US008906906B2

(12) United States Patent
Chaltin et al.

(10) Patent No.: US 8,906,906 B2
(45) Date of Patent: Dec. 9, 2014

(54) VIRAL REPLICATION INHIBITORS

(75) Inventors: Patrick Chaltin, Zetrud-Lumay (BE); Zeger Debyser, Heverlee (BE); Marc De Maeyer, Vaalbeek (BE); Arnaud Marchand, Korbeek-Lo (BE); Damien Marchand, Kessel-Lo (BE); Wim Smets, Kessel-Lo (BE); Arnout Voet, Zwevegem (BE); Frauke Christ, Heverlee (BE)

(73) Assignee: Katholieke Universiteit Leuven, Leuven (BE)

( * ) Notice: Subject to any disclaimer, the term of this patent is extended or adjusted under 35 U.S.C. 154(b) by 226 days.

(21) Appl. No.: 13/388,712

(22) PCT Filed: Aug. 5, 2010

(86) PCT No.: PCT/EP2010/061453
§ 371 (c)(1),
(2), (4) Date: Feb. 3, 2012

(87) PCT Pub. No.: WO2011/015641
PCT Pub. Date: Feb. 10, 2011

(65) Prior Publication Data
US 2012/0129840 A1    May 24, 2012

(30) Foreign Application Priority Data

Aug. 5, 2009  (GB) .................................. 0913636.7

(51) Int. Cl.
C07D 239/26    (2006.01)
A61K 31/505    (2006.01)
C07D 239/42    (2006.01)

(52) U.S. Cl.
CPC ............ *C07D 239/42* (2013.01); *C07D 239/26* (2013.01)
USPC ................... 514/217.06; 514/218; 514/235.8; 514/252.14; 514/269; 514/275; 540/575; 540/600; 544/122; 544/295; 544/320; 544/330; 544/331; 544/332

(58) Field of Classification Search
USPC .......... 540/575, 600; 544/122, 295, 320, 330, 544/331, 332; 514/217.06, 218, 235.8, 514/252.14, 269, 275
See application file for complete search history.

(56) References Cited

U.S. PATENT DOCUMENTS

| | | | | | |
|---|---|---|---|---|---|
| 3,502,673 | A | * | 3/1970 | Hepworth et al. ............ | 544/319 |
| 5,336,677 | A | * | 8/1994 | Sarantakis et al. ............ | 514/256 |
| 5,474,996 | A | * | 12/1995 | Caille et al. ................... | 514/256 |
| 7,125,880 | B1 | | 10/2006 | Chen | |
| 2004/0147547 | A1 | | 7/2004 | Hu et al. | |
| 2006/0040984 | A1 | * | 2/2006 | Luckhurst et al. ............ | 514/316 |

FOREIGN PATENT DOCUMENTS

| | | |
|---|---|---|
| CA | 2186536 | 3/1997 |
| CS | 231636 | 4/1984 |
| DE | 10-2007-061766 | 6/2009 |
| EP | 237963 | 9/1987 |
| EP | 169712 | 12/1990 |
| EP | 0634405 | 1/1995 |
| EP | 0667343 | 8/1995 |
| EP | 0731095 | 9/1996 |
| EP | 0941994 | 9/1999 |
| EP | 1015444 | 5/2003 |
| EP | 1505068 | 2/2005 |
| EP | 1471057 | 1/2006 |
| EP | 1375486 | 10/2008 |
| EP | 2006288 | 12/2008 |
| WO | WO96/02519 | 2/1996 |
| WO | WO96/32383 | 10/1996 |
| WO | WO97/25324 | 7/1997 |
| WO | WO98/07705 | 2/1998 |
| WO | WO00/43387 | 7/2000 |
| WO | WO01/14371 | 3/2001 |
| WO | WO01/53263 | 7/2001 |
| WO | WO01/98301 | 12/2001 |
| WO | WO02/102313 | 12/2002 |
| WO | WO2004/052315 | 6/2004 |
| WO | WO2004/069838 | 8/2004 |
| WO | WO2005/018645 | 3/2005 |
| WO | WO2005/042488 | 5/2005 |
| WO | WO2005/076861 | 8/2005 |
| WO | WO2006/033796 | 3/2006 |
| WO | WO2006/063732 | 6/2006 |

(Continued)

OTHER PUBLICATIONS

Goff, PubMed Abstract (J Gene Med 3(6):517-28), Nov.-Dec. 2001.*
Bosseray et al., PubMed Abstract (Pathol Biol (Paris) 50(8):483-92), Oct. 2002.*
Razonable et al., PubMed Abstract (Herpes 10(3):60-5), Dec. 2003.*
Douglas, Jr. Introduction to Viral Diseases, Cecil Textbook of Medicine, 20th Edition, vol. 2, pp. 1739-1747, 1996.*
Arutyunyan et al., CAPLUS Abstract 150:398461 (2008).*
Grimstrup et al., Exploration of SAR features by modifications of thiazoleacetic acids as CRTH2 antagonists, Bioorganic & Medicinal Chemistry Letters, 20(5), pp. 1638-1641, Jan. 2010.*

(Continued)

*Primary Examiner* — Deepak Rao
(74) *Attorney, Agent, or Firm* — Ropes & Gray LLP; Jane T. Gunnison; Ryan Murphey

(57) ABSTRACT

The present invention relates to a series of novel compounds having antiviral activity, more specifically HIV (Human Immunodeficiency Virus) replication inhibiting properties. The invention also relates to methods for the preparation of such compounds, as well as to novel intermediates useful in one or more steps of such syntheses. The invention also relates to pharmaceutical compositions comprising an effective amount of such compounds as active ingredients. This invention further relates to the use of such compounds as medicines or in the manufacture of a medicament useful for the treatment of animals suffering from viral infections, in particular HIV infection. This invention further relates to methods for the treatment of viral infections in animals by the administration of a therapeutical amount of such compounds, optionally combined with one or more other drugs having antiviral activity.

14 Claims, No Drawings

(56) References Cited

FOREIGN PATENT DOCUMENTS

| WO | WO2006/078834 | | 7/2006 |
|---|---|---|---|
| WO | WO2006/089053 | | 8/2006 |
| WO | WO2007/062677 | | 6/2007 |
| WO | WO2007/131350 | | 11/2007 |
| WO | WO2008/016522 | | 2/2008 |
| WO | WO2008/058285 | | 5/2008 |
| WO | WO2008/069609 | | 6/2008 |
| WO | WO2009/062285 | | 5/2009 |
| WO | WO2009/062288 | | 5/2009 |
| WO | WO2009/062289 | | 5/2009 |
| WO | WO2009/062308 | | 5/2009 |
| WO | WO 2010/089391 | * | 8/2010 |
| WO | WO2010/130842 | | 11/2010 |
| WO | WO2011/076765 | | 6/2011 |

OTHER PUBLICATIONS

Yamanaka et al., "Reactivity of active oxygen species generated in the EuCl3 catalytic system for monooxygenation of hydrocarbons," J. Chem. Soc., Perkin Trans. 2, 2511-2515 (1996).

Itoh et al., "The synthesis of 5-substituted 1,2,3-triazines with ketene silyl acetals and ceric ammonium nitrate," Chem. Pharm. Bull., 43(5), 881-883 (1995).

Bahekar et al., "Synthesis and anti-inflammatory activity of some [2-amino-6-(4-substituted aryl)-4-(4-substituted phenyl)-1,6-dihydropyrimidine-5-yl]-acetic acid derivatives," Acta. Pharma., 53(3):223-229 (2003).

El-Essawy, "Synthesis of Novel Acyclonucleosides Analogs of Pyridothienopyrimidine as Antiviral Agents," Nucleosides Nucleotides Nucleic Acids, 24(8):1265-1276 (2005).

Ryabukhin et al., "Heterocyclic Ortho-Aminocarbonyl Compounds in the Friedländer Reaction Promoted by Chlorotrimethylsilane," Heterocycles, 71(11):2397-2411 (2007).

Banker et al, Modern Pharmaceutics, 3ed., Marcel Dekker, New York, pp. 451 and 596 (1996).

Chemical Abstracts Service US Database registry Nos. 117646-31-8 and 107250-17-9 (accession Nos. 109:230768 and 106:131331) (1988).

Chemical Abstracts RN 556020-24-7 5,6, 7 ,8-tetrahydro-2-(4-iodophenyl)-4-phenyl-[Benzothieno[2,3-b]pyridine-3-acetic acid, Jul. 28, 2003.

Henze et al., "The number of structurally isomeric alcohols of the methanol series," J. Amer. Chem. Soc., 3042-3046 (1931).

Online "http://web.archive.org/web/20070630171813/http://www.enamine.net/index.php?option=com_content&task=view&id=22&menuid=51&PHPSESSID=64a4f248f69d671a413f487bb62c4d90" dated Jun. 30, 2007, accessed Nov. 9, 2011.

Online "http://web.archive.org/web/20030923140513/http://ambinter.com/" accessed Sep. 3, 2013.

Wolff, "Burger's Medicinal Chemistry, 5ed, Part 1", John Wiley & Sons, pp. 975-977 (1995).

Zhou "Anti-AIDS agents 79. Design, synthesis, molecular modeling and structure-activity relationships of novel dicamphanoyl-20,20-dimethyldihydropyranochromone (DCP) analogs as potent anti-HIV agents," Bioorganic & Medicinal Chemistry 18:6678-6689 (2010).

Chemical Abstracts Registry No. 105175-78-8:1,6-dihydro-α-4-dimethyl-2-(methylthio)-6-oxo-5-pyrimidineacetic acid, Apr. 16, 1984.

Chemical Abstracts Registry No. 351380-60-4: 4-[[1-(hydroxymethyl)propyl]amino]-α-2-dimethyl-6-(2,4,6-trimethylphenoxy)-ethyl ester-5-pyrimidineacetic acid, Jul. 26, 2001.

Garcia et al., Aminopyrimidines as electron-rich azadienes: extension of the synthetic potential of hetero Diels-Alder reactions under acidic conditions, Synlett 1:57-60 (2001).

Sakamoto et al.,Cross-coupling of N-heteroaryl halides with active methylene compounds in the presence of tetrakis(triphenylphosphine)palladium, Chem. Pharm. Bull. 36(5):1664-1669 (1988).

Zhang and Sui, A convenient synthesis of 3-pyridinal- and 3-pyrimidinylcoumarins, Synthesis 15:2568-2572 (2006).

Chemical Abstracts Registry No. 754922-72-0 [5-Pyrimidineacetic acid, 4-[(4-chlorophenyl)thio]-2- (methylthio)-.alpha.-(2,2,2-trifluro-1-hydroxyethylidene)-(CA Index Name) (2004).

Smrz et al., 5(OR 4)-Arylthio-2-methylthiopyrimidines as potential intermediates in the synthesis of tricyclic pyrimido systems, Collection Czechoslow. Chem. Commun. 41:2771-2787 (1975).

* cited by examiner

VIRAL REPLICATION INHIBITORS

RELATED APPLICATIONS

This application is a national stage filing under 35 U.S.C. 371 of International Application PCT/EP2010/061453, filed Aug. 5, 2010, which claims the benefit of GB 0913636.7, filed Aug. 5, 2009, the specifications of which are incorporated by reference herein. International Application PCT/EP2010/061453 was published under PCT Article 21(2) in English.

FIELD OF THE INVENTION

The present invention relates to a series of novel compounds having antiviral activity, more specifically HIV (Human Immunodeficiency Virus) replication inhibiting activity. The invention also relates to methods for the preparation of such compounds, as well as to novel intermediates useful in one or more steps of such syntheses. The invention also relates to pharmaceutical compositions comprising an effective amount of such compounds as active ingredients. This invention further relates to the compounds for use as a medicine and to the use of such compounds in the manufacture of a medicament, more in particular useful for the prevention or treatment of animals (including mammals and humans) suffering from viral infections, in particular HIV infection. This invention further relates to methods for the prevention or treatment of viral infections in animals by the administration of a therapeutically effective amount of such compounds, optionally combined with one or more other drugs having antiviral activity.

BACKGROUND OF THE INVENTION

A retrovirus designated human immunodeficiency virus (HIV) is the etiological agent of the complex disease that includes progressive destruction of the immune system (acquired immune deficiency syndrome, hereinafter AIDS) and degeneration of the central and peripheral nervous system. There are two types of HIV, HIV-1 and HIV-2, the latter producing a less severe disease than the former. Being a retrovirus, its genetic material is in the form of RNA (ribonucleic acid) consisting of two single RNA strands. Coexisting with RNA are reverse transcriptase (having polymerase and ribonuclease activity), integrase, a protease and other proteins.

It is known in the art that some antiviral compounds which act as inhibitors of HIV replication are effective agents in the treatment of AIDS and similar diseases. Drugs that are known and approved for the treatment of HIV-infected patients belong to one of the following classes:

nucleoside reverse transcriptase (RT) inhibitors such as, but not limited to, azidothymidine (AZT), and lamivudine (3TC), nucleotide reverse transcriptase inhibitors such as, but not limited to, tenofovir (R-PMPA), non-nucleoside reverse transcriptase inhibitors such as, but not limited to, nevirapine, efavirenz, protease inhibitors such as, but not limited to, nelfinavir, saquinavir, ritonavir and amprenavir, fusion inhibitors such as enfuvirtide, and integrase inhibitors such as raltegravir or elvitegravir.

Replication of the human immunodeficiency virus type 1 (hereinafter referred as HIV-1) can be drastically reduced in infected patients by combining potent antiviral drugs targeted at multiple viral targets, as reviewed by Vandamme et al. in *Antiviral Chem. Chemother.* (1998) 9:187-203.

Multiple-drug combination regimes can reduce viral load below the detection limit of the most sensitive tests. Nevertheless low level ongoing replication has been shown to occur, possibly in sanctuary sites, leading to the emergence of drug-resistant strains, according to Perelson et al. in *Nature* (1997) 387:123-124. Furthermore the selectivity of many antiviral agents is rather low, possibly making them responsible for side-effects and toxicity. Moreover, HIV can develop resistance to most, if not all, currently approved antiviral drugs, according to Schmit et al. in *J. Infect. Dis.* (1996) 174:962-968. It is well documented that the ability of HIV to rapidly evolve drug resistance, together with toxicity problems resulting from known drugs, requires the development of additional classes of antiviral drugs.

As a summary, there is still a stringent need in the art for potent inhibitors of HIV. Therefore a goal of the present invention is to satisfy this urgent need by identifying efficient pharmaceutically active ingredients that are active against HIV, less toxic, more stable (i.e. chemically stable, metabolically stable), effective against viruses resistant to currently available drugs and/or which are more resistant to virus mutations than existing antiviral drugs and that can be useful, either alone or in combination with other active ingredients, for the treatment of retroviral infections, in particular lentiviral infections, and more particularly HIV infections, in mammals and more specifically in humans. It is also known to the skilled in the art that the physicochemical properties of known drugs as well as their ADME-Tox (administration, distribution, metabolism, excretion) properties may limit or prohibit their use in the treatment of diseases. Therefore, a problem of existing drugs that can be overcome with the compounds of the invention can be selected from poor or inadequate physicochemical or ADME-Tox properties such as solubility, LogP, CYP inhibition, hepatic stability, plasmatic stability, among others. Furthermore, another goal of the present invention is to complement existing antiviral drugs in such a way that the resulting drug combination has improved activity or improved resistance to virus mutation than each of the individual compounds.

The prior art describes one 5-pyrimidineacetic acid derivative as a reactant for the preparation of small organic molecules (Kuno, Atsushi et al, Chemical & Pharmaceutical Bulletin (1992), 40(9), 2423-31; EP169712) and no mention is made of use as a medicament.

SUMMARY OF THE INVENTION

The present invention is based on the unexpected finding that at least one of the above-mentioned problems can be solved by a novel class of pyrimidine derivatives.

The present invention provides new antiviral agents, especially anti-retroviral agents, and more particularly anti-HIV compounds. These compounds are pyrimidines, or analogues or derivatives thereof, which have been shown to possess antiviral activity, more specifically against HIV. The present invention demonstrates that these compounds efficiently inhibit the replication of HIV. Therefore, these pyrimidine derivatives constitute a useful class of new potent antiviral compounds that can be used in the treatment and/or prevention of viral infections in animals, mammals and humans, more specifically for the treatment and/or prevention of HIV in humans.

The present invention furthermore relates to the compounds for use as a medicine, to the use of such compounds as medicines, more specifically as antiviral agents, and to their use for the manufacture of medicaments for treating and/or preventing viral infections, in particular retroviral infections such as, but not limited to, HIV in humans. The invention also relates to methods for the preparation of all such compounds and to pharmaceutical compositions comprising them in an antiviral effective amount.

The present invention also relates to a method of treatment or prevention of viral infections, in particular retroviral infections such as, but not limited to HIV in humans by the administration of one or more such compounds, optionally in combination with one or more other antiviral agents, to a patient in need thereof.

One aspect of the present invention is the provision of novel compounds (being pyrimidine derivatives), said compounds having a structure according to the formula (A1):

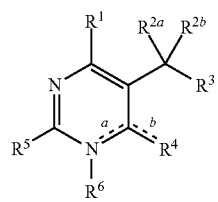

(A1)

wherein,
each dotted line represents an optional double bond, whereby if the dotted line "a" forms a double bond, the dotted line "b" does not form a double bond and whereby if the dotted line "b" forms a double bond, the dotted line "a" does not form a double bond;

$R^1$ is independently selected from alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl or heterocycle-heteroalkynyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more $Z^1$;

each of $R^{2a}$ and $R^{2b}$ is independently selected from hydrogen; cyano; alkyl; alkenyl; alkynyl; heteroalkyl; heteroalkenyl; heteroalkynyl; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl or $R^{2a}$ and $R^{2b}$ can be taken together to form vinyl, vinylalkyl or vinylheteroalkyl;

wherein said alkyl, alkenyl, alkynyl, heteroalkyl, heteroalkenyl, heteroalkynyl, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl or heterocycle-heteroalkynyl, vinyl, vinylalkyl or vinylheteroalkyl, can be unsubstituted or substituted with one or more $Z^1$;

or
$R^{2a}$ and $R^7$ or $R^{2b}$ and $R^7$ can be taken together to form a 4, 5, 6 or 7-membered lactone;

$R^3$ is independently selected from —CN; —CONH$_2$; —COOR$^7$; —C(O)NHCN; —C(O)NHOH; —S(O)$_2$OH; —S(O)$_2$NHZ$^4$; —P(O)(OH)NH$_2$; —P(O)(OH)O-alkyl; —P(O)(O-alkyl)$_2$; —P(O)OH$_2$; —NHC(O)NHS(O)$_2$-aryl; —NHC(O)NHS(O)$_2$-heteroaryl; —C(O)NHS(O)$_2$-aryl; —C(O)NHS(O)$_2$-heteroaryl; —S(O)$_2$NHS(O)$_2$-aryl; —S(O)$_2$NHS(O)$_2$-heteroaryl; or from the following structures:

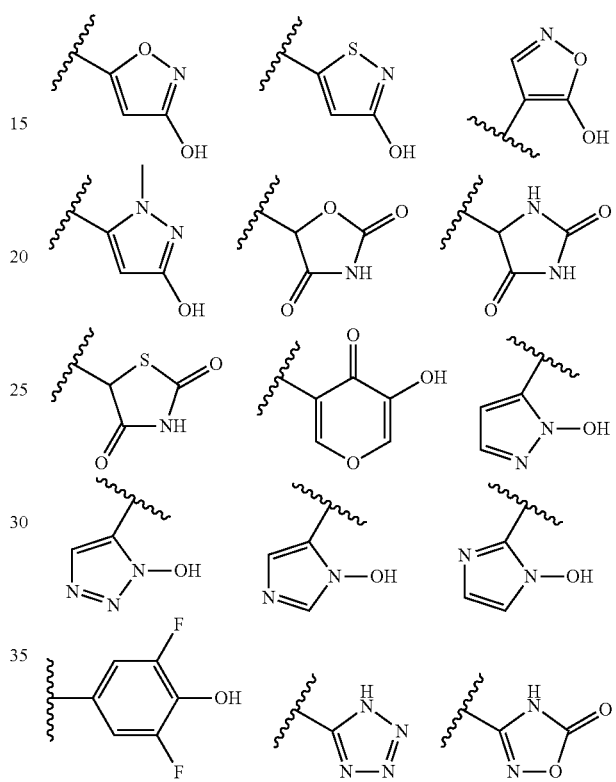

when the dotted line "a" forms a double bond, $R^4$ is independently selected from hydrogen; halogen; cyano; hydroxyl; alkyl; alkenyl, alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; and heterocycle-alkynyl; heterocycle-heteroalkyl; heterocycle-heteroalkenyl; and heterocycle-heteroalkynyl; and when the dotted line "b" forms a double bond, $R^4$ is independently selected from O and S;

wherein said alkyl, alkenyl, alkynyl, heteroalkyl, heteroalkenyl, heteroalkynyl, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl or heterocycle-heteroalkynyl can be unsubstituted or substituted with one or more $Z^1$;

when the dotted line "a" forms a double bond, $R^6$ is not present and when the dotted line "b" forms a double bond, $R^6$ is independently selected from hydrogen; alkyl; alkenyl, alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; heterocycle-heteroalkynyl;

wherein said alkyl, alkenyl, alkynyl, heteroalkyl, heteroalkenyl, heteroalkynyl, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl or heterocycle-heteroalkynyl can be unsubstituted or substituted with one or more $Z^1$;

$R^5$ is selected from halogen; cyano; —$NR^{10}R^{11}$; alkyl; alkenyl; alkynyl; heteroalkyl; heteroalkenyl; heteroalkynyl; aryl; arylalkyl; arylalkenyl; arylalkynyl; arylheteroalkyl; arylheteroalkenyl; arylheteroalkynyl; heterocycle; heterocycle-alkyl; heterocycle-alkenyl; heterocycle-alkynyl; heterocycle-heteroalkyl, heterocycle-heteroalkenyl, or heterocycle-heteroalkynyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more $R^{20}$;

each $R^{10}$ and $R^{11}$ is independently selected from hydrogen; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl; or $R^{10}$ and $R^{11}$ can be taken together with the nitrogen to which they are attached to in order to form a 4-, 5-, 6-, 7- or 8-membered heterocycle which can be unsubstituted or substituted with one or more $R^{20}$;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more $R^{20}$;

each $R^{20}$ is independently selected from the group consisting of halogen; —$OR^{21}$; =O; —$SR^{21}$; =S; —$S(O)R^{22}$; —$S(O)_2R^{22}$; —$S(O)_2NR^{23}R^{24}$; trifluoromethyl; nitro; —$NR^{23}R^{24}$; —$NR^{21}S(O)_2R^{22}$; cyano; —$NR^{21}C(O)R^{22}$; —$NR^{21}C(O)NR^{23}R^{24}$; —$C(O)OR^{21}$; —$C(O)NR^{23}R^{24}$; —$C(O)R^{22}$; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more $Z^1$;

each $R^{21}$ is independently selected from hydrogen; alkyl; alkenyl; alkynyl; heteroalkyl; heteroalkenyl; heteroalkynyl; aryl; arylalkyl; arylalkenyl; arylalkynyl; arylheteroalkyl; arylheteroalkenyl; arylheteroalkynyl; heterocycle; heterocycle-alkyl; heterocycle-alkenyl; heterocycle-alkynyl; heterocycle-heteroalkyl; heterocycle-heteroalkenyl; and heterocycle-heteroalkynyl;

wherein said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, heterocycle, heterocycle-alkyl, heterocycle-alkenyl, heterocycle-alkynyl, heterocycle-heteroalkyl, heterocycle-heteroalkenyl, and heterocycle-heteroalkynyl can be unsubstituted or substituted with one or more $Z^1$;

each $R^{22}$ is independently selected from hydrogen; hydroxyl; alkyl; alkenyl; alkynyl; heteroalkyl; heteroalkenyl; heteroalkynyl; aryl; arylalkyl; arylalkenyl; arylalkynyl; arylheteroalkyl; arylheteroalkenyl; arylheteroalkynyl; heterocycle; heterocycle-alkyl; heterocycle-alkenyl; heterocycle-alkynyl; heterocycle-heteroalkyl; heterocycle-heteroalkenyl; and heterocycle-heteroalkynyl;

wherein said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, heterocycle, heterocycle-alkyl, heterocycle-alkenyl, heterocycle-alkynyl, heterocycle-heteroalkyl, heterocycle-heteroalkenyl, and heterocycle-heteroalkynyl can be unsubstituted or substituted with one or more $Z^1$;

each $R^{23}$ and $R^{24}$ is independently selected from hydrogen; alkyl; alkenyl; alkynyl; heteroalkyl; heteroalkenyl; heteroalkynyl; aryl; arylalkyl; arylalkenyl; arylalkynyl; arylheteroalkyl; arylheteroalkenyl; arylheteroalkynyl; heterocycle; heterocycle-alkyl; heterocycle-alkenyl; heterocycle-alkynyl; heterocycle-heteroalkyl; heterocycle-heteroalkenyl; and heterocycle-heteroalkynyl; or $R^{23}$ and $R^{24}$ can be taken together with the nitrogen to which they are attached to in order to form a 4-, 5-, 6-, 7- or 8-membered heterocycle which can be unsubstituted or substituted with one or more $Z^1$;

wherein said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, heterocycle, heterocycle-alkyl, heterocycle-alkenyl, heterocycle-alkynyl, heterocycle-heteroalkyl, heterocycle-heteroalkenyl, and heterocycle-heteroalkynyl can be unsubstituted or substituted with one or more $Z^1$;

each $Z^1$ is independently selected from the group consisting of hydrogen; halogen; —$OZ^2$; =O; —$SZ^2$; =S; —$S(O)Z^3$; —$S(O)_2Z^3$; —$S(O)_2NZ^4Z^5$; trifluoromethyl; nitro; —$NZ^4Z^5$; —$NZ^2S(O)_2Z^3$; cyano; —$NZ^2C(O)Z^3$; —$NZ^2C(O)NZ^4Z^5$; —$C(O)OZ^2$; —$C(O)NZ^4Z^5$; —$C(O)Z^3$; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl;

wherein said alkyl, alkenyl, alkynyl, heteroalkyl, heteroalkenyl, heteroalkynyl, aryl, heterocycle, arylalkyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more $Z^{11}$;

or two $Z^1$ on the same carbon atom or nitrogen atom can be taken together with the 4-, 5-, 6-, 7- or 8-membered ring they are attached to form a spiro-cycloalkyl; a spiro-cycloalkenyl; a spiro-cycloalkynyl; or a saturated or unsaturated spiro-heterocycle;

each $Z^{11}$ is independently selected from the group consisting of hydrogen; halogen; —$OZ^{12}$; =O; —$SZ^{12}$; =S; —$S(O)Z^{13}$; —$S(O)_2Z^{13}$; —$S(O)_2NZ^{14}Z^{15}$; trifluoromethyl; nitro; —$NZ^{14}Z^{15}$; —$NZ^{12}S(O)_2Z^{13}$; cyano; —$NZ^{12}C(O)Z^{13}$; —$NZ^{12}C(O)NZ^{14}Z^{15}$; —$C(O)OZ^{12}$; —$C(O)NZ^{14}Z^{15}$; —$C(O)Z^{13}$; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from the group of alkyl, alkenyl, alkynyl, heteroalkyl, heteroalkenyl, heteroalkynyl, hydroxyl, =O, halogen, —SH, =S, trifluoromethyl, —O-alkyl, —$OCF_3$, cyano, nitro, —C(O)OH or —$NH_2$;

each $R^7$, $Z^2$ and $Z^{12}$ is independently selected from hydrogen; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with alkyl, alkenyl, alkynyl, heteroalkyl, heteroalkenyl, heteroalkynyl, hydroxyl, =O, halogen, —SH, =S, trifluoromethyl, —O-alkyl, —$OCF_3$, cyano, nitro, —C(O)OH or —$NH_2$;

each $Z^3$ and $Z^{13}$ is independently selected from hydroxyl; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more selected from the group of alkyl, alkenyl, alkynyl, heteroalkyl, heteroalkenyl, heteroalkynyl, hydroxyl, =O, halogen, —SH, =S, trifluoromethyl, —O-alkyl, —$OCF_3$, cyano, nitro, —C(O)OH or —$NH_2$;

each $Z^4$, $Z^5$, $Z^{14}$ and $Z^{15}$ is independently selected from hydrogen; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more selected from the group of alkyl, alkenyl, alkynyl, heteroalkyl, heteroalkenyl, heteroalkynyl, hydroxyl, =O, halogen, —SH, =S, trifluoromethyl, —O-alkyl, —$OCF_3$, cyano, nitro, —C(O)OH or —$NH_2$;

or wherein $Z^4$ and $Z^5$, and $Z^{14}$ and $Z^{15}$ respectively, can be taken together in order to form a (4-, 5-, 6-, 7-, or 8-membered) heterocycle which can be unsubstituted or substituted with alkyl, alkenyl, alkynyl, heteroalkyl, heteroalkenyl, heteroalkynyl, hydroxyl, halogen, —SH, trifluoromethyl, —O-alkyl, —$OCF_3$, cyano, nitro, —C(O)OH or —$NH_2$;

and isomers (in particular stereo-isomers or tautomers), solvates, hydrates, salts (in particular pharmaceutically acceptable salts) or prodrugs thereof.

In a particular embodiment of the invention, the compounds are novel pyrimidine derivatives, said compounds having a structure according to the formula (A):

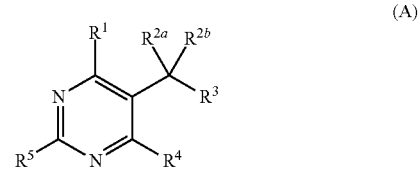

(A)

wherein, $R^1$ is independently selected from cycloalkyl; cycloalkenyl; cycloalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl or heterocycle-heteroalkynyl;

and wherein said cycloalkyl, cycloalkenyl, cycloalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more $Z^1$;

each of $R^{2a}$ and $R^{2b}$ is independently selected from hydrogen; cyano; alkyl; alkenyl; alkynyl; heteroalkyl; heteroalkenyl; heteroalkynyl; aryl; arylalkyl; arylalkenyl; arylalkynyl; arylheteroalkyl; arylheteroalkenyl; arylheteroalkynyl; heterocycle; heterocycle-alkyl; heterocycle-alkenyl; heterocycle-alkynyl; heterocycle-heteroalkyl, heterocycle-heteroalkenyl, or heterocycle-heteroalkynyl; or $R^{2a}$ and $R^{2b}$ can be taken together to form vinyl or vinylalkyl;

and wherein said alkyl, alkenyl, alkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more $Z^1$;

$R^3$ is independently selected from —C(O)OH; —C(O)OR$^7$; —C(O)NHCN; —S(O)$_2$OH; —S(O)$_2$OZ$^2$; —S(O)$_2$NHZ$^4$; —P(O)(OH)NH$_2$; —P(O)(OH)O-alkyl; —NHC(O)NHS(O)$_2$-aryl; —NHC(O)NHS(O)$_2$-heteroaryl; —C(O)NHS(O)$_2$-aryl; —C(O)NHS(O)$_2$-heteroaryl; —S(O)$_2$NHS(O)$_2$-aryl; —S(O)$_2$NHS(O)$_2$-heteroaryl; or from the following structures:

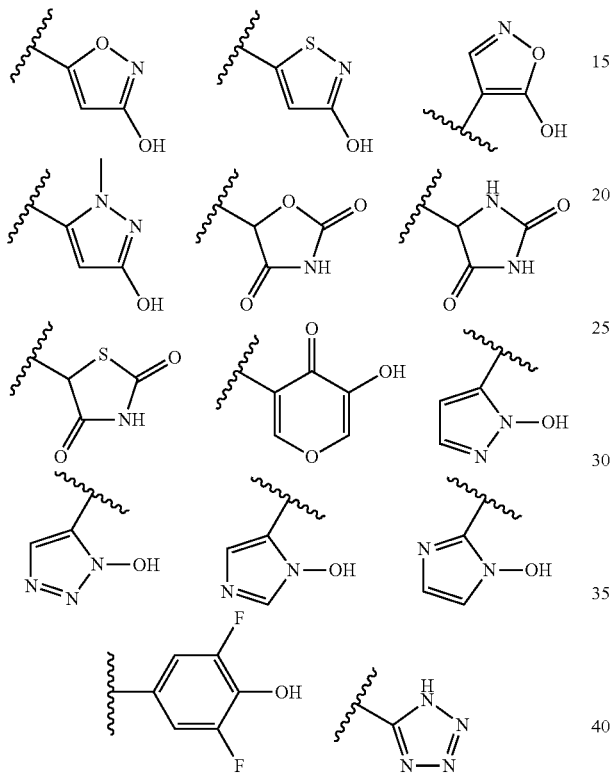

$R^4$ is independently selected from hydrogen; alkyl; alkenyl or alkynyl; wherein said alkyl, alkenyl or alkynyl can be unsubstituted or substituted with one or more $Z^1$;

$R^5$ is selected from halogen; cyano; —NR$^{10}$R$^{11}$; alkyl; alkenyl; alkynyl; heteroalkyl; heteroalkenyl; heteroalkynyl; aryl; arylalkyl; arylalkenyl; arylalkynyl; arylheteroalkyl; arylheteroalkenyl; arylheteroalkynyl; heterocycle; heterocycle-alkyl; heterocycle-alkenyl; heterocycle-alkynyl; heterocycle-heteroalkyl, heterocycle-heteroalkenyl, or heterocycle-heteroalkynyl;
wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more $R^{20}$;
each $R^{10}$ and $R^{11}$ is independently selected from hydrogen; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl; or $R^{10}$ and $R^{11}$ can be taken together with the nitrogen to which they are attached to form a (5-, 6-, or 7-membered) heterocycle which can be unsubstituted or substituted with one or more $R^{20}$;
wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more $R^{20}$;

each $R^{20}$ is independently selected from the group consisting of halogen; —OR$^{21}$; =O; —SR$^{21}$; =S; —S(O)R$^{22}$; —S(O)$_2$R$^{22}$; —S(O)$_2$NR$^{23}$R$^{24}$; trifluoromethyl; nitro; —NR$^{23}$R$^{24}$; —NR$^{21}$S(O)$_2$R$^{22}$; cyano; —C(O)OR$^{21}$; —C(O)NR$^{23}$R$^{24}$; —C(O)R$^{22}$; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl;
and wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more $Z^1$;

each $R^{21}$ is independently selected from hydrogen; alkyl; alkenyl; alkynyl; heteroalkyl; heteroalkenyl; heteroalkynyl; aryl; arylalkyl; arylalkenyl; arylalkynyl; arylheteroalkyl; arylheteroalkenyl; arylheteroalkynyl; heterocycle; heterocycle-alkyl; heterocycle-alkenyl; heterocycle-alkynyl; heterocycle-heteroalkyl; heterocycle-heteroalkenyl; and heterocycle-heteroalkynyl;
wherein said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, heterocycle, heterocycle-alkyl, heterocycle-alkenyl, heterocycle-alkynyl, heterocycle-heteroalkyl, heterocycle-heteroalkenyl, and heterocycle-heteroalkynyl can be unsubstituted or substituted with one or more $Z^1$;

each $R^{22}$ is independently selected from hydrogen; hydroxyl; alkyl; alkenyl; alkynyl; heteroalkyl; heteroalkenyl; heteroalkynyl; aryl; arylalkyl; arylalkenyl; arylalkynyl; arylheteroalkyl; arylheteroalkenyl; arylheteroalkynyl; heterocycle; heterocycle-alkyl; heterocycle-alkenyl; heterocycle-alkynyl; heterocycle-heteroalkyl; heterocycle-heteroalkenyl; and heterocycle-heteroalkynyl;
wherein said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, heterocycle, heterocycle-alkyl, heterocycle-alkenyl, heterocycle-alkynyl, heterocycle-heteroalkyl, heterocycle-heteroalkenyl, and heterocycle-heteroalkynyl can be unsubstituted or substituted with one or more $Z^1$;

each $R^{23}$ and $R^{24}$ is independently selected from hydrogen; alkyl; alkenyl; alkynyl; heteroalkyl; heteroalkenyl; heteroalkynyl; aryl; arylalkyl; arylalkenyl; arylalkynyl; arylheteroalkyl; arylheteroalkenyl; arylheteroalkynyl;

heterocycle; heterocycle-alkyl; heterocycle-alkenyl; heterocycle-alkynyl; heterocycle-heteroalkyl; heterocycle-heteroalkenyl; and heterocycle-heteroalkynyl;

and wherein said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, heterocycle, heterocycle-alkyl, heterocycle-alkenyl, heterocycle-alkynyl, heterocycle-heteroalkyl, heterocycle-heteroalkenyl, and heterocycle-heteroalkynyl can be unsubstituted or substituted with one or more $Z^1$;

and wherein $R^{23}$ and $R^{24}$ can be taken together in order to form a (5-, 6-, or 7-membered) heterocycle which can be unsubstituted or substituted with one or more $Z^1$;

each $Z^1$ is independently selected from the group consisting of hydrogen; halogen; —$OZ^2$; =O; —$SZ^2$; =S; —$S(O)Z^3$; —$S(O)_2Z^3$; —$S(O)_2NZ^4Z^5$; trifluoromethyl; nitro; —$NZ^4Z^5$; —$NZ^2S(O)_2Z^3$; cyano; —$C(O)OZ^2$; —$C(O)NZ^4Z^5$; —$C(O)Z^3$; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl;

and wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from the group of alkyl, alkenyl, alkynyl, hydroxyl, =O, halogen, —SH, =S, trifluoromethyl, —O-alkyl, —$OCF_3$, cyano, nitro, —C(O)OH or $NH_2$;

each $R^7$ and $Z^2$ is independently selected from hydrogen; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with alkyl, alkenyl, alkynyl, hydroxyl, =O, halogen, —SH, =S, trifluoromethyl, —O-alkyl, —$OCF_3$, cyano, nitro, —C(O)OH or $NH_2$;

each $Z^3$ is independently selected from hydroxyl; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more selected from the group of alkyl, alkenyl, alkynyl, hydroxyl, =O, halogen, —SH, =S, trifluoromethyl, —O-alkyl, —$OCF_3$, cyano, nitro, —C(O)OH or $NH_2$;

each $Z^4$ and $Z^5$ is independently selected from hydrogen; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more selected from the group of alkyl, alkenyl, alkynyl, hydroxyl, =O, halogen, —SH, =S, trifluoromethyl, —O-alkyl, —$OCF_3$, cyano, nitro, —C(O)OH or $NH_2$;

and wherein $Z^4$ and $Z^5$ can be taken together in order to form a (5-, 6-, or 7-membered) heterocycle which can be unsubstituted or substituted with alkyl, alkenyl, alkynyl, hydroxyl, halogen, —SH, trifluoromethyl, —O-alkyl, —$OCF_3$, cyano, nitro, —C(O)OH or —$NH_2$;

and isomers (in particular stereo-isomers or tautomers), solvates, hydrates, salts (in particular pharmaceutically acceptable salts) or prodrugs thereof.

In a particular embodiment, the compounds of the invention are not selected from the group of:

2-(2-(bis(4-methoxyphenyl)amino)-4-(3-fluorophenyl) pyrimidin-5-yl)acetic acid;

2-(2-(bis(4-fluorophenyl)amino)-4-(3-fluorophenyl)pyrimidin-5-yl)acetic acid;

3'-((2-butyl-5-(carboxymethyl)-6-chloropyrimidin-4-yl) methyl)biphenyl-2-carboxylic acid;

2-(4-chloro-6-(methyl(2-oxo-2-(pyrrolidin-1-yl)ethyl) amino)-2-(4-(nicotinamido)benzyl)pyrimidin-5-yl)acetic acid;

2-(2-(bis(4-fluorophenyl)methyl)-4-(3-fluorophenyl)pyrimidin-5-yl)acetic acid;

2-(6-(2-(4-aminophenyl)prop-1-enyl)-2-methyl-4-oxo-1, 4-dihydropyrimidin-5-yl)propanoic acid;

2-(2-methyl-4-oxo-6-(2-phenylprop-1-enyl)-1,4-dihydropyrimidin-5-yl)propanoic acid;

2-(6-(2-(4-chlorophenyl)prop-1-enyl)-2-methyl-4-oxo-1, 4-dihydropyrimidin-5-yl)propanoic acid;

2-(6-(2-(4-aminophenyl)prop-1-enyl)-2-methyl-4-oxo-1, 4-dihydropyrimidin-5-yl)acetic acid;

2-(6-(2-(4-chlorophenyl)prop-1-enyl)-2-methyl-4-oxo-1, 4-dihydropyrimidin-5-yl)acetic acid;

2-(2-(hydroxymethyl)-4-oxo-6-phenyl-1,4-dihydropyrimidin-5-yl)hexanoic acid;

2-(2-(hydroxymethyl)-4-oxo-6-phenyl-1,4-dihydropyrimidin-5-yl)propanoic acid;

2-(2-(hydroxymethyl)-4-oxo-6-phenyl-1,4-dihydropyrimidin-5-yl)acetic acid;

2-(4-(pyridin-2-ylamino)-2-(3,4,5-trimethoxyphenylamino)pyrimidin-5-yl)acetic acid;

2-(4-cyclopropyl-2-(4-(trifluoromethyl)phenyl)pyrimidin-5-yl)acetic acid;

2-(2-(4-(3,4-dichlorobenzamido)benzyl)-4-methyl-6-(pyrrolidin-1-yl)pyrimidin-5-yl)acetic acid;

2-(2-(4-(2-naphthamido)benzyl)-4-methyl-6-(pyrrolidin-1-yl)pyrimidin-5-yl)acetic acid;
2-(2-(4-(2-naphthamido)benzyl)-4-(dimethylamino)-6-(piperidin-1-yl)pyrimidin-5-yl)acetic acid;
2-(2-(4-(2-naphthamido)benzyl)-4-(dimethylamino)-6-(pyrrolidin-1-yl)pyrimidin-5-yl)acetic acid;
2-(2-(4-(2-naphthamido)benzyl)-4-(dimethylamino)-6-morpholinopyrimidin-5-yl)acetic acid;
2-(4-chloro-2-(4-(3-chloro-4-methoxybenzamido)benzyl)-6-(pyrrolidin-1-yl)pyrimidin-5-yl)acetic acid;
2-(4-chloro-2-(4-(4-(methylthio)benzamido)benzyl)-6-(pyrrolidin-1-yl)pyrimidin-5-yl)acetic acid;
(S)-1-(2-(4-(2-naphthamido)benzyl)-5-(carboxymethyl)-6-chloropyrimidin-4-yl)pyrrolidine-2-carboxylic acid;
2-(2-(4-(2-naphthamido)benzyl)-4-chloro-6-(3-hydroxypyrrolidin-1-yl)pyrimidin-5-yl)acetic acid;
2-(2-(4-(2-naphthamido)benzyl)-4-chloro-6-(2,5-dihydro-1H-pyrrol-1-yl)pyrimidin-5-yl)acetic acid;
2-(2-(4-(2-naphthamido)benzyl)-4-chloro-6-(piperidin-1-yl)pyrimidin-5-yl)acetic acid;
2-(2-(4-(2-naphthamido)benzyl)-4-chloro-6-morpholinopyrimidin-5-yl)acetic acid;
2-(2-(4-(2-naphthamido)benzyl)-4-chloro-6-(cyclohexyl(methyl)amino)pyrimidin-5-yl)acetic acid;
2-(2-(4-(2-naphthamido)benzyl)-4-chloro-6-(pyrrolidin-1-yl)pyrimidin-5-yl)acetic acid;
2-(2-(4-(2-naphthamido)benzyl)-4-(methyl(2-oxo-2-(pyrrolidin-1-yl)ethyl)amino)pyrimidin-5-yl)acetic acid;
2-(4-chloro-2-(4-(3,4-dichlorobenzamido)benzyl)-6-(pyrrolidin-1-yl)pyrimidin-5-yl)acetic acid;
(E)-2-(4-chloro-2-(4-cinnamamidobenzyl)-6-(pyrrolidin-1-yl)pyrimidin-5-yl)acetic acid;
2-(4-chloro-2-(4-(4-methoxy-3,5-dimethylbenzamido)benzyl)-6-(pyrrolidin-1-yl)pyrimidin-5-yl)acetic acid;
2-(4-chloro-2-(4-(4-methoxy-3-nitrobenzamido)benzyl)-6-(pyrrolidin-1-yl)pyrimidin-5-yl)acetic acid;
2-(2-(1H-pyrrol-1-yl)benzamido)benzyl)-4-chloro-6-(pyrrolidin-1-yl)pyrimidin-5-yl)acetic acid;
2-(4-chloro-2-(4-(4-isopropoxybenzamido)benzyl)-6-(pyrrolidin-1-yl)pyrimidin-5-yl)acetic acid;
2-(4-chloro-2-(4-(4-phenoxybenzamido)benzyl)-6-(pyrrolidin-1-yl)pyrimidin-5-yl)acetic acid;
2-(2-(4-(4-acetamidobenzamido)benzyl)-4-chloro-6-(pyrrolidin-1-yl)pyrimidin-5-yl)acetic acid;
2-(4-chloro-2-(4-(4-nitrobenzamido)benzyl)-6-(pyrrolidin-1-yl)pyrimidin-5-yl)acetic acid;
2-(4-chloro-2-(4-(4-guanidinobenzamido)benzyl)-6-(pyrrolidin-1-yl)pyrimidin-5-yl)acetic acid;
2-(2-(4-(2-naphthamido)benzyl)-4-chloro-6-(methyl(2-oxo-2-(pyrrolidin-1-yl)ethyl)amino)pyrimidin-5-yl)acetic acid;
2-(4-(4-chlorophenylthio)-2-(methylthio)pyrimidin-5-yl)-4,4,4-trifluoro-3-hydroxybut-2-enoic acid;
2-(4-(4-((4-(3,4-dichlorophenoxy)piperidin-1-yl)methyl)piperidin-1-yl)-2,6-dimethoxypyrimidin-5-yl)acetic acid;
2,2'-(6,6'-diphenyl-2,2'-dithioxo-1,1',2,2'-tetrahydro-4,4'-bipyrimidine-5,5'-diyl)diacetic acid;
2,2'-(2,2'-diamino-6,6'-diphenyl-4,4'-bipyrimidine-5,5'-diyl)diacetic acid;
2-(2-(5,6-dimethyl-1H-benzo[d]imidazol-2-ylamino)-4-oxo-6-phenyl-1,4-dihydropyrimidin-5-yl)acetic acid;
2-(2-(1H-benzo[d]imidazol-1-yl)-4,6-dimorpholinopyrimidin-5-yl)acetic acid;
2-(4-((2'-(1H-tetrazol-5-yl)biphenyl-4-yl)methylamino)-2,6-dimethylpyrimidin-5-yl)acetic acid;
2-(2-butyl-4-chloro-6-((2'-(thiazol-5-yl)biphenyl-4-yl)methyl)pyrimidin-5-yl)acetic acid;
4'-((2-butyl-5-(carboxymethyl)-6-ethoxypyrimidin-4-yl)methyl)biphenyl-2-carboxylic acid;
4',4''-(2-butyl-5-(carboxymethyl)pyrimidine-4,6-diyl)bis(methylene)dibiphenyl-2-carboxylic acid;
4'-((2-butyl-5-(carboxymethyl)-6-oxo-3,6-dihydropyrimidin-4-yl)methyl)biphenyl-2-carboxylic acid;
4'-((2-butyl-5-(carboxymethyl)-6-chloropyrimidin-4-yl)methyl)biphenyl-2-carboxylic acid;
4-((2-butyl-5-(carboxymethyl)-6-chloropyrimidin-4-yl)methyl)benzoic acid;
2-(4-methyl-6-(3-nitrophenyl)-2-phenylpyrimidin-5-yl)acetic acid;
sodium 2-(4-(4-chlorophenylthio)-2-(methylthio)pyrimidin-5-yl)-4,4,4-trifluoro-3-hydroxybut-2-enoate; and
2-(4-(4-chlorophenylthio)-2-(methylthio)pyrimidin-5-yl)acetic acid.

In another particular embodiment, the compounds are not selected from a compound according to formula (A1) or (A) or other formulae herein wherein $R^{2a}$ and $R^{2b}$ are hydrogen, $R^3$ is COOH and:

$R^1$ is m-fluorophenyl, $R^4$ is hydrogen and $R^5$ is unsubstituted or substituted diphenylamino; or $R^1$ is unsubstituted or substituted biphenylmethylene or biphenylmethyleneamino, $R^4$ is halogen, alkyl, heteroalkyl, hydroxyl, or carboxybiphenylmethylene and $R^5$ is alkyl; or $R^1$ is unsubstituted or substituted p-pyridylcarboxamidephenylmethylene, $R^4$ is halogen and $R^5$ is substituted heterocycleheteroalkyl; or $R^1$ is unsubstituted phenyl, $R^4$ is hydroxyl and $R^5$ is hydroxymethyl; or $R^1$ is unsubstituted pyridylamino, $R^4$ is hydrogen, and $R^5$ is trimethoxyphenylamino; or $R^1$ is unsubstituted cyclopropyl, $R^4$ is hydrogen, and $R^5$ is trifluoromethylphenyl; or $R^1$ is selected from unsubstituted or substituted pyrolidin-1-yl, pyrolin-1-yl, piperidin-1-yl, morpholin-4-yl, cyclohexylamino, or 1-(pyrolidin-1-yl)-2-methylamino-ethan-1-one, $R^4$ is selected from alkyl, dialkylamino or halogen, and $R^5$ is selected from substituted aryl-C(O)NH-phenylmethylene or arylalkenyl- C(O)NH-phenylmethylene; or $R^1$ is substituted piperidin-1-yl-methylene-piperidin-1-yl, $R^4$ is methoxy, and $R^5$ is methoxy; or $R^1$ is unsubstituted phenyl, $R^4$ is 2-amino-5-acetic acid-6phenyl-pyrimidin-4-yl, and $R^5$ is amino; or $R^1$ is unsubstituted phenyl, $R^4$ is hydroxyl, and $R^5$ is substituted 2-aminobenzimidazole; or $R^1$ is unsubstituted morpholin-4-yl, $R^4$ is morpholin-4-yl, and $R^5$ is benzimidazol-1-yl; or $R^1$ is p-carboxylic acid-phenylmethylene, $R^4$ is halogen and $R^5$ is n-butyl; or $R^1$ is m-nitrophenyl, $R^4$ is methyl, and $R^5$ is phenyl; or $R^1$ is p-chlorothiophenoxy, $R^4$ is hydrogen and $R^5$ is methylthio.

In another particular embodiment, the compounds are not selected from a compound according to formula A1 wherein $R^{2b}$ is hydrogen, $R^3$ is COOH and:

$R^1$ is substituted styryl, $R^{2a}$ is methyl, $R^4$ is hydroxyl and $R^5$ is methyl; or $R^1$ is unsubstituted phenyl, $R^{2a}$ is alkyl, $R^4$ is hydroxyl and $R^5$ is hydroxymethylene; or $R^1$ is methyl, $R^{2a}$ is alkyl and $R^4$ is hydroxyl; or $R^1$ is unsubstituted or substituted styryl, $R^{2a}$ is methyl or phenyl, $R^4$ is hydroxyl and $R^5$ is methyl; or R$^1$ is 2-(furan-2-yl)vinyl, R$^{2a}$ is methyl or phenyl, R$^4$ is hydroxyl and R$^5$ is methyl; or R$^1$ is 2-(pyridinyl)vinyl, R$^{2a}$ is methyl or phenyl, R$^4$ is hydroxyl and R$^5$ is methyl; or R$^1$ is 2-(substituted naphthalen-1-yl)vinyl, R$^{2a}$ is methyl or phenyl, R$^4$ is hydroxyl and R$^5$ is methyl; or R$^1$ is 2-(2,4-dioxo-1,2,3,4-tetrahydropyrimidin-5-yl)vinyl, R$^{2a}$ is methyl or phenyl, R$^4$ is hydroxyl and R$^5$ is methyl; or R$^1$ is 2-(unsubstituted or substituted phenyl)prop-1-enyl, R$^{2a}$ is methyl or phenyl, R$^4$ is hydroxyl and R$^5$ is methyl; or R$^1$ is pentyl, R$^{2a}$ is methyl, R$^4$ is hydroxyl and R$^5$ is amino.

In yet another particular embodiment, the compounds are not selected from a compound according to formula (A1) or (A) or other formulae herein wherein R$^{2a}$ and R$^{2b}$ are taken together to form trifluoromethyl-hydroxy-vinyl, R$^3$ is COOH, R$^1$ is p-chlorothiophenoxy, R$^4$ is hydrogen and R$^5$ is methylthio.

In a particular embodiment, R$^1$ is selected from cycloalkyl; cycloalkenyl; cycloalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl or heterocycle-heteroalkynyl; wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more Z$^1$. In yet another particular embodiment, R$^1$ is selected from aryl, arylalkyl, —O-aryl, —S-aryl, —NH-aryl, heterocycle, heterocyclealkyl, —O-heterocycle, —S-heterocycle, —NH-heterocycle, yet in a more particular embodiment R$^1$ is selected from phenyl, wherein said aryl, arylalkyl, —O-aryl, —S-aryl, —NH-aryl, heterocycle, heterocyclealkyl, —O-heterocycle, —S-heterocycle, —NH-heterocycle or phenyl can be unsubstituted or substituted, in a particular embodiment substituted with one or more Z$^1$. In another particular embodiment, R$^1$ is selected from aryl, arylalkyl, —O-aryl, or heterocycle, wherein said aryl, arylalkyl, —O-aryl, or heterocycle can be unsubstituted or substituted with 1, 2 or 3 substituents selected from the group consisting of halogen; hydroxy; trifluoromethyl; and alkyl. Preferably, R$^1$ is selected from benzothiazolyl, quinolinyl, piperidinyl, 1-H-azepinyl, 4-methyl-piperazinyl, naphtyl, benzothiophenyl, benzofuranyl, indazolyl, N-methyl-indazolyl, chromanyl, 4H-isoquinolinyl, isochromanyl, 5F, 8Me-isochromanyl, 5Cl-isochromanyl, t-butyl, ethyl, phenyl, O-phenyl, and phenyl substituted with 1, 2 or 3 substituents independently selected from the group consisting of C$_1$-C$_4$ alkyl (preferably methyl or i-propyl), chloro, fluoro, hydroxy, methoxy, trifluoromethyll. More preferably, R$^1$ is selected from phenyl, O-phenyl, tol-4-yl, 3-hydroxyphenyl, 4-chloro-phenyl, 3,4-dimethylphenyl, 2-fluoro-4-chloro-phenyl, 2-fluoro-4-methyl-phenyl, 4-fluoro-4-hydroxy-phenyl, 4-trifluoromethyl-phenyl, 2-chloro-4-methyl-phenyl, 2-hydroxy-4-methyl-phenyl, 2-methoxy-4-chloro-phenyl, 2-methoxy-4-methyl-phenyl, 2-hydroxy-4-chloro-phenyl, 2,4-difluoro-phenyl, 2,4-dimethyl-phenyl, 2,4,5-trimethyl-phenyl, piperidin-1-yl; 3,4-dihydro-2H-benzo[b][1,4]dioxepin-7-yl, 4-methyl-3,4-dihydro-2H-benzo[b][1,4]oxazin-7-yl, 2-oxo-2,3-dihydro-1H-benzo[d]imidazol-5-yl, 3-oxo-2,3-dihydro-1H-inden-5-yl)-2-phenylpyrimidin-5-yl, 2-oxoindolin-6-yl, 1,2-dihydroacenaphthylen-5-yl, 2,3-dihydropyrano[4,3,2-de]quinolin-7-yl, and 8-fluoro-5-methylchroman-6-yl.

In yet another particular embodiment, one of R$^{2a}$ and R$^{2b}$ is not hydrogen. In another particular embodiment, one of R$^{2a}$ and R$^{2b}$ is hydrogen and the other of R$^{2a}$ and R$^{2b}$ is selected from alkyl, alkenyl, alkynyl, heteroalkyl, heteroalkenyl or heteroalkynyl. In a yet more particular embodiment, one of R$^{2a}$ and R$^{2b}$ is hydrogen and the other of R$^{2a}$ and R$^{2b}$ is selected from alkyl and heteroalkyl. In a yet more particular embodiment, one of R$^{2a}$ and R$^{2b}$ is hydrogen and the other of R$^{2a}$ and R$^{2b}$ is selected from alkyl and —O-alkyl. In another particular embodiment, one of R$^{2a}$ and R$^{2b}$ is hydrogen and the other of R$^{2a}$ and R$^{2b}$ is selected from C$_3$-C$_4$-alkyl, O—(C1-C4-alkyl), arylalkyl, O-alkylalkyl, trifluoromethylalkyl, preferably one of R$^{2a}$ and R$^{2b}$ is hydrogen and the other of R$^{2a}$ and R$^{2b}$ is selected from i-propyl, t-butyl, t-butoxy, benzyl, 2-methoxy-eth-1-yl, 3-trifluoromethyl-prop-1-yl.

In yet another particular embodiment, R$^3$ is selected from —C(O)OR$^7$, more particularly R$^3$ is —C(O)OH or —C(O)O-alkyl even more particularly R$^3$ is —C(O)OH or —C(O)OCH$_3$, and most particularly R$^3$ is —C(O)OH.

In yet another particular embodiment, the dotted line "a" forms a double bond, the dotted line "b" does not form a double bond and R$^4$ is selected from hydrogen and alkyl, more in particular is methyl or the dotted line "a" does not form a double bond, the dotted line "b" forms a double bond and R$^4$ is selected from oxygen and sulfur.

In yet another particular embodiment, R$^5$ is selected from —NR$^{10}$R$^{11}$; alkyl; alkenyl; alkynyl; heteroalkyl; heteroalkenyl; heteroalkynyl; aryl; arylalkyl; arylalkenyl; arylalkynyl; arylheteroalkyl; arylheteroalkenyl; arylheteroalkynyl; heterocycle; heterocycle-alkyl; heterocycle-alkenyl; heterocycle-alkynyl; heterocycle-heteroalkyl, heterocycle-heteroalkenyl, or heterocycle-heteroalkynyl; wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more R$^{20}$.

In another particular embodiment, R$^5$ is selected from —NR$^{10}$R$^{11}$; aryl; arylalkyl; —O-aryl; —S-aryl; and heterocycle; wherein said aryl, arylalkyl, —O-aryl, —S-aryl, NH-aryl, and heterocycle can be unsubstituted or substituted with one or more R$^{20}$. Preferably, R$^5$ is selected from NR$^{10}$R$^{11}$; aryl; arylalkyl; arylalkenyl; —O-aryl; S-aryl, NH-aryl, and heterocycle; wherein said aryl, arylalkyl, —O-aryl, S-aryl and heterocycle can be unsubstituted or substituted with one or more substituents independently selected from the group consisting of halogen; —OH; —O-phenyl, —N(CH$_3$)$_2$, NH(CO)(phenyl); —C(O)NH(C$_1$-C$_4$-alkyl); C$_1$-C$_4$-alkyl; phenyl; 1,2,4-oxadiazolyl; benzyl; phenylethylenyl, wherein said 1,2,4-oxadiazolyl is further substituted with one C1-C4-alkyl, preferably with isopropyl. More preferably, R$^5$ is selected from NR$^{10}$R$^{11}$; phenyl; benzyl; —O-phenyl; S-phenyl and heterocycle; wherein said phenyl; benzyl; —O-phenyl; S-phenyl and heterocycle can be unsubstituted or substituted with one or more substituents independently selected from the group consisting of halogen; —OH; —O-phenyl, —N(CH$_3$)$_2$, NH(CO)(phenyl); —C(O)NH(C$_1$-C$_4$-alkyl); C$_1$-C$_4$-alkyl; phenyl; 1,2,4-oxadiazolyl; benzyl; wherein said 1,2,4-oxadiazolyl is further substituted with one C1-C4-alkyl, preferably with isopropyl.

In a more particular embodiment, R$^5$ is —NR$^{10}$R$^{11}$ wherein R$^{10}$ and R$^{11}$ are as described herein, preferably each R$^{10}$ and R$^{11}$ is independently selected from hydrogen; alkyl; aryl; arylalkyl; or R$^{10}$ and R$^{11}$ can be taken together with the nitrogen to which they are attached to in order to form a 4-, 5-, 6-, 7- or 8-membered heterocycle which can be unsubstituted or substituted with one or more ;

In yet a more particular embodiment, $R^5$ is $—NR^{10}R^{11}$, whereby $R^{10}$ and $R^{11}$ are taken together with the nitrogen to which they are attached to form a 4-, 5-, 6-, 7- or 8-membered heterocycle, preferably a 5-, 6-, or 7-membered heterocycle which can be unsubstituted or substituted with one or more $R^{20}$ (wherein $R^{20}$ is as described herein, preferably each $R^{20}$ is independently selected from the group consisting of halogen; —O-aryl; alkyl; heterocycle (preferably 3-methyl-1,2,4-oxadiazol-5-yl); C(O)NH($C_1$-$C_4$-alkyl), NH(CO)(phenyl).

Preferably, the 5-, 6-, or 7-membered heterocycle is selected from the group consisting of N-piperidinyl, N-morpholinyl, 1,4-oxazin-4-yl, 3-dimethylaminopyrrolidin-1-yl, N-methyl-pyrazol-4-yl, 4-ethyl-1,4-diazepan-1-yl, wherein the N-piperidinyl is unsubstituted or substituted with a substituent selected from the group consisting of methyl, phenyl, O-phenyl, C(O)NH($C_1$-$C_4$-alkyl), NH(CO)(phenyl); and 3-methyl-1,2,4-oxadiazol-5-yl.

In another particular embodiment, $R^5$ is selected from N,N-dimethylamino, phenyl, benzyl, phenylethylenyl, tol-4-yl, phenylethyl, N-phenyl,N-methylamino, chlorophenyl, N-piperidinyl, N-morpholinyl, 3-dimethylaminopyrrolidin-1-yl, N-piperidinyl, N-methyl-pyrazol-4-yl, wherein the N-piperidinyl is unsubstituted or substituted with a substituent selected from the group consisting of methyl, phenyl, O-phenyl, C(O)NH($C_1$-$C_4$-alkyl), NH(CO)(phenyl); and 3-methyl-1,2,4-oxadiazol-5-yl.

In a particular embodiment, the dotted line "a" forms a double bond and $R^6$ is not present or the dotted line "a" does not form a double bond and $R^6$ is selected from hydrogen and alkyl. In another particular embodiment, the dotted line "b" forms a double bond and $R^4$ is O. In a more particular embodiment, the dotted line "b" forms a double bond and $R^4$ is O and $R^6$ is selected from alkyl and arylalkyl, particularly from C1-C4 alkyl and benzyl.

In another embodiment, the compounds of the invention have a structure according to formula (B1),

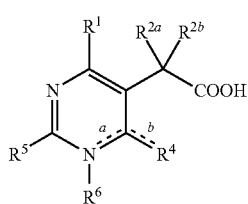

(B1)

wherein each of $R^1$, $R^{2a}$, $R^{2b}$, $R^4$, the dotted lines, $R^5$ and $R^6$ are as in formula (A1) or (A) and the embodiments described herein.

In another embodiment, the compounds of the invention have a structure according to formula (C1) or (C2),

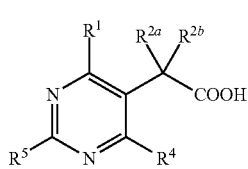

(C1)

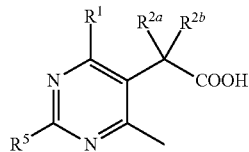

(C2)

wherein each of $R^1$, $R^{2a}$, $R^{2b}$, $R^4$ and $R^5$ are as in formula (A1) or (A) and the embodiments described herein.

In another embodiment, the compounds of the invention have a structure according to formula (D1), (D2), or (D3)

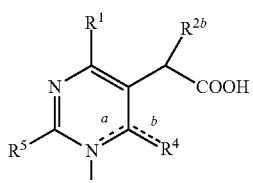

(D1)

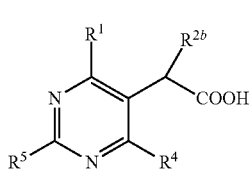

(D2)

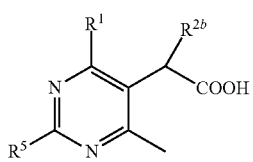

(D3)

wherein each of $R^1$, $R^{2b}$, $R^4$, the dotted lines, $R^5$ and $R^6$ are as in formula (A1) or (A) and the embodiments described herein.

In another embodiment, the compounds of the invention have a structure according to formula (E1), (E2) or (E3),

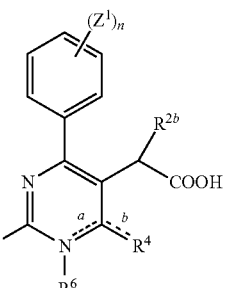

(E1)

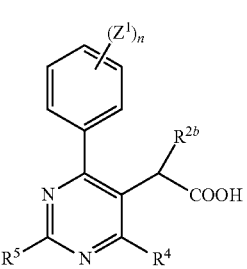

(E2)

-continued

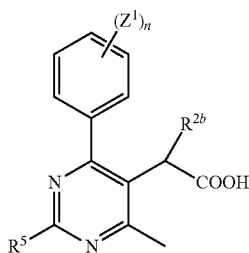
(E3)

wherein each of $R^{2b}$, $R^4$, the dotted lines, $R^5$, $R^6$ and $Z^1$ are as in formula (A1) or (A) and the embodiments described herein and n is selected from 0, 1, 2, 3, 4 and 5.

In another embodiment, the compounds of the invention have a structure according to formula (F1), (F2) or (F3),

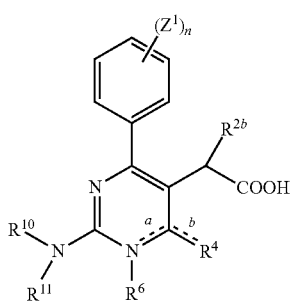
(F1)

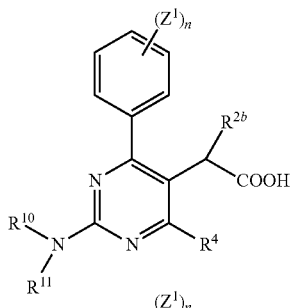
(F2)

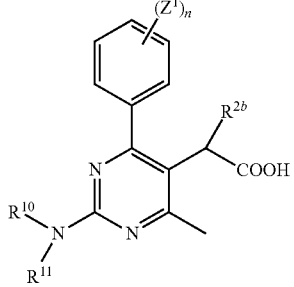
(F3)

wherein each of $R^{2b}$, $R^4$, $R^{10}$, $R^{11}$, the dotted lines, $R^5$, $R^6$ and $Z^1$ are as in formula (A1) or (A) and the embodiments described herein and n is selected from 0, 1, 2, 3, 4 and 5.

In another embodiment, the compounds of the invention have a structure according to formula (G1),

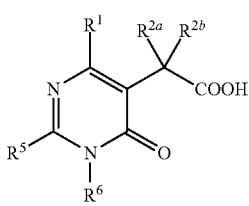
(G1)

wherein each of $R^1$, $R^{2a}$, $R^{2b}$, $R^5$ and $R^6$ are as in formula (A1) or (A) and the embodiments described herein.

In another embodiment, the compounds of the invention have a structure according to formula (H1), (H2) or (H3),

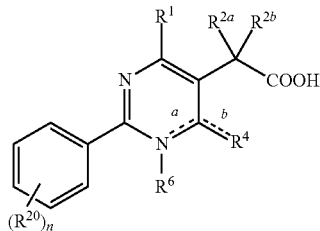
(H1)

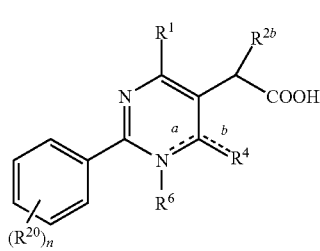
(H2)

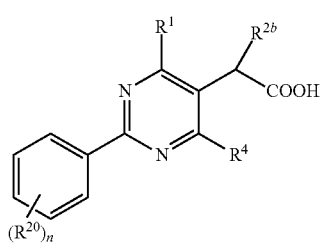
(H3)

wherein each of $R^1$, $R^{2a}$, $R^{2b}$, $R^4$, $R^{10}$, $R^{11}$, the dotted lines, $R^6$ and $R^{20}$ are as in formula (A1) or (A) and the embodiments described herein and n is selected from 0, 1, 2, 3, 4 and 5.

In another embodiment, the compounds of the invention have a structure according to formula (J1), (J2) or (J3),

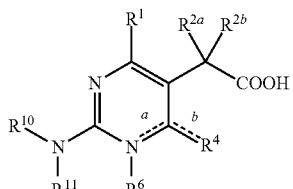
(J1)

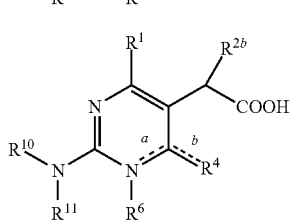
(J2)

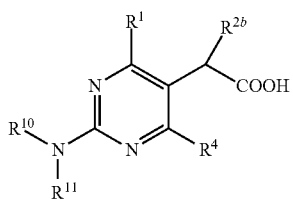
(J3)

wherein each of $R^{2a}$, $R^{2b}$, $R^4$, $R^{10}$, $R^{11}$, the dotted lines and $R^6$ are as in formula (A1) or (A) and the embodiments described herein.

Particular embodiments of this aspect are described in the claims and relate to subtypes of the compounds of the invention. In particular embodiments, the terms alkyl, alkenyl or alkynyl can be restricted to refer to their cyclic or acyclic subgroups (such as the acyclic alkyl or cycloalkyl for alkyl).

In a particular embodiment, the compounds of the present invention are selected from the list of:

methyl 2-(2-(dimethylamino)-4-methyl-6-phenylpyrimidin-5-yl)pentanoate;
2-(2-(dimethylamino)-4-methyl-6-phenylpyrimidin-5-yl) pentanoic acid;
methyl 2-(2-benzyl-4-methyl-6-phenylpyrimidin-5-yl) pentanoate;
2-(2-benzyl-4-methyl-6-phenylpyrimidin-5-yl)pentanoic acid;
(E)-methyl 2-(4-methyl-6-phenyl-2-styrylpyrimidin-5-yl) pentanoate;
(E)-2-(4-methyl-6-phenyl-2-styrylpyrimidin-5-yl)pentanoic acid;
methyl 2-(4-methyl-2-phenethyl-6-phenylpyrimidin-5-yl) pentanoate;
2-(4-methyl-2-phenethyl-6-phenylpyrimidin-5-yl)pentanoic acid;
methyl 2-(4-methyl-2,6-dip-tolylpyrimidin-5-yl)pentanoate;
2-(4-methyl-2,6-dip-tolylpyrimidin-5-yl)pentanoic acid;
methyl 2-(2-(cyclohexyl(methyl)amino)-4-methyl-6-p-tolylpyrimidin-5-yl)pentanoate;
2-(2-(cyclohexyl(methyl)amino)-4-methyl-6-p-tolylpyrimidin-5-yl)pentanoic acid;
methyl 2-(4-methyl-2-phenyl-6-p-tolylpyrimidin-5-yl) pentanoate;
2-(4-methyl-2-phenyl-6-p-tolylpyrimidin-5-yl)pentanoic acid;
methyl 2-(2-(2-chlorophenyl)-4-methyl-6-phenylpyrimidin-5-yl)pentanoate;
2-(2-(2-chlorophenyl)-4-methyl-6-phenylpyrimidin-5-yl) pentanoic acid;
methyl 2-(2-(2-chlorophenyl)-4-methyl-6-p-tolylpyrimidin-5-yl)pentanoate;
2-(2-(2-chlorophenyl)-4-methyl-6-p-tolylpyrimidin-5-yl) pentanoic acid;
methyl 2-(4-methyl-6-phenyl-2-(piperidin-1-yl)pyrimidin-5-yl)pentanoate;
2-(4-methyl-6-phenyl-2-(piperidin-1-yl)pyrimidin-5-yl) pentanoic acid;
methyl 2-(4-methyl-2-(piperidin-1-yl)-6-p-tolylpyrimidin-5-yl)pentanoate;
2-(4-methyl-2-(piperidin-1-yl)-6-p-tolylpyrimidin-5-yl) pentanoic acid;
methyl 2-(4-methyl-2,6-diphenylpyrimidin-5-yl)pentanoate;
2-(4-methyl-2,6-diphenylpyrimidin-5-yl)pentanoic acid;
methyl 2-(4-(3-hydroxyphenyl)-6-methyl-2-phenylpyrimidin-5-yl)pentanoate;
2-(4-(3-hydroxyphenyl)-6-methyl-2-phenylpyrimidin-5-yl)pentanoic acid;
methyl 2-(4-methyl-2-morpholino-6-p-tolylpyrimidin-5-yl)pentanoate;
2-(4-methyl-2-morpholino-6-p-tolylpyrimidin-5-yl)pentanoic acid;
methyl 2-(4-methyl-2-(pyrrolidin-1-yl)-6-p-tolylpyrimidin-5-yl)pentanoate;
2-(4-methyl-2-(pyrrolidin-1-yl)-6-p-tolylpyrimidin-5-yl) pentanoic acid;
methyl 2-(4-methyl-2-(4-methylpiperazin-1-yl)-6-p-tolylpyrimidin-5-yl)pentanoate;
2-(4-methyl-2-(4-methylpiperazin-1-yl)-6-p-tolylpyrimidin-5-yl)pentanoic acid;
methyl 2-(2-(3,5-dimethylpiperidin-1-yl)-4-methyl-6-p-tolylpyrimidin-5-yl)pentanoate;
2-(2-(3,5-dimethylpiperidin-1-yl)-4-methyl-6-p-tolylpyrimidin-5-yl)pentanoic acid;
methyl 2-(2-(azepan-1-yl)-4-methyl-6-p-tolylpyrimidin-5-yl)pentanoate;
2-(2-(azepan-1-yl)-4-methyl-6-p-tolylpyrimidin-5-yl) pentanoic acid;
methyl 2-(2-(3-(isobutylcarbamoyl)piperidin-1-yl)-4-methyl-6-p-tolylpyrimidin-5-yl)pentanoate;
2-(2-(3-(isobutylcarbamoyl)piperidin-1-yl)-4-methyl-6-p-tolylpyrimidin-5-yl)pentanoic acid;
methyl 2-(4-methyl-2-(3-methylpiperidin-1-yl)-6-p-tolylpyrimidin-5-yl)pentanoate;
2-(4-methyl-2-(3-methylpiperidin-1-yl)-6-p-tolylpyrimidin-5-yl)pentanoic acid;
methyl 2-(2-(3,4-dihydroisoquinolin-2(1H)-yl)-4-methyl-6-p-tolylpyrimidin-5-yl)pentanoate;
2-(2-(3,4-dihydroisoquinolin-2(1H)-yl)-4-methyl-6-p-tolylpyrimidin-5-yl)pentanoic acid;
methyl 2-(2-(4-benzyl-1,4-diazepan-1-yl)-4-methyl-6-p-tolylpyrimidin-5-yl)pentanoate;
2-(2-(4-benzyl-1,4-diazepan-1-yl)-4-methyl-6-p-tolylpyrimidin-5-yl)pentanoic acid;
methyl 2-(2-(3-(3-isopropyl-1,2,4-oxadiazol-5-yl)piperidin-1-yl)-4-methyl-6-p-tolylpyrimidin-5-yl)pentanoate;
2-(2-(3-(3-isopropyl-1,2,4-oxadiazol-5-yl)piperidin-1-yl)-4-methyl-6-p-tolylpyrimidin-5-yl)pentanoic acid;
methyl 2-(4-methyl-2-(3-phenoxypiperidin-1-yl)-6-p-tolylpyrimidin-5-yl)pentanoate;
2-(4-methyl-2-(3-phenoxypiperidin-1-yl)-6-p-tolylpyrimidin-5-yl)pentanoic acid;
methyl 2-(4-methyl-2-(3-phenylpiperidin-1-yl)-6-p-tolylpyrimidin-5-yl)pentanoate;
2-(4-methyl-2-(3-phenylpiperidin-1-yl)-6-p-tolylpyrimidin-5-yl)pentanoic acid;
methyl 2-(2-((S)-3-(dimethylamino)pyrrolidin-1-yl)-4-methyl-6-p-tolylpyrimidin-5-yl)pentanoate;
2-(2-((S)-3-(dimethylamino)pyrrolidin-1-yl)-4-methyl-6-p-tolylpyrimidin-5-yl)pentanoic acid;
methyl 2-(2-(4-benzamidopiperidin-1-yl)-4-methyl-6-p-tolylpyrimidin-5-yl)pentanoate;
2-(2-(4-benzamidopiperidin-1-yl)-4-methyl-6-p-tolylpyrimidin-5-yl)pentanoic acid;
methyl 2-(2-(4-ethyl-1,4-diazepan-1-yl)-4-methyl-6-p-tolylpyrimidin-5-yl)pentanoate;
2-(2-(4-ethyl-1,4-diazepan-1-yl)-4-methyl-6-p-tolylpyrimidin-5-yl)pentanoic acid;
methyl 2-(2-(indolin-1-yl)-4-methyl-6-p-tolylpyrimidin-5-yl)pentanoate;
2-(2-(indolin-1-yl)-4-methyl-6-p-tolylpyrimidin-5-yl) pentanoic acid;
methyl 2-(4-methyl-2-phenyl-6-(piperidin-1-yl)pyrimidin-5-yl)pentanoate;
2-(4-methyl-2-phenyl-6-(piperidin-1-yl)pyrimidin-5-yl) pentanoic acid;
methyl 2-(4-(azepan-1-yl)-6-methyl-2-phenylpyrimidin-5-yl)pentanoate;
2-(4-(azepan-1-yl)-6-methyl-2-phenylpyrimidin-5-yl) pentanoic acid;

methyl 2-(4-methyl-6-(4-methylpiperazin-1-yl)-2-phenylpyrimidin-5-yl)pentanoate;
2-(4-methyl-6-(4-methylpiperazin-1-yl)-2-phenylpyrimidin-5-yl)pentanoic acid;
methyl 2-(4-(3,4-dimethylphenyl)-6-methyl-2-phenylpyrimidin-5-yl)pentanoate;
2-(4-(3,4-dimethylphenyl)-6-methyl-2-phenylpyrimidin-5-yl)pentanoic acid;
methyl 2-(4-methyl-6-(naphthalen-2-yl)-2-phenylpyrimidin-5-yl)pentanoate;
2-(4-methyl-6-(naphthalen-2-yl)-2-phenylpyrimidin-5-yl)pentanoic acid;
methyl 2-(4-(2,3-dihydrobenzofuran-5-yl)-6-methyl-2-phenylpyrimidin-5-yl)pentanoate;
2-(4-(2,3-dihydrobenzofuran-5-yl)-6-methyl-2-phenylpyrimidin-5-yl)pentanoic acid;
methyl 2-(4-(benzofuran-5-yl)-6-methyl-2-phenylpyrimidin-5-yl)pentanoate;
2-(4-(benzofuran-5-yl)-6-methyl-2-phenylpyrimidin-5-yl)pentanoic acid;
methyl 2-(4-methyl-6-(1-methyl-1H-indol-5-yl)-2-phenylpyrimidin-5-yl)pentanoate;
2-(4-methyl-6-(1-methyl-1H-indol-5-yl)-2-phenylpyrimidin-5-yl)pentanoic acid;
methyl 2-(4-(3,4-dihydroisoquinolin-2(1H)-yl)-6-methyl-2-phenylpyrimidin-5-yl)pentanoate;
2-(4-(3,4-dihydroisoquinolin-2(1H)-yl)-6-methyl-2-phenylpyrimidin-5-yl)pentanoic acid;
methyl 2-(4-methyl-6-phenoxy-2-phenylpyrimidin-5-yl)pentanoate;
2-(4-methyl-6-phenoxy-2-phenylpyrimidin-5-yl)pentanoic acid;
methyl 2-(4-(1H-indol-5-yl)-6-methyl-2-phenylpyrimidin-5-yl)pentanoate;
2-(4-(1H-indol-5-yl)-6-methyl-2-phenylpyrimidin-5-yl)pentanoic acid;
methyl 2-(4-(1H-indol-6-yl)-6-methyl-2-phenylpyrimidin-5-yl)pentanoate;
2-(4-(1H-indol-6-yl)-6-methyl-2-phenylpyrimidin-5-yl)pentanoic acid;
methyl 2-(4-(3,4-dihydro-2H-benzo[b][1,4]dioxepin-7-yl)-6-methyl-2-phenylpyrimidin-5-yl)pentanoate;
2-(4-(3,4-dihydro-2H-benzo[b][1,4]dioxepin-7-yl)-6-methyl-2-phenylpyrimidin-5-yl)pentanoic acid;
methyl 2-(4-methyl-6-(4-methyl-3,4-dihydro-2H-benzo[b][1,4]oxazin-7-yl)-2-phenylpyrimidin-5-yl)pentanoate;
2-(4-methyl-6-(4-methyl-3,4-dihydro-2H-benzo[b][1,4]oxazin-7-yl)-2-phenylpyrimidin-5-yl)pentanoic acid;
methyl 2-(4-(benzo[b]thiophen-5-yl)-6-methyl-2-phenylpyrimidin-5-yl)pentanoate;
2-(4-(benzo[b]thiophen-5-yl)-6-methyl-2-phenylpyrimidin-5-yl)pentanoic acid;
methyl 2-(4-(chroman-6-yl)-6-methyl-2-phenylpyrimidin-5-yl)pentanoate;
2-(4-(chroman-6-yl)-6-methyl-2-phenylpyrimidin-5-yl)pentanoic acid;
methyl 2-(4-methyl-6-(1-methyl-1H-indol-6-yl)-2-phenylpyrimidin-5-yl)pentanoate;
2-(4-methyl-6-(1-methyl-1H-indol-6-yl)-2-phenylpyrimidin-5-yl)pentanoic acid;
methyl 2-(4-(4-chloro-2-fluorophenyl)-6-methyl-2-phenylpyrimidin-5-yl)pentanoate;
2-(4-(4-chloro-2-fluorophenyl)-6-methyl-2-phenylpyrimidin-5-yl)pentanoic acid;
methyl 2-(4-methyl-6-(1-methylindolin-5-yl)-2-phenylpyrimidin-5-yl)pentanoate;
2-(4-methyl-6-(1-methylindolin-5-yl)-2-phenylpyrimidin-5-yl)pentanoic acid;
methyl 2-(4-(2-fluoro-4-methylphenyl)-6-methyl-2-phenylpyrimidin-5-yl)pentanoate;
2-(4-(2-fluoro-4-methylphenyl)-6-methyl-2-phenylpyrimidin-5-yl)pentanoic acid;
methyl 2-(4-methyl-6-(2-oxo-2,3-dihydro-1H-benzo[d]imidazol-5-yl)-2-phenylpyrimidin-5-yl)pentanoate;
2-(4-methyl-6-(2-oxo-2,3-dihydro-1H-benzo[d]imidazol-5-yl)-2-phenylpyrimidin-5-yl)pentanoic acid;
methyl 2-(4-(4-chlorophenyl)-6-methyl-2-phenylpyrimidin-5-yl)pentanoate;
2-(4-(4-chlorophenyl)-6-methyl-2-phenylpyrimidin-5-yl)pentanoic acid;
methyl 2-(4-methyl-6-(2-oxoindolin-6-yl)-2-phenylpyrimidin-5-yl)pentanoate;
2-(4-methyl-6-(2-oxoindolin-6-yl)-2-phenylpyrimidin-5-yl)pentanoic acid;
methyl 2-(4-(4-isopropylphenyl)-6-methyl-2-phenylpyrimidin-5-yl)pentanoate;
2-(4-(4-isopropylphenyl)-6-methyl-2-phenylpyrimidin-5-yl)pentanoic acid;
methyl 2-(4-methyl-2-phenyl-6-(4-(trifluoromethyl)phenyl)pyrimidin-5-yl)pentanoate;
2-(4-methyl-2-phenyl-6-(4-(trifluoromethyl)phenyl)pyrimidin-5-yl)pentanoic acid;
methyl 2-(4-(4-chloro-2-methoxyphenyl)-6-methyl-2-phenylpyrimidin-5-yl)pentanoate;
2-(4-(4-chloro-2-methoxyphenyl)-6-methyl-2-phenylpyrimidin-5-yl)pentanoic acid;
2-(4-(4-chloro-2-hydroxyphenyl)-6-methyl-2-phenylpyrimidin-5-yl)pentanoic acid;
methyl 2-(4-methyl-6-(3-oxo-2,3-dihydro-1H-inden-5-yl)-2-phenylpyrimidin-5-yl)pentanoate;
2-(4-methyl-6-(3-oxo-2,3-dihydro-1H-inden-5-yl)-2-phenylpyrimidin-5-yl)pentanoic acid;
methyl 2-(4-(benzo[d]thiazol-6-yl)-6-methyl-2-phenylpyrimidin-5-yl)pentanoate;
2-(4-(benzo[d]thiazol-6-yl)-6-methyl-2-phenylpyrimidin-5-yl)pentanoic acid;
methyl 2-(4-benzyl-6-methyl-2-phenylpyrimidin-5-yl)pentanoate;
2-(4-benzyl-6-methyl-2-phenylpyrimidin-5-yl)pentanoic acid;
methyl 2-(4-(2-hydroxy-4-methylphenyl)-6-methyl-2-phenylpyrimidin-5-yl)pentanoate;
2-(4-(2-hydroxy-4-methylphenyl)-6-methyl-2-phenylpyrimidin-5-yl)pentanoic acid;
2-(4-(2-methoxy-4-methylphenyl)-6-methyl-2-phenylpyrimidin-5-yl)pentanoic acid;
methyl 4-methoxy-2-(4-methyl-2-(piperidin-1-yl)-6-p-tolylpyrimidin-5-yl)butanoate;
4-methoxy-2-(4-methyl-2-(piperidin-1-yl)-6-p-tolylpyrimidin-5-yl)butanoic acid;
methyl 6,6,6-trifluoro-2-(4-methyl-2-(piperidin-1-yl)-6-p-tolylpyrimidin-5-yl)hexanoate;
6,6,6-trifluoro-2-(4-methyl-2-(piperidin-1-yl)-6-p-tolylpyrimidin-5-yl)hexanoic acid;
methyl 2-(4-methyl-2-(piperidin-1-yl)-6-p-tolylpyrimidin-5-yl)-3-phenylpropanoate;
2-(4-methyl-2-(piperidin-1-yl)-6-p-tolylpyrimidin-5-yl)-3-phenylpropanoic acid;
methyl 3-methyl-2-(4-methyl-2-(piperidin-1-yl)-6-p-tolylpyrimidin-5-yl)pentanoate;
3-methyl-2-(4-methyl-2-(piperidin-1-yl)-6-p-tolylpyrimidin-5-yl)pentanoic acid;

methyl 2-(4-(2,4-difluorophenyl)-6-methyl-2-(piperidin-1-yl)pyrimidin-5-yl)pentanoate;
2-(4-(2,4-difluorophenyl)-6-methyl-2-(piperidin-1-yl)pyrimidin-5-yl)pentanoic acid;
methyl 2-(4-(2,4-dimethylphenyl)-6-methyl-2-(piperidin-1-yl)pyrimidin-5-yl)pentanoate;
2-(4-(2,4-dimethylphenyl)-6-methyl-2-(piperidin-1-yl)pyrimidin-5-yl)pentanoic acid;
methyl 2-(4-(4-isopropylphenyl)-6-methyl-2-(piperidin-1-yl)pyrimidin-5-yl)pentanoate;
2-(4-(4-isopropylphenyl)-6-methyl-2-(piperidin-1-yl)pyrimidin-5-yl)pentanoic acid;
methyl 2-(4-(2-fluoro-4-methoxyphenyl)-6-methyl-2-(piperidin-1-yl)pyrimidin-5-yl)pentanoate;
2-(4-(2-fluoro-4-methoxyphenyl)-6-methyl-2-(piperidin-1-yl)pyrimidin-5-yl)pentanoic acid;
methyl 2-(4-methyl-2-(piperidin-1-yl)-6-(quinolin-5-yl)pyrimidin-5-yl)pentanoate;
2-(4-methyl-2-(piperidin-1-yl)-6-(quinolin-5-yl)pyrimidin-5-yl)pentanoic acid;
methyl 2-(4-methyl-2-(piperidin-1-yl)-6-(quinolin-8-yl)pyrimidin-5-yl)pentanoate;
2-(4-methyl-2-(piperidin-1-yl)-6-(quinolin-8-yl)pyrimidin-5-yl)pentanoic acid;
methyl 2-(4-methyl-2-(piperidin-1-yl)-6-(2,4,5-trifluorophenyl)pyrimidin-5-yl)pentanoate;
2-(4-methyl-2-(piperidin-1-yl)-6-(2,4,5-trifluorophenyl)pyrimidin-5-yl)pentanoic acid;
methyl 2-(4-(2-chloro-4-methylphenyl)-6-methyl-2-(piperidin-1-yl)pyrimidin-5-yl)pentanoate;
2-(4-(2-chloro-4-methylphenyl)-6-methyl-2-(piperidin-1-yl)pyrimidin-5-yl)pentanoic acid;
methyl 2-(4-(4-chloro-2-fluorophenyl)-6-methyl-2-(piperidin-1-yl)pyrimidin-5-yl)pentanoate;
2-(4-(4-chloro-2-fluorophenyl)-6-methyl-2-(piperidin-1-yl)pyrimidin-5-yl)pentanoic acid;
methyl 2-(4-methyl-2,6-di(piperidin-1-yl)pyrimidin-5-yl)pentanoate;
2-(4-methyl-2,6-di(piperidin-1-yl)pyrimidin-5-yl)pentanoic acid;
methyl 2-(4-(1,2-dihydroacenaphthylen-5-yl)-6-methyl-2-(piperidin-1-yl)pyrimidin-5-yl)pentanoate;
2-(4-(1,2-dihydroacenaphthylen-5-yl)-6-methyl-2-(piperidin-1-yl)pyrimidin-5-yl)pentanoic acid;
methyl 4,4-dimethyl-2-(4-methyl-2-(piperidin-1-yl)-6-p-tolylpyrimidin-5-yl)pentanoate;
4,4-dimethyl-2-(4-methyl-2-(piperidin-1-yl)-6-p-tolylpyrimidin-5-yl)pentanoic acid;
methyl 2-tert-butoxy-2-(4-methyl-2-(piperidin-1-yl)-6-p-tolylpyrimidin-5-yl)acetate;
2-tert-butoxy-2-(4-methyl-2-(piperidin-1-yl)-6-p-tolylpyrimidin-5-yl)acetic acid;
methyl 2-(4-(2,3-dihydropyrano[4,3,2-de]quinolin-7-yl)-6-methyl-2-(piperidin-1-yl)pyrimidin-5-yl)pentanoate;
2-(4-(2,3-dihydropyrano[4,3,2-de]quinolin-7-yl)-6-methyl-2-(piperidin-1-yl)pyrimidin-5-yl)pentanoic acid;
methyl 2-(4-(8-fluoro-5-methylchroman-6-yl)-6-methyl-2-(piperidin-1-yl)pyrimidin-5-yl)pentanoate;
2-(4-(8-fluoro-5-methylchroman-6-yl)-6-methyl-2-(piperidin-1-yl)pyrimidin-5-yl)pentanoic acid;
methyl 2-(4-(5-chlorochroman-6-yl)-6-methyl-2-(piperidin-1-yl)pyrimidin-5-yl)pentanoate;
2-(4-(5-chlorochroman-6-yl)-6-methyl-2-(piperidin-1-yl)pyrimidin-5-yl)pentanoic acid;
2-(1-methyl-6-oxo-2-(piperidin-1-yl)-4-p-tolyl-1,6-dihydropyrimidin-5-yl)pentanoic acid;
2-(1-ethyl-6-oxo-2-(piperidin-1-yl)-4-p-tolyl-1,6-dihydropyrimidin-5-yl)pentanoic acid;
2-(1-benzyl-6-oxo-2-(piperidin-1-yl)-4-p-tolyl-1,6-dihydropyrimidin-5-yl)pentanoic acid;
methyl 2-tert-butoxy-2-(4-tert-butyl-6-methyl-2-(piperidin-1-yl)pyrimidin-5-yl)acetate;
2-tert-butoxy-2-(4-tert-butyl-6-methyl-2-(piperidin-1-yl)pyrimidin-5-yl)acetic acid;
methyl 2-(4-ethyl-6-methyl-2-phenylpyrimidin-5-yl)pentanoate; and
2-(4-ethyl-6-methyl-2-phenylpyrimidin-5-yl)pentanoic acid.

According to a second aspect, the invention relates to the compounds as described herein (more in particular of the formulae (A), (A1), (B), (B1), (C), (C1), (C2), (D), (D1), (D2), (D3), (E), (E1), (E2), (E3), (F), (F1), (F2), (F3), (G1), (H1), (H2), (H3), (J1), (J2), (J3), embodiments thereof and claims herein) for use as a medicament or a medicine, more in particular for use as an antiviral medicament and for the use in the prevention or treatment of a viral infection in a subject (animal, mammal or human).

The present invention also relates to the use of compounds of the formulae (A), (A1), (B), (B1), (C), (C1), (C2), (D), (D1), (D2), (D3), (E), (E1), (E2), (E3), (F), (F1), (F2), (F3), (G1), (H1), (H2), (H3), (J1), (J2), (J3), embodiments thereof and claims as antiviral compounds, more particularly as compounds active against retroviruses, yet more in particular against HIV. The invention also relates to the use of the compounds of the invention for the manufacture of a medicament or as a pharmaceutically active ingredient, especially as a virus replication inhibitor, for instance for the manufacture of a medicament or pharmaceutical composition having antiviral activity for the prevention and/or treatment of viral infections in humans, mammals and animals in general. The present invention further relates to a method of prevention or treatment of a viral infection, preferably a retroviral infection in an animal, including mammals, including a human, comprising administering to the animal in need of such treatment a therapeutically effective amount of a compound of the invention as an active ingredient, preferably in admixture with at least a pharmaceutically acceptable carrier.

Another aspect of the invention further relates to methods for the preparation of compounds of formulae and claims herein. Also the intermediates used in the preparation methods described herein are aspects of the present invention.

One embodiment relates to a method for the preparation of the compounds according to the invention comprising the steps of:
  Preparing a substituted or non-substituted 2-(4-oxo-2-thioxo-1,2,3,4-tetrahydropyrimidin-5-yl)acetic acid derivative.
  Converting a substituted or non-substituted 2-(4-oxo-2-thioxo-1,2,3,4-tetrahydropyrimidin-5-yl)acetic acid derivative into a substituted or non-substituted 2-(2,4-dioxo-1,2,3,4-tetrahydropyrimidin-5-yl)acetic acid derivative which is ultimately converted in a substituted or non-substituted 2-(pyrimidin-5-yl)acetate.
  Preparing a substituted or non-substituted 2-(6-oxo-1,6-dihydropyrimidin-5-yl)acetic acid derivative.
  Converting a substituted or non-substituted 2-(6-oxo-1,6-dihydropyrimidin-5-yl)acetic acid derivative into a substituted or non-substituted 2-(pyrimidin-5-yl)acetate.
  Substituting a 2-(pyrimidin-5-yl)acetate derivative on position 2 and/or 4 of the pyrimidine moiety and/or on position 2 of the acetate side chain sequentially and in a specific manner (amination, alkylation, arylation) with suitable chemical reagents to obtain the desired compounds.

Hydrolyzing the obtained compounds in the previous step to obtain the desired 2-(pyrimidin-5-yl)acetic acid derivatives.

Yet another aspect of the present invention relates to pharmaceutical compositions comprising the compounds of the invention according to formulae, embodiments thereof and claims herein in a mixture with at least a pharmaceutically acceptable carrier, the active ingredient preferably being in a concentration range of about 0.1 to 100% by weight, and to the use of these derivatives namely as drugs useful for the treatment of subjects suffering from a viral infection, in particular a retroviral infection.

The invention further relates to the use of a composition comprising (a) one or more compounds of the invention (of formulae and claims herein), and (b) one or more viral inhibitors as biologically active agents in respective proportions such as to provide a synergistic effect against a viral infection in a mammal, for instance in the form of a combined preparation for simultaneous, separate or sequential use in viral infection therapy. Within the framework of this embodiment of the invention, the viral enzyme inhibitors used as a therapeutically active ingredients (b) may belong to categories already known in the art. In a particular embodiment, the compounds of the present invention can be combined with the following compounds:

nucleoside reverse transcriptase (RT) inhibitors such as, but not limited to, azidothymidine (AZT), and lamivudine (3TC), nucleotide reverse transcriptase inhibitors such as, but not limited to, tenofovir (R-PMPA), non-nucleoside reverse transcriptase inhibitors such as, but not limited to, nevirapine, efavirenz, protease inhibitors such as, but not limited to, nelfinavir, saquinavir, ritonavir and amprenavir, fusion inhibitors such as enfuvirtide, or integrase inhibitors such as raltegravir or elvitegravir.

More generally, the invention relates to the compounds of formulae, embodiments and claims herein being useful as agents having biological activity or as diagnostic agents. Any of the uses mentioned with respect to the present invention may be restricted to a non-medical use, a non-therapeutic use, a non-diagnostic use, or exclusively an in vitro use, or a use related to cells remote from an animal.

The invention further relates to the use of the compounds of the invention as chemical tools for virology and biochemistry. In particular, they can be used as research tools to investigate HIV biology.

DETAILED DESCRIPTION OF THE INVENTION

The present invention will be described with respect to particular embodiments but the invention is not limited thereto.

It is to be noticed that the term "comprising", used in the claims, should not be interpreted as being restricted to the means listed thereafter; it does not exclude other elements or steps.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments. Where an indefinite or definite article is used when referring to a singular noun e.g. "a" or "an", "the", this includes a plural of that noun unless something else is specifically stated.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects.

In each of the following definitions, the number of carbon atoms represents the maximum number of carbon atoms generally optimally present in the substituent or linker; it is understood that where otherwise indicated in the present application, the number of carbon atoms represents the optimal maximum number of carbon atoms for that particular substituent or linker.

The term "leaving group" or "LG" as used herein means a chemical group which is susceptible to be displaced by a nucleophile or cleaved off or hydrolyzed in basic or acidic conditions. In a particular embodiment, a leaving group is selected from a halogen atom (e.g., Cl, Br, I) or a sulfonate (e.g., mesylate, tosylate, triflate).

The term "protecting group" refers to a moiety of a compound that masks or alters the properties of a functional group or the properties of the compound as a whole. The chemical substructure of a protecting group varies widely. One function of a protecting group is to serve as intermediates in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g. alcohols, be physiologically acceptable, although in general it is more desirable if the products are pharmacologically innocuous.

The term "hydrocarbyl", "$C_{1-18}$ hydrocarbyl", "hydrocarbyl group" or "$C_{1-18}$ hydrocarbyl group" as used herein refers to $C_1$-$C_{18}$ normal, secondary, tertiary, unsaturated or saturated, non-aromatic, acyclic or cyclic, hydrocarbons and combinations thereof. This term therefore comprises alkyl, alkenyl, alkynyl, cycloalkyl, cycloalkenyl and cycloalkynyl.

The terminology "heterohydrocarbyl", "hetero $C_{1-18}$ hydrocarbyl", "heterohydrocarbyl group", "hetero $C_{1-18}$ hydrocarbyl group" or "hydrocarbyl group which optionally includes one or more heteroatoms, said heteroatoms being selected from the atoms consisting of O, S, and N" as used herein, refers to a hyrdocarbyl group where one or more carbon atoms are replaced by an oxygen, nitrogen or sulphur atom(s) and thus includes heteroalkyl, heteroalkenyl, heteroalkynyl and non-aromatic heterocycle. This term therefore comprises as an example alkoxy, alkenyloxy, $C_w$alkyl-O—$C_{18-w}$alkyl, $C_w$alkenyl-O-alkyl, $C_w$alkyl-NH—$C_{18-w}$alkenyl, among others, wherein w is selected from any number between 1 and 18.

The term "alkyl" or "$C_{1-18}$ alkyl" as used herein means $C_1$-$C_{18}$ normal, secondary, or tertiary, linear or cyclic, branched or straight hydrocarbon with no site of unsaturation. Examples are methyl, ethyl, 1-propyl (n-propyl), 2-propyl (iPr), 1-butyl, 2-methyl-1-propyl(i-Bu), 2-butyl (s-Bu), 2-dimethyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, cyclopropylethylene, methylcyclopropylene, 2,3-dimethyl-2-butyl, 3,3-dimethyl-2-butyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, cyclopropyl, cyclobutyl, cyclopentyl and cyclohexyl. In a particular embodiment, the term alkyl refers to $C_{1-12}$ hydrocarbons, yet more in particular to $C_{1-6}$ hydrocarbons as further defined herein above.

The term "acyclic alkyl" as used herein means $C_1$-$C_{18}$ normal, secondary, or tertiary, linear, branched or straight, hydrocarbon with no site of unsaturation. Examples are methyl, ethyl, 1-propyl, 2-propyl (iPr), 1-butyl, 2-methyl-1-propyl(i-Bu), 2-butyl (s-Bu), 2-methyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl and n-icosyl.

The term "cycloalkyl" or "$C_{3-18}$ cycloalkyl" as used herein and unless otherwise stated means a saturated hydrocarbon monovalent radical having from 3 to 18 carbon atoms consisting of or comprising a $C_{3-10}$ monocyclic or $C_{7-18}$ polycyclic saturated hydrocarbon, such as for instance cyclopropyl, cyclobutyl, cyclopentyl, cyclopropylethylene, methylcyclopropylene, cyclohexyl, cycloheptyl, cyclooctyl, cyclooctylmethylene, norbornyl, fenchyl, trimethyltricycloheptyl, decalinyl, adamantyl and the like.

The term "alkenyl" or "$C_{2-18}$alkenyl" as used herein is $C_2$-$C_{18}$ normal, secondary or tertiary, linear or cyclic, branched or straight hydrocarbon with at least one site (usually 1 to 3, preferably 1) of unsaturation, namely a carbon-carbon, sp2 double bond. Examples include, but are not limited to: ethylene or vinyl (—CH=CH$_2$), allyl (—CH$_2$CH=CH$_2$), cyclopentenyl (—C$_5$H$_7$), cyclohexenyl (—C$_6$H$_9$), cyclopentenylpropylene, methylcyclohexenylene and 5-hexenyl (—CH$_2$CH$_2$CH$_2$CH$_2$CH=CH$_2$). The double bond may be in the cis or trans configuration. In a particular embodiment, the term alkenyl refers to $C_{1-12}$ hydrocarbons, yet more in particular to $C_{1-6}$ hydrocarbons as further defined herein above.

The term "acyclic alkenyl" as used herein refers to $C_2$-$C_{18}$ normal, secondary or tertiary, linear, branched or straight hydrocarbon with at least one site (usually 1 to 3, preferably 1) of unsaturation, namely a carbon-carbon, sp2 double bond. Examples include, but are not limited to: ethylene or vinyl (—CH=CH$_2$), allyl (—CH$_2$CH=CH$_2$) and 5-hexenyl (—CH$_2$CH$_2$CH$_2$CH$_2$CH=CH$_2$). The double bond may be in the cis or trans configuration.

The term "cycloalkenyl" as used herein refers to a non-aromatic hydrocarbon radical having from 3 to 18 carbon atoms with at least one site (usually 1 to 3, preferably 1) of unsaturation, namely a carbon-carbon, sp2 double bond and consisting of or comprising a $C_{3-10}$ monocyclic or $C_{7-18}$ polycyclic hydrocarbon. Examples include, but are not limited to: cyclopentenyl (—C$_5$H$_7$), cyclopentenylpropylene, methylcyclohexenylene and cyclohexenyl (—C$_6$H$_9$). The double bond may be in the cis or trans configuration.

The term "alkynyl" or "$C_{2-18}$alkynyl" as used herein refers to $C_2$-$C_{18}$ normal, secondary, tertiary, linear or cyclic, branched or straight hydrocarbon with at least one site (usually 1 to 3, preferably 1) of unsaturation, namely a carbon-carbon, sp triple bond. Examples include, but are not limited to: ethynyl (—C≡CH), 3-ethyl-cyclohept-1-ynylene, 4-cyclohept-1-yn-methylene and 1-propynyl (propargyl, —CH$_2$C≡CH). In a particular embodiment, the term alkenyl refers to $C_{1-12}$ hydrocarbons, yet more in particular to $C_{1-6}$ hydrocarbons as further defined herein above.

The term "acyclic alkynyl" as used herein refers to $C_2$-$C_{18}$ normal, secondary, tertiary, linear, branched or straight hydrocarbon with at least one site (usually 1 to 3, preferably 1) of unsaturation, namely a carbon-carbon, sp triple bond. Examples include, but are not limited to: ethynyl (—C≡CH) and 1-propynyl (propargyl, —CH$_2$C≡CH).

The term "cycloalkynyl" as used herein refers to a non-aromatic hydrocarbon radical having from 3 to 18 carbon atoms with at least one site (usually 1 to 3, preferably 1) of unsaturation, namely a carbon-carbon, sp triple bond and consisting of or comprising a $C_{3-10}$ monocyclic or $C_{7-18}$ polycyclic hydrocarbon. Examples include, but are not limited to: cyclohept-1-yne, 3-ethyl-cyclohept-1-ynylene, 4-cyclohept-1-yn-methylene and ethylene-cyclohept-1-yne.

The term "alkylene" as used herein each refer to a saturated, branched or straight chain hydrocarbon radical of 1-18 carbon atoms (more in particular $C_{1-12}$ or $C_{1-6}$ carbon atoms), and having two monovalent radical centers derived by the removal of two hydrogen atoms from the same or two different carbon atoms of a parent alkane. Typical alkylene radicals include, but are not limited to: methylene (—CH$_2$—) 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like.

The term "alkenylene" as used herein each refer to a branched or straight chain hydrocarbon radical of 2-18 carbon atoms (more in particular $C_{2-12}$ or $C_{2-6}$ carbon atoms) with at least one site (usually 1 to 3, preferably 1) of unsaturation, namely a carbon-carbon, sp2 double bond, and having two monovalent radical centers derived by the removal of two hydrogen atoms from the same or two different carbon atoms of a parent alkene.

The term "alkynylene" as used herein each refer to a branched or straight chain hydrocarbon radical of 2-18 carbon atoms (more in particular $C_{2-12}$ or $C_{2-6}$ carbon atoms) with at least one site (usually 1 to 3, preferably 1) of unsaturation, namely a carbon-carbon, sp triple bond, and having two monovalent radical centers derived by the removal of two hydrogen atoms from the same or two different carbon atoms of a parent alkyne.

The term "heteroalkyl" as used herein refers to an acyclic alkyl wherein one or more carbon atoms are replaced by an oxygen, nitrogen or sulphur atom. In other words, this term means that —$CH_3$ can be replaced by $NH_2$, and —$CH_2$— by —NH—, —O— or —S—. The heteroatoms may be positioned at the beginning of the acyclic alkyl chain, in the acyclic alkyl chain or at the end of the acyclic alkyl chain. Examples of heteroalkyl include methoxy, methylthio, ethoxy, propoxy, $CH_3$—O—$CH_2$—, $CH_3$—S—$CH_2$—, $CH_3$—$CH_2$—O—$CH_2$—, $CH_3$—NH—, $(CH_3)_2$—N—, $(CH_3)_2$—$CH_2$—NH—$CH_2$—$CH_2$—, among many other examples.

The term "heteroalkenyl" as used herein refers to an acyclic alkenyl wherein one or more carbon atoms are replaced by an oxygen, nitrogen or sulphur atom. In other words, this term means that —$CH_3$ can be replaced by $NH_2$, —$CH_2$— by —NH—, —O— or —S—, and a —CH= by —N=. The heteroatoms may be positioned at the beginning of the acyclic alkenyl chain, in the acyclic alkenyl chain or at the end of the acyclic alkenyl chain. Examples of heteroalkenyl include $CH_3$—O—$CH_2$—N=, $CH_3$—N=$CH_2$—, $CH_3$—NH—N=, $(CH_3)_2$—$CH_2$—N=CH—$CH_2$—, among many other examples.

The term "heteroalkynyl" as used herein refers to an acyclic alkynyl wherein one or more carbon atoms are replaced by an oxygen, nitrogen or sulphur atom. In other words, this term means that —$CH_3$ can be replaced by $NH_2$, —$CH_2$— by —NH—, —O— or —S—, a —CH= by —N= and ≡CH by ≡N. The heteroatoms may be positioned at the beginning of the acyclic alkynyl chain, in the acyclic alkynyl chain or at the end of the acyclic alkynyl chain. Examples of heteroalkynyl include NC—$CH_2$—, NC—$CH_2$—N=$CH_2$—, or NC—$CH_2$—NH—N=, among many other examples.

The term "heteroalkylene" as used herein refers to an alkylene wherein one or more carbon atoms are replaced by an oxygen, nitrogen or sulphur atom. In other words, this term means that —$CH_3$ can be replaced by $NH_2$ and —$CH_2$— by —NH—, —O— or —S—. The heteroatoms may be positioned at the beginning of the alkylene chain, in the alkylene chain or at the end of the alkylene chain. Examples of heteroalkylene include —$CH_2$—O—, —$CH_2$—S—, $CH_2$—$CH_2$—O—, —$CH_2$—O—$CH_2$—, —$CH_2$—S—$CH_2$—, —CH($NH_2$)—S—$CH_2$—, —$CH_2$—$CH_2$—O—$CH_2$—, —$CH_2$—NH—, —$CH_2$—N($CH_3$)—, among many other examples.

The term "heteroalkenylene" as used herein refers to an alkenylene wherein one or more carbon atoms are replaced by an oxygen, nitrogen or sulphur atom. In other words, this term means that —$CH_3$ can be replaced by $NH_2$, —$CH_2$—by —NH—, —O— or —S—, and a —CH= by —N=. The heteroatoms may be positioned at the beginning of the acyclic alkenylene chain, in the acyclic alkenylene chain or at the end of the acyclic alkenylene chain. Examples of heteroalkenylene include —$CH_2$—O—$CH_2$—N=, —$CH_2$—N=$CH_2$—, —$CH_2$—NH—N=, —CH($CH_3$)—N=CH—$CH_2$—, among many other examples.

The term "heteroalkynylene" as used herein refers to an alkynylene wherein one or more carbon atoms are replaced by an oxygen, nitrogen or sulphur atom. In other words, this term means that —$CH_3$ can be replaced by $NH_2$, —$CH_2$— by —NH—, —O— or —S—, a —CH= by —N= and ≡CH by ≡N. The heteroatoms may be positioned at the beginning of the alkynyl ene chain, in the alkynylene chain or at the end of the alkynylene chain. Examples of heteroalkynylene include NC—CH—, —CH(NC)—N=$CH_2$—, or —CH(NC)—NH—N=, —CH(NC)—$CH_2$—O—$CH_2$— among many other examples.

The term "aryl" as used herein means a aromatic hydrocarbon radical of 6-20 carbon atoms derived by the removal of hydrogen from a carbon atom of a parent aromatic ring system. Typical aryl groups include, but are not limited to 1 ring, or 2 or 3 rings fused together, radicals derived from benzene, naphthalene, anthracene, biphenyl, and the like. In a particular embodiment, the term "parent aromatic ring system" means a monocyclic aromatic ring system or a bi- or tricyclic ring system of which at least one ring is aromatic. Therefore, in this embodiment, typical aryl groups include, but are not limited to 1 ring, or 2 or 3 rings fused together, radicals derived from benzene, naphthalene, anthracene, biphenyl, 2,3-dihydro-1H-indenyl, 5,6,7,8-tetrahydronaphthalenyl, 1,2,6,7,8,8a-hexahydroacenaphthylenyl, 1,2-dihydroacenaphthylenyl, and the like.

The term "arylalkyl" or "arylalkyl-" as used herein refers to an acyclic alkyl radical in which one of the hydrogen atoms bonded to a carbon atom, typically a terminal or sp3 carbon atom, is replaced with an aryl radical. Typical arylalkyl groups include, but are not limited to, benzyl, 2-phenylethan-1-yl, 2-phenylethen-1-yl, naphthylmethyl, 2-naphthylethyl, and the like. The arylalkyl group comprises 6 to 20 carbon atoms, e.g. the alkyl moiety of the arylalkyl group is 1 to 6 carbon atoms and the aryl moiety is 6 to 14 carbon atoms.

The term "arylalkenyl" or "arylalkenyl-" as used herein refers to an acyclic alkenyl radical in which one of the hydrogen atoms bonded to a carbon atom, is replaced with an aryl radical. The arylalkenyl group comprises 6 to 20 carbon atoms, e.g. the alkenyl moiety of the arylalkenyl group is 1 to 6 carbon atoms and the aryl moiety is 6 to 14 carbon atoms.

The term "arylalkynyl" or "arylalkynyl-" as used herein refers to an acyclic alkynyl radical in which one of the hydrogen atoms bonded to a carbon atom, is replaced with an aryl radical. The arylalkynyl group comprises 6 to 20 carbon atoms, e.g. the alkynyl moiety of the arylalkynyl group is 1 to 6 carbon atoms and the aryl moiety is 6 to 14 carbon atoms.

The term "arylheteroalkyl" or "arylheteroalkyl-" as used herein refers to a heteroalkyl radical in which one of the hydrogen atoms bonded to a carbon atom, typically a terminal or sp3 carbon atom, is replaced with an aryl radical. The arylheteroalkyl group comprises 6 to 20 carbon atoms, e.g. the heteroalkyl moiety of the arylheteroalkyl group is 1 to 6 carbon atoms and the aryl moiety is 6 to 14 carbon atoms.

The term "arylheteroalkenyl" or "arylheteroalkenyl-" as used herein refers to a heteroalkenyl radical in which one of the hydrogen atoms bonded to a carbon atom, is replaced with an aryl radical. The arylheteroalkenyl group comprises 6 to 20 carbon atoms, e.g. the heteroalkenyl moiety of the arylheteroalkenyl group is 1 to 6 carbon atoms and the aryl moiety is 6 to 14 carbon atoms.

The term "arylheteroalkynyl" or "arylheteroalkynyl-" as used herein refers to a heteroalkynyl radical in which one of the hydrogen atoms bonded to a carbon atom, is replaced with an aryl radical. The arylheteroalkynyl group comprises 6 to 20 carbon atoms, e.g. the heteroalkynyl moiety of the arylheteroalkynyl group is 1 to 6 carbon atoms and the aryl moiety is 6 to 14 carbon atoms.

The term "heterocycle" as used herein means a saturated, unsaturated or aromatic ring system of 3 to 18 atoms including at least one N, O, S, or P. Heterocycle thus include heteroaryl groups. Heterocycle as used herein includes by way of example and not limitation these heterocycles described in Paquette, Leo A. "Principles of Modern Heterocyclic Chemistry" (W.A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; Katritzky, Alan R., Rees, C. W. and Scriven, E. "Comprehensive Heterocyclic Chemistry" (Pergamon Press, 1996); and J. Am. Chem. Soc. (1960) 82:5566. In a particular embodiment, the term means pyridyl, dihydroypyridyl, tetrahydropyridyl (piperidyl), thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl, isatinoyl, 2,3-dihydropyrano[4,3,2-de]quinolinyl, chromanyl, 3,4-dihydro-2H-benzo[b][1,4] oxazinyl, 1,2,3,4-tetrahydroquinolinyl and 2,3-dihydrobenzofuranyl. Preferably it means pyridyl, dihydroypyridyl, tetrahydropyridyl (piperidyl), thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl, and isatinoyl.

The term "heteroaryl" means an aromatic ring system of 5 to 18 atoms including at least one N, O, S, or P and thus refers to aromatic heterocycles. Examples of heteroaryl include but are not limited to pyridyl, dihydropyridyl, pyridazinyl, pyrimidinyl, pyrazinyl, s-triazinyl, oxazolyl, imidazolyl, thiazolyl, isoxazolyl, pyrazolyl, isothiazolyl, furyl, thienyl, and pyrrolyl.

The term "non-aromatic heterocycle" as used herein means a saturated or unsaturated non-aromatic ring system of 3 to 18 atoms including at least one N, O, S, or P.

The term "heterocycle-alkyl" or "heterocycle-alkyl-" as used herein refers to an acyclic alkyl radical in which one of the hydrogen atoms bonded to a carbon atom, typically a terminal or sp3 carbon atom, is replaced with a heterocyle radical. An example of a heterocycle-alkyl group is 2-pyridyl-methylene. The heterocycle-alkyl group comprises 6 to 20 atoms, e.g. the alkyl moiety of the heterocycle-alkyl group is 1 to 6 carbon atoms and the heterocycle moiety is 3 to 14 atoms.

The term "heterocycle-alkenyl" or "heterocycle-alkenyl-" as used herein refers to an acyclic alkenyl radical in which one of the hydrogen atoms bonded to a carbon atom, is replaced with an heterocycle radical. The heterocycle-alkenyl group comprises 6 to 20 atoms, e.g. the alkenyl moiety of the heterocycle-alkenyl group is 1 to 6 carbon atoms and the heterocycle moiety is 3 to 14 atoms.

The term "heterocycle-alkynyl" or "heterocycle-alkynyl-" as used herein refers to an acyclic alkynyl radical in which one of the hydrogen atoms bonded to a carbon atom, is replaced with a heterocycle radical. The heterocycle-alkynyl group comprises 6 to 20 atoms, e.g. the alkynyl moiety of the heterocycle-alkynyl group is 1 to 6 carbon atoms and the heterocycle moiety is 3 to 14 atoms.

The term "heterocycle-heteroalkyl" or "heterocycle-heteroalkyl-" as used herein refers to a heteroalkyl radical in which one of the hydrogen atoms bonded to a carbon atom, typically a terminal or sp3 carbon atom, is replaced with a heterocyle radical. The heterocycle-heteroalkyl group comprises 6 to 20 atoms, e.g. the heteroalkyl moiety of the heterocycle-heteroalkyl group is 1 to 6 carbon atoms and the heterocycle moiety is 3 to 14 atoms.

The term "heterocycle-heteroalkenyl" or "heterocycle-heteroalkenyl-" as used herein refers to a heteroalkenyl radical in which one of the hydrogen atoms bonded to a carbon atom, is replaced with an heterocycle radical. The heterocycle-heteroalkenyl group comprises 6 to 20 atoms, e.g. the heteroalkenyl moiety of the heterocycle-heteroalkenyl group is 1 to 6 carbon atoms and the heterocycle moiety is 3 to 14 atoms.

The term "heterocycle-heteroalkynyl" or "heterocycle-heteroalkynyl-" as used herein refers to a heteroalkynyl radical in which one of the hydrogen atoms bonded to a carbon atom, is replaced with a heterocycle radical. The heterocycle-heteroalkynyl group comprises 6 to 20 atoms, e.g. the heteroalkynyl moiety of the heterocycle-heteroalkynyl group is 1 to 6 carbon atoms and the heterocycle moiety is 3 to 14 atoms.

The term "heteroaryl-alkyl" or "heteroaryl-alkyl-" as used herein refers to an acyclic alkyl radical in which one of the hydrogen atoms bonded to a carbon atom, typically a terminal or sp3 carbon atom, is replaced with a heteraryl radical. An example of a heteroaryl-alkyl group is 2-pyridyl-methylene. The heteroaryl-alkyl group comprises 6 to 20 atoms, e.g. the alkyl moiety of the heteroaryl-alkyl group is 1 to 6 carbon atoms and the heteroaryl moiety is 5 to 14 atoms.

The term "heteroaryl-alkenyl" or "heteroaryl-alkenyl-" as used herein refers to an acyclic alkenyl radical in which one of the hydrogen atoms bonded to a carbon atom, is replaced with an heteroaryl radical. The heteroaryl-alkenyl group comprises 6 to 20 atoms, e.g. the alkenyl moiety of the heteroaryl-alkenyl group is 1 to 6 carbon atoms and the heteroaryl moiety is 5 to 14 atoms.

The term "heteroaryl-alkynyl" or "heteroaryl-alkynyl-" as used herein refers to an acyclic alkynyl radical in which one of the hydrogen atoms bonded to a carbon atom, is replaced with a heteroaryl radical. The heteroaryl-alkynyl group comprises 6 to 20 atoms, e.g. the alkynyl moiety of the heteroaryl-alkynyl group is 1 to 6 carbon atoms and the heteroaryl moiety is 5 to 14 atoms.

The term "heteroaryl-heteroalkyl" or "heteroaryl-heteroalkyl-" as used herein refers to a heteroalkyl radical in which one of the hydrogen atoms bonded to a carbon atom, typically a terminal or sp3 carbon atom, is replaced with a heterocyle radical. The heteroaryl-heteroalkyl group comprises 6 to 20 atoms, e.g. the heteroalkyl moiety of the heteroaryl-heteroalkyl group is 1 to 6 carbon atoms and the heteroaryl moiety is 5 to 14 atoms.

The term "heteroaryl-heteroalkenyl" or "heteroaryl-heteroalkenyl-" as used herein refers to a heteroalkenyl radical in which one of the hydrogen atoms bonded to a carbon atom, is replaced with an heteroaryl radical. The heteroaryl-heteroalkenyl group comprises 6 to 20 atoms, e.g. the heteroalkenyl moiety of the heteroaryl-heteroalkenyl group is 1 to 6 carbon atoms and the heteroaryl moiety is 5 to 14 atoms.

The term "heteroaryl-heteroalkynyl" or "heteroaryl-heteroalkynyl-" as used herein refers to a heteroalkynyl radical in which one of the hydrogen atoms bonded to a carbon atom, is replaced with a heteroaryl radical. The heteroaryl-heteroalkynyl group comprises 6 to 20 atoms, e.g. the heteroalkynyl moiety of the heteroaryl-heteroalkynyl group is 1 to 6 carbon atoms and the heteroaryl moiety is 5 to 14 atoms.

The term "non-aromatic heterocycle-alkyl" or "non-aromatic heterocycle-alkyl-" as used herein refers to an acyclic alkyl radical in which one of the hydrogen atoms bonded to a carbon atom, typically a terminal or sp3 carbon atom, is replaced with a non-aromatic heterocycle radical. The non-aromatic heterocycle-alkyl group comprises 6 to 20 atoms, e.g. the alkyl moiety of the non-aromatic heterocycle-alkyl group is 1 to 6 carbon atoms and the non-aromatic heterocycle moiety is 3 to 14 atoms.

The term "non-aromatic heterocycle-alkenyl" or "non-aromatic heterocycle-alkenyl-" as used herein refers to an acyclic alkenyl radical in which one of the hydrogen atoms bonded to a carbon atom, is replaced with an non-aromatic heterocycle radical. The non-aromatic heterocycle-alkenyl group comprises 6 to 20 atoms, e.g. the alkenyl moiety of the non-aromatic heterocycle-alkenyl group is 1 to 6 carbon atoms and the non-aromatic heterocycle moiety is 3 to 14 atoms.

The term "non-aromatic heterocycle-alkynyl" or "non-aromatic heterocycle-alkynyl-" as used herein refers to an acyclic alkynyl radical in which one of the hydrogen atoms bonded to a carbon atom, is replaced with a non-aromatic heterocycle radical. The non-aromatic heterocycle-alkynyl group comprises 6 to 20 atoms, e.g. the alkynyl moiety of the non-aromatic heterocycle-alkynyl group is 1 to 6 carbon atoms and the non-aromatic heterocycle moiety is 3 to 14 atoms.

The term "non-aromatic heterocycle-heteroalkyl" or "non-aromatic heterocycle-heteroalkyl-" as used herein refers to a heteroalkyl radical in which one of the hydrogen atoms bonded to a carbon atom, typically a terminal or sp3 carbon atom, is replaced with a heterocyle radical. The non-aromatic heterocycle-heteroalkyl group comprises 6 to 20 atoms, e.g. the heteroalkyl moiety of the non-aromatic heterocycle-heteroalkyl group is 1 to 6 carbon atoms and the non-aromatic heterocycle moiety is 3 to 14 atoms.

The term "non-aromatic heterocycle-heteroalkenyl" or "non-aromatic heterocycle-heteroalkenyl-" as used herein refers to a heteroalkenyl radical in which one of the hydrogen atoms bonded to a carbon atom, is replaced with an non-aromatic heterocycle radical. The non-aromatic heterocycle-heteroalkenyl group comprises 6 to 20 atoms, e.g. the heteroalkenyl moiety of the non-aromatic heterocycle-heteroalkenyl group is 1 to 6 carbon atoms and the non-aromatic heterocycle moiety is 3 to 14 atoms.

The term "non-aromatic heterocycle-heteroalkynyl" or "non-aromatic heterocycle-heteroalkynyl-" as used herein refers to a heteroalkynyl radical in which one of the hydrogen atoms bonded to a carbon atom, is replaced with a non-aromatic heterocycle radical. The non-aromatic heterocycle-heteroalkynyl group comprises 6 to 20 atoms, e.g. the heteroalkynyl moiety of the non-aromatic heterocycle-heteroalkynyl group is 1 to 6 carbon atoms and the non-aromatic heterocycle moiety is 3 to 14 atoms.

By way of example, carbon bonded heterocyclic rings are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl. By way of example, nitrogen bonded heterocyclic rings are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

As used herein and unless otherwise stated, the terms "alkoxy", "cyclo-alkoxy", "aryloxy", "arylalkyloxy", "heterocycleoxy", "alkylthio", "cycloalkylthio", "arylthio", "arylalkylthio" and "heterocyclethio" refer to substituents wherein an alkyl group, respectively a cycloalkyl, aryl, arylalkyl or heterocycle (each of them such as defined herein), are attached to an oxygen atom or a sulfur atom through a single bond, such as but not limited to methoxy, ethoxy, propoxy, butoxy, thioethyl, thiomethyl, phenyloxy, benzyloxy, mercaptobenzyl and the like. The same definitions will apply for alkenyl and alkynyl radicals in stead of alkyl.

As used herein and unless otherwise stated, the term halogen means any atom selected from the group consisting of fluorine (F), chlorine (Cl), bromine (Br) and iodine (I).

The terminology regarding a chemical group "which optionally includes one or more heteroatoms, said heteroatoms being selected from the atoms consisting of O, S, and N" as used herein, refers to a group where one or more carbon atoms are replaced by an oxygen, nitrogen or sulphur atom and thus includes, depending on the group to which is referred, heteroalkyl, heteroalkenyl, heteroalkynyl, heteroalkyl, heteroalkenyl, heteroalkynyl, cycloheteroalkyl, cycloheteroalkenyl, cycloheteroalkynyl, heteroaryl, arylheteroalkyl, heteroarylalkyl, heteroarylheteroalkyl, arylheteroalkenyl, heteroarylalkenyl, heteroarylheteroalkenyl, heteroarylheteroalkenyl, arylheteroalkynyl, heteroarylalkynyl, heteroarylheteroalkynyl, among others. In other words, this term means that —CH$_3$ can be replaced by —NH$_2$, —CH$_2$— by —NH—, —O— or —S—, a —CH= by —N= and =CH by =N. This term therefore comprises, depending on the group to which is referred, as an example alkoxy, alkenyloxy, alkynyloxy, alkyl-O-alkylene, alkenyl-O-alkylene, arylalkoxy, benzyloxy, heterocycle-heteroalkyl, heterocycle-alkoxy, among others. As an example, the terminology "alkyl which optionally includes one or more heteroatoms, said heteroatoms being selected from the atoms consisting of O, S, and N" therefore refers to heteroalkyl, meaning an alkyl which comprises one or more heteroatoms in the hydrocarbon chain, whereas the heteroatoms may be positioned at the beginning of the hydrocarbon chain, in the hydrocarbon chain or at the end of the hydrocarbon chain. Examples of heteroalkyl include methoxy, methylthio, ethoxy, propoxy, $CH_3$—O—$CH_2$—, $CH_3$—S—$CH_2$—, $CH_3$—$CH_2$—O—$CH_2$—, $CH_3$—NH—, $(CH_3)_2$—N—, $(CH_3)_2$—$CH_2$—NH—$CH_2$—$CH_2$—, among many other examples. As an example, the terminology "arylalkylene which optionally includes one or more heteroatoms in the alkylene chain, said heteroatoms being selected from the atoms consisting of O, S, and N" therefore refers to arylheteroalkylene, meaning an arylalkylene which comprises one or more heteroatoms in the hydrocarbon chain, whereas the heteroatoms may be positioned at the beginning of the hydrocarbon chain, in the hydrocarbon chain or at the end of the hydrocarbon chain. "Arylheteroalkylene" thus includes aryloxy, arylalkoxy, aryl-alkyl-NH— and the like and examples are phenyloxy, benzyloxy, aryl-$CH_2$—S—$CH_2$—, aryl-$CH_2$—O—$CH_2$—, aryl-NH—$CH_2$— among many other examples. The same counts for "heteroalkenylene", "heteroalkynylene", and other terms used herein when referred to "which optionally includes one or more heteroatoms, said heteroatoms being selected from the atoms consisting of O, S, and N".

The terminology regarding a chemical group "wherein optionally two or more hydrogen atoms on a carbon atom or heteroatom of said group can be taken together to form a =O or =S" as used herein, refers to a group where two or more hydrogen atoms on a carbon atom or heteroatom of said group are taken together to form =O or =S. In other words, the expression means that a carbon atom or heteroatom of said group can be oxidized to form a C=O, C=S, N=O, N=S, S=O or $S(O)_2$. As an example, the terminology refers to "an alkyl wherein optionally two or more hydrogen atoms on a carbon atom or heteroatom of said alkyl can be taken together to form a =O or =S", includes among other examples $CH_3$—C(O)—$CH_2$—, $CH_3$—C(O)—, $CH_3$—C(S)—$CH_2$—, $CH_3$—$S(O)_2$—$CH_2$— and $(CH_3)_2$—$CH_2$—C(O)—$CH_2$—$CH_2$—.

The combination for a group "which optionally includes one or more heteroatoms, said heteroatoms being selected from the atoms consisting of O, S, and N" and "wherein optionally two or more hydrogen atoms on a carbon atom or heteroatom of said group can be taken together to form a =O or =S" can combine the two aspects described herein above and includes, if the group referred to is alkyl, among other examples $CH_3$—C(O)O—, $CH_3$—C(O)O—$CH_2$—, $CH_3$—NH—C(O)—, $CH_3$—C(O)—NH— $CH_3$—NH—C(O)—$CH_2$—, $CH_3$—NH—C(S)—$CH_2$—, $CH_3$—NH—C(S)—NH—$CH_2$—, $CH_3$—NH—$S(O)_2$— and $CH_3$—NH—$S(O)_2$—NH—$CH_2$—.

As used herein with respect to a substituting group, and unless otherwise stated, the terms "substituted" such as in "substituted alkyl", "substituted alkenyl", "substituted alkynyl", "substituted aryl", "substituted heterocycle", "substituted arylalkyl", "substituted heterocycle-alkyl" and the like refer to the chemical structures defined herein, and wherein the said hydrocarbyl, heterohydrocarbyl group and/or the said aryl or heterocycle may be optionally substituted with one or more substituents (preferable 1, 2, 3, 4, 5 or 6), meaning that one or more hydrogen atoms are each independently replaced with a substituent. Typical substituents include, but are not limited to and in a particular embodiment said substituents are being independently selected from the group consisting of halogen, amino, hydroxyl, sulfhydryl, alkyl, alkoxy, alkenyl, alkenyloxy, alkynyl, alkynyloxy, cycloalkyl, cycloalkenyl, cycloalkynyl, heteroalkyl, heteroalkenyl, heteroalkynyl, aryl, heterocycle, arylalkyl, arylalkenyl, arylalkynyl, heterocycle-alkyl, heterocycle-alkenyl and heterocycle-alkynyl, —X, —Z, —O$^-$, —OZ, =O, —SZ, —S$^-$, =S, —NZ$_2$, —N$^+$Z$_3$, =NZ, =N—OZ, —CX$_3$ (e.g. trifluoromethyl), —CN, —OCN, —SCN, —N=C=O, —N=C=S, —NO, —NO$_2$, =N$_2$, —N$_3$, —NZC(O)Z, —NZC(S)Z, —NZC(O)O$^-$, —NZC(O)OZ, —NZC(S)OZ, —NZC(O)NZZ, NZC(NZ)Z, NZC(NZ)NZZ, —C(O)NZZ, —C(NZ)Z, —$S(O)_2$O$^-$, —$S(O)_2$OZ, —$S(O)_2$Z, —OS(O)$_2$OZ, —OS(O)$_2$Z, —OS(O)$_2$O$^-$, —$S(O)_2$NZ, —S(O)Z, —OP(O)(OZ)$_2$, —P(O)(OZ)$_2$, —P(O)(O$^-$)$_2$, —P(O)(OZ)(O$^-$), —P(O)(OH)$_2$, —C(O)Z, —C(O)X, —C(S)Z, —C(O)OZ, —C(O)O$^-$, —C(S)OZ, —C(O)SZ, —C(S)SZ, —C(O)NZZ, —C(S)NZZ, —C(NZ)NZZ, —OC(O)Z, —OC(S)Z, —OC(O)O$^-$, —OC(O)OZ, —OC(S)OZ, wherein each X is independently a halogen selected from F, Cl, Br, or I; and each Z is independently —H, alkyl, alkenyl, alkynyl, heteroalkyl, heteroalkenyl, heteroalkynyl, aryl, heterocycle, protecting group or prodrug moiety, while two Z bonded to a nitrogen atom can be taken together with the nitrogen atom to which they are bonded to form a heterocycle. Alkyl(ene), alkenyl(ene), and alkynyl(ene) groups may also be similarly substituted.

Any substituent designation that is found in more than one site in a compound of this invention shall be independently selected.

Substituents optionally are designated with or without bonds. Regardless of bond indications, if a substituent is polyvalent (based on its position in the structure referred to), then any and all possible orientations of the substituent are intended.

As an example, if reference is made to an alkyl which can be substituted with certain substituents selected from the group of alkyl, alkenyl, alkynyl, heteroalkyl, heteroalkenyl, heteroalkynyl, hydroxyl, =O, halogen, =SH, =S, trifluoromethyl, —O-alkyl, —OCF$_3$, cyano, nitro, —C(O)OH or NH$_2$; then this includes as examples F—$CH_2$—, $CH_3$—C(O)—, $CH_3$—CH(NH$_2$)—, NH$_2$C(O)—, CF$_3$—$CH_2$—$CH_2$—CH(CN)—, among many other examples.

As an example, if reference is made to a heteroalkyl which can be substituted with certain substituents selected from the group of alkyl, alkenyl, alkynyl, heteroalkyl, heteroalkenyl, heteroalkynyl, hydroxyl, =O, halogen, =SH, =S, trifluoromethyl, —O-alkyl, —OCF$_3$, cyano, nitro, —C(O)OH or —NH$_2$; then this includes as examples F—$CH_2$—$CH_2$—NH—, $CH_3$—C(O)—, $CH_3$—C(O)O—, $CH_3$—C(S)O—, $CH_3$—C(O)NH—, NH$_2$C(O)—$CH_2$—S—, CF$_3$—$CH_2$—O—CH(CN)—, $CH_3$—$CH_2$—$S(O)_2$—NH—, among many other examples.

As used herein and unless otherwise stated, the term "solvate" includes any combination which may be formed by a derivative of this invention with a suitable inorganic solvent (e.g. hydrates) or organic solvent, such as but not limited to alcohols, ketones, esters, ethers, nitriles and the like.

The compounds of the invention are pyrimidine derivatives and have a structure according to the formulae and embodiments described in the summary of the invention.

More in particular, one aspect of the present invention is the provision of novel pyrimidine derivatives, said compounds having a structure according to the formula (A):

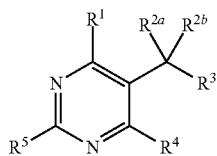

(A)

wherein, $R^1$ is independently selected from cycloalkyl; cycloalkenyl; cycloalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl or heterocycle-heteroalkynyl;

and wherein said cycloalkyl, cycloalkenyl, cycloalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more $Z^1$;

each of $R^{2a}$ and $R^{2b}$ is independently selected from hydrogen; cyano; alkyl; alkenyl; alkynyl; heteroalkyl; heteroalkenyl; heteroalkynyl; aryl; arylalkyl; arylalkenyl; arylalkynyl; arylheteroalkyl; arylheteroalkenyl; arylheteroalkynyl; heterocycle; heterocycle-alkyl; heterocycle-alkenyl; heterocycle-alkynyl; heterocycle-heteroalkyl, heterocycle-heteroalkenyl, or heterocycle-heteroalkynyl; or $R^{2a}$ and $R^{2b}$ can be taken together to form vinyl or vinylalkyl;

and wherein said alkyl, alkenyl, alkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more $Z^1$;

$R^3$ is independently selected from —C(O)OH; —C(O)OZ$^2$; —C(O)NHCN; —S(O)$_2$OH; —S(O)$_2$OZ$^2$; —S(O)$_2$NHZ$^4$; —P(O)(OH)NH$_2$; —P(O)(OH)O-alkyl; —NHC(O)NHS(O)$_2$-aryl; —NHC(O)NHS(O)$_2$-heteroaryl; —C(O)NHS(O)$_2$-aryl; —C(O)NHS(O)$_2$-heteroaryl; —S(O)$_2$NHS(O)$_2$-aryl; —S(O)$_2$NHS(O)$_2$-heteroaryl; or from the following structures:

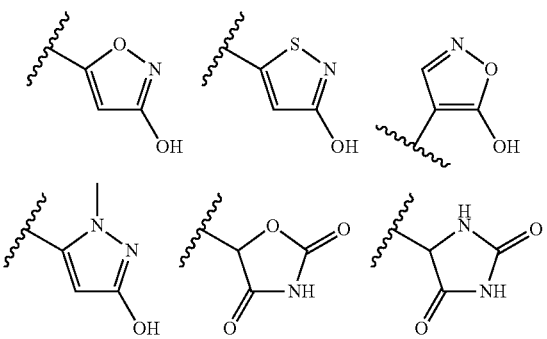

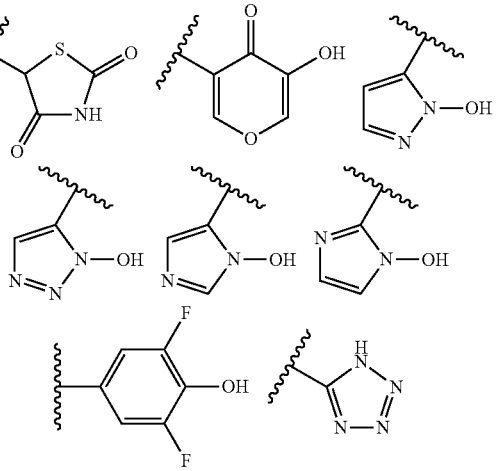

$R^4$ is independently selected from hydrogen; alkyl; alkenyl or alkynyl; wherein said alkyl, alkenyl or alkynyl can be unsubstituted or substituted with one or more $Z^1$;

$R^5$ is selected from halogen; cyano; —NR$^{10}$R$^{11}$; alkyl; alkenyl; alkynyl; heteroalkyl; heteroalkenyl; heteroalkynyl; aryl; arylalkyl; arylalkenyl; arylalkynyl; arylheteroalkyl; arylheteroalkenyl; arylheteroalkynyl; heterocycle; heterocycle-alkyl; heterocycle-alkenyl; heterocycle-alkynyl; heterocycle-heteroalkyl, heterocycle-heteroalkenyl, or heterocycle-heteroalkynyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more $R^{20}$;

each $R^{10}$ and $R^{11}$ is independently selected from hydrogen; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl; or $R^{10}$ and $R^{11}$ can be taken together with the nitrogen to which they are attached to form a (5-, 6-, or 7-membered) heterocycle which can be unsubstituted or substituted with one or more $R^{20}$;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more $R^{20}$;

each $R^{20}$ is independently selected from the group consisting of halogen; —OR$^{21}$; =O; —SR$^{21}$; =S; —S(O)R$^{22}$; —S(O)$_2$R$^{22}$; —S(O)$_2$NR$^{23}$R$^{24}$; trifluoromethyl; nitro; —NR$^{23}$R$^{24}$; —NR$^{21}$S(O)$_2$R$^{22}$; cyano; —C(O)OR$^{21}$; —C(O)NR$^{23}$R$^{24}$; —C(O)R$^{22}$; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl;
- and wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more $Z^1$;

each $R^{21}$ is independently selected from hydrogen; alkyl; alkenyl; alkynyl; heteroalkyl; heteroalkenyl; heteroalkynyl; aryl; arylalkyl; arylalkenyl; arylalkynyl; arylheteroalkyl; arylheteroalkenyl; arylheteroalkynyl; heterocycle; heterocycle-alkyl; heterocycle-alkenyl; heterocycle-alkynyl; heterocycle-heteroalkyl; heterocycle-heteroalkenyl; and heterocycle-heteroalkynyl;
- wherein said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, heterocycle, heterocycle-alkyl, heterocycle-alkenyl, heterocycle-alkynyl, heterocycle-heteroalkyl, heterocycle-heteroalkenyl, and heterocycle-heteroalkynyl can be unsubstituted or substituted with one or more $Z^1$;

each $R^{22}$ is independently selected from hydrogen; hydroxyl; alkyl; alkenyl; alkynyl; heteroalkyl; heteroalkenyl; heteroalkynyl; aryl; arylalkyl; arylalkenyl; arylalkynyl; arylheteroalkyl; arylheteroalkenyl; arylheteroalkynyl; heterocycle; heterocycle-alkyl; heterocycle-alkenyl; heterocycle-alkynyl; heterocycle-heteroalkyl; heterocycle-heteroalkenyl; and heterocycle-heteroalkynyl;
- wherein said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, heterocycle, heterocycle-alkyl, heterocycle-alkenyl, heterocycle-alkynyl, heterocycle-heteroalkyl, heterocycle-heteroalkenyl, and heterocycle-heteroalkynyl can be unsubstituted or substituted with one or more $Z^1$;

each $R^{23}$ and $R^{24}$ is independently selected from hydrogen; alkyl; alkenyl; alkynyl; heteroalkyl; heteroalkenyl; heteroalkynyl; aryl; arylalkyl; arylalkenyl; arylalkynyl; arylheteroalkyl; arylheteroalkenyl; arylheteroalkynyl; heterocycle; heterocycle-alkyl; heterocycle-alkenyl; heterocycle-alkynyl; heterocycle-heteroalkyl; heterocycle-heteroalkenyl; and heterocycle-heteroalkynyl;
- and wherein said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, heterocycle, heterocycle-alkyl, heterocycle-alkenyl, heterocycle-alkynyl, heterocycle-heteroalkyl, heterocycle-heteroalkenyl, and heterocycle-heteroalkynyl can be unsubstituted or substituted with one or more $Z^1$;
- and wherein $R^{104}$ and $R^{105}$ can be taken together in order to form a (5-, 6-, or 7-membered) heterocycle which can be unsubstituted or substituted with one or more $Z^1$;

each $Z^1$ is independently selected from the group consisting of hydrogen; halogen; $-OZ^2$; $=O$; $-SZ^2$; $=S$; $-S(O)Z^3$; $-S(O)_2Z^3$; $-S(O)_2NZ^4Z^5$; trifluoromethyl; nitro; $-NZ^4Z^5$; $-NZ^2S(O)_2Z^3$; cyano; $-C(O)OZ^2$; $-C(O)NZ^4Z^5$; $-C(O)Z^3$; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl;
- and wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from the group of alkyl, alkenyl, alkynyl, hydroxyl, $=O$, halogen, $-SH$, $=S$, trifluoromethyl, $-O$-alkyl, $-OCF_3$, cyano, nitro, $-C(O)OH$ or $NH_2$;

each $Z^2$ is independently selected from hydrogen; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl;
- wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with alkyl, alkenyl, alkynyl, hydroxyl, $=O$, halogen, $-SH$, $=S$, trifluoromethyl, $-O$-alkyl, $-OCF_3$, cyano, nitro, $-C(O)OH$ or $NH_2$;

each $Z^3$ is independently selected from hydroxyl; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl;
- wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more selected from the group of alkyl, alkenyl, alkynyl, hydroxyl, $=O$, halogen, $-SH$, $=S$, trifluoromethyl, $-O$-alkyl, $-OCF_3$, cyano, nitro, $-C(O)OH$ or $NH_2$;

each $Z^4$ and $Z^5$ is independently selected from hydrogen; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl;
- wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more selected from the group of alkyl, alkenyl, alkynyl, hydroxyl, $=O$, halogen, —SH, =S, trifluoromethyl, —O-alkyl, —OCF$_3$, cyano, nitro, —C(O)OH or NH$_2$;

and wherein $Z^4$ and $Z^5$ can be taken together in order to form a (5-, 6-, or 7-membered) heterocycle which can be unsubstituted or substituted with alkyl, alkenyl, alkynyl, hydroxyl, halogen, —SH, trifluoromethyl, —O-alkyl, —OCF$_3$, cyano, nitro, —C(O)OH or —NH$_2$;

and isomers (in particular stereo-isomers or tautomers), solvates, hydrates, salts (in particular pharmaceutically acceptable salts) or prodrugs thereof.

In a particular embodiment, the compounds of the invention are not 4-methyl-6-(3-nitrophenyl)-2-phenyl-5-pyrimidineacetic acid.

In a particular embodiment, $R^1$ is selected from aryl or heteroaryl and yet in a more particular embodiment is selected from phenyl, wherein said aryl, heteroaryl or phenyl can be unsubstituted or substituted, in a particular embodiment substituted with one or more $Z^1$.

In yet another particular embodiment, one of $R^{2a}$ and $R^{2b}$ is not hydrogen. In another particular embodiment, one of $R^{2a}$ and $R^{2b}$ is hydrogen and the other of $R^{2a}$ and $R^{2b}$ is selected from alkyl, alkenyl, alkynyl, heteroalkyl, heteroalkenyl or heteroalkynyl. In a yet more particular embodiment, one of $R^{2a}$ and $R^{2b}$ is hydrogen and the other of $R^{2a}$ and $R^{2b}$ is selected from alkyl and heteroalkyl.

In yet another particular embodiment, $R^3$ is selected from —C(O)O$Z^2$, more in particular is —C(O)OH.

In yet another particular embodiment, $R^4$ is selected from hydrogen and alkyl, more in particular is methyl.

In yet another particular embodiment, $R^5$ is selected from —N$R^{10}R^{11}$; alkyl; alkenyl; alkynyl; heteroalkyl; heteroalkenyl; heteroalkynyl; aryl; arylalkyl; arylalkenyl; arylalkynyl; arylheteroalkyl; arylheteroalkenyl; arylheteroalkynyl; heterocycle; heterocycle-alkyl; heterocycle-alkenyl; heterocycle-alkynyl; heterocycle-heteroalkyl, heterocycle-heteroalkenyl, or heterocycle-heteroalkynyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more $R^{20}$.

In a more particular embodiment, $R^5$ is —N$R^{10}R^{11}$ wherein $R^{10}$ and $R^{11}$ are as described herein. In yet a more particular embodiment, $R^5$ is —N$R^{10}R^{11}$, whereby $R^{10}$ and $R^{11}$ are taken together with the nitrogen to which they are attached to form a (5-, 6-, or 7-membered) heterocycle which can be unsubstituted or substituted with one or more $R^{20}$ (wherein $R^{20}$ is as described herein).

In another embodiment, the compounds of the invention have a structure according to formula (B),

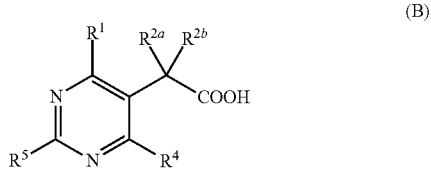

(B)

wherein each of $R^1$, $R^{2a}$, $R^{2b}$, $R^4$ and $R^5$ are as in formula (A) and the embodiments described herein.

In another embodiment, the compounds of the invention have a structure according to formula (C),

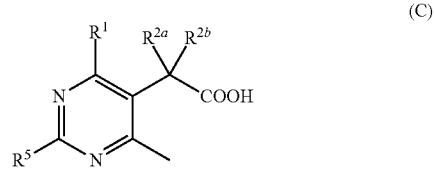

(C)

wherein each of $R^1$, $R^{2a}$, $R^{2b}$ and $R^5$ are as in formula (A) and the embodiments described herein.

In another embodiment, the compounds of the invention have a structure according to formula (D),

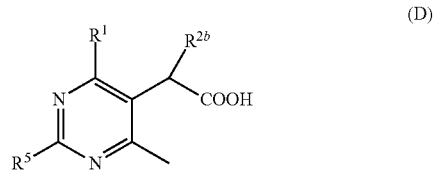

(D)

wherein each of $R^1$, $R^{2b}$ and $R^5$ are as in formula (A) and the embodiments described herein.

In another embodiment, the compounds of the invention have a structure according to formula (E),

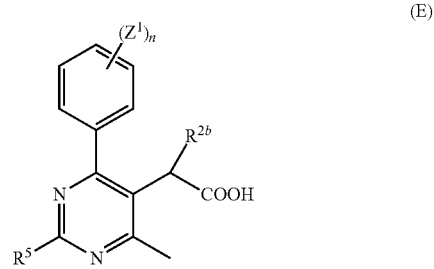

(E)

wherein each of $R^{2b}$, $R^5$ and $Z^1$ are as in formula (A) and the embodiments described herein and n is selected from 0, 1, 2, 3, 4 and 5.

In another embodiment, the compounds of the invention have a structure according to formula (F),

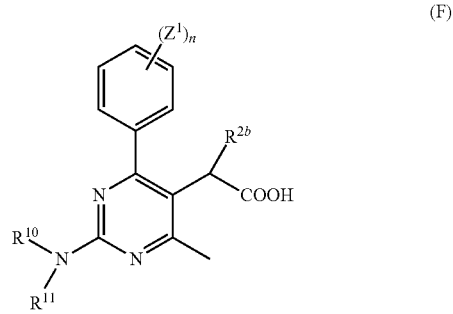

(F)

wherein each of $R^{2b}$, $R^{10}$, $R^{11}$ and $Z^1$ are as in formula (A) and the embodiments described herein and n is selected from 0, 1, 2, 3, 4 and 5.

Particular embodiments of this aspect are described in the claims and relate to subtypes of the compounds of the invention. In particular embodiments, the terms alkyl, alkenyl or alkynyl can be restricted to refer to their cyclic or acyclic subgroups (such as the acyclic alkyl or cycloalkyl for alkyl).

In a particular embodiment, the compounds of the present invention are selected from the list of:
- methyl 2-(2-(dimethylamino)-4-methyl-6-phenylpyrimidin-5-yl)pentanoate
- 2-(2-(dimethylamino)-4-methyl-6-phenylpyrimidin-5-yl)pentanoic acid
- methyl 2-(2-benzyl-4-methyl-6-phenylpyrimidin-5-yl)pentanoate
- 2-(2-benzyl-4-methyl-6-phenylpyrimidin-5-yl)pentanoic acid
- (E)-methyl 2-(4-methyl-6-phenyl-2-styrylpyrimidin-5-yl)pentanoate
- (E)-2-(4-methyl-6-phenyl-2-styrylpyrimidin-5-yl)pentanoic acid
- methyl 2-(4-methyl-2-phenethyl-6-phenylpyrimidin-5-yl)pentanoate
- 2-(4-methyl-2-phenethyl-6-phenylpyrimidin-5-yl)pentanoic acid
- methyl 2-(4-methyl-2,6-dip-tolylpyrimidin-5-yl)pentanoate
- 2-(4-methyl-2,6-dip-tolylpyrimidin-5-yl)pentanoic acid
- methyl 2-(2-(cyclohexyl(methyl)amino)-4-methyl-6-p-tolylpyrimidin-5-yl)pentanoate
- 2-(2-(cyclohexyl(methyl)amino)-4-methyl-6-p-tolylpyrimidin-5-yl)pentanoic acid
- methyl 2-(4-methyl-2-phenyl-6-p-tolylpyrimidin-5-yl)pentanoate
- 2-(4-methyl-2-phenyl-6-p-tolylpyrimidin-5-yl)pentanoic acid
- methyl 2-(2-(2-chlorophenyl)-4-methyl-6-phenylpyrimidin-5-yl)pentanoate
- 2-(2-(2-chlorophenyl)-4-methyl-6-phenylpyrimidin-5-yl)pentanoic acid
- methyl 2-(2-(2-chlorophenyl)-4-methyl-6-p-tolylpyrimidin-5-yl)pentanoate
- 2-(2-(2-chlorophenyl)-4-methyl-6-p-tolylpyrimidin-5-yl)pentanoic acid
- methyl 2-(4-methyl-6-phenyl-2-(piperidin-1-yl)pyrimidin-5-yl)pentanoate
- 2-(4-methyl-6-phenyl-2-(piperidin-1-yl)pyrimidin-5-yl)pentanoic acid
- methyl 2-(4-methyl-2-(piperidin-1-yl)-6-p-tolylpyrimidin-5-yl)pentanoate
- 2-(4-methyl-2-(piperidin-1-yl)-6-p-tolylpyrimidin-5-yl)pentanoic acid
- methyl 2-(4-methyl-2,6-diphenylpyrimidin-5-yl)pentanoate
- 2-(4-methyl-2,6-diphenylpyrimidin-5-yl)pentanoic acid
- methyl 2-(4-(3-hydroxyphenyl)-6-methyl-2-phenylpyrimidin-5-yl)pentanoate
- 2-(4-(3-hydroxyphenyl)-6-methyl-2-phenylpyrimidin-5-yl)pentanoic acid
- methyl 2-(4-methyl-2-morpholino-6-p-tolylpyrimidin-5-yl)pentanoate
- 2-(4-methyl-2-morpholino-6-p-tolylpyrimidin-5-yl)pentanoic acid
- methyl 2-(4-methyl-2-(pyrrolidin-1-yl)-6-p-tolylpyrimidin-5-yl)pentanoate
- 2-(4-methyl-2-(pyrrolidin-1-yl)-6-p-tolylpyrimidin-5-yl)pentanoic acid
- methyl 2-(4-methyl-2-(4-methylpiperazin-1-yl)-6-p-tolylpyrimidin-5-yl)pentanoate
- 2-(4-methyl-2-(4-methylpiperazin-1-yl)-6-p-tolylpyrimidin-5-yl)pentanoic acid
- methyl 2-(2-(3,5-dimethylpiperidin-1-yl)-4-methyl-6-p-tolylpyrimidin-5-yl)pentanoate
- 2-(2-(3,5-dimethylpiperidin-1-yl)-4-methyl-6-p-tolylpyrimidin-5-yl)pentanoic acid
- methyl 2-(2-(azepan-1-yl)-4-methyl-6-p-tolylpyrimidin-5-yl)pentanoate
- 2-(2-(azepan-1-yl)-4-methyl-6-p-tolylpyrimidin-5-yl)pentanoic acid.

The compounds of the invention optionally are bound covalently to an insoluble matrix and used for affinity chromatography (separations, depending on the nature of the groups of the compounds, for example compounds with pendant aryl are useful in hydrophobic affinity separations.

The compounds of the invention are employed for the treatment or prophylaxis of viral infections, more particularly retroviral infections, in particular HIV infections. When using one or more compounds of the invention and of the formulae as defined herein:
- the compound(s) may be administered to the animal or mammal (including a human) to be treated by any means well known in the art, i.e. orally, intranasally, subcutaneously, intramuscularly, intradermally, intravenously, intra-arterially, parenterally or by catheterization.
- the therapeutically effective amount of the preparation of the compound(s), especially for the treatment of viral infections in humans and other mammals, preferably is a retroviral replication inhibiting amount of the formulae as defined herein and corresponds to an amount which ensures a plasma level of between 1 μg/ml and 100 mg/ml, optionally of 10 mg/ml.

The present invention further relates to a method for preventing or treating a viral infections in a subject or patient by administering to the patient in need thereof a therapeutically effective amount of the pyrimidines of the present invention. The therapeutically effective amount of the compound(s), especially for the treatment of viral infections in humans and other mammals, preferably is a retroviral replication inhibiting amount. The suitable dosage is usually in the range of 0.001 mg to 60 mg, optionally 0.01 mg to 10 mg, optionally 0.1mg to 1 mg per day per kg bodyweight for humans. Depending upon the pathologic condition to be treated and the patient's condition, the said effective amount may be divided into several sub-units per day or may be administered at more than one day intervals.

As is conventional in the art, the evaluation of a synergistic effect in a drug combination may be made by analyzing the quantification of the interactions between individual drugs, using the median effect principle described by Chou et al. in *Adv. Enzyme Reg.* (1984) 22:27. Briefly, this principle states that interactions (synergism, additivity, antagonism) between two drugs can be quantified using the combination index (hereinafter referred as CI) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon CI<1, CI=1, or CI>1, respectively.

Synergistic activity of the pharmaceutical compositions or combined preparations of this invention against viral infection may also be readily determined by means of one or more tests such as, but not limited to, the isobologram method, as previously described by Elion et al. in *J. Biol. Chem.* (1954) 208:477-488 and by Baba et al. in *Antimicrob. Agents Chemother.* (1984) 25:515-517, using $EC_{50}$ for calculating the fractional inhibitory concentration (hereinafter referred as FIC). When the minimum FIC index corresponding to the FIC of combined compounds (e.g., $FIC_x+FIC_y$) is equal to 1.0, the combination is said to be additive; when it is between 1.0 and 0.5, the combination is defined as subsynergistic, and when it is lower than 0.5, the combination is by defined as synergistic. When the minimum FIC index is between 1.0 and 2.0, the combination is defined as subantagonistic and, when it is higher than 2.0, the combination is defined as antagonistic.

This principle may be applied to a combination of different antiviral drugs of the invention or to a combination of the antiviral drugs of the invention with other drugs that exhibit anti-HIV activity.

The invention thus relates to a pharmaceutical composition or combined preparation having synergistic effects against a viral infection and containing:
Either:
A)
(a) a combination of two or more of the pyrimidine derivatives of the present invention, and
(b) optionally one or more pharmaceutical excipients or pharmaceutically acceptable carriers,
for simultaneous, separate or sequential use in the treatment or prevention of a retroviridae infection
or
B)
(c) one or more antiviral agents, and
(d) at least one of the pyrimidines derivatives of the present invention, and
(e) optionally one or more pharmaceutical excipients or pharmaceutically acceptable carriers,
for simultaneous, separate or sequential use in the treatment or prevention of a retroviridae infection.

Suitable antiviral agents for inclusion into the synergistic antiviral compositions or combined preparations of this invention include, for instance, tenofovir, azidothymidine (AZT), lamivudine (3TC), nevirapine, efavirenz, nelfinavir, saquinavir, ritonavir, amprenavir, enfuvirtide, raltegravir or elvitegravir.

The pharmaceutical composition or combined preparation with synergistic activity against viral infection according to this invention may contain the pyrimidines derivatives of the present invention over a broad content range depending on the contemplated use and the expected effect of the preparation. Generally, the content of the pyrimidines derivatives of the present invention of the combined preparation is within the range of 0.1 to 99.9% by weight, preferably from 1 to 99% by weight, more preferably from 5 to 95% by weight.

According to a particular embodiment of the invention, the compounds of the invention may be employed in combination with other therapeutic agents for the treatment or prophylaxis of retroviral infections, more preferably HIV. The invention therefore relates to the use of a composition comprising:
(a) one or more compounds of the formulae herein, and
(b) one or more retroviral enzyme inhibitors as biologically active agents in respective proportions such as to provide a synergistic effect against a viral infection, particularly a retroviral infection in a mammal, for instance in the form of a combined preparation for simultaneous, separate or sequential use in viral infection therapy, such as of HIV.

More generally, the invention relates to the compounds of formulae (A), (A1), (B), (B1), (C), (C1), (C2), (D), (D1), (D2), (D3), (E), (E1), (E2), (E3), (F), (F1), (F2), (F3), (G1), (H1), (H2), (H3), (J1), (J2), (J3) and embodiments thereof being useful as agents having biological activity (particularly antiviral activity) or as diagnostic agents. Any of the uses mentioned with respect to the present invention may be restricted to a non-medical use, a non-therapeutic use, a non-diagnostic use, or exclusively an in vitro use, or a use related to cells remote from an animal.

Those of skill in the art will also recognize that the compounds of the invention may exist in many different protonation states, depending on, among other things, the pH of their environment. While the structural formulae provided herein depict the compounds in only one of several possible protonation states, it will be understood that these structures are illustrative only, and that the invention is not limited to any particular protonation state—any and all protonated forms of the compounds are intended to fall within the scope of the invention.

The term "pharmaceutically acceptable salts" as used herein means the therapeutically active non-toxic salt forms which the compounds of formulae herein are able to form. Therefore, the compounds of this invention optionally comprise salts of the compounds herein, especially pharmaceutically acceptable non-toxic salts containing, for example, $Na^+$, $Li^+$, $K^+$, $Ca^{2+}$ and $Mg^{2+}$. Such salts may include those derived by combination of appropriate cations such as alkali and alkaline earth metal ions or ammonium and quaternary amino ions with an acid anion moiety, typically a carboxylic acid. The compounds of the invention may bear multiple positive or negative charges. The net charge of the compounds of the invention may be either positive or negative. Any associated counter ions are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion. Moreover, as the compounds can exist in a variety of different forms, the invention is intended to encompass not only forms of the compounds that are in association with counter ions (e.g., dry salts), but also forms that are not in association with counter ions (e.g., aqueous or organic solutions). Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound. In addition, salts may be formed from acid addition of certain organic and inorganic acids to basic centers, typically amines, or to acidic groups. Examples of such appropriate acids include, for instance, inorganic acids such as hydrohalogen acids, e.g. hydrochloric or hydrobromic acid, sulfuric acid, nitric acid, phosphoric acid and the like; or organic acids such as, for example, acetic, propanoic, hydroxyacetic, 2-hydroxypropanoic, 2-oxopropanoic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclohexanesulfamic, salicylic (i.e. 2-hydroxybenzoic), p-aminosalicylic and the like. Furthermore, this term also includes the solvates which the compounds of formulae herein as well as their salts are able to form, such as for example hydrates, alcoholates and the like. Finally, it is to be understood that the compositions herein comprise compounds of the invention in their unionized, as well as zwitterionic form, and combinations with stoichiometric amounts of water as in hydrates.

Also included within the scope of this invention are the salts of the parental compounds with one or more amino acids, especially the naturally-occurring amino acids found as protein components. The amino acid typically is one bearing a side chain with a basic or acidic group, e.g., lysine, arginine or glutamic acid, or a neutral group such as glycine, serine, threonine, alanine, isoleucine, or leucine.

The compounds of the invention also include physiologically acceptable salts thereof. Examples of physiologically acceptable salts of the compounds of the invention include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound containing a hydroxy group include the anion of said compound in combination with a suitable cation such as $Na^+$ and $NX_4^+$ (wherein X typically is independently selected from H or a $C_1$-$C_4$ alkyl group). However, salts of acids or bases which are not physiologically acceptable may also find use, for example, in the preparation or purification of a physiologically acceptable compound. All salts, whether or not derived from a physiologically acceptable acid or base, are within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

The term "isomers" as used herein means all possible isomeric forms, including tautomeric and stereochemical forms, which the compounds of formulae herein may possess, but not including position isomers. Typically, the structures shown herein exemplify only one tautomeric or resonance form of the compounds, but the corresponding alternative configurations are contemplated as well. Unless otherwise stated, the chemical designation of compounds denotes the mixture of all possible stereochemically isomeric forms, said mixtures containing all diastereomers and enantiomers (since the compounds of formulae herein may have at least one chiral center) of the basic molecular structure, as well as the stereochemically pure or enriched compounds. More particularly, stereogenic centers may have either the R- or S-configuration, and multiple bonds may have either cis- or trans-configuration.

Pure isomeric forms of the said compounds are defined as isomers substantially free of other enantiomeric or diastereomeric forms of the same basic molecular structure. In particular, the term "stereoisomerically pure" or "chirally pure" relates to compounds having a stereoisomeric excess of at least about 80% (i.e. at least 90% of one isomer and at most 10% of the other possible isomers), preferably at least 90%, more preferably at least 94% and most preferably at least 97%. The terms "enantiomerically pure" and "diastereomerically pure" should be understood in a similar way, having regard to the enantiomeric excess, respectively the diastereomeric excess, of the mixture in question.

Separation of stereoisomers is accomplished by standard methods known to those in the art. One enantiomer of a compound of the invention can be separated substantially free of its opposing enantiomer by a method such as formation of diastereomers using optically active resolving agents ("Stereochemistry of Carbon Compounds," (1962) by E. L. Eliel, McGraw Hill; Lochmuller, C. H., (1975) J. Chromatogr., 113:(3) 283-302). Separation of isomers in a mixture can be accomplished by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure enantiomers, or (3) enantiomers can be separated directly under chiral conditions. Under method (1), diastereomeric salts can be formed by reaction of enantiomerically pure chiral bases such as brucine, quinine, ephedrine, strychnine, a-methyl-b-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts. Alternatively, by method (2), the substrate to be resolved may be reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester or Mosher ester, a-methoxy-a-(trifluoromethyl)phenyl acetate (Jacob III. (1982) J. Org. Chem. 47:4165), of the racemic mixture, and analyzing the NMR spectrum for the presence of the two atropisomeric diastereomers. Stable diastereomers can be separated and isolated by normal- and reverse-phase chromatography following methods for separation of atropisomeric naphthyl-isoquinolines (Hoye, T., WO 96/15111). Under method (3), a racemic mixture of two asymmetric enantiomers is separated by chromatography using a chiral stationary phase. Suitable chiral stationary phases are, for example, polysaccharides, in particular cellulose or amylose derivatives. Commercially available polysaccharide based chiral stationary phases are ChiralCel™ CA, OA, OB5, OC5, OD, OF, OG, OJ and OK, and Chiralpak™ AD, AS, OP(+) and OT(+). Appropriate eluents or mobile phases for use in combination with said polysaccharide chiral stationary phases are hexane and the like, modified with an alcohol such as ethanol, isopropanol and the like. ("Chiral Liquid Chromatography" (1989) W. J. Lough, Ed. Chapman and Hall, New York; Okamoto, (1990) "Optical resolution of dihydropyridine enantiomers by High-performance liquid chromatography using phenylcarbamates of polysaccharides as a chiral stationary phase", J. of Chromatogr. 513:375-378).

The terms cis and trans are used herein in accordance with Chemical Abstracts nomenclature and include reference to the position of the substituents on a ring moiety. The absolute stereochemical configuration of the compounds of formula (1) may easily be determined by those skilled in the art while using well-known methods such as, for example, X-ray diffraction.

The compounds of the invention may be formulated with conventional carriers and excipients, which will be selected in accordance with standard practice. Tablets will contain excipients, glidants, fillers, binders and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkylmethylcellulose, stearic acid and the like.

Subsequently, the term "pharmaceutically acceptable carrier" as used herein means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders.

Suitable pharmaceutical carriers for use in the said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents may also be prepared by micronisation, for instance in view to obtain them in the form of microspheres usually having a diameter of about 1 to 10 gm, namely for the manufacture of microcapsules for controlled or sustained release of the active ingredients.

Suitable surface-active agents, also known as emulgent or emulsifier, to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable from coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcoholamine salts of dodecylbenzene sulphonic acid or dibutyl-naphthalenesulphonic acid or a naphthalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidyl-choline, dipalmitoylphosphatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol -polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, particularly halides, having 4 hydrocarbon radicals optionally substituted with halo, phenyl, substituted phenyl or hydroxy; for instance quaternary ammonium salts containing as N-substituent at least one C8C22 alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbucw', 2 d ed. (Hanser Verlag, Vienna, 1981) and "Encyclopaedia of Surfactants, (Chemical Publishing Co., New York, 1981).

Compounds of the invention and their physiologically acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

While it is possible for the active ingredients to be administered alone, it is preferable to present them as pharmaceutical formulations. The formulations, both for veterinary and for human use, of the present invention comprise at least one active ingredient, as above described, together with one or more pharmaceutically acceptable carriers therefore and optionally other. therapeutic ingredients. The carrier(s) optimally are "acceptable" in the sense of being compatible with the other ingredients of the formulation and not deleterious to the recipient thereof. The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein. For infections of the eye or other external tissues e.g. mouth and skin, the formulations are optionally applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Optionally, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

The choice of suitable oils or fats for the formulation is based on achieving the desired cosmetic properties, since the solubility of the active compound in most oils likely to be used in pharmaceutical emulsion formulations is very low. Thus the cream should optionally be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is optionally present in such formulations in a concentration of 0.5 to 20%, advantageously 0.5 to 10% particularly about 1.5% w/w. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate. Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

Compounds of the invention can be used to provide controlled release pharmaceutical formulations containing as active ingredient one or more compounds of the invention ("controlled release formulations") in which the release of the active ingredient can be controlled and regulated to allow less frequency dosing or to improve the pharmacokinetic or toxicity profile of a given invention compound. Controlled release formulations adapted for oral administration in which discrete units comprising one or more compounds of the invention can be prepared according to conventional methods.

Additional ingredients may be included in order to control the duration of action of the active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulphate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition may require protective coatings. Pharmaceutical forms suitable for injectionable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof.

In view of the fact that, when several active ingredients are used in combination, they do not necessarily bring out their joint therapeutic effect directly at the same time in the mammal to be treated, the corresponding composition may also be in the form of a medical kit or package containing the two ingredients in separate but adjacent repositories or compartments. In the latter context, each active ingredient may therefore be formulated in a way suitable for an administration route different from that of the other ingredient, e.g. one of them may be in the form of an oral or parenteral formulation whereas the other is in the form of an ampoule for intravenous injection or an aerosol.

Another embodiment of this invention relates to various precursor or "prodrug" forms of the compounds of the present invention. It may be desirable to formulate the compounds of the present invention in the form of a chemical species which itself is not significantly biologically-active, but which when delivered to the animal will undergo a chemical reaction catalyzed by the normal function of the body of the animal, inter alia, enzymes present in the stomach or in blood serum, said chemical reaction having the effect of releasing a compound as defined herein. The term "pro-drug" thus relates to these species which are converted in vivo into the active pharmaceutical ingredient.

The prodrugs of the present invention can have any form suitable to the formulator, for example, esters are non-limiting common pro-drug forms. In the present case, however, the pro-drug may necessarily exist in a form wherein a covalent bond is cleaved by the action of an enzyme present at the target locus. For example, a C—C covalent bond may be selectively cleaved by one or more enzymes at said target locus and, therefore, a pro-drug in a form other than an easily hydrolysable precursor, inter alia an ester, an amide, and the like, may be used. The counterpart of the active pharmaceutical ingredient in the pro-drug can have different structures such as an amino acid or peptide structure, alkyl chains, sugar moieties and others as known in the art.

For the purpose of the present invention the term "therapeutically suitable prodrug" is defined herein as "a compound modified in such a way as to be transformed in vivo to the therapeutically active form, whether by way of a single or by multiple biological transformations, when in contact with the tissues of the animal, mammal or human to which the pro-drug has been administered, and without undue toxicity, irritation, or allergic response, and achieving the intended therapeutic outcome".

More specifically the term "prodrug", as used herein, relates to an inactive or significantly less active derivative of a compound such as represented by the structural formula (I), which undergoes spontaneous or enzymatic transformation within the body in order to release the pharmacologically active form of the compound. For a comprehensive review, reference is made to Rautio J. et al. ("Prodrugs: design and clinical applications" Nature Reviews Drug Discovery, 2008, doi: 10.1038/nrd2468).

The compounds of the invention can be prepared while using a series of chemical reactions well known to those skilled in the art, altogether making up the process for preparing said compounds and exemplified further. The processes described further are only meant as examples and by no means are meant to limit the scope of the present invention.

The compounds of the present invention can be prepared according to the following general procedures depicted hereunder:

Scheme 1:

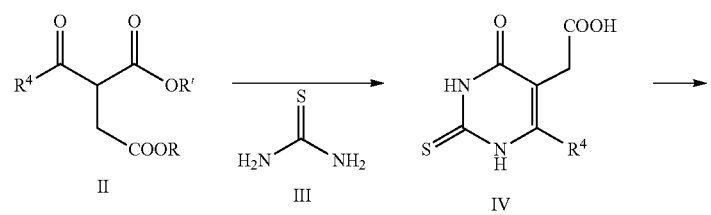

-continued

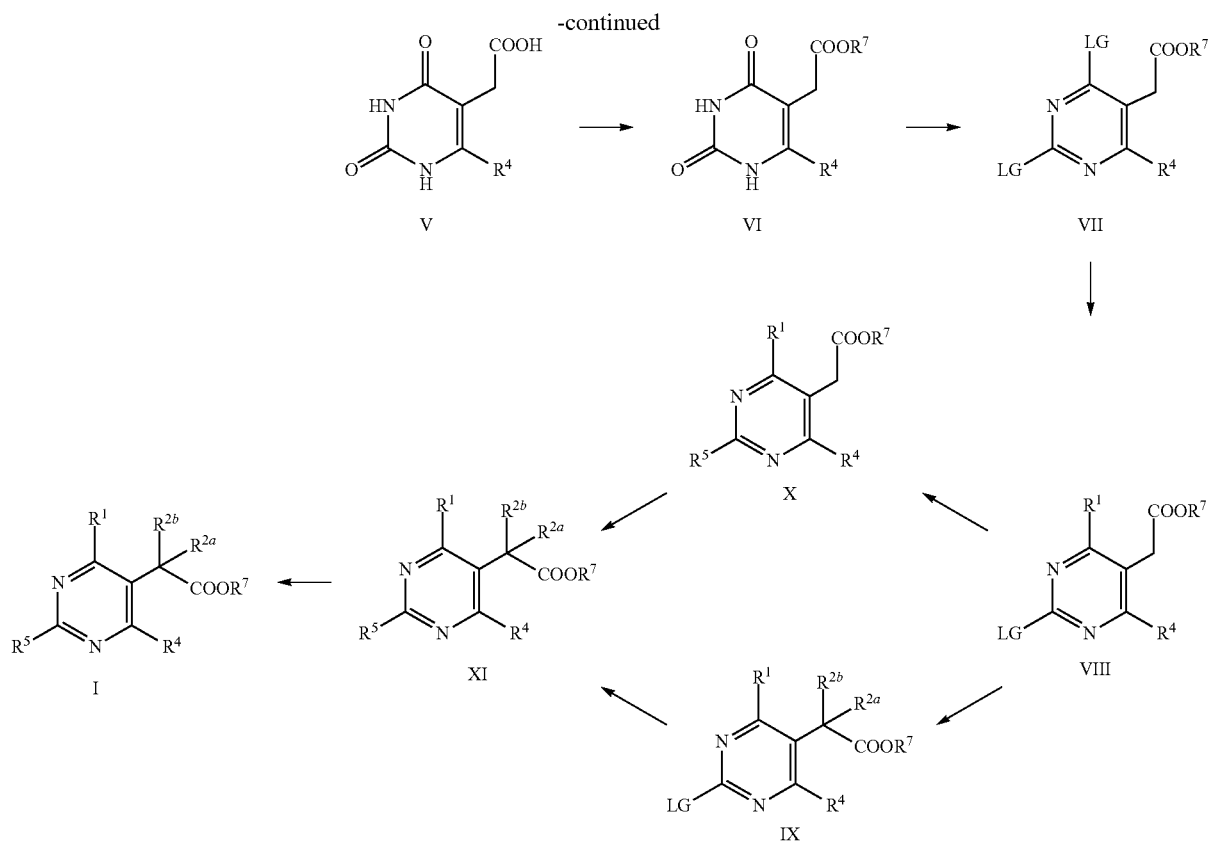

Scheme 1: all $R^1$, $R^{2a}$, $R^{2b}$, $R^4$, $R^5$, $R^7$ and LG are as described for the compounds of the present invention and its embodiments and formulae.

Condensation of intermediates II (commercially available or synthesized by procedures known to the skilled in the art or as set forth in the examples below) wherein R and R' is independently an ester protecting group (e.g., methyl, ethyl, tert-butyl, benzy and the like) with thiourea III in the presence of a strong base (e.g., sodium methoxide, sodium ethoxide, KOH and the like) in a polar protic solvent (e.g., methanol, ethanol, . . . ) or in a polar aprotic solvent (e.g., DMF, DMAc, NMP and the like) at a temperature raising from 60° C. to 100° C., provides the desired intermediates of formula IV. More detailed synthetic procedures can be found in the following reference (Journal fuer Praktische Chemie, 2000, 342 (5), 504-507). Intermediates of formula IV are then converted into intermediates of formula V by treatment in an aqueous acidic medium (most preferably using choloracetic acid) at high temperature (most preferably 100° C.). Intermediates of formula V are converted in intermediates of formula VI by standard procedures known to the skilled in the art and wherein R is an ester protecting group (e.g., methyl, ethyl, tert-butyl, benzy and the like). The intermediates VI are then converted in intermediates of formula VII by procedures known to the skilled in the art or as set forth in the examples below, and wherein LG is a leaving group only selected from halogen. Coupling of intermediates VII with a suitable $R^1$ precursor by procedures known to the skilled in the art or as set forth in examples below, provides intermediates of formula VIII which can be converted in intermediates of formula X, using a suitable $R^5$ precursor by procedures known to the skilled in the art or as set forth in examples below. Alkylation of intermediates X, by procedures known to the skilled in the art or as set forth in the examples below, provides compounds of formula XI, which are hydrolyzed to the desired compounds of formula I. Alternatively, alkylation of intermediates VIII, by procedures known to the skilled in the art or as set forth in the examples below, provides intermediates of formula IX. Condensation of intermediates IX with a suitable $R^5$ precursor by procedures known to the skilled in the art or as set forth in examples below, provides also compounds of general formula XI.

Alternatively, compounds of general formula I can also be prepared as outlined in Scheme 2 below.

Scheme 2:

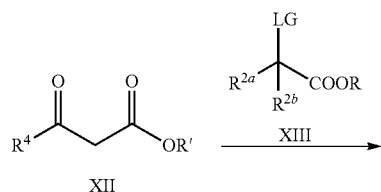

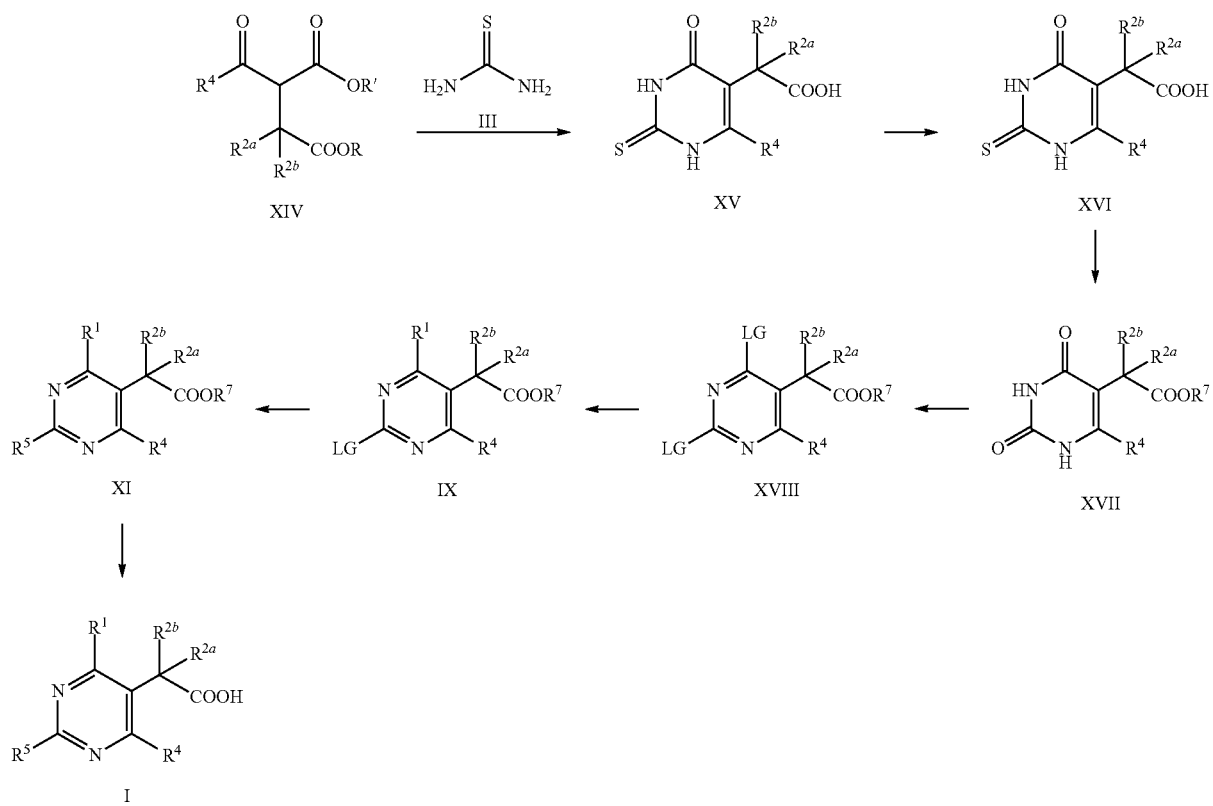

Scheme 2: all $R^1$, $R^{2a}$, $R^{2b}$, $R^4$, $R^5$, $R^7$ and LG are as described for the compounds of the present invention and its embodiments and formulae.

Condensation of intermediates of formula XII (commercially available or synthesized by procedures known to the skilled in the art), wherein R' is an ester protecting group (e.g., methyl, ethyl, tert-butyl, benzy and the like), with intermediates of formula XIII (commercially available or synthesized by procedures known to the skilled in the art), wherein R is an ester protecting group (e.g., methyl, ethyl, tert-butyl, benzy and the like), provides intermediates of formula XIV which is condensed with thiourea III in the presence of a strong base (e.g., sodium methoxide, sodium ethoxide, KOH and the like) in a polar protic solvent (e.g., methanol, ethanol and the like) or in a polar aprotic solvent (e.g., DMF, DMAc, NMP and the like) at a temperature raising from 60° C. to 100° C., to furnish the desired intermediates of formula XV. Intermediates of formula XV are then converted into intermediates of formula XVI by treatment in an aqueous acidic medium (most preferably using choloracetic acid) at high temperature (most preferably 100° C.). Intermediates of formula XVI are converted in intermediates of formula XVII by standard procedures known to the skilled in the art and wherein R is an ester protecting group (e.g., methyl, ethyl, tert-butyl, benzy and the like). The intermediates XVII are then converted in intermediates of formula XVIII by procedures known to the skilled in the art or as set forth in the examples below, and wherein LG is a leaving group only selected from halogen. Coupling of intermediates XVIII with a suitable $R^1$ precursor by procedures known to the skilled in the art or as set forth in examples below, provides intermediates of formula IX which can ultimately be converted into compounds XI and I as described here above (Scheme 1).

Alternatively, compounds of general formula I can also be prepared as outlined in Scheme 3 below.

Scheme 3:

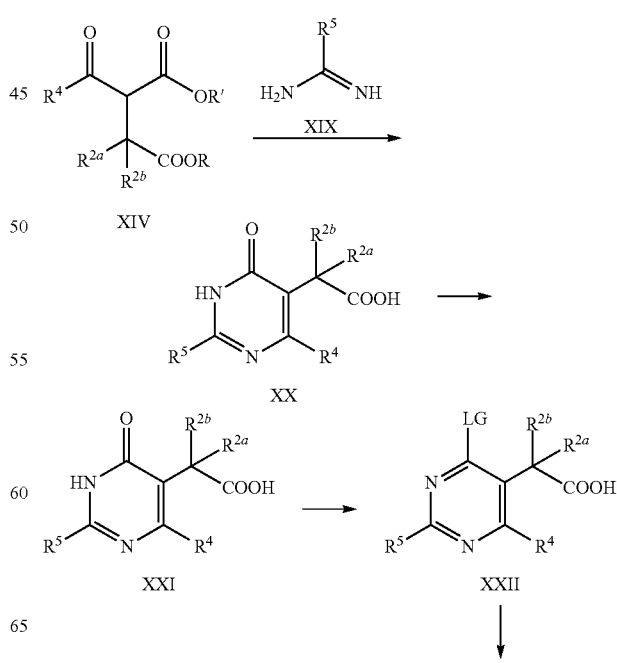

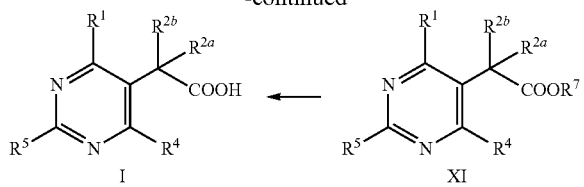

Scheme 3: all $R^1$, $R^{2a}$, $R^{2b}$, $R^4$, $R^5$, $R^7$ and LG are as described for the compounds of the present invention and its embodiments and formulae.

Condensation of intermediates of formula XIV, wherein R and R' is independently an ester protecting group (e.g., methyl, ethyl, tert-butyl, benzy and the like), with intermediates of formula XIX (commercially available or synthesized by procedures known to the skilled in the art), in the presence of a strong base (e.g., sodium methoxide, sodium ethoxide, KOH and the like) in a polar protic solvent (e.g., methanol, ethanol and the like) or in a polar aprotic solvent (e.g., DMF, DMAc, NMP and the like) at a temperature raising from 60° C. to 100° C., provides intermediates of formula XX, which are converted in intermediates of formula XXI by standard procedures known to the skilled in the art and wherein R is an ester protecting group (e.g., methyl, ethyl, tert-butyl, benzy and the like). The intermediates XXI are then converted in intermediates of formula XXII by procedures known to the skilled in the art or as set forth in the examples below, and wherein LG is a leaving group only selected from halogen. Coupling of intermediates XXII with a suitable $R^1$ precursor by procedures known to the skilled in the art or as set forth in examples below, provides intermediates of formula XI which can be hydrolyzed in compounds of formula I as described here above (Scheme 1).

Condensation of intermediates of formula II, wherein R and R' is independently an ester protecting group (e.g., methyl, ethyl, tert-butyl, benzy and the like), with intermediates of formula XIX (commercially available or synthesized by procedures known to the skilled in the art), in the presence of a strong base (e.g., sodium methoxide, sodium ethoxide, KOH and the like) in a polar protic solvent (e.g., methanol, ethanol and the like) or in a polar aprotic solvent (e.g., DMF, DMAc, NMP and the like) at a temperature raising from 60° C. to 100° C., provides intermediates of formula XXIII, which are converted in intermediates of formula XXIV by standard procedures known to the skilled in the art and wherein R is an ester protecting group (e.g., methyl, ethyl, tert-butyl, benzy and the like). The intermediates XXIV are then converted in intermediates of formula XXV by procedures known to the skilled in the art or as set forth in the examples below, and wherein LG is a leaving group only selected from halogen. Coupling of intermediates XXV with a suitable $R^1$ precursor by procedures known to the skilled in the art or as set forth in examples below, provides intermediates of formula X which can ultimately be converted in compounds XI and I as described here above (Scheme 1). Alternatively, alkylation of intermediates XXV, by procedures known to the skilled in the art or as set forth in the examples below, provides compounds of formula XXII, which can ultimately be converted in compounds XI and I as described here above (Scheme 3).

Scheme 4:

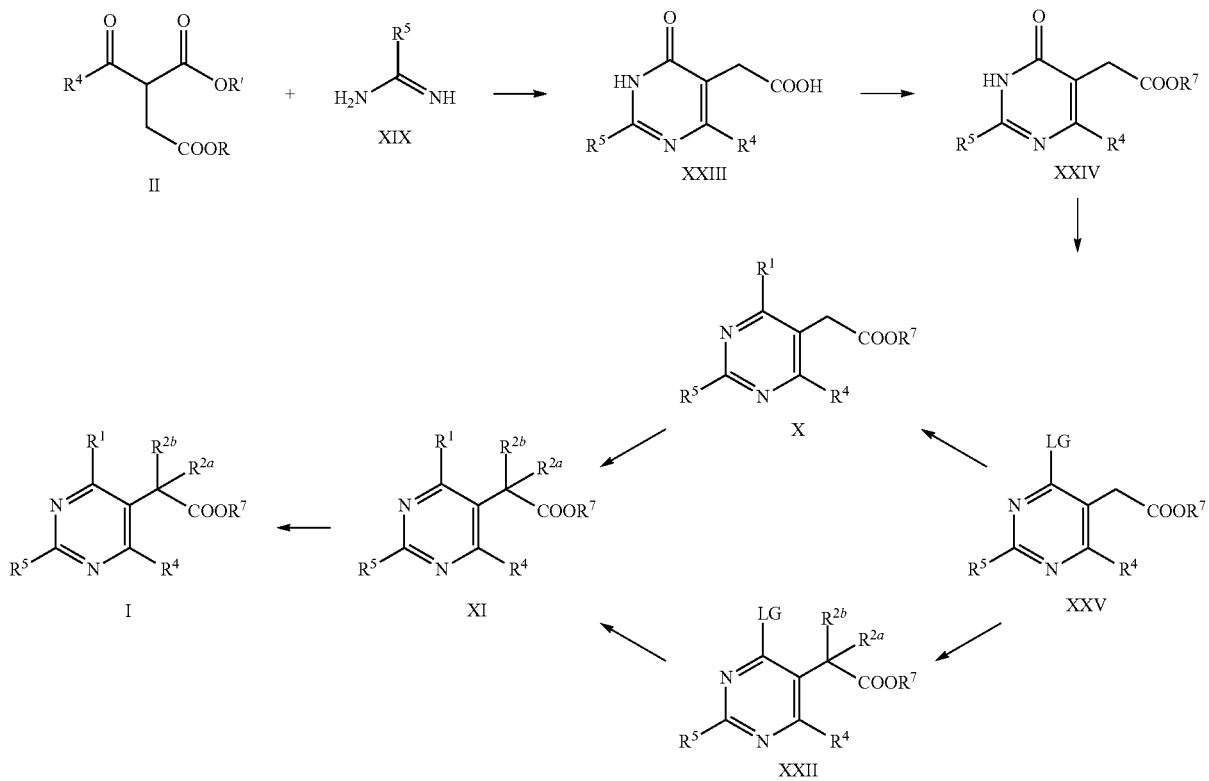

Scheme 4: all $R^1$, $R^{2a}$, $R^{2b}$, $R^4$, $R^5$, $R^7$ and LG are as described for the compounds of the present invention and its embodiments and formulae.

Scheme 5

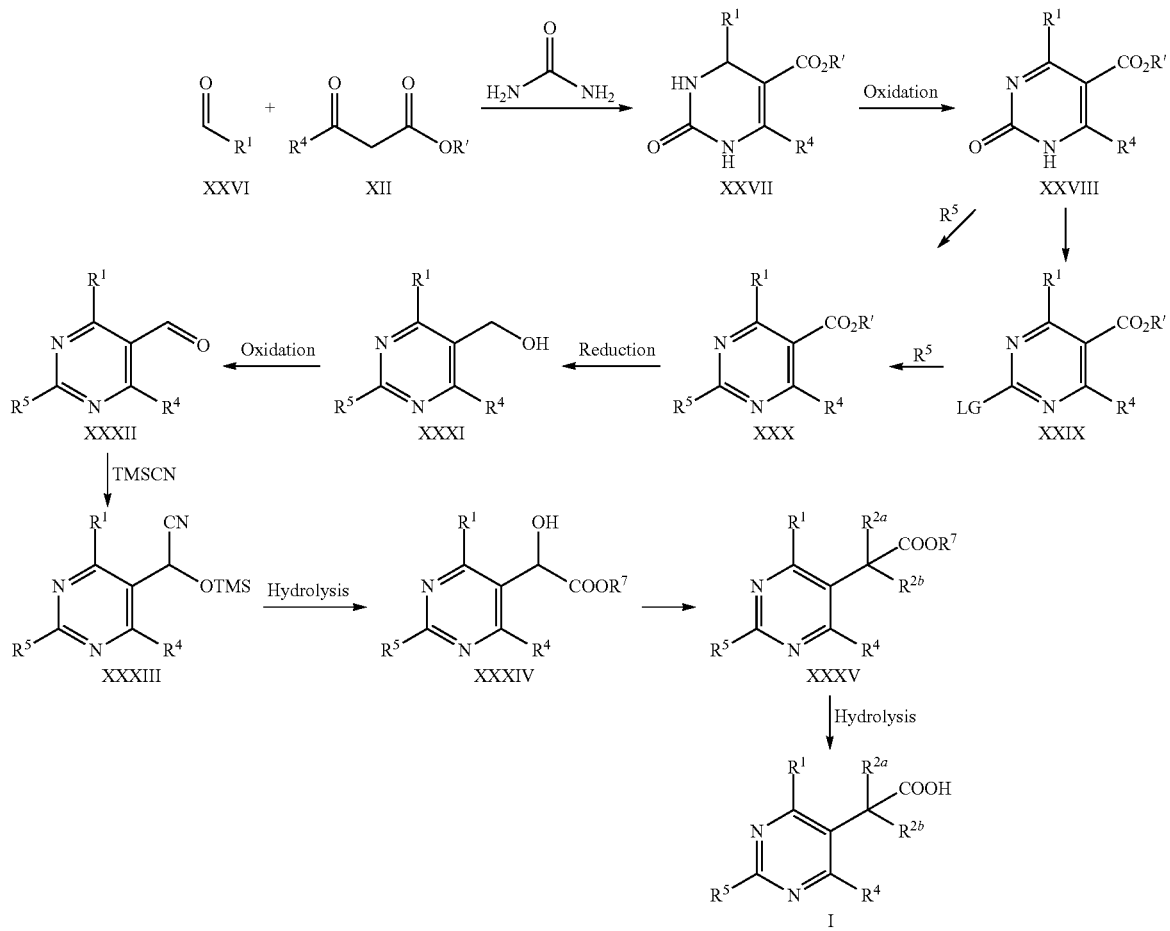

Scheme 5: all $R^1$, $R^{2a}$, $R^{2b}$, $R^4$, $R^5$, $R^7$ and LG are as described for the compounds of the present invention and its embodiments and formulae.

In a first step, derivatives of formula XII (commercially available or prepared by procedures known to the skilled in the art), wherein R' is an ester protecting group (e.g., methyl, ethyl and the like) can be reacted with aldehydes of formula XXVI (or protected aldehydes such as an acetal) and urea in the presence of a metal derived salt (e.g., boron trifluoride, iron chloride, barium chloride, copper chloride, copper nitrate . . . ) and an acid (e.g., acetic acid, lactic acid, lewis acid, . . . ) in a polar protic solvent (e.g., methanol, ethanol, acetic acid, water, . . . ) or in a polar aprotic solvent (e.g., tetrahydrofuran, DMF, dimethylacetamide and the like) at a temperature raising from 60° C. to 130° C., to yield the expected 2-oxo-1,2,3,4-tetrahydropyrimidine-5-carboxyester derivatives of formula XXVII. More detailed information can be found in the following references (Phosphorus, Sulfur and Silicon and the Related Elements (2010), 185(2), 325-329 or Synthesis (2004), (8), 1239-1242). Intermediates of formula XXVII are then oxidized in intermediates of formula XXVIII by procedures known to the skilled in the art or as set forth in the examples below. Compounds of general formula XXX may be obtained by reacting intermediates of formula XXVIII with a suitable $R^5$ precursor according to the general peptide coupling procedures known to the skilled in the art. Alternatively, intermediates XXVIII can be converted into intermediates XXIX by procedures known to the skilled in the art or as set forth in the examples below, and wherein LG is a leaving group only selected from halogen. It is known for the skilled in the art that when LG is a chlorine atom, this atom can be exchange for a more reactive halogen atom (bromine or iodine) using substitution reactions which are known to the skilled in the art or as set forth in the examples below. Coupling of intermediates XXIX with a suitable $R^5$ precursor by procedures known to the skilled in the art (amination, Suzuki coupling, Negishi coupling, Stille coupling and the like) provides intermediates of formula XXX. Intermediates of formula XXX can then be converted into intermediates of formula XXXI by reduction of the ester functionality using standard reducing agents (LiAlH$_4$ and most preferably DIBAL) in polar aprotic solvents (e.g., THF, dichloromethane and the like) at a temperature ranging from −78° C. to 0° C. (most preferably −78° C.). Intermediates of formula XXXI are then oxidized in intermediates of formula XXXII by procedures known to the skilled in the art or as set forth in the examples below. Addition of trimethylsilylcyanide on intermediates XXXII in the presence of zinc iodide provides intermediates of formula XXXIII, which are immediately hydrolyzed under acidic conditions to provide intermediates of formula XXXIV. Intermediates of general formula XXXV may be obtained by reacting intermediates of formula XXXIV with suitable R²ᵃLG and or R²ᵇLG, in the presence of a strong base (e.g., NaH, LiHMDS, DBU and the like) in a polar aprotic solvent (e.g., THF, dichloromethane, DMF and the like) at a temperature raising from −78° C. to 80° C. (most preferably −78° C.). Alternatively, compounds of general formula XXXV may also be obtained in acidic conditions by reacting an alkene (e.g., ethylene, isoprene and the like) or an alkene precursor (e.g., isopropyl acetate, tert-butyl acetate, and the like). In another embodiment, the hydroxyl function of intermediates XXXIV may also be contion reactions which are known to the skilled in the art. This keto function can then be subjected to reductive amination conditions to provide the desired compounds of formula XXXV. Additionally, this keto function may undergo a nucleophilic attack using suitable precursors of $R^{2a}$ and or $R^{2b}$ following reactions which are known to the skilled in the art to provide the desired compounds of formula XXXV. Compounds XXXV can be converted in the desired compounds of formula I using standard hydrolysis conditions.

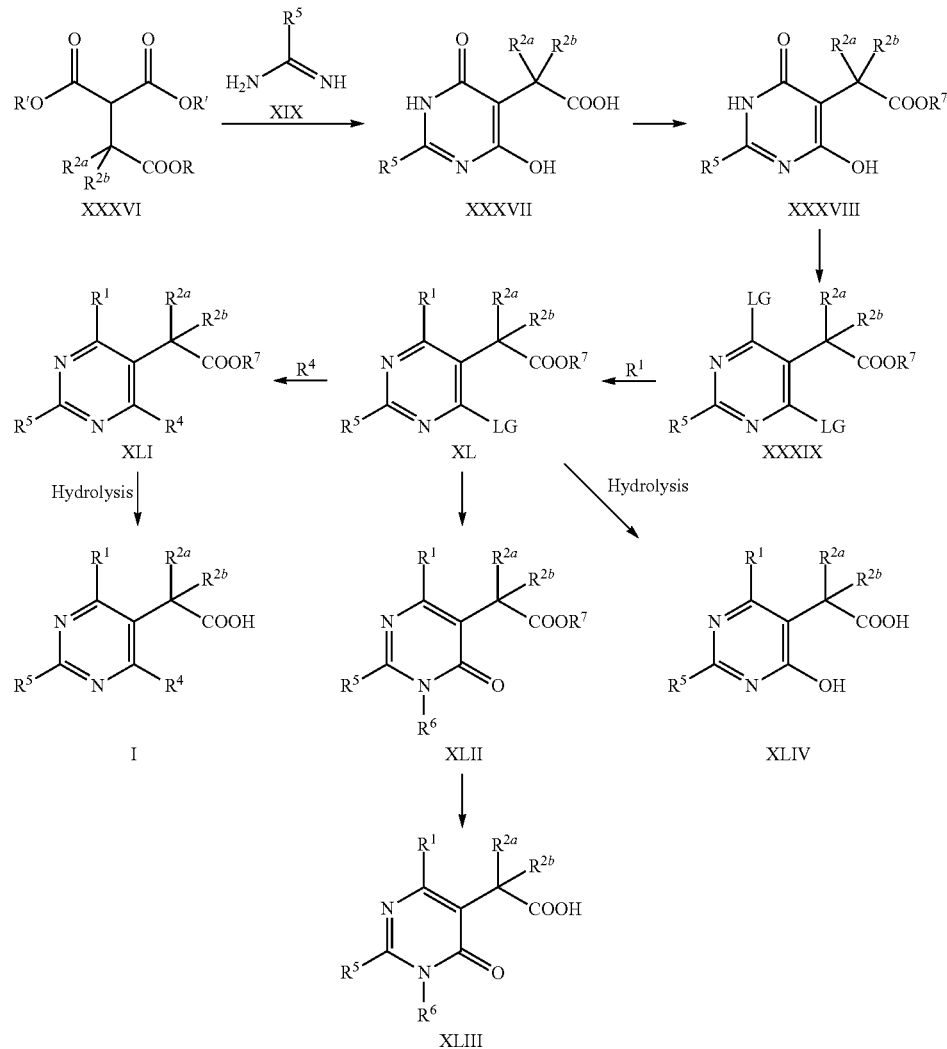

Scheme 6: all $R^1$, $R^{2a}$, $R^{2b}$, $R^4$, $R^5$, $R^7$ and LG are as described for the compounds of the present invention and its embodiments and formulae.

verted into a leaving group selected from sulfonates (e.g., mesylate, tosylate and the like) or from halogen atom (e.g., chlorine, bromine, iodine) following procedures known to the skilled in the art or as set forth in the examples below. This leaving group can then undergo a nucleophilic substitution using suitable precursors of $R^{2a}$ and or $R^{2b}$ following reactions which are known to the skilled in the art to provide the desired compounds of formula XXXV. Alternatively, the hydroxyl function of intermediates XXXIV may also be converted into a keto (C═O) function following standard oxida- In a first step, derivatives of formula XXXVI (commercially available or synthesized by procedures known to the skilled in the art), wherein R and R' is an ester protecting group (e.g., methyl, ethyl and the like) can be reacted with an amidine of formula XIX and a strong base (e.g., sodium methoxide, potassium methoxide, sodium ethoxide, . . . ) in a polar protic solvent (e.g., methanol, ethanol, . . . ) at a temperature raising from 60° C. to 100° C., to yield the expected pyrimidine derivative of formula XXXVII which can be converted in intermediates of formula XXXVIII by procedures known to the skilled in the art or as set forth in the examples below. Intermediates of general formula XXXVIII can be converted into intermediates XXXIX by procedures known to the skilled in the art or as set forth in the examples below, and wherein LG is a leaving group only selected from halogen. It is known for the skilled in the art that when LG is a chlorine atom, this atom can be exchange for a more reactive halogen atom (bromine or iodine) using substitution reactions which are known to the skilled in the art or as set forth in the examples below. Coupling of intermediates XXIX with a suitable $R^1$ precursor by procedures known to the skilled in the art (amination, Suzuki coupling, Negishi coupling, Stille coupling and the like) provides compounds of formula XL, which can be converted in the desired compounds of formula XLIV using standard hydrolysis conditions. Alternatively, intermediates XL can be reacted with a suitable $R^4$ precursor by procedures known to the skilled in the art (amination, Suzuki coupling, Negishi coupling, Stille coupling and the like) to provide compounds of formula XLI, which can be converted in the desired compounds of formula I using standard hydrolysis conditions. In another way, intermediates of formula XL can be hydrolyzed under acidic conditions and immediately reacted with suitable $R^6LG$ derivatives in the presence of a strong base (e.g., NaH, LiHMDS, DBU and the like) in a polar aprotic solvent (e.g., THF, dichloromethane, DMF and the like) at a temperature raising from −78° C. to 80° C. Compound of general formula XLII can be converted in the desired compounds of formula XLIII using standard hydrolysis conditions.

For the synthesis of compounds of the invention wherein $R^3$ is different from —COOH or —COOR, the same procedure can be used as provided in schemes 1, 2, 3 and 4 whereby the compounds of formula II is replaced by $R^4C(O)CH(CO_2R')CH_2R^3$, compound of formula XIV is replaced by $R^4C(O)CH(CO_2R')CR^{2a}R^{2b}R^3$ (commercially available or synthesized by procedures known to the skilled in the art).

EXAMPLES

The following examples are provided for the purpose of illustrating the present invention and by no means should be interpreted to limit the scope of the present invention.

Part A represent the preparation of the compounds (intermediates and final compounds) whereas Part B describes the (antiviral) activity of the pyrimidine derivatives of the invention.

TABLE 1A

Structures of example compounds of the invention and their respective codes.

| Code | Structure | $R^1$ | $R^{2a}$ | $R^{2b}$ | $R^3$ | $R^4$ | $R^5$ |
|------|-----------|-------|----------|----------|-------|-------|-------|
| Cpd 1 | 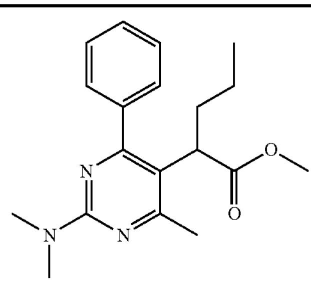 | phenyl | propyl | H | –C(O)O–Me | Me | –N(Me)– |
| Cpd 2 | 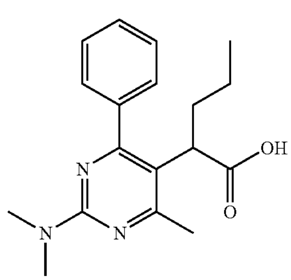 | phenyl | propyl | H | –C(O)OH | Me | –N(Me)– |
| Cpd 3 | 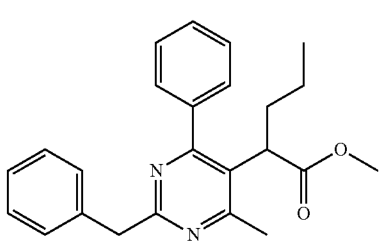 | phenyl | propyl | H | –C(O)O–Me | Me | –CH2–phenyl |

TABLE 1A-continued
Structures of example compounds of the invention and their respective codes.
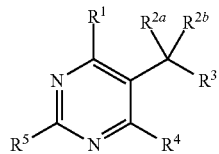
| Code | Structure | $R^1$ | $R^{2a}$ | $R^{2b}$ | $R^3$ | $R^4$ | $R^5$ |
|---|---|---|---|---|---|---|---|
| Cpd 4 | 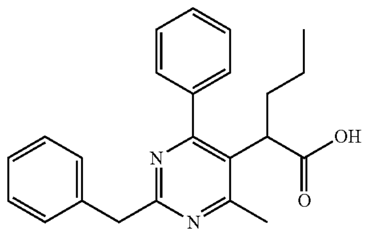 | phenyl | propyl | H | COOH | Me | benzyl |
| Cpd 5 | 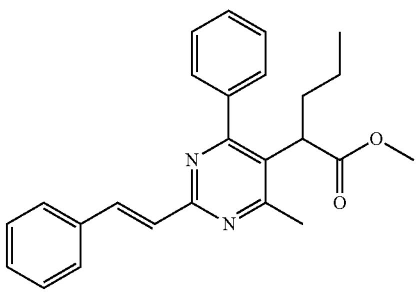 | phenyl | propyl | H | COOMe | Me | styryl |
| Cpd 6 | 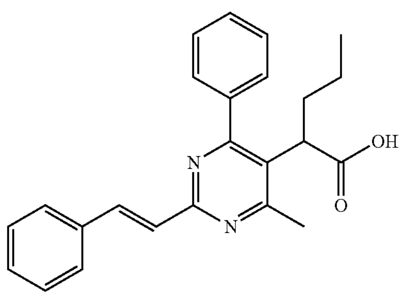 | phenyl | propyl | H | COOH | Me | styryl |
| Cpd 7 | 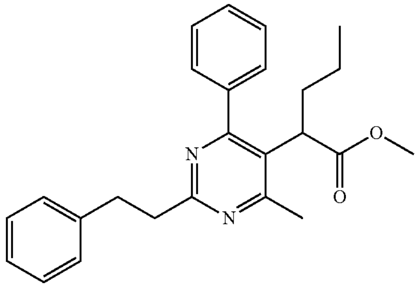 | phenyl | propyl | H | COOMe | Me | phenethyl |

TABLE 1A-continued

Structures of example compounds of the invention and their respective codes.

| Code | Structure | R¹ | R²ᵃ | R²ᵇ | R³ | R⁴ | R⁵ |
|---|---|---|---|---|---|---|---|
| Cpd 8 | 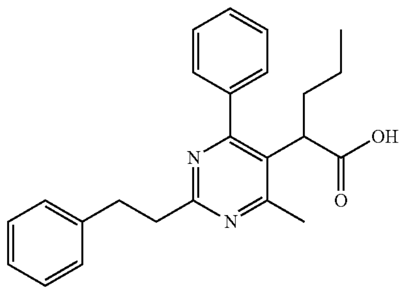 | phenyl | propyl | H | COOH | Me | phenethyl |
| Cpd 9 | 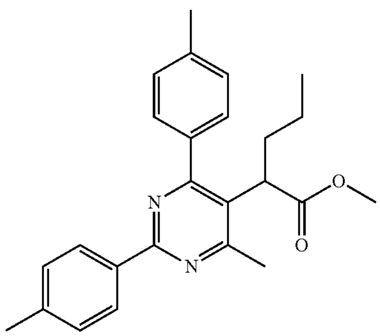 | 4-tolyl | propyl | H | COOMe | Me | 4-tolyl |
| Cpd 10 | 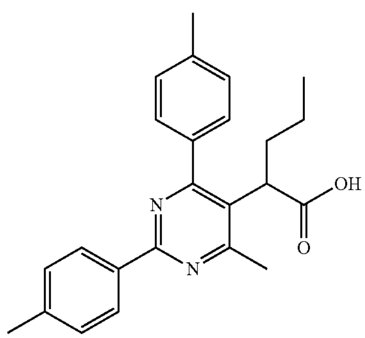 | 4-tolyl | propyl | H | COOH | Me | 4-tolyl |
| Cpd 11 | 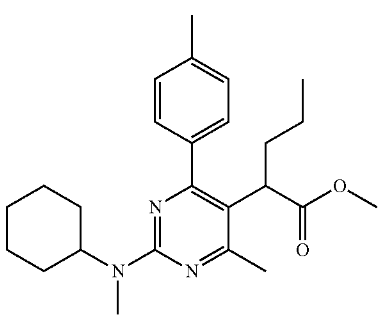 | 4-tolyl | propyl | H | COOMe | Me | N(cyclohexyl)(Me) |

TABLE 1A-continued

Structures of example compounds of the invention and their respective codes.

| Code | Structure | R¹ | R²ᵃ | R²ᵇ | R³ | R⁴ | R⁵ |
|---|---|---|---|---|---|---|---|
| Cpd 12 | 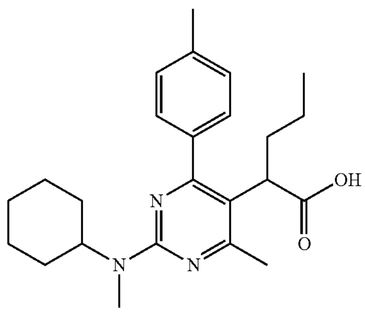 | 4-methylphenyl | propyl | H | -CH(COOH)- | Me | N(Me)(cyclohexyl) |
| Cpd 13 | 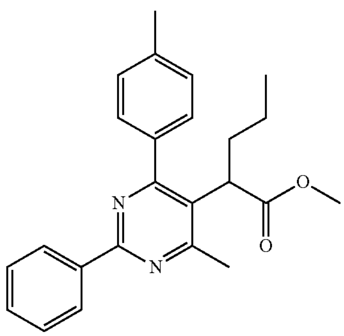 | 4-methylphenyl | propyl | H | -CH(COOMe)- | Me | phenyl |
| Cpd 14 | 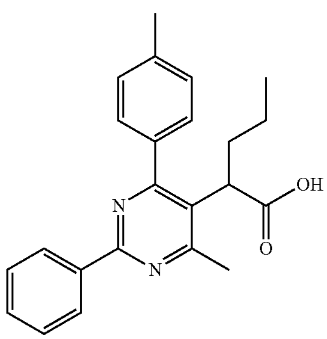 | 4-methylphenyl | propyl | H | -CH(COOH)- | Me | phenyl |
| Cpd 15 | 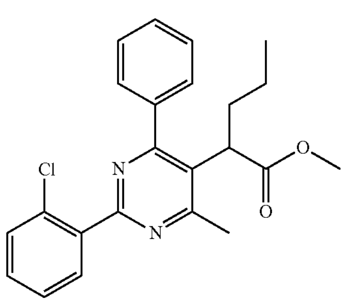 | phenyl | propyl | H | -CH(COOMe)- | Me | 2-chlorophenyl |

TABLE 1A-continued

Structures of example compounds of the invention and their respective codes.

| Code | Structure | R¹ | R²ᵃ | R²ᵇ | R³ | R⁴ | R⁵ |
|------|-----------|----|----|----|----|----|----|
| Cpd 16 | 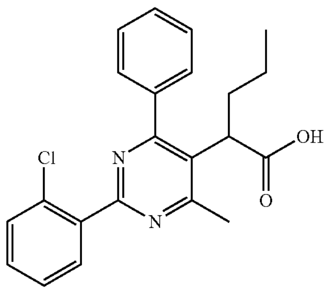 | phenyl | n-propyl | H | -CH(CO OH)- | Me | 2-chlorophenyl |
| Cpd 17 | 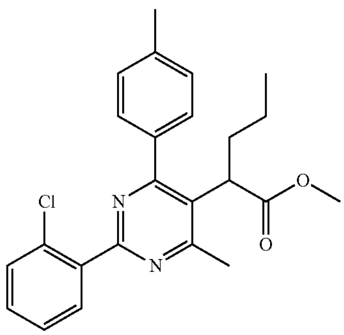 | 4-methylphenyl | n-propyl | H | -CH(C(O)OMe)- | Me | 2-chlorophenyl |
| Cpd 18 | 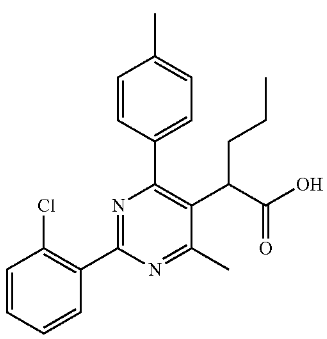 | 4-methylphenyl | n-propyl | H | -CH(CO OH)- | Me | 2-chlorophenyl |
| Cpd 19 | 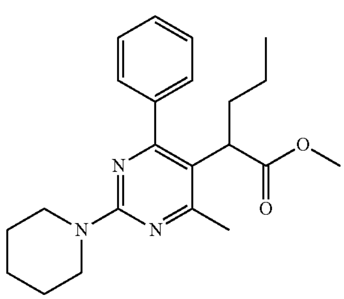 | phenyl | n-propyl | H | -CH(C(O)OMe)- | Me | piperidin-1-yl |

TABLE 1A-continued

Structures of example compounds of the invention and their respective codes.

| Code | Structure | R¹ | R²ᵃ | R²ᵇ | R³ | R⁴ | R⁵ |
|---|---|---|---|---|---|---|---|
| Cpd 20 | 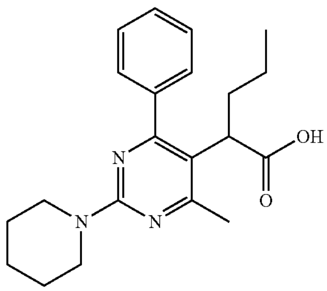 | phenyl | propyl | H | –CH(Me)–C(=O)OH | Me | piperidinyl |
| Cpd 21 | 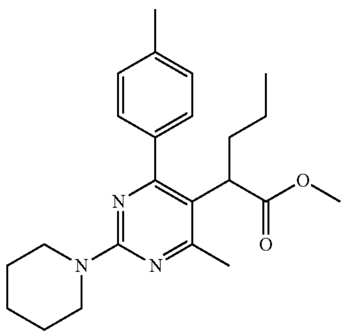 | p-tolyl | propyl | H | –CH(Me)–C(=O)OMe | Me | piperidinyl |
| Cpd 22 | 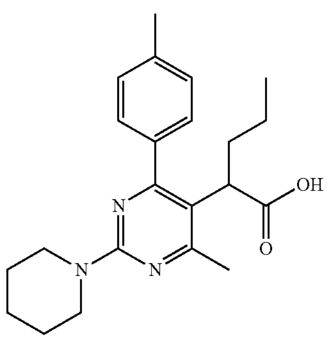 | p-tolyl | propyl | H | –CH(Me)–C(=O)OH | Me | piperidinyl |
| Cpd 23 | 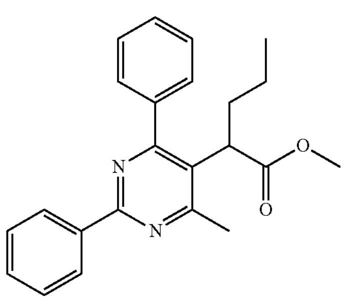 | phenyl | propyl | H | –CH(Me)–C(=O)OMe | Me | phenyl |

TABLE 1A-continued
Structures of example compounds of the invention and their respective codes.
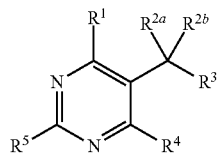
| Code | Structure | R¹ | R²ᵃ | R²ᵇ | R³ | R⁴ | R⁵ |
|---|---|---|---|---|---|---|---|
| Cpd 24 | 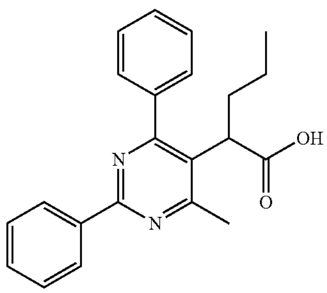 | phenyl | phenyl | H | -C(=O)OH | Me | phenyl |
| Cpd 25 | 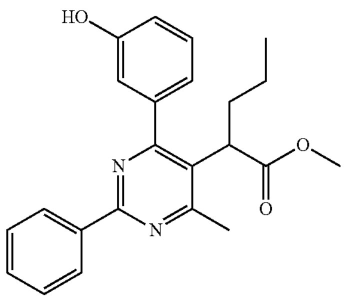 | 3-hydroxyphenyl | 3-hydroxyphenyl | H | -C(=O)OMe | Me | phenyl |
| Cpd 26 | 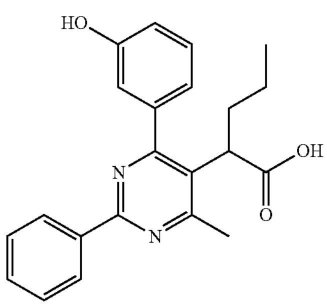 | 3-hydroxyphenyl | 3-hydroxyphenyl | H | -C(=O)OH | Me | phenyl |
| Cpd 27 | 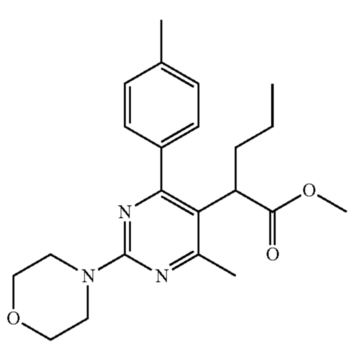 | 4-methylphenyl | 4-methylphenyl | H | -C(=O)OMe | Me | morpholinyl |

TABLE 1A-continued

Structures of example compounds of the invention and their respective codes.

| Code | Structure | R¹ | R²ᵃ | R²ᵇ | R³ | R⁴ | R⁵ |
|---|---|---|---|---|---|---|---|
| Cpd 28 | 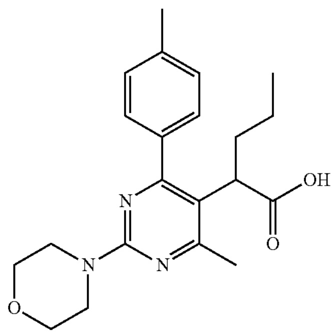 [SMILES: CCCC(C(=O)O)c1c(C)nc(N2CCOCC2)nc1-c1ccc(C)cc1] | p-tolyl | p-tolyl | propyl | H | -CH(CO₂H)- | Me, morpholinyl-CH- |
| Cpd 29 | 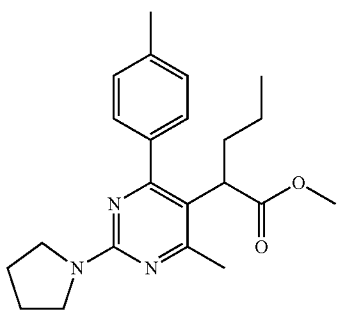 [SMILES: CCCC(C(=O)OC)c1c(C)nc(N2CCCC2)nc1-c1ccc(C)cc1] | p-tolyl | p-tolyl | propyl | H | -CH(CO₂Me)- | Me, pyrrolidinyl |
| Cpd 30 | 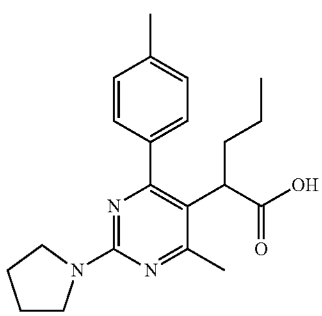 [SMILES: CCCC(C(=O)O)c1c(C)nc(N2CCCC2)nc1-c1ccc(C)cc1] | p-tolyl | p-tolyl | propyl | H | -CH(CO₂H)- | Me, pyrrolidinyl |
| Cpd 31 | 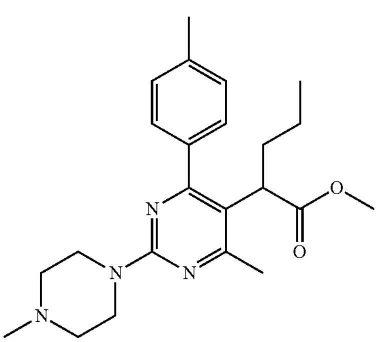 | p-tolyl | p-tolyl | propyl | H | -CH(CO₂Me)- | Me, 4-methylpiperazinyl |

TABLE 1A-continued
Structures of example compounds of the invention and their respective codes.
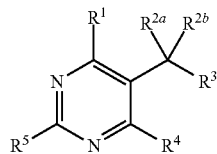
| Code | Structure | R¹ | R²ᵃ | R²ᵇ | R³ | R⁴ | R⁵ |
|---|---|---|---|---|---|---|---|
| Cpd 32 | 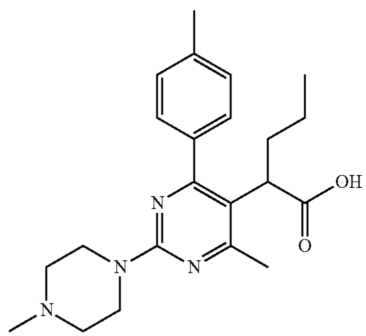 | | | | H | | Me |
| Cpd 33 | 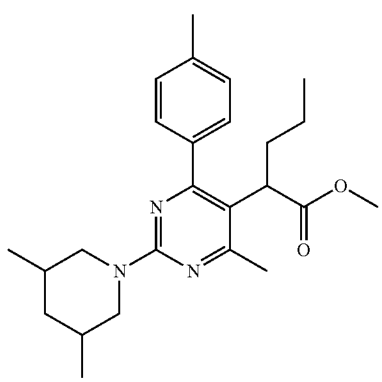 | | | | H | | Me |
| Cpd 34 | 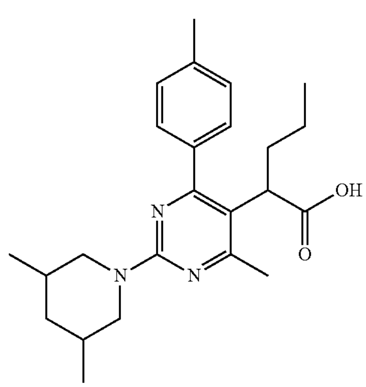 | | | | H | | Me |

TABLE 1A-continued

Structures of example compounds of the invention and their respective codes.

| Code | Structure | R¹ | R²ᵃ | R²ᵇ | R³ | R⁴ | R⁵ |
|---|---|---|---|---|---|---|---|
| Cpd 35 | | p-tolyl | p-tolyl | n-propyl | H | -C(=O)OMe | Me | azepan-1-yl |
| Cpd 36 | | p-tolyl | p-tolyl | n-propyl | H | -C(=O)OH | Me | azepan-1-yl |

TABLE 1B

Structures of example compounds of the invention and their respective codes.

| Code | Structure |
|---|---|
| Cpd 37 | 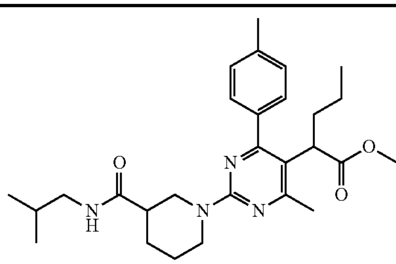 |
| Cpd 38 | 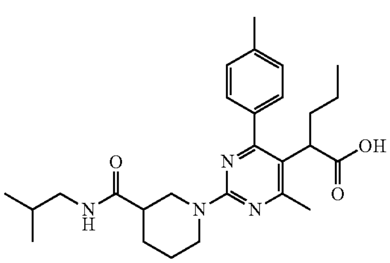 [SMILES: CCCC(C(=O)O)c1c(C)nc(N2CCCC(C(=O)NCC(C)C)C2)nc1-c1ccc(C)cc1] |

TABLE 1B-continued

Structures of example compounds of the invention and their respective codes.

| Code | Structure |
|---|---|
| Cpd 39 | 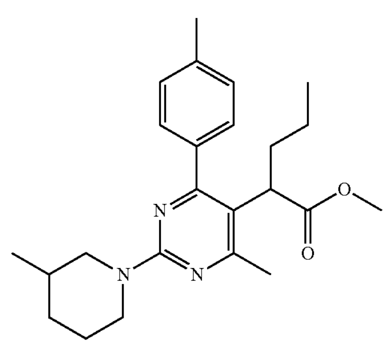 |

TABLE 1B-continued

Structures of example compounds of
the invention and their respective codes.

| Code | Structure |
| --- | --- |
| Cpd 40 | 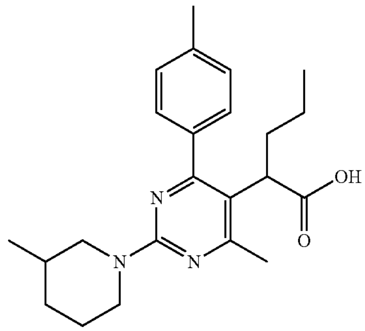 [SMILES: CCCC(C(=O)O)c1c(C)nc(N2CCCC(C)C2)nc1-c1ccc(C)cc1] |
| Cpd 41 | 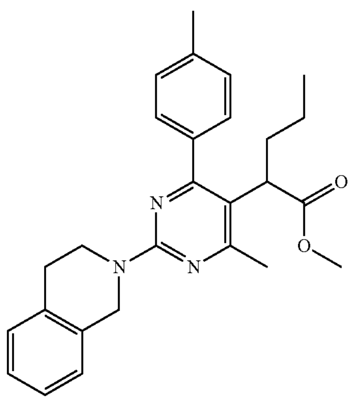 [SMILES: CCCC(C(=O)OC)c1c(C)nc(N2CCc3ccccc3C2)nc1-c1ccc(C)cc1] |
| Cpd 42 | 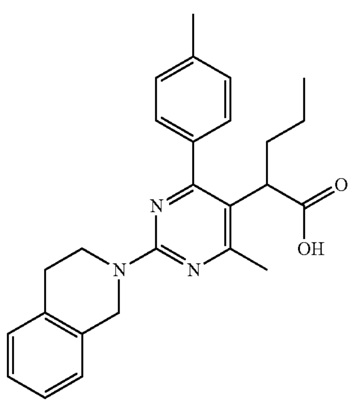 [SMILES: CCCC(C(=O)O)c1c(C)nc(N2CCc3ccccc3C2)nc1-c1ccc(C)cc1] |
| Cpd 43 | 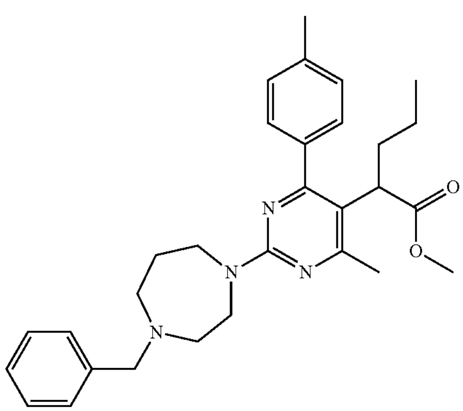 [SMILES: CCCC(C(=O)OC)c1c(C)nc(N2CCCN(Cc3ccccc3)CC2)nc1-c1ccc(C)cc1] |
| Cpd 44 | |
| Cpd 45 | |
| Cpd 46 | |
| Cpd 47 | |

TABLE 1B-continued

Structures of example compounds of the invention and their respective codes.

| Code | Structure |
|------|-----------|
| Cpd 48 | 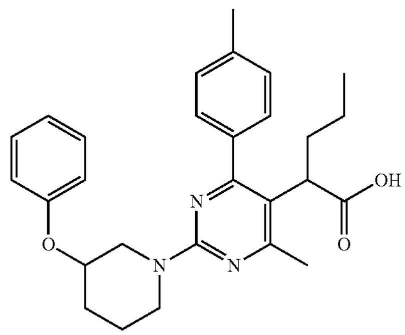 [SMILES: CCCC(C(=O)O)c1c(C)nc(N2CCCC(Oc3ccccc3)C2)nc1-c1ccc(C)cc1] |
| Cpd 49 | 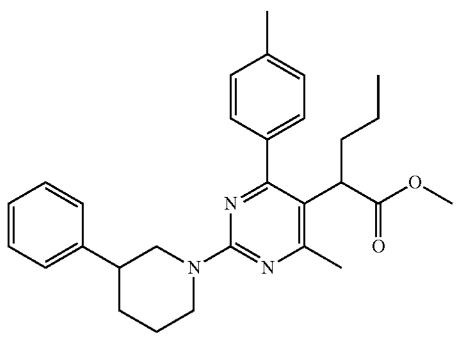 [SMILES: CCCC(C(=O)OC)c1c(C)nc(N2CCCC(c3ccccc3)C2)nc1-c1ccc(C)cc1] |
| Cpd 50 | 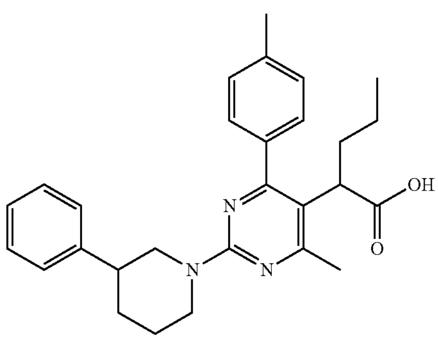 [SMILES: CCCC(C(=O)O)c1c(C)nc(N2CCCC(c3ccccc3)C2)nc1-c1ccc(C)cc1] |
| Cpd 51 | 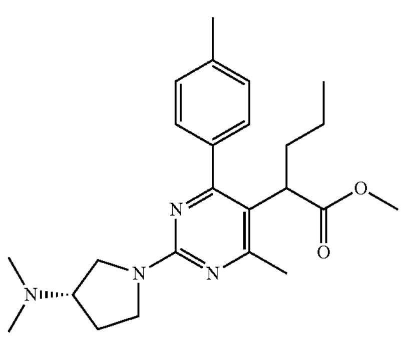 |
| Cpd 52 | |
| Cpd 53 | |
| Cpd 54 | |
| Cpd 55 | |

TABLE 1B-continued
Structures of example compounds of the invention and their respective codes.
| Code | Structure |
|------|-----------|
| Cpd 56 | 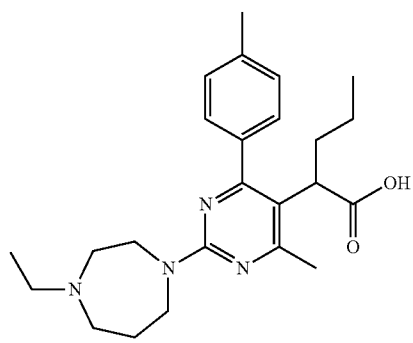 [SMILES: CCCC(C(=O)O)c1c(C)nc(N2CCCN(CC)CC2)nc1-c1ccc(C)cc1] |
| Cpd 57 | 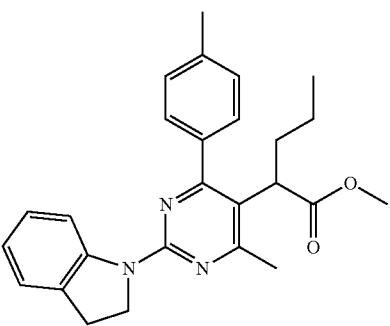 [SMILES: CCCC(C(=O)OC)c1c(C)nc(N2CCc3ccccc32)nc1-c1ccc(C)cc1] |
| Cpd 58 | 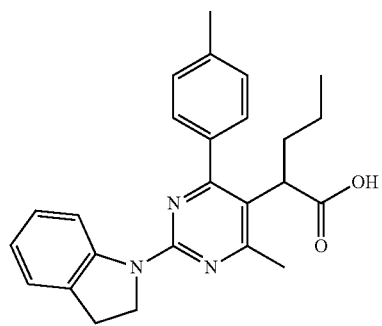 [SMILES: CCCC(C(=O)O)c1c(C)nc(N2CCc3ccccc32)nc1-c1ccc(C)cc1] |
| Cpd 59 | 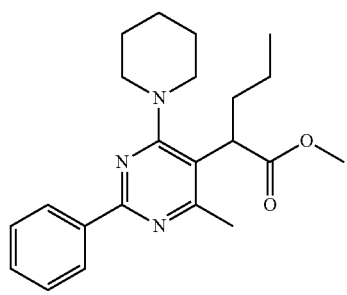 [SMILES: CCCC(C(=O)OC)c1c(C)nc(-c2ccccc2)nc1N1CCCCC1] |
TABLE 1B-continued
Structures of example compounds of the invention and their respective codes.
| Code | Structure |
|------|-----------|
| Cpd 60 | 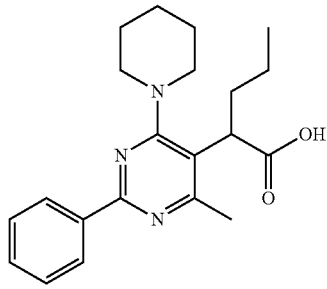 [SMILES: CCCC(C(=O)O)c1c(C)nc(-c2ccccc2)nc1N1CCCCC1] |
| Cpd 61 | 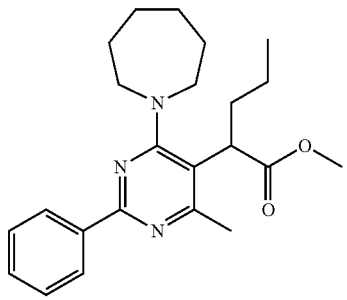 [SMILES: CCCC(C(=O)OC)c1c(C)nc(-c2ccccc2)nc1N1CCCCCC1] |
| Cpd 62 | 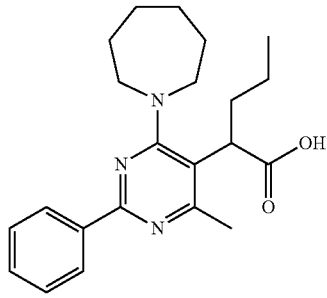 [SMILES: CCCC(C(=O)O)c1c(C)nc(-c2ccccc2)nc1N1CCCCCC1] |
| Cpd 63 | 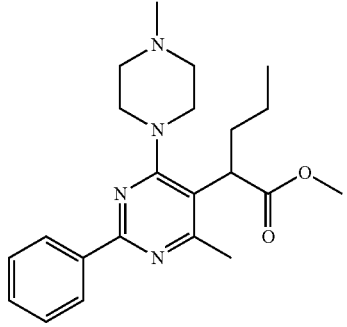 [SMILES: CCCC(C(=O)OC)c1c(C)nc(-c2ccccc2)nc1N1CCN(C)CC1] |

TABLE 1B-continued
Structures of example compounds of the invention and their respective codes.
| Code | Structure |
|---|---|
| Cpd 64 | 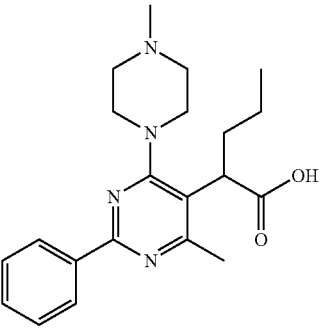 [SMILES: CCCC(C(=O)O)c1c(C)nc(-c2ccccc2)nc1N1CCN(C)CC1] |
| Cpd 65 | 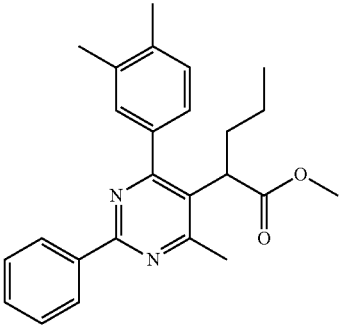 [SMILES: CCCC(C(=O)OC)c1c(C)nc(-c2ccccc2)nc1-c1ccc(C)c(C)c1] |
| Cpd 66 | 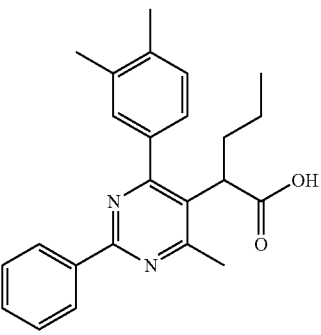 [SMILES: CCCC(C(=O)O)c1c(C)nc(-c2ccccc2)nc1-c1ccc(C)c(C)c1] |
| Cpd 67 | 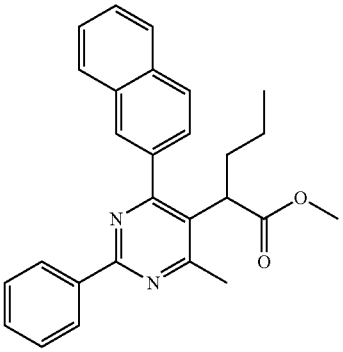 [SMILES: CCCC(C(=O)OC)c1c(C)nc(-c2ccccc2)nc1-c1ccc2ccccc2c1] |
| Cpd 68 | 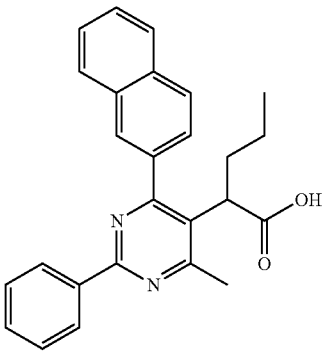 [SMILES: CCCC(C(=O)O)c1c(C)nc(-c2ccccc2)nc1-c1ccc2ccccc2c1] |
| Cpd 69 | 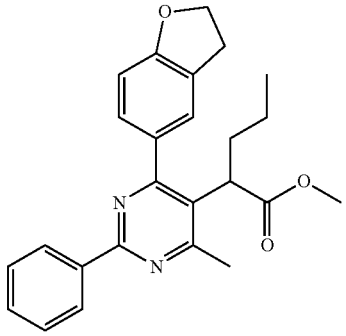 [SMILES: CCCC(C(=O)OC)c1c(C)nc(-c2ccccc2)nc1-c1ccc2c(c1)CCO2] |
| Cpd 70 | 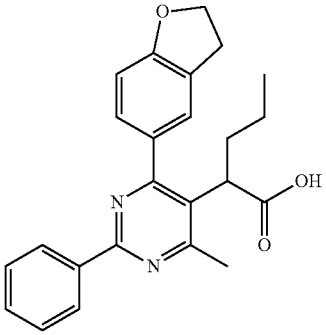 [SMILES: CCCC(C(=O)O)c1c(C)nc(-c2ccccc2)nc1-c1ccc2c(c1)CCO2] |
| Cpd 71 | 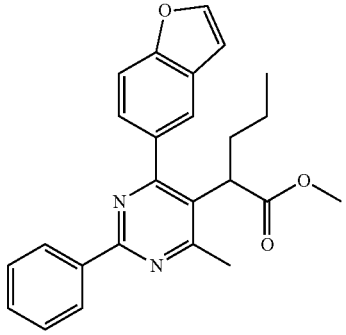 [SMILES: CCCC(C(=O)OC)c1c(C)nc(-c2ccccc2)nc1-c1ccc2occc2c1] |

TABLE 1B-continued

Structures of example compounds of the invention and their respective codes.

| Code | Structure |
|---|---|
| Cpd 72 | 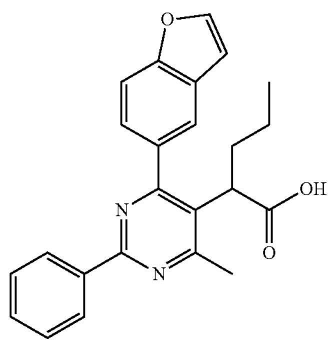 [SMILES: CCCC(C(=O)O)c1c(C)nc(-c2ccccc2)nc1-c1ccc2occc2c1] |
| Cpd 73 | 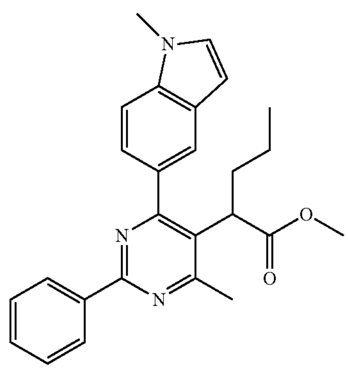 [SMILES: CCCC(C(=O)OC)c1c(C)nc(-c2ccccc2)nc1-c1ccc2c(ccn2C)c1] |
| Cpd 74 | 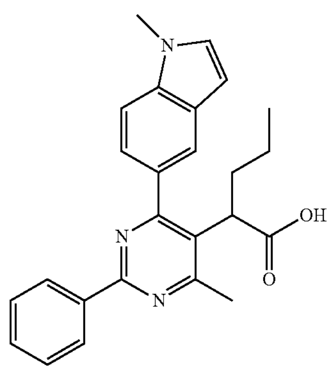 [SMILES: CCCC(C(=O)O)c1c(C)nc(-c2ccccc2)nc1-c1ccc2c(ccn2C)c1] |
| Cpd 75 | 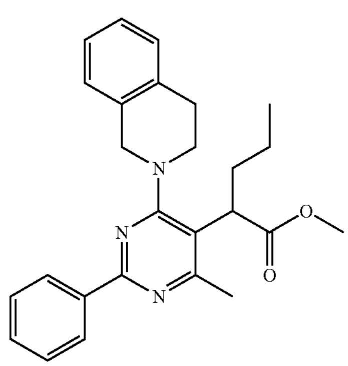 [SMILES: CCCC(C(=O)OC)c1c(C)nc(-c2ccccc2)nc1N1CCc2ccccc2C1] |
| Cpd 76 | |
| Cpd 77 | |
| Cpd 78 | |
| Cpd 79 | |

TABLE 1B-continued

Structures of example compounds of the invention and their respective codes.

| Code | Structure |
|------|-----------|
| Cpd 80 | 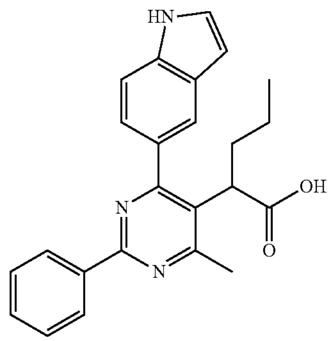 |
| Cpd 81 | 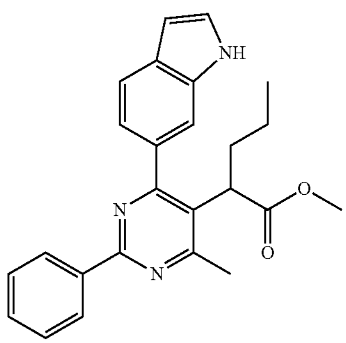 [SMILES: CCCC(C(=O)OC)c1c(C)nc(-c2ccccc2)nc1-c1ccc2cc[nH]c2c1] |
| Cpd 82 | 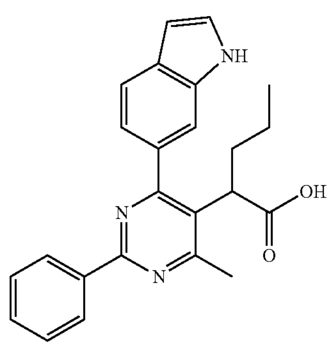 [SMILES: CCCC(C(=O)O)c1c(C)nc(-c2ccccc2)nc1-c1ccc2cc[nH]c2c1] |
| Cpd 83 | 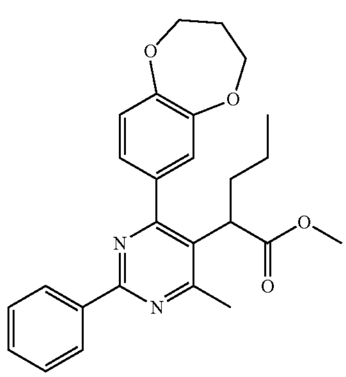 [SMILES: CCCC(C(=O)OC)c1c(C)nc(-c2ccccc2)nc1-c1ccc2c(c1)OCCCO2] |
| Cpd 84 | |
| Cpd 85 | |
| Cpd 86 | |
| Cpd 87 | |

TABLE 1B-continued
Structures of example compounds of
the invention and their respective codes.
| Code | Structure |
|---|---|
| Cpd 88 | 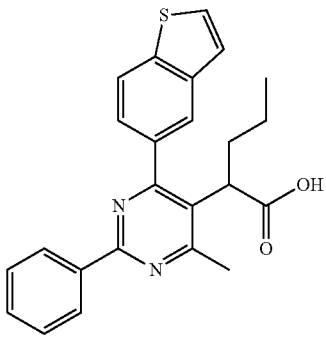 [SMILES: CCCC(C(=O)O)c1c(C)nc(-c2ccccc2)nc1-c1ccc2sccc2c1] |
| Cpd 89 | 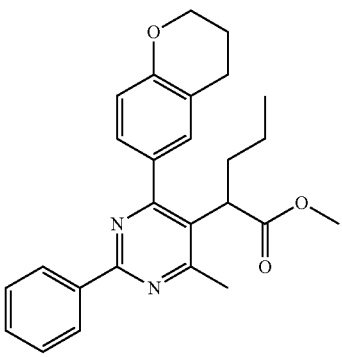 [SMILES: CCCC(C(=O)OC)c1c(C)nc(-c2ccccc2)nc1-c1ccc2c(c1)CCCO2] |
| Cpd 90 | 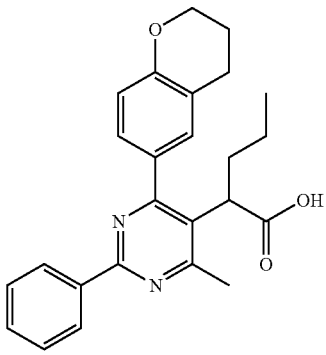 [SMILES: CCCC(C(=O)O)c1c(C)nc(-c2ccccc2)nc1-c1ccc2c(c1)CCCO2] |
| Cpd 91 | 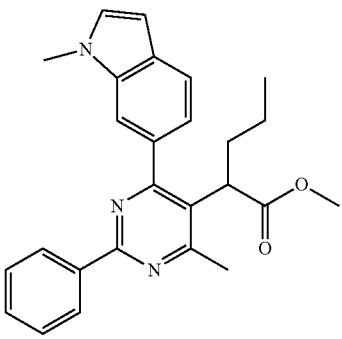 [SMILES: CCCC(C(=O)OC)c1c(C)nc(-c2ccccc2)nc1-c1ccc2ccn(C)c2c1] |
TABLE 1B-continued
Structures of example compounds of
the invention and their respective codes.
| Code | Structure |
|---|---|
| Cpd 92 | 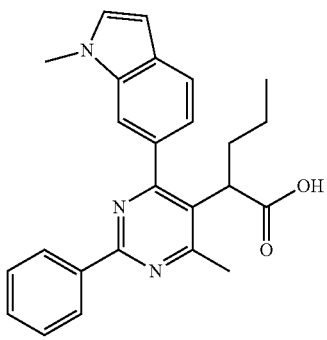 [SMILES: CCCC(C(=O)O)c1c(C)nc(-c2ccccc2)nc1-c1ccc2ccn(C)c2c1] |
| Cpd 93 | 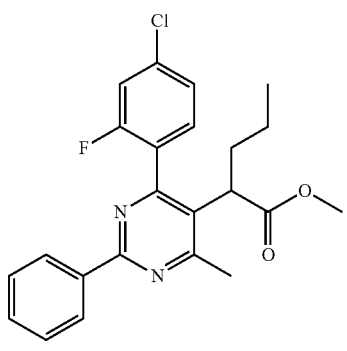 [SMILES: CCCC(C(=O)OC)c1c(C)nc(-c2ccccc2)nc1-c1ccc(Cl)cc1F] |
| Cpd 94 | 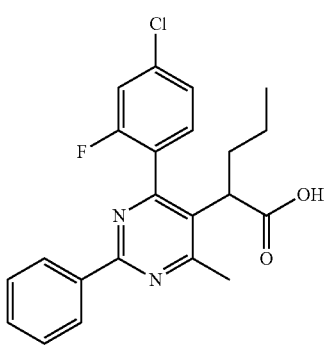 [SMILES: CCCC(C(=O)O)c1c(C)nc(-c2ccccc2)nc1-c1ccc(Cl)cc1F] |
| Cpd 95 | 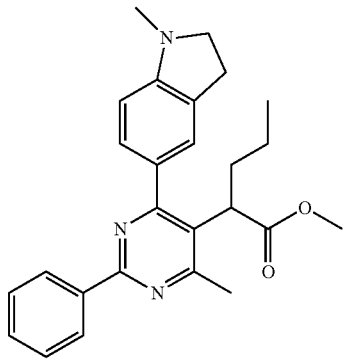 [SMILES: CCCC(C(=O)OC)c1c(C)nc(-c2ccccc2)nc1-c1ccc2c(c1)CCN2C] |

TABLE 1B-continued
Structures of example compounds of the invention and their respective codes.
| Code | Structure |
|---|---|
| Cpd 96 | 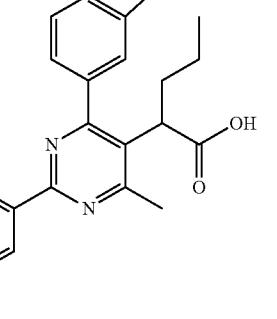 |
| Cpd 97 | 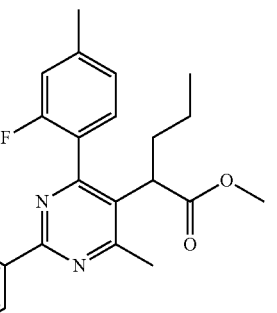 |
| Cpd 98 | 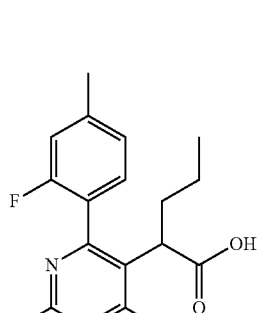 |
| Cpd 99 | 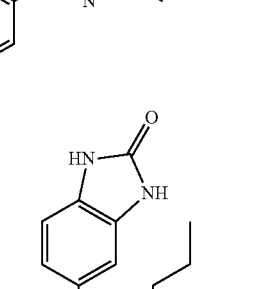 |
| Cpd 100 | 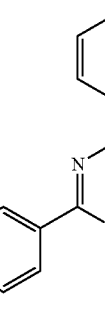 |
| Cpd 101 | 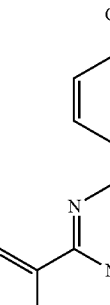 |
| Cpd 102 | 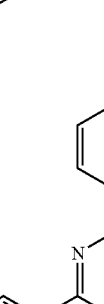 |
| Cpd 103 |  |

TABLE 1B-continued
Structures of example compounds of the invention and their respective codes.
| Code | Structure |
|---|---|
| Cpd 104 | 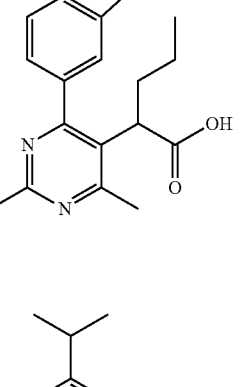 |
| Cpd 105 | 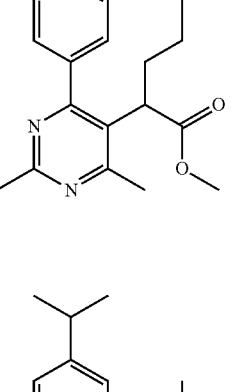 |
| Cpd 106 | 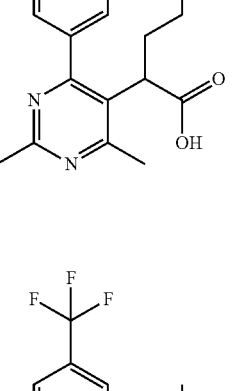 |
| Cpd 107 | 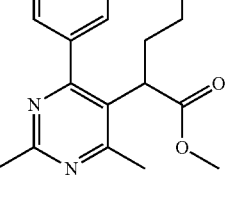 |
| Cpd 108 | 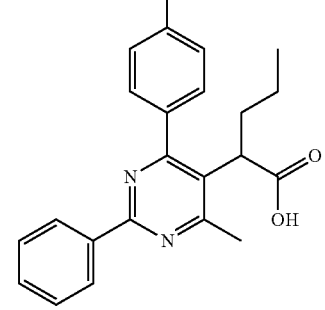 |
| Cpd 109 | 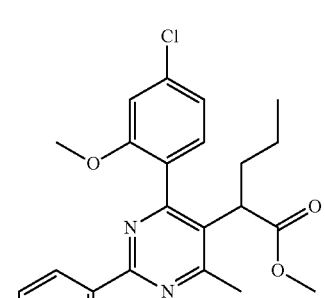 |
| Cpd 110 | 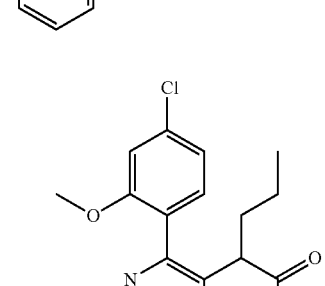 |
| Cpd 111 | 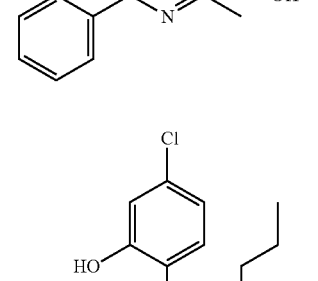 |

TABLE 1B-continued
Structures of example compounds of the invention and their respective codes.
| Code | Structure |
|------|-----------|
| Cpd 112 | 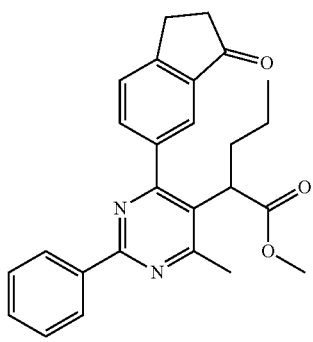 [SMILES: CCCC(C(=O)OC)c1c(C)nc(-c2ccccc2)nc1-c1ccc2c(c1)C(=O)CC2] |
| Cpd 113 | 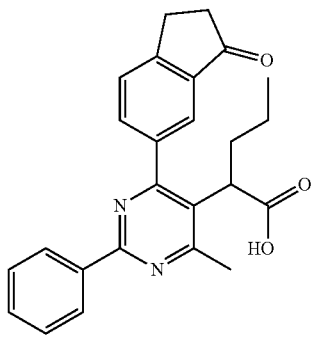 [SMILES: CCCC(C(=O)O)c1c(C)nc(-c2ccccc2)nc1-c1ccc2c(c1)C(=O)CC2] |
| Cpd 114 | 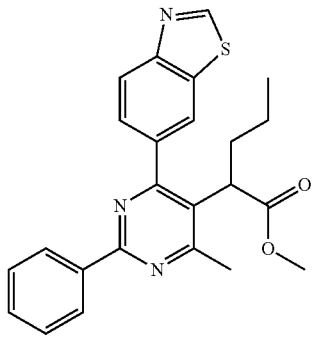 [SMILES: CCCC(C(=O)OC)c1c(C)nc(-c2ccccc2)nc1-c1ccc2ncsc2c1] |
| Cpd 115 | 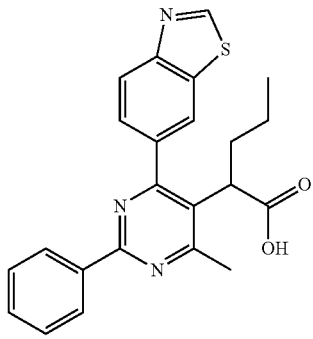 [SMILES: CCCC(C(=O)O)c1c(C)nc(-c2ccccc2)nc1-c1ccc2ncsc2c1] |
| Cpd 116 | 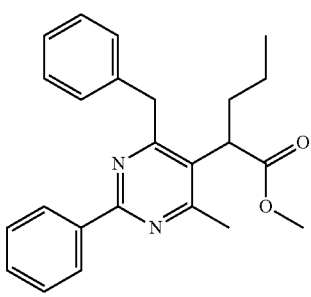 [SMILES: CCCC(C(=O)OC)c1c(C)nc(-c2ccccc2)nc1Cc1ccccc1] |
| Cpd 117 | 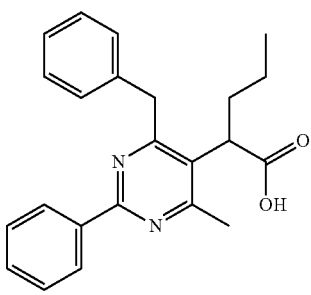 [SMILES: CCCC(C(=O)O)c1c(C)nc(-c2ccccc2)nc1Cc1ccccc1] |
| Cpd 118 | 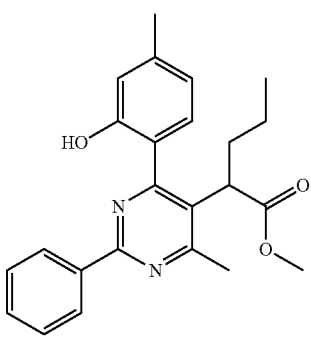 [SMILES: CCCC(C(=O)OC)c1c(C)nc(-c2ccccc2)nc1-c1ccc(C)cc1O] |
| Cpd 119 | 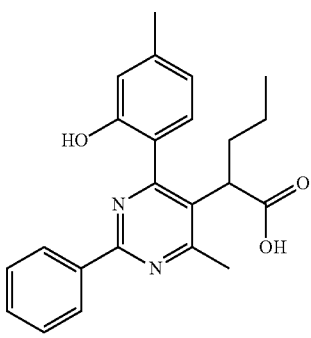 [SMILES: CCCC(C(=O)O)c1c(C)nc(-c2ccccc2)nc1-c1ccc(C)cc1O] |

TABLE 1B-continued

Structures of example compounds of the invention and their respective codes.

| Code | Structure |
|---|---|
| Cpd 120 | 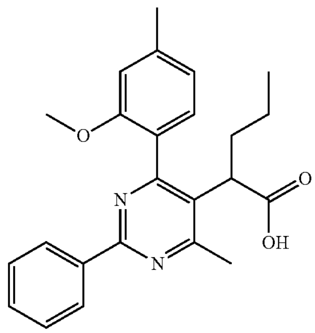 [SMILES: CCCC(C(=O)O)c1c(C)nc(-c2ccccc2)nc1-c1ccc(C)cc1OC] |
| Cpd 121 | 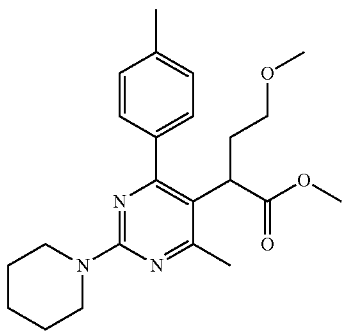 [SMILES: COCCC(C(=O)OC)c1c(C)nc(N2CCCCC2)nc1-c1ccc(C)cc1] |
| Cpd 122 | 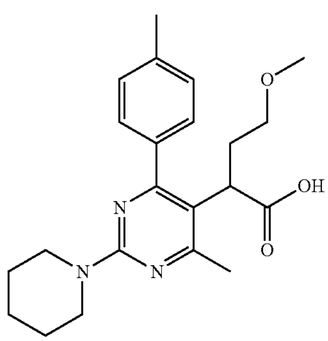 [SMILES: COCCC(C(=O)O)c1c(C)nc(N2CCCCC2)nc1-c1ccc(C)cc1] |
| Cpd 123 | 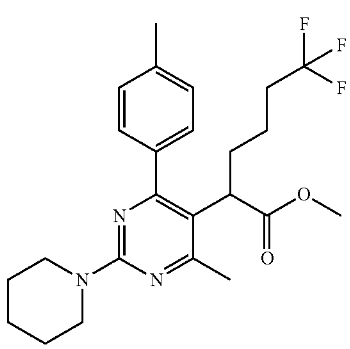 [SMILES: COC(=O)C(CCCC(F)(F)F)c1c(C)nc(N2CCCCC2)nc1-c1ccc(C)cc1] |
| Cpd 124 | 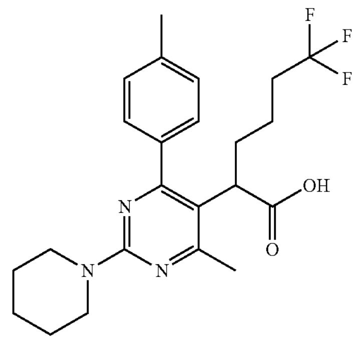 [SMILES: Cc1ccc(-c2nc(N3CCCCC3)nc(C)c2C(CCCC(F)(F)F)C(=O)O)cc1] |
| Cpd 125 | 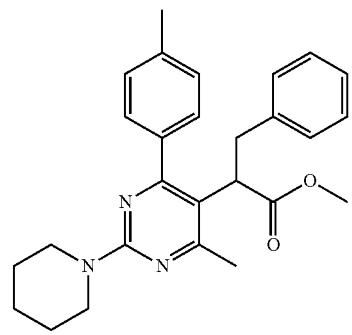 [SMILES: COC(=O)C(Cc1ccccc1)c1c(C)nc(N2CCCCC2)nc1-c1ccc(C)cc1] |
| Cpd 126 | 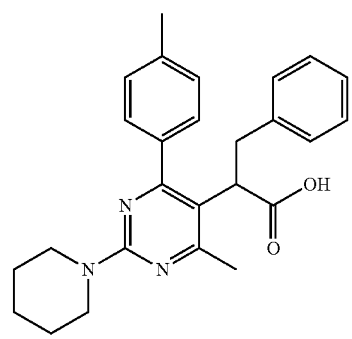 [SMILES: Cc1ccc(-c2nc(N3CCCCC3)nc(C)c2C(Cc2ccccc2)C(=O)O)cc1] |
| Cpd 127 | 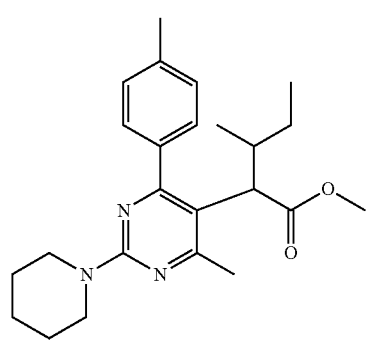 [SMILES: CCC(C)C(C(=O)OC)c1c(C)nc(N2CCCCC2)nc1-c1ccc(C)cc1] |

TABLE 1B-continued

Structures of example compounds of the invention and their respective codes.

| Code | Structure |
| --- | --- |
| Cpd 128 | 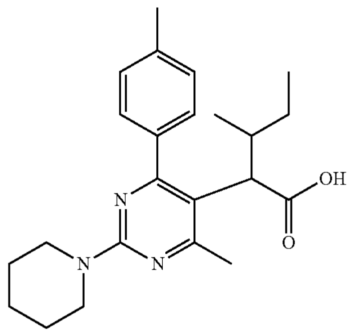 [SMILES: CCC(C)C(C(=O)O)c1c(C)nc(N2CCCCC2)nc1-c1ccc(C)cc1] |
| Cpd 129 | 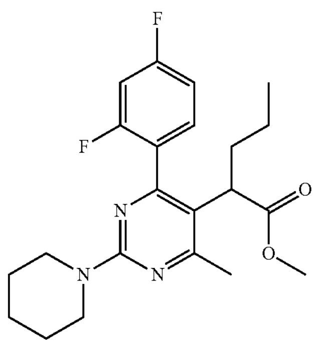 [SMILES: CCCC(C(=O)OC)c1c(C)nc(N2CCCCC2)nc1-c1ccc(F)cc1F] |
| Cpd 130 | 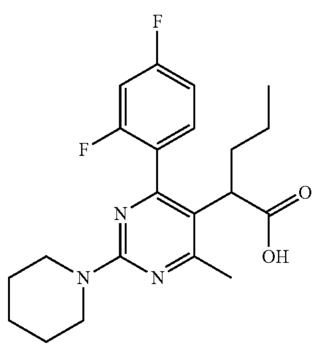 [SMILES: CCCC(C(=O)O)c1c(C)nc(N2CCCCC2)nc1-c1ccc(F)cc1F] |
| Cpd 131 | 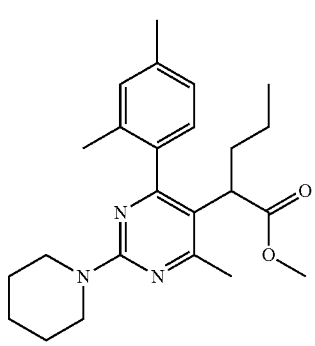 [SMILES: CCCC(C(=O)OC)c1c(C)nc(N2CCCCC2)nc1-c1ccc(C)cc1C] |
| Cpd 132 | |
| Cpd 133 | |
| Cpd 134 | |
| Cpd 135 | |

TABLE 1B-continued
Structures of example compounds of the invention and their respective codes.
| Code | Structure |
|---|---|
| Cpd 136 | 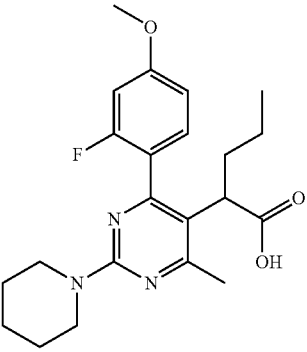 [SMILES: CCCC(C(=O)O)c1c(C)nc(N2CCCCC2)nc1-c1ccc(OC)cc1F] |
| Cpd 137 | 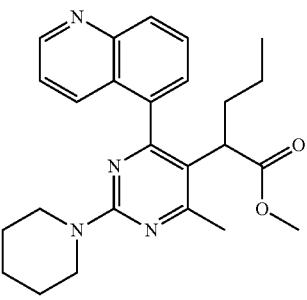 [SMILES: CCCC(C(=O)OC)c1c(C)nc(N2CCCCC2)nc1-c1cccc2ncccc12] |
| Cpd 138 | 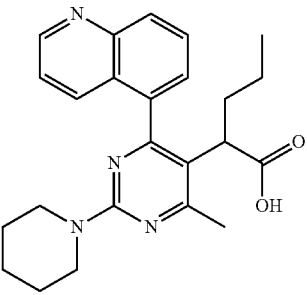 [SMILES: CCCC(C(=O)O)c1c(C)nc(N2CCCCC2)nc1-c1cccc2ncccc12] |
| Cpd 139 | 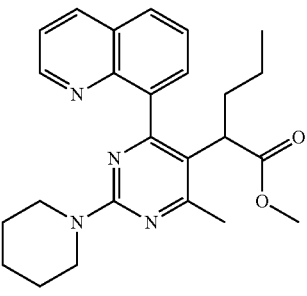 [SMILES: CCCC(C(=O)OC)c1c(C)nc(N2CCCCC2)nc1-c1cccc2cccnc12] |
| Cpd 140 | 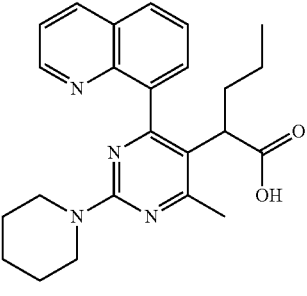 [SMILES: CCCC(C(=O)O)c1c(C)nc(N2CCCCC2)nc1-c1cccc2cccnc12] |
| Cpd 141 | 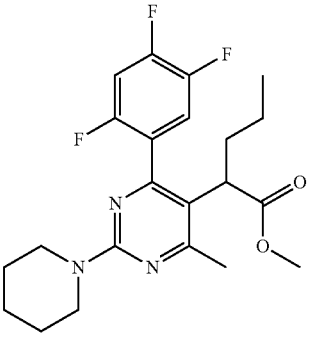 [SMILES: CCCC(C(=O)OC)c1c(C)nc(N2CCCCC2)nc1-c1cc(F)c(F)cc1F] |
| Cpd 142 | 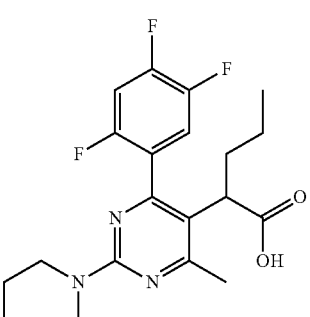 |
| Cpd 143 | 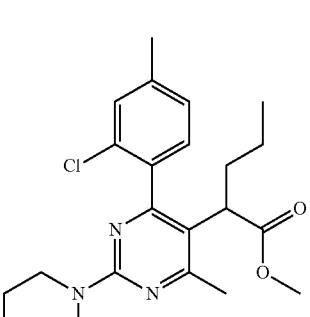 |
| Cpd 144 | 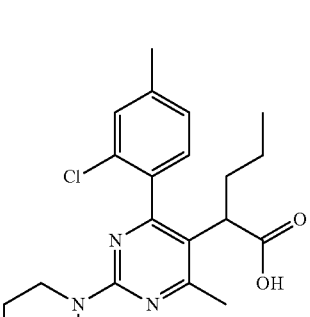 |

TABLE 1B-continued
Structures of example compounds of the invention and their respective codes.
| Code | Structure |
|---|---|
| Cpd 145 | 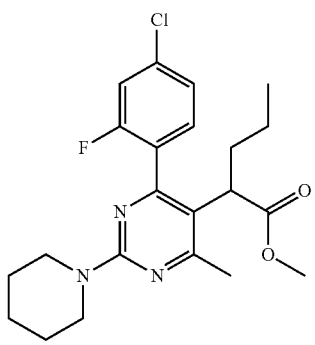 [SMILES: CCCC(C(=O)OC)c1c(C)nc(N2CCCCC2)nc1-c1ccc(Cl)cc1F] |
| Cpd 146 | 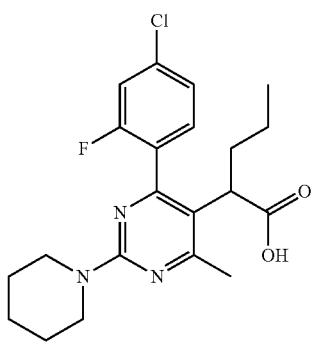 [SMILES: CCCC(C(=O)O)c1c(C)nc(N2CCCCC2)nc1-c1ccc(Cl)cc1F] |
| Cpd 147 | 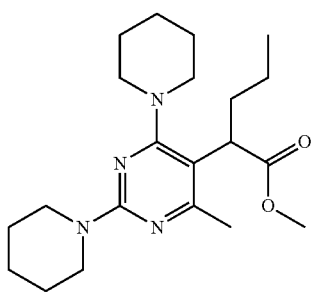 [SMILES: CCCC(C(=O)OC)c1c(C)nc(N2CCCCC2)nc1N1CCCCC1] |
| Cpd 148 | 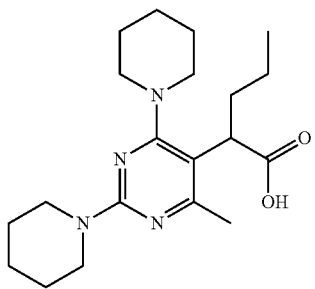 [SMILES: CCCC(C(=O)O)c1c(C)nc(N2CCCCC2)nc1N1CCCCC1] |
| Cpd 149 | 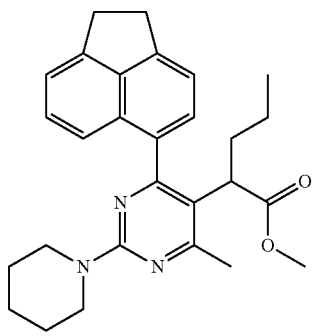 [SMILES: CCCC(C(=O)OC)c1c(C)nc(N2CCCCC2)nc1-c1ccc2c3c(cccc13)CC2] |
| Cpd 150 | 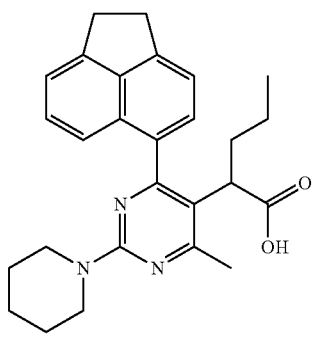 [SMILES: CCCC(C(=O)O)c1c(C)nc(N2CCCCC2)nc1-c1ccc2c3c(cccc13)CC2] |
| Cpd 151 | 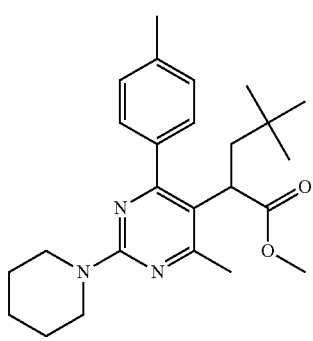 [SMILES: COC(=O)C(CC(C)(C)C)c1c(C)nc(N2CCCCC2)nc1-c1ccc(C)cc1] |
| Cpd 152 | 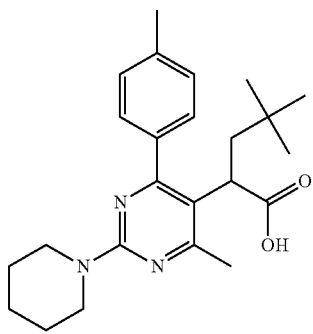 [SMILES: Cc1ccc(-c2nc(N3CCCCC3)nc(C)c2C(CC(C)(C)C)C(=O)O)cc1] |

TABLE 1B-continued

Structures of example compounds of the invention and their respective codes.

| Code | Structure |
| --- | --- |
| Cpd 153 | 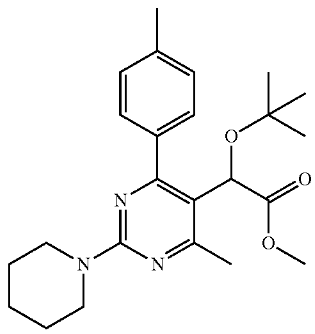 [SMILES: COC(=O)C(OC(C)(C)C)c1c(C)nc(N2CCCCC2)nc1-c1ccc(C)cc1] |
| Cpd 154 | 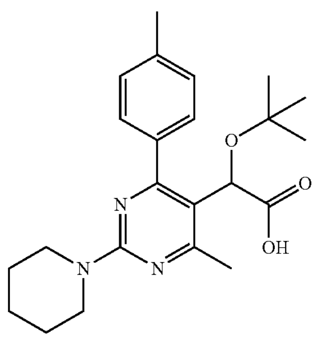 [SMILES: Cc1ccc(-c2nc(N3CCCCC3)nc(C)c2C(OC(C)(C)C)C(=O)O)cc1] |
| Cpd 155 | 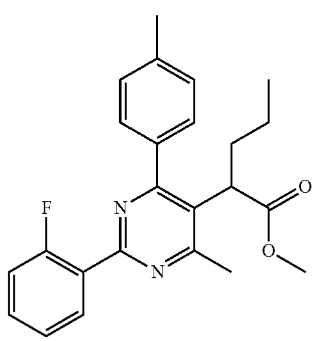 [SMILES: CCCC(C(=O)OC)c1c(C)nc(-c2ccccc2F)nc1-c1ccc(C)cc1] |
| Cpd 156 | 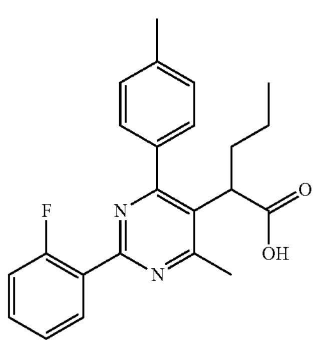 [SMILES: CCCC(C(=O)O)c1c(C)nc(-c2ccccc2F)nc1-c1ccc(C)cc1] |
| Cpd 157 | |
| Cpd 158 | |
| Cpd 159 | |
| Cpd 160 | |

TABLE 1B-continued
Structures of example compounds of the invention and their respective codes.
| Code | Structure |
|---|---|
| Cpd 161 | 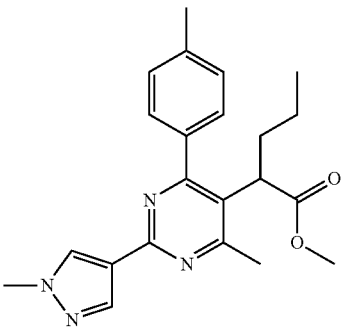 |
| Cpd 162 | 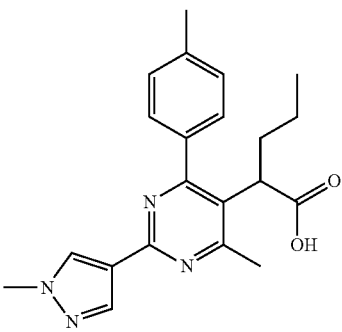 [SMILES: CCCC(C(=O)O)c1c(C)nc(-c2cnn(C)c2)nc1-c1ccc(C)cc1] |
| Cpd 163 | 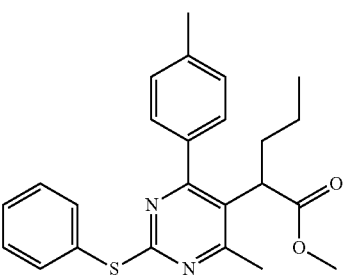 [SMILES: CCCC(C(=O)OC)c1c(C)nc(Sc2ccccc2)nc1-c1ccc(C)cc1] |
| Cpd 164 | 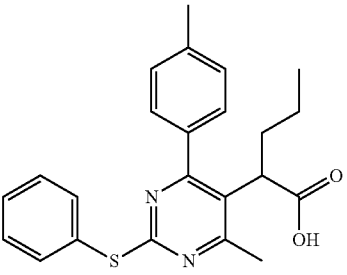 [SMILES: CCCC(C(=O)O)c1c(C)nc(Sc2ccccc2)nc1-c1ccc(C)cc1] |
| Cpd 165 | 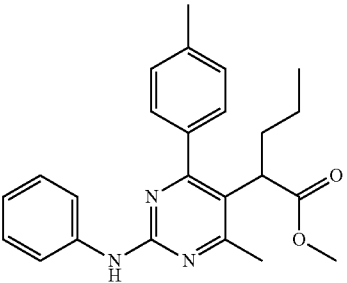 [SMILES: CCCC(C(=O)OC)c1c(C)nc(Nc2ccccc2)nc1-c1ccc(C)cc1] |
| Cpd 166 | 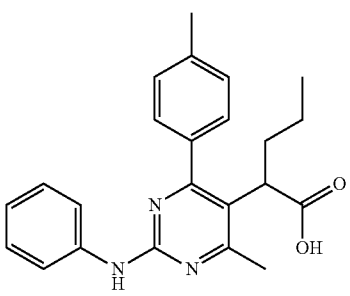 [SMILES: CCCC(C(=O)O)c1c(C)nc(Nc2ccccc2)nc1-c1ccc(C)cc1] |
| Cpd 167 | 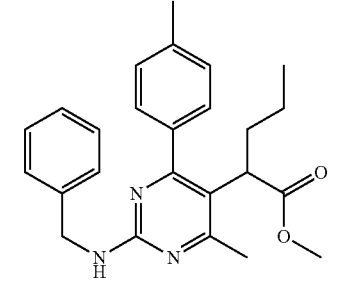 [SMILES: CCCC(C(=O)OC)c1c(C)nc(NCc2ccccc2)nc1-c1ccc(C)cc1] |
| Cpd 168 | 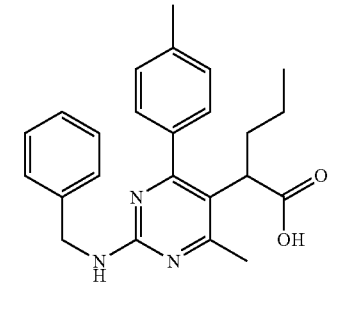 [SMILES: CCCC(C(=O)O)c1c(C)nc(NCc2ccccc2)nc1-c1ccc(C)cc1] |
| Cpd 169 | 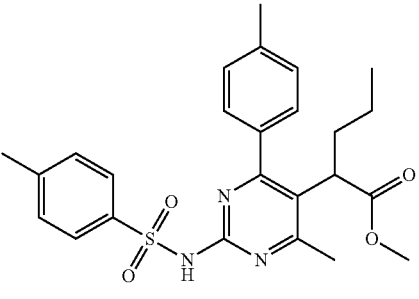 |
| Cpd 170 | 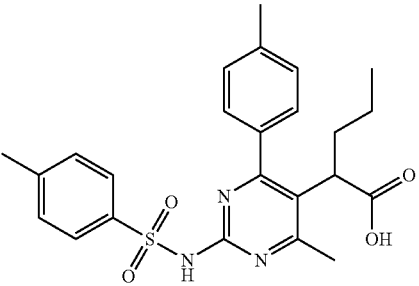 [SMILES: CCCC(C(=O)O)c1c(C)nc(NS(=O)(=O)c2ccc(C)cc2)nc1-c1ccc(C)cc1] |

TABLE 1B-continued
Structures of example compounds of the invention and their respective codes.
| Code | Structure |
|---|---|
| Cpd 171 | 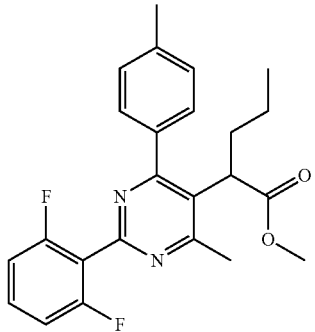 [SMILES: CCCC(C(=O)OC)c1c(C)nc(-c2c(F)cccc2F)nc1-c1ccc(C)cc1] |
| Cpd 172 | 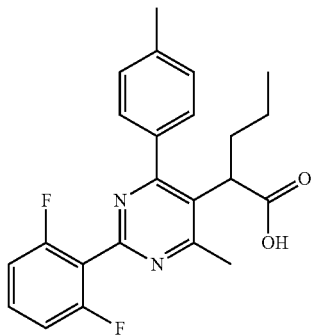 [SMILES: CCCC(C(=O)O)c1c(C)nc(-c2c(F)cccc2F)nc1-c1ccc(C)cc1] |
| Cpd 173 | 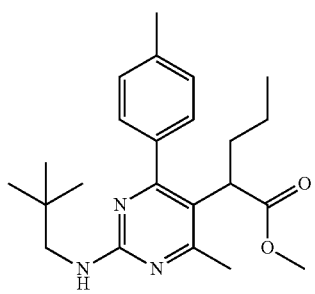 [SMILES: CCCC(C(=O)OC)c1c(C)nc(NCC(C)(C)C)nc1-c1ccc(C)cc1] |
| Cpd 174 | 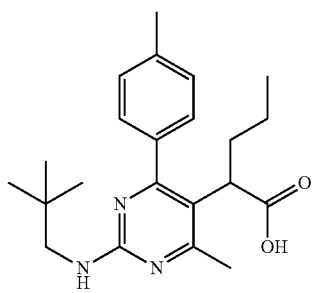 [SMILES: CCCC(C(=O)O)c1c(C)nc(NCC(C)(C)C)nc1-c1ccc(C)cc1] |
TABLE 1B-continued
Structures of example compounds of the invention and their respective codes.
| Code | Structure |
|---|---|
| Cpd 175 | 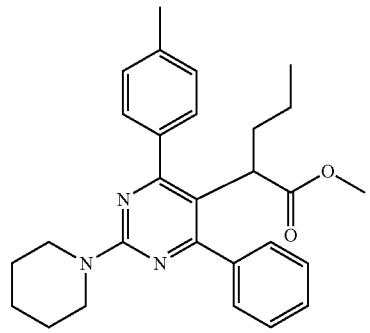 [SMILES: CCCC(C(=O)OC)c1c(-c2ccccc2)nc(N2CCCCC2)nc1-c1ccc(C)cc1] |
| Cpd 176 | 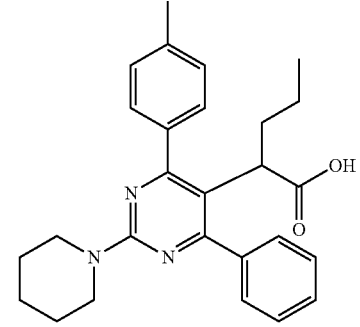 [SMILES: CCCC(C(=O)O)c1c(-c2ccccc2)nc(N2CCCCC2)nc1-c1ccc(C)cc1] |
| Cpd 177 | 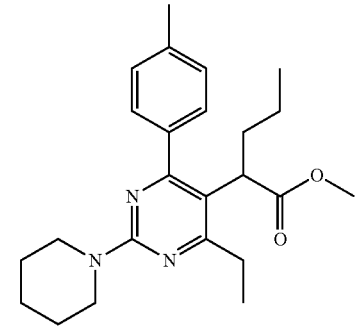 [SMILES: CCCC(C(=O)OC)c1c(CC)nc(N2CCCCC2)nc1-c1ccc(C)cc1] |
| Cpd 178 | 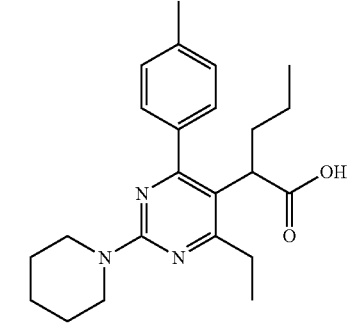 [SMILES: CCCC(C(=O)O)c1c(CC)nc(N2CCCCC2)nc1-c1ccc(C)cc1] |

TABLE 1B-continued

Structures of example compounds of the invention and their respective codes.

| Code | Structure |
|---|---|
| Cpd 179 | 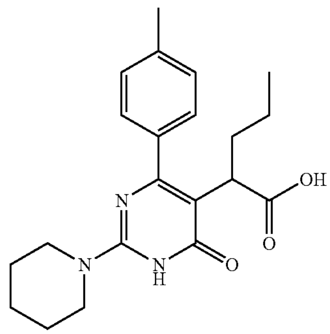 [SMILES: CCCC(C(=O)O)c1c(-c2ccc(C)cc2)nc(N2CCCCC2)[nH]c1=O] |
| Cpd 180 | 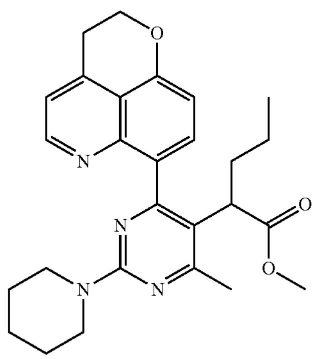 [SMILES: CCCC(C(=O)OC)c1c(C)nc(N2CCCCC2)nc1-c1ccc2c3c(ccnc13)CCO2] |
| Cpd 181 | 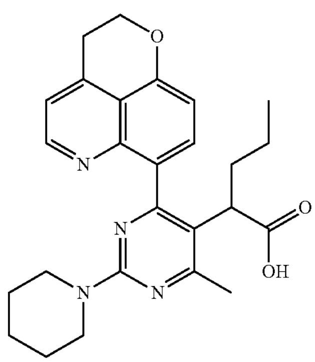 [SMILES: CCCC(C(=O)O)c1c(C)nc(N2CCCCC2)nc1-c1ccc2c3c(ccnc13)CCO2] |
| Cpd 182 | 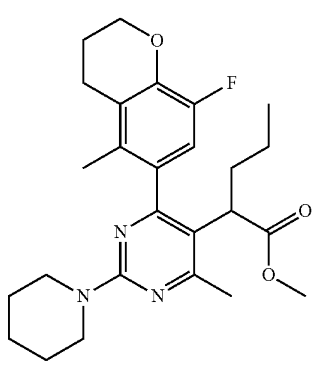 [SMILES: CCCC(C(=O)OC)c1c(C)nc(N2CCCCC2)nc1-c1cc(F)c2c(c1C)CCCO2] |
| Cpd 183 | |
| Cpd 184 | |
| Cpd 185 | |
| Cpd 186 | |

TABLE 1B-continued

Structures of example compounds of the invention and their respective codes.

| Code | Structure |
|---|---|
| Cpd 187 | 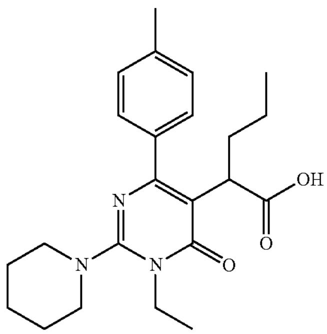 [SMILES: CCCC(C(=O)O)c1c(-c2ccc(C)cc2)nc(N2CCCCC2)n(CC)c1=O] |
| Cpd 188 | 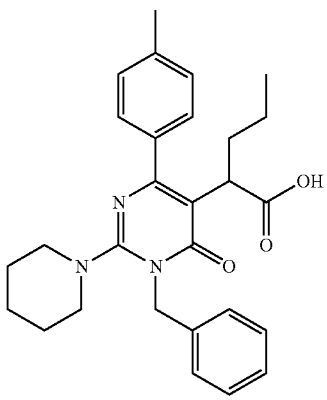 [SMILES: CCCC(C(=O)O)c1c(-c2ccc(C)cc2)nc(N2CCCCC2)n(Cc2ccccc2)c1=O] |
| Cpd 189 | 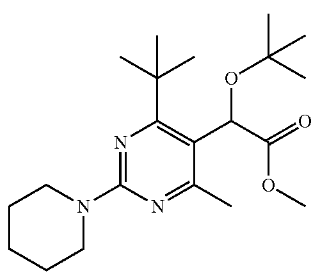 [SMILES: COC(=O)C(OC(C)(C)C)c1c(C)nc(N2CCCCC2)nc1C(C)(C)C] |
| Cpd 190 | 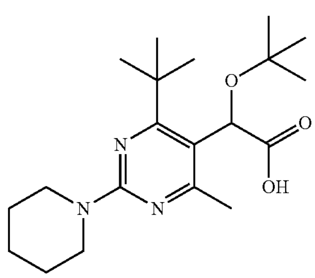 [SMILES: Cc1nc(N2CCCCC2)nc(C(C)(C)C)c1C(OC(C)(C)C)C(=O)O] |
| Cpd 191 | 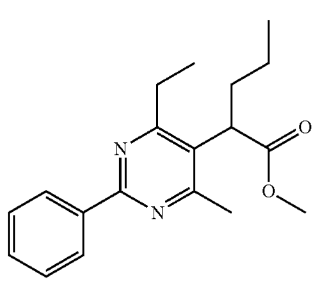 [SMILES: CCCC(C(=O)OC)c1c(C)nc(-c2ccccc2)nc1CC] |
| Cpd 192 | |

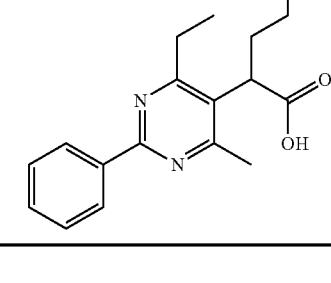

Part A

All the preparative HPLC purifications mentioned in this experimental part have been carried out with the following system: a Waters 2489 UV/Visible Detector, a Waters 2545 Binary Gradient Module, a Waters Fraction Collector III and a Waters Dual Flex Injector.

The separations were performed with a X-Bridge Prep C18, 100×19 mm, 5 μm column equipped with a X-Bridge C18, 5 μm, 19×10 mm Guard column.

Elutions were carried out with the gradient described in the following tables, and detection wavelengths were fixed at 210 and 254 nm:

HPLC Method 1:

| Time (min) | Flow Rate ml/min | Solvent A % | Solvent B % |
|---|---|---|---|
| 0 | 20 | 50 | 50 |
| 2.00 | 20 | 50 | 50 |
| 9.00 | 20 | 10 | 90 |
| 11.00 | 20 | 10 | 90 |
| 11.20 | 20 | 50 | 50 |
| 16.00 | 20 | 50 | 50 |

Solvent A: Formic Acid LC-MS grade 0.1% in milliQ water
Solvent B: Acetonitrile HPLC grade.

HPLC Method 2:

| Time (min) | Flow Rate (mL/min) | Solvent A (%) | Solvent B (%) |
|---|---|---|---|
| 0 | 20 | 80 | 20 |
| 2.00 | 20 | 80 | 20 |
| 8.00 | 20 | 10 | 90 |
| 10.80 | 20 | 10 | 90 |
| 11.00 | 20 | 80 | 20 |
| 16.00 | 20 | 80 | 20 |

Solvent A: Formic Acid LC-MS grade 0.1% in milliQ water
Solvent B: Acetonitrile HPLC grade.

HPLC Method 3:

| Time (min) | Flow Rate ml/min | Solvent A % | Solvent B % |
|---|---|---|---|
| 0 | 20 | 50 | 50 |
| 2.00 | 20 | 50 | 50 |
| 9.00 | 20 | 10 | 90 |
| 11.00 | 20 | 10 | 90 |
| 11.20 | 20 | 50 | 50 |

| Time (min) | Flow Rate ml/min | Solvent A % | Solvent B % |
|---|---|---|---|
| 16.00 | 20 | 50 | 50 |

Solvent A: Ammonium Acetate puriss p.a. for HPLC 10 mM in milliQ water, adjusted at pH 10 with Ammonium Hydroxide puriss p.a. for HPLC.
Solvent B: Acrtonitrile HPLC grade.

HPLC Method 4:

| Time (min) | Flow Rate (mL/min) | Solvent A (%) | Solvent B (%) |
|---|---|---|---|
| 0 | 20 | 80 | 20 |
| 2.00 | 20 | 80 | 20 |
| 8.00 | 20 | 10 | 90 |
| 10.80 | 20 | 10 | 90 |
| 11.00 | 20 | 80 | 20 |
| 16.00 | 20 | 80 | 20 |

Solvent A: Ammonium Acetate puriss p.a. for HPLC 10 mM in milliQ water, adjusted at pH 10 with Ammonium Hydroxide puriss p.a. for HPLC.
Solvent B: Acrtonitrile HPLC grade.

HPLC Method 5:

| Time (min) | Flow Rate (ml/min) | Solvent A (%) | Solvent B (%) |
|---|---|---|---|
| 0 | 20 | 95 | 5 |
| 2.00 | 20 | 95 | 5 |
| 8.00 | 20 | 50 | 50 |
| 9.00 | 20 | 10 | 90 |
| 11.80 | 20 | 10 | 90 |
| 12.00 | 20 | 95 | 5 |
| 16.00 | 20 | 95 | 5 |

Solvent A: Ammonium Acetate puriss p.a. for HPLC 10 mM in milliQ water, adjusted at pH 10 with Ammonium Hydroxide puriss p.a. for HPLC.
Solvent B: Acrtonitrile HPLC grade.

General Method A for the Preparation of methyl 2-(4-methyl-6-p-tolylpyrimidin-5-yl)pentanoate derivatives An amine (1.20 mmol, 5 eq) was added to a solution of methyl 2-(2-chloro-4-methyl-6-p-tolylpyrimidin-5-yl)pentanoate (HPLC purity 79.5%, 0.239 mmol, 1 eq) in tetrahydrofuran (0.12 mol/L) in a microwave vial. The vial was irradiated in a microwave oven at 100° C. for 1 hour. The reaction mixture was diluted with a saturated solution of sodium hydrogen carbonate and extracted twice with ethyl acetate. Combined organic extracts were washed with brine and concentrated under reduced pressure. The residue was purified by flash chromatography.

General Method B for the Hydrolysis of methyl 2-(4-methyl-6-p-tolylpyrimidin-5-yl)pentanoate derivatives A solution of sodium hydroxide 5N (0.370 mL; 1.85 mmol; 10 eq) was added to a mixture of methyl 2-(4-methyl-6-p-tolylpyrimidin-5-yl)pentanoate (0.185 mmol; 1 eq) and methanol (2 mL; 0.09 mmol/mL). The mixture was refluxed for 18 h and then concentrated under reduced pressure. The residue was dissolved in water and the pH of the solution was adjusted between 2 and 3 by addition of a solution of hydrochloric acid 6N. The precipitate was collected by filtration and dried under reduced pressure over phosphorus pentoxide to give the desired compound.

General Method C

To a solution of methyl 2-(2-chloro-4-methyl-6-p-tolylpyrimidin-5-yl)pentanoate (1 eq) and triethyl amine (5 eq) in tetrahydrofuran (2 mL/mmol of the limiting reagent) in a sealed tube was added an amine (3 eq). The vial was sealed and irradiated in a microwave oven at 100° C. for 1 h. The reaction mixture was diluted with a saturated solution of sodium hydrogen carbonate and extracted twice with ethyl acetate. The combined organic extracts were washed with a saturated solution of sodium chloride, dried over sodium sulphate, filtered and concentrated under reduced pressure.

General Method D

A solution of sodium hydroxide 10N (10 eq) was added to a mixture of a methyl or an ethyl ester (1 eq) in methanol (10 mL/mmol of the limiting reagent). The mixture was heated at 100° C. in a sealed tube until disappearance of the limiting reagent and then concentrated under reduced pressure. The residue was dissolved in water and the pH of the solution was adjusted between 2 and 3 by addition of a solution of hydrochloric acid 6N until a precipitate was formed. The precipitate was collected by filtration and dried under reduced pressure over phosphorus pentoxide to give the desired compound.

General Method E

To a sonicated solution of methyl 2-(4-chloro-6-methyl-2-substituted-pyrimidin-5-yl)pentanoate (1 equivalent) and arylboronic acid (1.5 to 3 equivalents) in a mixture of DME-water (3:1) were added palladiumtetrakistriphenylphosphine (0.1 to 0.2 equivalent) and diisopropylethylamine (2 to 4 equivalents). The solution was stirred under microwave irradiation at 130° C. until disappearance of the limiting compound. The mixture was diluted with a saturated solution of sodium chloride solution and was extracted with ethyl acetate. The combined organic layers were dried over magnesium sulphate, filtered and concentrated under reduced pressure. The residue was purified by flash chromatography on silica gel to afford the expected product.

Example 1

Preparation of 2-(6-Methyl-4-oxo-2-thioxo-1,2,3,4-tetrahydropyrimidin-5-yl)acetic acid Thiourea (4.00 g; 52.5 mmol) and dimethyl acetylsuccinate (9.41 g; 50 mmol) were added at room temperature to a solution of sodium methoxide (22.87 ml; 100 mmol) in methanol (18 ml) and the mixture is stirred under reflux for 18 h. After cooling, the precipitate was filtered off and added with stirring to a hydrochloric acid solution (12N) at 0° C. The white precipitate was filtered, washed with water and dried under reduced pressure over phosphorus pentoxide to give 7.3 g (73%) of title compound as a white powder.

Example 2

Preparation of 2-(6-methyl-2,4-dioxo-1,2,3,4-tetrahydropyrimidin-5-yl)acetic acid A 10% aq chloroacetic acid solution (150 mL; 159 mmol) was added to 2-(6-methyl-4-oxo-2-thioxo-1,2,3,4-tetrahydropyrimidin-5-yl)acetic acid (7.3 g; 36.5 mmol). The mixture was stirred under reflux for 24 h and cooled in an ice-bath. The formed solid was collected by filtration, washed with water and dried under reduced pressure to give 5.17 g (77%) of the title compound as a white solid.

Example 3

Preparation of Methyl 2-(6-methyl-2,4-dioxo-1,2,3,4-tetrahydropyrimidin-5-yl)acetate 2-(6-Methyl-2,4-dioxo-1,2,3,4-tetrahydropyrimidin-5-yl)acetic acid (5.17 g; 28,1 mmol) was suspended in methanol (70.2 mL) and to the stirred mixture was added thionyl chloride (40.7 ml; 562 mmol) dropwise at 0° C. The mixture was stirred under reflux for 12 h. After cooling, the white precipitate was filtered off, washed with methanol and dried under reduced pressure with phosphorus pentoxide to give 5.4 g (97%) of the title compound as a white solid.

$^1$H NMR (DMSO-$d_6$) δ 11.06 (1H, s); 10.81 (1H, s); 3.59 (3H, s); 3.30 (2H, s); 2.04 (3H, s).

Example 4

Preparation of Methyl 2-(2,4-dichloro-6-methylpyrimidin-5-yl)acetate

Methyl 2-(6-methyl-2,4-dioxo-1,2,3,4-tetrahydropyrimidin-5-yl)acetate (5.4 g; 27.2 mmol) is dissolved in a mixture of phosphorus oxychloride (38.2 mL; 409 mmol) and N,N'-dimethyl aniline (4.82 mL; 38.1 mmol). The mixture is stirred at reflux (115° C.) for 2 h. The reaction mixture was concentrated under reduced pressure. Ice was added to the remaining solution. The suspension was extracted with diethyl ether (2×150 ml) and the combined organic layers were washed with brine. The organic layer was dried with magnesium sulphate. The crude material was purified by flash chromatography on silica gel using a linear gradient of ethylacetate (5-40%) in heptane to give 5.88 g (92%) of the title compound as a white solid.

Example 5

Preparation of Methyl 2-(2-chloro-4-methyl-6-phenylpyrimidin-5-yl)acetate

To a suspension of methyl 2-(2,4-dichloro-6-methylpyrimidin-5-yl)acetate (4.42 g; 18.80 mmol) in a mixture of degassed DME (75 mL) and water (25 mL) was added phenyl boronic acid (5.73 g; 47 mmol), Tetrakis(triphenylphosphine) palladium(0) (2 g; 1.731 mmol) and diisopropyl ethylamine (12.96 mL; 75 mmol). The reaction was stirred under reflux for 3.5 h. The reaction mixture was partitioned between brine and ethyl acetate. The phases were separated and the water layer was extracted with ethyl acetate. The combined organic layers were dried over magnesium sulphate and concentrated under reduced pressure. The crude material was purified by flash chromatography on silica gel using a linear gradient of ethylacetate (5-40%) in heptane to give 3.44 g (65%) of the title compound as a white solid. ESI/APCI(+): 277 (M+H).

Example 6

Preparation of Methyl 2-(2-chloro-4-methyl-6-phenylpyrimidin-5-yl)pentanoate

A solution of methyl 2-(2-chloro-4-methyl-6-phenylpyrimidin-5-yl)acetate (2.5 g; 9.03 mmol) in dry DMF (45 mL) was cooled to −15° C. LHMDS (10.84 mL; 10.84 mmol; 1M in THF) was added dropwise and the mixture was stirred at −15° C. for 15 min followed by the dropwise addition of iodopropane (1.765 mL; 18.07 mmol). After stirring for 2 h at −15° C. the mixture was allowed to warm up to room temperature. After 1 h the reaction was quenched by adding a saturated solution of ammonium chloride. The mixture was extracted twice with ethyl acetate and the combined organic layers were washed with brine, dried over magnesium sulphate and concentrated under reduced pressure. The crude material was purified by flash chromatography on silica gel using a linear gradient of ethylacetate (2-20%) in heptane to give 0.98 g (25%) of the title compound as a yellow oil. ESI/APCI(+): 319 (M+H).

Example 7

Preparation of Methyl 2-(2-chloro-4-methyl-6-phenylpyrimidin-5-yl)acetate

To a suspension of methyl 2-(2,4-dichloro-6-methylpyrimidin-5-yl)acetate (4 g; 17.02 mmol) in a mixture of degassed DME (75 mL) and water (25 mL) was added p-tolylboronic acid (4.63 g; 34 mmol), Tetrakis(triphenylphosphine) palladium(0) (2 g; 1.731 mmol) and diisopropyl ethylamine (11.73 mL; 68.1 mmol). The reaction was stirred under reflux for 3.5 h. The reaction mixture was then partitioned between brine and ethyl acetate. The phases were separated and the water layer was extracted with ethyl acetate. The combined organic layers were dried with magnesium sulphate and concentrated under reduced pressure. The crude material was purified by flash chromatography on silica gel using a linear gradient of ethylacetate (5-40%) in heptane to give 3.82 g (61%) of the title compound as a white solid (purity: 80%). ESI/APCI(+): 291 (M+H).

Example 8

Preparation of Methyl 2-(2-chloro-4-methyl-6-p-tolylpyrimidin-5-yl)pentanoate

A solution of methyl 2-(2-chloro-4-methyl-6-p-tolylpyrimidin-5-yl)acetate (2.5 g; 8.60 mmol) in dry DMF (40 mL) was cooled to −78° C. LHMDS (9.46 mL; 9.46 mmol; 1M in THF) was added dropwise and the mixture was stirred at −78° C. for 15 min followed by the dropwise addition of iodopropane (1.260 ml; 12.90 mmol). After stirring for 2 h at −15° C. the mixture was allowed to warm up to room temperature. After 1 h the reaction was quenched by adding a saturated solution of ammonium chloride. The mixture was extracted twice with ethyl acetate and the combined organic layers were washed with brine, dried over magnesium sulphate and concentrated under reduced pressure. The crude material was purified by flash chromatography on silica gel using a linear gradient of ethylacetate (2-10%) in heptane to give 1.131 g (37%) of the title compound as a yellow oil. ESI/APCI(+): 333 (M+H).

Example 9

Preparation of Dimethyl 2-acetyl-3-propylsuccinate

To a solution of ethyl acetoacetate (64 mL; 504 mmol) in dry DMF (240 mL) under a nitrogen atmosphere was added potassium carbonate (69.6 g; 504 mmol), which has been dried at 120° C. for 12 h before its use. After stirring for 15 minutes at room temperature, ethyl 2-bromovalerate (81.6 mL; 480 mmol) was slowly added under nitrogen and the mixture was vigorously stirred at room temperature for 20 h.

The reaction mixture was poured in water (240 mL) and neutralized by adding HCl 2N. The product was extracted with diethyl ether (2×240 mL) and the combined organic layers were dried over magnesium sulphate and concentrated under reduced pressure. The crude yellow oil was purified by distillation under reduced pressure (160° C./6 mbar) to give 61.8 g of the title compound as a colorless liquid (HPLC purity 60%). ESI/APCI(+): 259 (M+H);

Example 10

Preparation of Methyl 2-(4-methyl-6-oxo-2-phenyl-1,6-dihydropyrimidin-5-yl)pentanoate Step 1:
To a solution of benzamidine hydrochloride (9.2 g; 50 mmol) in methanol (46 mL) was slowly added a solution of sodium methoxide (25%) (23 mL; 100 mmol) and dimethyl 2-acetyl-3-propylsuccinate (60%) (19.2 g; 50 mmol). The reaction mixture was heated at reflux for 18 h, and after cooling, the white precipitate was filtered and washed with a small volume of methanol. The solid was dried and carefully added to a cold hydrochloric 12N solution (25 mL). The suspension was stirred for one minute at 0° C., filtered and washed with a small amount of methanol. The precipitate was dried under reduced pressure over phosphorus pentoxide to provide 17.16 g of the expected 2-(4-methyl-6-oxo-2-phenyl-1,6-dihydropyrimidin-5-yl)pentanoic acid as a white powder which was used without further purification. ESI/APCI(+): 287 (M+H); ESI/APCI(−): 285 (M−H). $^1$H NMR (DMSO-d6) δ 8.08 (2H, d, $H_{arom.}$); 7.70 (1H, m, $H_{arom.}$); 7.60 (2H, m, $H_{arom.}$); 3.76 (1H, m, $CH_\alpha$); 2.48 (3H, s, $CH_3$); 1.98 (1H, m, $CH_\beta$); 1.72 (1H, m, $CH_{\beta'}$); 1.14 (2H, m, $CH_{2\gamma}$); 0.87 (3H, t, $CH_{3\delta}$).
Step 2:
The 2-(4-methyl-6-oxo-2-phenyl-1,6-dihydropyrimidin-5-yl)pentanoic acid (17.16 g) was suspended in dry methanol (150 mL) and thionyl chloride (87 mL; 120 mmol) was added dropwise. The stirred reaction mixture was heated at reflux for 18 h. After cooling, the white precipitate was filtered off, washed with methanol and the filtrate was concentrated under reduced pressure. The residue was suspended in ethyl acetate (25 mL) and heptane (50 mL) was added. The white precipitate was filtered and dried under reduced pressure. The filtrate was concentrated and the residue was precipitate another time with the same procedure to furnish 12.1 g (80% overall yield) of the title compound as a white powder. ESI/APCI(+): 301 (M+H); ESI/APCI(−): 299 (M−H).

Example 11

Preparation of Methyl 2-(2-(dimethylamino)-4-methyl-6-phenylpyrimidin-5-yl)pentanoate Step 1:
Methyl 2-(2-chloro-4-methyl-6-phenylpyrimidin-5-yl)acetate (1 g; 3.61 mmol) was added to a 20 mL tube and dimethylamine (7.23 mL; 14.46 mmol; 2M in THF) was added. The reaction was heated under microwave irradiation at 100° C. for 1 h. The reaction mixture was diluted with ethyl acetate and washed with saturated sodium hydrogen carbonate solution. The water layer was back-extracted with ethyl acetate and the combined organic layers were dried with magnesium sulphate, filtered and concentrated under reduced pressure. The residue was purified by flash chromatography on silica gel eluting with a gradient of ethyl acetate (5-40%) in heptane to give 900 mg (86%) of the title compound as a white solid.
Step 2:
A solution of methyl 2-(2-(dimethylamino)-4-methyl-6-phenylpyrimidin-5-yl)acetate (750 mg; 2.63 mmol) in dry DMF (13 mL) was cooled to −15° C. LHMDS (2.89 mL, 2.89 mmol; 1M in THF) was added dropwise and the mixture was stirred at −15° C. for 15 min followed by the dropwise addition of iodopropane (0.385 mL; 3.94 mmol), after stirring for 2 h at −15° C. the mixture was allowed to warm up to room temperature. After 1 h the reaction was quenched by adding a saturated solution of ammonium chloride. The mixture was extracted twice with ethyl acetate and the combined organic layers were washed with brine, dried over magnesium sulphate and concentrated under reduced pressure. The crude material was purified by flash chromatography on silica gel using a linear gradient of ethylacetate (2-20%) in heptane to give 680 mg (79%) of the title compound as a white solid. $^1$H NMR ($CDCl_3$) δ 7.46-7.40 (5H, m); 3.82 (1H, dd, J=6.1, 8.2 Hz); 3.69 (3H, s); 3.19 (6H, s); 2.31 (3H, s); 2.08-1.96 (1H, m); 1.62-1.47 (1H, m); 1.02-0.92 (2H, m); 0.65 (3H, t, J=7.1 Hz).

Example 12

Preparation of 2-(2-(dimethylamino)-4-methyl-6-phenylpyrimidin-5-yl)pentanoic acid A solution of methyl 2-(2-(dimethylamino)-4-methyl-6-phenylpyrimidin-5-yl)pentanoate (100 mg; 0.305 mmol) in THF (1 mL) and 2N sodium hydroxide solution (1.5 mL; 3 mmol) was placed in a sealed tube and irradiated in a microwave oven at 100° C. for 1 h and stirred overnight at room temperature. The reaction mixture was concentrated under reduced pressure and diluted with water. 1N Hydrochloric acid was added dropwise until the product precipitated. The solid was filtered and dried under reduced pressure to give 66 mg (69%) of the title compound as a white solid. ESI/APCI (+): 314 (M+H).

Example 13

Preparation of Methyl 2-(2-benzyl-4-methyl-6-phenylpyrimidin-5-yl)pentanoate

THF (4 ml) was added to an argon purged glass tube (20 mL) containing methyl 2-(2-chloro-4-methyl-6-phenylpyrimidin-5-yl)pentanoate (135 mg; 0.423 mmol) and tetrakis(triphenylphosphine) palladium(0) (24.47 mg; 0.021 mmol). The mixture was stirred at room temperature for 10 min and, after dissolution of the solids, benzylzinc bromide (1.694 ml; 0.847 mmol; 0,5 M in THF) was added dropwise. Stirring at room temperature was continued for 15 min followed by stirring at 60° C. for 8 h. The reaction was quenched by adding a saturated ammonium chloride solution. To this suspension was added a saturated disodium ethylenediamine tetraacetate solution and the mixture was stirred at room temperature for 15 min. The mixture was extracted twice with ethyl acetate and the organic layers were washed with brine and dried over magnesium sulphate. The crude material was purified by flash chromatography on silica gel using a linear gradient of ethylacetate (2-20%) in heptane to give 101 mg (64%) of the title compound. ESI/APCI(+): 375 (M+H). ESI/APCI(−): 373 (M−H).

131

Example 14

Preparation of 2-(2-Benzyl-4-methyl-6-phenylpyrimidin-5-yl)pentanoic acid

A solution of methyl 2-(2-benzyl-4-methyl-6-phenylpyrimidin-5-yl)pentanoate (67 mg; 0.17 mmol) in ethanol (1 mL), tetrahydrofuran (1 mL) and 2N sodium hydroxide solution (0.895 mL; 1.789 mmol) was stirred for 40 h at room temperature. The reaction mixture was concentrated under reduced pressure, diluted with water and acidified with a 6N hydrochloric acid solution. The suspension was extracted twice with ethyl acetate and the organic layers were washed with water and dried by filtration over a phase separater filter (PS1). The crude material was purified first by flash chromatography on silica gel using a linear gradient of methanol (1-10%) in dichloromethane and then by preparative thick layer chromatography on silica gel eluting with 10% methanol in dichloromethane to give 25 mg (37%) of the title compound as a colorless oil. ESI/APCI(+): 361 (M+H).

Example 15

Preparation of (E)-Methyl 2-(4-methyl-6-phenyl-2-styrylpyrimidin-5-yl)pentanoate Methyl 2-(2-chloro-4-methyl-6-phenylpyrimidin-5-yl)pentanoate (308 mg; 0.966 mmol), trans-beta-styrylboronic acid (429 mg; 2.90 mmol) and tetrakis(triphenylphosphine)palladium(0) (112 mg; 0.097 mmol) were placed in a 5 mL reaction tube and dissolved in a mixture of degassed DME (3 mL) and water (1 mL). N,N-Diisopropylethylamine (0.594 mL; 3.86 mmol) was added, the tube was sealed and irradiated in a microwave oven at 100° C. for 30 min. The reaction mixture was partitioned between brine and ethyl acetate, the phases were separated and the water layer was extracted with ethyl acetate. The combined organic layers were dried over magnesium sulphate and concentrated under reduced pressure. The crude material was purified by flash chromatography on silica gel using a linear gradient of ethylacetate (1-10%) in heptane to give 215 mg (54%) of the title compound as a colorless oil. ESI/APCI(+): 387 (M+H); 409 (M+Na). ESI/APCI(−): 385 (M−H). $^1$H NMR (DMSO-d6) δ 7.89 (1H, d); 7.73 (2H, d); 7.34-7.54 (8H, m); 7.26 (1H, d); 3.95 (1H, t); 3.68 (3H, s); 2.45 (3H, s); 1.99 (1H, m); 1.57 (1H, m); 0.94 (2H, m); 0.61 (3H, t).

Example 16

Preparation of (E)-2-(4-methyl-6-phenyl-2-styrylpyrimidin-5-yl)pentanoic acid

A solution of (E)-methyl 2-(4-methyl-6-phenyl-2-styrylpyrimidin-5-yl)pentanoate (73 mg; 0.189 mmol) in ethanol (1 mL), tetrahydrofuran (1 mL) and 2N sodium hydroxide solution (0.944 mL; 1.889 mmol) was stirred for 24 h at room temperature. The reaction mixture was concentrated under reduced pressure, diluted with water and acidified with a 6N hydrochloric acid solution. The formed suspension was extracted twice with ethyl acetate and the organic layers were washed with water and dried by filtration over a phase separater filter (PS1). The crude material was purified first by flash chromatography on silica gel using a linear gradient of methanol (1-10%) in dichloromethane and then by preparative thick layer chromatography on silica gel

132 eluting with 10% methanol in dichloromethane to give 29 mg (40%) of the title compound as a colorless oil. ESI/APCI(+): 373 (M+H).

Example 17

Preparation of Methyl 2-(4-methyl-2-phenethyl-6-phenylpyrimidin-5-yl)pentanoate

To a suspension of (E)-methyl 2-(4-methyl-6-phenyl-2-styrylpyrimidin-5-yl)pentanoate (91 mg; 0.235 mmol) in ethanol (2 mL) was added 10% Pd/C. The solution was deoxygenated and back filled with a nitrogen atmosphere twice. The solution was then degassed, back filled with hydrogen gas and allowed to react at room temperature overnight. The reaction mixture was filtered using a syringe filter and the solvent was removed under reduced pressure. The crude material was purified by flash chromatography on silica gel using a linear gradient of ethylacetate (5-30%) in heptane to give 91 mg of the title compound which was immediately used in the next step. ESI/APCI(+): 389 (M+H).

Example 18

Preparation of 2-(4-methyl-2-phenethyl-6-phenylpyrimidin-5-yl)pentanoic acid

A solution of methyl 2-(4-methyl-2-phenethyl-6-phenylpyrimidin-5-yl)pentanoate (91 mg; 0.235 mmol) in ethanol (1.5 mL), tetrahydrofuran (0.5 mL) and 2N sodium hydroxide solution (1.5 mL; 3.0 mmol) was stirred for 24 h at room temperature. The reaction mixture was concentrated under reduced pressure, diluted with water and acidified with a 6N hydrochloric acid. The suspension was extracted twice with ethyl acetate and the organic layers were washed with water and dried by filtration over a phase separater filter (PS1). The crude material was first purified by flash chromatography on silica gel using a linear gradient of methanol (1-10%) in dichloromethane and then by preparative thick layer chromatography on silica gel eluting with 10% methanol in dichloromethane to give 24 mg (26%) of the title compound as a colorless oil. ESI/APCI(+): 375 (M+H). ESI/APCI(−): 373 (M−H).

Example 19

Preparation of Methyl 2-(2-(2-chlorophenyl)-4-methyl-6-phenylpyrimidin-5-yl)pentanoate Methyl 2-(2-chloro-4-methyl-6-phenylpyrimidin-5-yl)pentanoate (100 mg; 0.314 mmol), 2-chlorophenylboronic acid (73.6 mg; 0.471 mmol) and tetrakis(triphenylphosphine)palladium(0) (36.2 mg; 0.031 mmol) were placed in a 5 mL reaction tube and dissolved in a mixture of degassed DME (1.50 mL) and water (0.5 mL). N,N-Diisopropylethylamine (0.193 mL; 1.255 mmol) was added, the tube was sealed and irradiated in a microwave oven at 130° C. for 1 h. The reaction mixture was partitioned between brine and ethyl acetate, the phases were separated and the water layer was extracted with ethyl acetate. The combined organic layers were dried over magnesium sulphate and concentrated under reduced pressure. The crude material was purified by flash chromatography on silica gel using a linear gradient of ethylacetate (2-20%) in heptane to give 82 mg (66%) of the title compound. ESI/APCI(+): 395 (M+H).

Example 20

Preparation of 2-(2-(2-chlorophenyl)-4-methyl-6-phenylpyrimidin-5-yl)pentanoic acid To a solution of methyl 2-(4-methyl-2-phenyl-6-p-tolylpyrimidin-5-yl)pentanoate (82 mg; 0.208 mmol) in methanol (2.077 mL) was added a 10 N sodium hydroxide solution (208 µL; 2.077 mmol) and the mixture was heated to 100° C. overnight. The reaction mixture was concentrated under reduced pressure, diluted with water and acidified with a 6N hydrochloric acid. The suspension was extracted twice with ethyl acetate and the organic layers were washed with water and dried by filtration over a phase separator filter (PS1). The crude material was purified by flash chromatography on silica gel using a linear gradient of methanol (1-10%) in dichloromethane to give 67 mg (85%) of the title compound. ESI/APCI(+): 381 (M+H). ESI/APCI(−): 379 (M−H).

Example 21

Preparation of Methyl 2-(4-methyl-6-phenyl-2-(piperidin-1-yl)pyrimidin-5-yl)pentanoate Step 1:
A mixture of methyl 2-(2-chloro-4-methyl-6-phenylpyrimidin-5-yl)acetate (200 mg; 0.723 mmol) and piperidine (0.286 mL; 2.89 mmol) in THF (2 mL) was placed in a sealed tube and heated via microwave irradiation at 110° C. for 1 h. The reaction mixture was diluted with a saturated sodium hydrogen carbonate solution and extracted twice with ethyl acetate. The organic layers were combined, washed with brine, dried over magnesium sulphate and concentrated under vacuum. The crude material was purified by flash chromatography on silica gel using a linear gradient of ethylacetate (2-20%) in heptane to give 158 mg (63%) of methyl 2-(4-methyl-6-phenyl-2-(piperidin-1-yl)pyrimidin-5-yl)acetate. ESI/APCI(+): 326 (M+H).
Step 2:
A solution of methyl 2-(4-methyl-6-phenyl-2-(piperidin-1-yl)pyrimidin-5-yl)acetate (150 mg; 0.461 mmol) in dry DMF (2.5 mL) was cooled to −15° C. LHMDS (0.507 mL; 0.507 mmol; 1M in THF) was added dropwise and the mixture was stirred at −15° C. for 15 min followed by the dropwise addition of iodopropane (0.068 mL; 0.691 mmol), After stirring for 2 h at −15° C. the mixture was allowed to warm up to room temperature. After 1 h the reaction was quenched by adding a saturated solution of ammonium chloride. The mixture was extracted twice with ethyl acetate and the combined organic layers were washed with brine, dried over magnesium sulphate and concentrated under reduced pressure. The crude material was purified by flash chromatography on silica gel using a linear gradient of ethylacetate (2-10%) in heptane to give 48 mg (28%) of the title compound as a yellow oil. ESI/APCI(+): 368 (M+H).

Example 22

Preparation of 2-(4-methyl-6-phenyl-2-(piperidin-1-yl)pyrimidin-5-yl)pentanoic acid To a solution of methyl 2-(4-methyl-6-phenyl-2-(piperidin-1-yl)pyrimidin-5-yl)pentanoate (48 mg; 0.131 mmol) in methanol (1.306 mL) was added a 10 N sodium hydroxide solution (131 µL; 1.306 mmol) and the mixture was heated at 100° C. for 18 h. The volatiles were removed under reduced pressure and the residue was dissolved in water, the mixture was then acidified by adding 6N hydrochloric acid until a precipitate formed. The solid was isolated by filtration and dried under reduced pressure over phosphorus pentoxide to give 37 mg (80%) of the title compound as a white solid. ESI/APCI(+): 354 (M+H). $^1$H NMR (DMSO-d6) δ 12.58 (1H, br s); 7.44 (5H, m); 3.71 (4H, m); 3.63 (1H, m); 2.28 (3H, s); 1.88 (1H, m); 1.60 (2H, m); 1.50 (4H, m); 1.43 (1H, m); 0.90 (2H, m); 0.57 (3H, t).

Example 23

Preparation of Methyl 2-(4-methyl-2,6-diphenylpyrimidin-5-yl)pentanoate

Step 1:
Methyl 2-(2-chloro-4-methyl-6-phenylpyrimidin-5-yl)acetate (200 mg; 0.723 mmol), benzeneboronic acid (264 mg; 2.168 mmol), tetrakis(triphenylphosphine) palladium(0) (84 mg; 0.072 mmol) were placed in a 5 mL reaction tube and dissolved in a mixture of degassed DME (3 mL) and water (1 mL). N,N-Diisopropylethylamine (0.444 mL; 2.89 mmol) was added, the tube was sealed and irradiated in a microwave oven at 130° C. for 1 h. The reaction mixture was partitioned between brine and ethyl acetate, the phases were separated and the water layer was extracted with ethyl acetate. The combined organic layers were dried over magnesium sulphate and concentrated under reduced pressure. The crude material was purified by flash chromatography on silica gel using a linear gradient of ethylacetate (5-40%) in heptane to give 212 mg (91%) of methyl 2-(4-methyl-2,6-diphenylpyrimidin-5-yl)acetate as a white solid. ESI/APCI(+): 319 (M+H).
Step 2:
A solution of methyl 2-(4-methyl-2,6-diphenylpyrimidin-5-yl)acetate (150 mg; 0.471 mmol) in dry DMF (2.5 mL) was cooled to −15° C. LHMDS (0.518 mL; 0.518 mmol; 1M in THF) was added dropwise and the mixture was stirred at −15° C. for 15 min followed by the dropwise addition of iodopropane (0.069 mL; 0.707 mmol), after stirring for 2 h at −15° C. the mixture was allowed to warm to room temperature. After 1 h the reaction was quenched by adding a saturated solution of ammonium chloride. The mixture was extracted twice with ethyl acetate and the combined organic layers were washed with brine and dried over magnesium sulphate and concentrated under reduced pressure. The crude material was purified by flash chromatography on silica gel using a linear gradient of ethylacetate (1-10%) in heptane to give 94 mg (54%) of the title compound as a colorless oil. ESI/APCI(+): 361 (M+H).

Example 24

Preparation of 2-(4-methyl-2,6-diphenylpyrimidin-5-yl)pentanoic acid

To a solution of methyl 2-(4-methyl-2,6-diphenylpyrimidin-5-yl)pentanoate (80 mg; 0.222 mmol) in dioxane (1.5 mL) was added a 10 N sodium hydroxide solution (222 µL; 2.219 mmol) and the mixture was heated at 100° C. for 48 h. After removing the solvent under reduced pressure, the residue was dissolved in water, and acidified with a 6N hydrochloric acid. The precipitate was filtered, washed with water and dried under reduced pressure over phosphorus pentoxide to give 62 mg (80%) of the title compound as a white solid. ESI/APCI(+): 347 (M+H). ESI/APCI(−): 713 (2M−H+Na); 301 (M−CO$_2$H).

Example 25

Preparation of Methyl 2-(4-methyl-2,6-dip-tolylpyrimidin-5-yl)pentanoate

Methyl 2-(2-chloro-4-methyl-6-p-tolylpyrimidin-5-yl) pentanoate (100 mg; 0.30 mmol), 4-tolylboronic acid (123 mg; 0.901 mmol) and tetrakis(triphenylphosphine) palladium (0) (34.7 mg; 0.030 mmol) were placed in a 5 mL reaction tube and dissolved in a mixture of degassed DME (1.50 mL) and water (0.5 mL). N,N-diisopropylethylamine (0.185 mL; 1.202 mmol) was added, the tube was sealed and irradiated in a microwave oven at 130° C. for 1 h. The reaction mixture was partitioned between brine and ethyl acetate, the phases were separated and the water layer was extracted with ethyl acetate. The combined organic layers were dried over magnesium sulphate and concentrated under reduced pressure. The crude material was purified by flash chromatography on silica gel using a linear gradient of ethylacetate (2-20%) in heptane to give 86 mg (74%) of the title compound. ESI/APCI(+): 389 (M+H).

Example 26

Preparation of 2-(4-methyl-2,6-dip-tolylpyrimidin-5-yl)pentanoic acid

To a solution of methyl 2-(4-methyl-2,6-dip-tolylpyrimidin-5-yl)pentanoate (86 mg; 0.221 mmol) in methanol (2.214 ml) was added a 10 N sodium hydroxide solution (221 µl; 2.21 mmol) and the mixture was heated at 100° C. overnight. The volatiles were removed under reduced pressure and the mixture was acidified by adding 6N hydrochloric acid. The suspension was extracted twice with ethyl acetate. The combined organic layers were washed with brine, dried over magnesium sulphate and concentrated under reduced pressure.

The compound was precipitated from a mixture of ethyl acetate and heptane and the formed solid was triturated with heptane to give 73 mg (88%) of the title compound as a white solid. ESI/APCI(+): 375 (M+H).

Example 27

Preparation of Methyl 2-(2-(cyclohexyl(methyl) amino)-4-methyl-6-p-tolylpyrimidin-5-yl)pentanoate A mixture of methyl 2-(2-chloro-4-methyl-6-p-tolylpyrimidin-5-yl)pentanoate (100 mg; 0.30 mmol) and N-methylcyclohexanamine (0.158 mL; 1.202 mmol) in THF (1 mL) was placed in a sealed tube and heated at 100° C. for 18 h. The reaction mixture was diluted with a saturated sodium hydrogen carbonate solution and extracted twice with ethyl acetate. The organic layers were combined, washed with brine, dried over magnesium sulphate and concentrated under reduced pressure. The crude material was purified by flash chromatography on silica gel using a linear gradient of ethylacetate (2-20%) in heptane to give 61 mg (49%) of the title compound.

Example 28

Preparation of 2-(2-(cyclohexyl(methyl)amino)-4-methyl-6-p-tolylpyrimidin-5-yl)pentanoic acid To a solution of methyl 2-(2-(cyclohexyl(methyl)amino)-4-methyl-6-p-tolylpyrimidin-5-yl)pentanoate (61 mg; 0.15 mmol) in methanol (1.5 mL) was added a 10 N sodium hydroxide solution (149 µL; 1.489 mmol) and the mixture was heated at 100° C. for 18 h. The volatiles were removed under reduced pressure and the mixture was acidified by adding 6N hydrochloric acid. The suspension was extracted twice with ethyl acetate. The combined organic layers were washed with brine, dried over magnesium sulphate and concentrated under reduced pressure. The compound was precipitated from a mixture of ethyl acetate and heptane and the formed solid was triturated with heptane to give 40 mg (68%) of the title compound as a white solid. ESI/APCI(+): 396 (M+H). ESI/APCI(−): 350 (M−CO$_2$H); 394 (M−H).

Example 29

Preparation of Methyl 2-(4-methyl-2-phenyl-6-p-tolylpyrimidin-5-yl)pentanoate Methyl 2-(2-chloro-4-methyl-6-p-tolylpyrimidin-5-yl) pentanoate (100 mg; 0.30 mmol), benzeneboronic acid (110 mg; 0.901 mmol) and tetrakis(triphenylphosphine) palladium (0) (34.7 mg; 0.030 mmol) were placed in a 5 mL reaction tube and dissolved in a mixture of degassed DME (1.50 mL) and water (0.5 mL). N,N-Diisopropylethylamine (0.185 mL; 1.202 mmol) was added, the tube was sealed and irradiated in a microwave oven at 130° C. for 1 h. The reaction mixture was partitioned between brine and ethyl acetate, the phases were separated and the water layer was extracted with ethyl acetate. The combined organic layers were dried over magnesium sulphate and concentrated under reduced pressure. The crude material was purified by flash chromatography on silica gel using a linear gradient of ethylacetate (1-10%) in heptane to give 100 mg (89%) of the title compound. ESI/APCI(+): 375 (M+H).

Example 30

Preparation of 2-(4-methyl-2-phenyl-6-p-tolylpyrimidin-5-yl)pentanoic acid

To a solution of methyl 2-(4-methyl-2-phenyl-6-p-tolylpyrimidin-5-yl)pentanoate (80 mg; 0.214 mmol) in tetrahydrofuran (2.136 mL) was added a 10 N sodium hydroxide solution (214 µL; 2.136 mmol) and the mixture was heated at 100° C. for 18 h. The volatiles were removed under reduced pressure and the mixture was acidified by adding 6N hydrochloric acid. The suspension was extracted twice with ethyl acetate. The combined organic layers were washed with a saturated sodium chloride solution, dried over magnesium sulphate and concentrated under reduced pressure to give 31 mg (40%) of the title compound as a white solid. ESI/APCI(+): 361 (M+H).

Example 31

Preparation of Methyl 2-(2-(2-chlorophenyl)-4-methyl-6-p-tolylpyrimidin-5-yl)pentanoate Methyl 2-(2-chloro-4-methyl-6-p-tolylpyrimidin-5-yl) pentanoate (100 mg; 0.300 mmol), 2-chlorophenylboronic acid (141 mg; 0.901 mmol), tetrakis(triphenylphosphine) palladium(0) (34.7 mg; 0.030 mmol) were placed in a 5 mL reaction tube and dissolved in a mixture of degassed DME (1.50 mL) and water (0.5 mL). N,N-Diisopropylethylamine (0.185 mL; 1.202 mmol) was added, the tube was sealed and irradiated in a microwave oven at 130° C. for 40 min. The reaction mixture was partitioned between brine and ethyl acetate, the phases were separated and the water layer was extracted with ethyl acetate. The combined organic layers were dried over magnesium sulphate and concentrated under reduced pressure. The crude material was purified by flash chromatography on silica gel using a linear gradient of ethylacetate (2-20%) in heptane to give 100 mg (81%) of the title compound. ESI/APCI(+): 409 (M+H).

Example 32

Preparation of 2-(2-(2-chlorophenyl)-4-methyl-6-p-tolylpyrimidin-5-yl)pentanoic acid To a solution of methyl 2-(2-(2-chlorophenyl)-4-methyl-6-p-tolylpyrimidin-5-yl)pentanoate (27 mg; 0.066 mmol) in methanol (660 µL) was added a 10 N sodium hydroxide solution (66 µL; 0.66 mmol) and the mixture was heated at 100° C. for 18 h. The volatiles were removed under reduced pressure and the mixture was acidified by adding 6N hydrochloric acid. The suspension was extracted twice with ethyl acetate. The combined organic layers were washed with a saturated sodium chloride solution, dried over magnesium sulphate and concentrated under reduced pressure to give 19 mg (72%) of the title compound as a white solid. ESI/APCI(+): 395 (M+H).

Example 33

Preparation of Methyl 2-(4-methyl-2-(piperidin-1-yl)-6-p-tolylpyrimidin-5-yl)pentanoate Step 1:
A mixture of methyl 2-(2-chloro-4-methyl-6-phenylpyrimidin-5-yl)acetate (200 mg; 0.688 mmol) and piperidine (0.272 mL; 2.75 mmol) in THF (2 mL) was placed in a sealed tube and heated under microwave irradiation at 110° C. for 1 h. The reaction mixture was diluted with a saturated sodium hydrogen carbonate solution and extracted twice with ethyl acetate. The organic layers were combined, washed with brine, dried over magnesium sulphate and concentrated under reduced pressure. The crude material was purified by flash chromatography on silica gel using a linear gradient of ethylacetate (2-20%) in heptane to give 186 mg (87%) of methyl 2-(4-methyl-2-(piperidin-1-yl)-6-p-tolylpyrimidin-5-yl)acetate. ESI/APCI(+): 340 (M+H).
Step 2:
A solution of methyl 2-(4-methyl-2-(piperidin-1-yl)-6-p-tolylpyrimidin-5-yl)acetate (160 mg; 0.471 mmol) in dry DMF (2.5 mL) was cooled to −15° C. LHMDS (0.519 mL; 0.519 mmol; 1M in THF) was added dropwise and the mixture was stirred at −15° C. for 15 min followed by the dropwise addition of iodopropane (0.069 mL; 0.707 mmol), after stirring for 2 h at −15° C. the mixture was allowed to warm up to room temperature. After 1 h the reaction was quenched by adding a saturated solution of ammonium chloride. The mixture was extracted twice with ethyl acetate and the combined organic layers were washed with brine, dried over magnesium sulphate and concentrated under reduced pressure. The crude material was purified by flash chromatography on silica gel using a linear gradient of ethylacetate (2-10%) in heptane to give 63 mg (34%) of the title compound as a yellow oil. ESI/APCI(+): 382 (M+H).

Example 34

Preparation of 2-(4-methyl-2-(piperidin-1-yl)-6-p-tolylpyrimidin-5-yl)pentanoic acid To a solution of methyl 2-(4-methyl-2-(piperidin-1-yl)-6-p-tolylpyrimidin-5-yl)pentanoate (63 mg; 0.16 mmol) in methanol (1.651 mL) was added a 10 N sodium hydroxide solution (165 µL; 1.651 mmol) and the mixture was heated at 100° C. for 18 h. The volatiles were removed under reduced pressure and the residue was dissolved in water, the mixture was then acidified by adding 6N hydrochloric acid until a precipitate formed. The solid was isolated by filtration and dried under reduced pressure over phosphorus pentoxide to give 47.6 mg (77%) of the title compound as a white solid. ESI/APCI(+): 368 (M+H). ESI/APCI(−): 366. 1H NMR (DMSO-d6) δ 7.29 (4H, m); 3.71 (4H, m); 3.68 (1H, m); 2.35 (3H, s); 2.28 (3H, s); 1.89 (1H, m); 1.60 (2H, m); 1.50 (4H, m); 1.44 (1H, m); 0.89 (2H, m); 0.59 (3H, t).

Example 35

Preparation of methyl 2-(4-(3-(methoxymethoxy)phenyl)-6-methyl-2-phenylpyrimidin-5-yl)pentanoate Step 1:
To a suspension of methyl 2-(2,4-dichloro-6-methylpyrimidin-5-yl)acetate (0.5 g; 2.127 mmol) in a mixture of degassed DME (75 mL) and water (25 mL) was added 3-hydroxyphenylboronic acid (0.587 g; 4.25 mmol), tetrakis(triphenylphosphine) palladium(0) (0.246 g; 0.213 mmol) and diisopropyl ethylamine (1.466 ml; 8.51 mmol). The reaction was heated under reflux for 3.5 h. The reaction mixture was partitioned between brine and ethyl acetate. The phases were separated and the water layer was extracted with ethyl acetate. The combined organic layers were dried with magnesium sulphate and concentrated under reduced pressure. The crude material was purified by flash chromatography on silica gel using a linear gradient of ethylacetate (5-40%) in heptane to give 189 mg (28%) of the title compound as a white solid. ESI/APCI(+): 293 (M+H).
Step 2:
Methyl 2-(2-chloro-4-(3-hydroxyphenyl)-6-methylpyrimidin-5-yl)acetate (189 mg; 0.646 mmol), benzeneboronic acid (236 mg; 1.937 mmol) and tetrakis(triphenylphosphine) palladium(0) (74.6 mg; 0.065 mmol) were placed in a 5 mL reaction tube and dissolved in a mixture of degassed DME (2.40 mL) and water (0.80 mL). N,N-Diisopropylethylamine (0.397 mL, 2.58 mmol) was added, the tube was sealed and irradiated in a microwave oven at 130° C. for 30 min. The reaction mixture was partitioned between brine and ethyl acetate, the phases were separated and the water layer was extracted with ethyl acetate. The combined organic layers were dried over magnesium sulphate and concentrated under reduced pressure. The crude material was purified by flash chromatography on silica gel using a linear gradient of ethylacetate (10-80%) in heptane to give 172 mg (75%) of the title compound. ESI/APCI(+): 335 (M+H).
Step 3:
Methyl 2-(4-(3-hydroxyphenyl)-6-methyl-2-phenylpyrimidin-5-yl)acetate (150 mg; 0.449 mmol), bromo(methoxy)methane (73.3 µL; 0.897 mmol) and N,N-Diisopropylethylamine (116 µL; 0.673 mmol) were added to a flask at room temperature, dissolved in tetrahydrofuran (449 µL) and heated to reflux for 1 h. The reaction mixture was cooled to room temperature. The salts were removed by filtration and the filtrate was washed with water, brine, dried over magnesium sulphate and concentrated under reduced pressure. The crude material was purified by flash chromatography on silica gel using a linear gradient of ethylacetate (10-80%) in heptane to give 86 mg (49%) of the title compound as a colorless oil. ESI/APCI(+): 378 (M+H).

Step 4:

A solution of methyl 2-(4-(3-(methoxymethoxy)phenyl)-6-methyl-2-phenylpyrimidin-5-yl)acetate (79 mg; 0.209 mmol) in dry DMF (1 mL) was cooled to −15° C. (acetone/ice). LHMDS (0.230 mL; 0.230 mmol; 1M in THF) was added dropwise and the mixture was stirred at −15° C. for 15 min followed by the dropwise addition of iodopropane (0.031 mL; 0.313 mmol), after stirring for 2 h at −15° C. the mixture was allowed to warm to room temperature. After 1 h the reaction was quenched by adding a saturated solution of ammonium chloride. The mixture was extracted twice with ethyl acetate and the combined organic layers were washed with brine, dried over magnesium sulphate and concentrated under reduced pressure. The crude material was purified by flash chromatography on silica gel using a linear gradient of ethylacetate (2-10%) in heptane to give 65 mg (73%) of the title compound as a colorless oil. ESI/APCI(+): 421 (M+H).

Example 36

Preparation of 2-(4-(3-hydroxyphenyl)-6-methyl-2-phenylpyrimidin-5-yl)pentanoic acid Methyl 2-(4-(3-(methoxymethoxy)phenyl)-6-methyl-2-phenylpyrimidin-5-yl)pentanoate (60 mg; 0.143 mmol) was dissolved in methanol (1.5 mL) and 12N hydrochloric acid (10 μL; 0.120 mmol) was added. The mixture was heated at 60° C. for 3 h until the deprotection was finished (monitored by TLC). The mixture was basified with an excess 10N sodium hydroxide solution and stirred in a sealed tube at 80° C. for 18 h. The volatiles were removed under reduced pressure, the residue was dissolved in water and acidified with a 6N hydrochloric acid solution. The precipitate was filtered, washed with water and dried under reduced pressure over phosphorus pentoxide to give 37 mg (71%) of the title compound as a yellowish solid. ESI/APCI(+): 363 (M+H). ESI/APCI(−): 723 (2M−H).

Example 37

Preparation of Methyl 2-(4-methyl-2-morpholino-6-p-tolylpyrimidin-5-yl)pentanoate Methyl 2-(4-methyl-2-morpholino-6-p-tolylpyrimidin-5-yl)pentanoate was prepared according to the general method A starting from morpholine (0.107 mL; 1.20 mmol) and methyl 2-(2-chloro-4-methyl-6-p-tolylpyrimidin-5-yl)pentanoate (0.100 g; 0.239 mmol) in tetrahydrofuran (2 mL). Purification by flash-chromatography on silica gel using a gradient of ethyl acetate (5-25%) in heptane furnished 74 mg (81%) of the title compound as an oil. ESI/APCI(+): 384 (M+H).

Example 38

Preparation of 2-(4-methyl-2-morpholino-6-p-tolylpyrimidin-5-yl)pentanoic acid 2-(4-methyl-2-morpholino-6-p-tolylpyrimidin-5-yl)pentanoic acid was prepared according to the general method B starting from methyl 2-(4-methyl-2-morpholino-6-p-tolylpyrimidin-5-yl)pentanoate (71 mg; 0.185 mmol). 58 mg (85%) of the title compound was obtained as a white solid. ESI/APCI(+): 370 (M+H). ESI/APCI(−): 368 (M−H).

Example 39

Preparation of Methyl 2-(4-methyl-2-(4-methylpiperazin-1-yl)-6-p-tolylpyrimidin-5-yl)pentanoate Methyl 2-(4-methyl-2-(4-methylpiperazin-1-yl)-6-p-tolylpyrimidin-5-yl)pentanoate was prepared according to the general method A starting from 1-methylpiperazine (0.132 mL; 1.18 mmol) and methyl 2-(2-chloro-4-methyl-6-p-tolylpyrimidin-5-yl)pentanoate (0.098 g; 0.235 mmol) in tetrahydrofuran (2 mL). Purification by flash-chromatography on silica gel using a gradient of methanol (0-6%) in dichloromethane furnished 68 mg (74%) of the title compound as an oil. ESI/APCI(+): 397 (M+H)a). ESI/APCI(−): 395 (M−H).

Example 40

Preparation of Methyl 2-(4-methyl-2-(pyrrolidin-1-yl)-6-p-tolylpyrimidin-5-yl)pentanoate Methyl 2-(4-methyl-2-(pyrrolidin-1-yl)-6-p-tolylpyrimidin-5-yl)pentanoate was prepared according to the general method A starting from pyrrolidine (0.111 mL; 1.32 mmol) and methyl 2-(2-chloro-4-methyl-6-p-tolylpyrimidin-5-yl)pentanoate (0.110 g; 0.264 mmol) in tetrahydrofuran (2 mL). Purification by flash-chromatography on silica gel using a gradient of ethyl acetate (5-20%) in heptane furnished 90 mg (93%) of the title compound as an oil. ESI/APCI(+): 368 (M+H), 390 (M+Na). ESI/APCI(−): 366 (M−H).

Example 41

Preparation of Methyl 2-(2-(azepan-1-yl)-4-methyl-6-p-tolylpyrimidin-5-yl)pentanoate Methyl 2-(2-(azepan-1-yl)-4-methyl-6-p-tolylpyrimidin-5-yl)pentanoate was prepared according to the general method A starting from azepane (0.152 mL; 1.32 mmol) and methyl 2-(2-chloro-4-methyl-6-p-tolylpyrimidin-5-yl)pentanoate (0.110 g; 0.264 mmol) in tetrahydrofuran (2 mL). Purification by flash-chromatography on silica gel using a gradient of ethyl acetate (5-15%) in heptane furnished 91 mg (87%) of the title compound as an oil. ESI/APCI(+): 396(M+H), 418 (M+Na). ESI/APCI(−): 394 (M−H).

Example 42

Preparation of 2-(2-(azepan-1-yl)-4-methyl-6-p-tolylpyrimidin-5-yl)pentanoic acid 2-(2-(azepan-1-yl)-4-methyl-6-p-tolylpyrimidin-5-yl)pentanoic acid was prepared according to the general method B starting from methyl 2-(2-(azepan-1-yl)-4-methyl-6-p-tolylpyrimidin-5-yl)pentanoate (90 mg; 0.227 mmol). 64 mg (74%) of the title compound was obtained as a white solid. ESI/APCI(+): 382 (M+H). ESI/APCI(−): 380(M−H).

Example 43

Preparation of Methyl 2-(2-(3,5-dimethylpiperidin-1-yl)-4-methyl-6-p-tolylpyrimidin-5-yl)pentanoate Methyl 2-(2-(3,5-dimethylpiperidin-1-yl)-4-methyl-6-p-tolylpyrimidin-5-yl)pentanoate was prepared according to the general method A starting from 3,5-Dimethylpiperidine (0.183 mL; 1.32 mmol) and methyl 2-(2-chloro-4-methyl-6- p-tolylpyrimidin-5-yl)pentanoate (0.110 g; 0.264 mmol) in tetrahydrofuran (2 mL). Purification by flash-chromatography on silica gel using a gradient of ethyl acetate (5-15%) in heptane furnished 100 mg (92%) of the title compound as an oil. ESI/APCI(+): 410 (M+H), 432 (M+Na). ESI/APCI(−): 408 (M−H).

Example 44

Preparation of 2-(4-methyl-2-(4-methylpiperazin-1-yl)-6-p-tolylpyrimidin-5-yl)pentanoic acid To a solution of methyl 2-(4-methyl-2-(4-methylpiperazin-1-yl)-6-p-tolylpyrimidin-5-yl)pentanoate (0.042 g; 0.105 mmol) in methanol (2 mL) was added a solution of sodium hydroxide 5N (0.131 mL; 0.656 mmol) and the reaction mixture was heated to reflux for 48 h. The volatiles were removed under reduced pressure, the residue dissolved in water and the pH was adjusted to 5 by addition of a solution of hydrochloric acid 2N. The formed precipitate was collected by filtration and dried under reduced pressure. Purification by preparative HPLC (HPLC method 4) furnished 0.043 g (58%) of the title compound as a solid.
ESI/APCI(+): 383 (M+H);
ESI/APCI(−): 381 (M−H), 337 (M−CO$_2$).

Example 45

Preparation of 2-(4-methyl-2-(pyrrolidin-1-yl)-6-p-tolylpyrimidin-5-yl)pentanoic acid To a solution of methyl 2-(4-methyl-2-(pyrrolidin-1-yl)-6-p-tolylpyrimidin-5-yl)pentanoate (0.090 g; 0.227 mmol) in methanol (3 mL) was added a solution of sodium hydroxide 5N (0.490 mL; 2.45 mmol) and the reaction mixture was heated to reflux for 18 h. The volatiles were removed under reduced pressure, the residue was dissolved in water and the pH of the solution was adjusted between 2 and 3 by addition of a solution of hydrochloric acid 6N. The formed precipitate was collected by filtration and dried under reduced pressure over P$_2$O$_5$ to give 0.058 g (67%) of the title compound as a white solid.
ESI/APCI(+): 354 (M+H).

Example 46

Preparation of 2-(2-(3,5-dimethylpiperidin-1-yl)-4-methyl-6-p-tolylpyrimidin-5-yl)pentanoic acid To a solution of methyl 2-(2-(3,5-dimethylpiperidin-1-yl)-4-methyl-6-p-tolylpyrimidin-5-yl)pentanoate (0.090 g; 0.227 mmol) in methanol (3 mL) was added a solution of sodium hydroxide 5N (0.488 mL; 2.44 mmol) and the reaction mixture was heated to reflux for 18 h. The volatiles were removed under reduced pressure, the residue was dissolved in water and the pH of the solution was adjusted between 2 and 3 by addition of a solution of hydrochloric acid 6N. The formed precipitate was collected by filtration and dried under reduced pressure over P$_2$O$_5$ to give 0.067 g (69%) of the title compound as a white solid.
ESI/APCI(+): 396 (M+H).

Example 47

Preparation of Methyl 2-(2-(3-(isobutylcarbamoyl)piperidin-1-yl)-4-methyl-6-p-tolylpyrimidin-5-yl)pentanoate A mixture of methyl 2-(2-chloro-4-methyl-6-p-tolylpyrimidin-5-yl)pentanoate (0.100 g; 0.300 mmol), N-isobutylpiperidine-3-carboxamide hydrochloride (0.198 g; 0.901 mmol) and triethylamine (0.211 mL; 1.50 mmol) in a mixture of tetrahydrofuran (2 mL) and DMF (0.4 mL) was heated at 110° C. in a sealed tube for 18 h. After cooling, the reaction mixture was diluted in a saturated solution of sodium hydrogen carbonate and extracted twice with ethyl acetate. The organic layer was washed with brine, dried over sodium sulphate, filtered and concentrated under reduced pressure. Purification by flash-chromatography on silica gel using a gradient of ethyl acetate (2-40%) in heptane (with 0.5% of triethyl amine) furnished 0.150 g (quantitative) of the title compound as a yellow oil.
ESI/APCI(+): 481 (M+H) (M+Na).

Example 48

Preparation of 2-(2-(3-(isobutylcarbamoyl)piperidin-1-yl)-4-methyl-6-p-tolylpyrimidin-5-yl)pentanoic acid To a solution of methyl 2-(2-(3-(isobutylcarbamoyl)piperidin-1-yl)-4-methyl-6-p-tolylpyrimidin-5-yl)pentanoate (0.150 g; 0.191 mmol) in methanol (4.60 mL) was added a solution sodium hydroxide 5% (4.60 mL, 5.75 mmol) and the reaction mixture stirred at room temperature for 4 days, then heated for 18 h at 50° C. The volatiles were removed under reduced pressure, the residue was dissolved in water and the aqueous solution was washed with diethylether (3 times). The pH of the aqueous solution was adjusted between 2 and 3 by addition of a solution of hydrochloric acid 6N and the formed precipitate was collected by filtration. Purification by preparative HPLC (HPLC method 4) furnished 0.10 g (11%) of the title compound as a white solid.
ESI/APCI(+): 467 (M+H);
ESI/APCI(−): 465 (M−H).

Example 49

Preparation of Methyl 2-(4-methyl-2-(3-methylpiperidin-1-yl)-6-p-tolylpyrimidin-5-yl)pentanoate A mixture of methyl 2-(2-chloro-4-methyl-6-p-tolylpyrimidin-5-yl)pentanoate (0.100 g; 0.300 mmol), 3-methylpiperidine (0.106 mL; 0.901 mmol) and triethylamine (0.211 mL; 1.50 mmol) in a mixture of tetrahydrofuran (2 mL) and DMF (0.4 mL) was heated at 110° C. in a sealed tube for 18 h. After cooling, the reaction mixture was diluted in a saturated solution of sodium hydrogen carbonate and extracted twice with ethyl acetate. The organic layer was washed with brine, dried over sodium sulphate, filtered and concentrated under reduced pressure. Purification by flash-chromatography on silica gel using a gradient of ethyl acetate (2-20%) in heptane furnished 0.067 g (57%) of the title compound as a yellow oil.
ESI/APCI(+): 396 (M+H).

Example 50

Preparation of 2-(4-methyl-2-(3-methylpiperidin-1-yl)-6-p-tolylpyrimidin-5-yl)pentanoic acid To a solution of methyl 2-(4-methyl-2-(3-methylpiperidin-1-yl)-6-p-tolylpyrimidin-5-yl)pentanoate (0.067 g; 0.169 mmol) in methanol (4.1 mL) was added a solution of sodium hydroxide 5% (4.1 mL, 5.12 mmol) and the mixture was stirred at room temperature for 4 days. The volatiles were removed under reduced pressure, the residue dissolved in water and the pH was adjusted between 2 and 3 by addition of a solution of hydrochloric acid 6N. The formed precipitate was collected by filtration. Purification by preparative HPLC (HPLC method 3) furnished 0.004 g (6%) of the title compound as a solid.

ESI/APCI(+): 382 (M+H).
ESI/APCI(−): 380 (M−H).

Example 51

Preparation of 2-(6-methyl-4-oxo-2-thio-1,2,3,4-tetrahydropyrimidin-5-yl)pentanoic acid To a suspension of sodium methoxide (9.19 g; 170.17 mmol) in methanol (100 mL) were added thiourea (6.80 g; 89.08 mmol) and diethyl 2-acetyl-3-propylsuccinate (purity ca 66%; 33.30 g; 85.08 mmol). The mixture was heated under reflux (oil bath 80° C.) for 21 h and, then concentrated under reduced pressure. The residue was triturated in diethyl ether (400 mL) and the formed precipitate was collected by filtration, suspended in diethyl ether (100 mL) and acidified with a solution of hydrochloric acid (4N in dioxane) (40 mL). The mixture was stirred at room temperature for 30 min and the precipitate was collected by filtration and dried under reduced pressure at 50° C. to give 9.95 g of a white solid, which was used as such in the next step. The filtrate was concentrated under reduced pressure to furnish 4.56 g of the title compound, as an oily residue (67% global yield).

ESI/APCI(−): 241 (M−H).

Example 52

Preparation of 2-(6-methyl-2,4-dioxo-1,2,3,4-tetrahydropyrimidin-5-yl)pentanoic acid A solution of 2-chloroacetic acid (8.85 g; 93.69 mmol) in water (100 mL) was added to 2-(6-methyl-4-oxo-2-thio-1,2,3,4-tetrahydropyrimidin-5-yl)pentanoic acid (4.54 g; 18.74 mmol) and the mixture was heated to reflux for 20 h. After cooling, the reaction mixture was extracted several times with ethyl acetate, the organics were combined, dried over magnesium sulphate and concentrated under reduced pressure to give 6.82 g of a crude oil, which was used in the next step without further purification.

ESI/APCI(+): 227 (M+H); 249 (M+Na);
ESI/APCI(−): 225(M−H).

Example 53

Preparation of Methyl 2-(6-methyl-2,4-dioxo-1,2,3,4-tetrahydropyrimidin-5-yl)pentanoate To a cold (0° C.) solution of 2-(6-methyl-2,4-dioxo-1,2,3,4-tetrahydropyrimidin-5-yl)pentanoic acid (4.24 g; 18.74 mmol) was added thionyl chloride (27.27 mL; 374.84 mmol) dropwise in methanol (70 mL). The mixture was refluxed for 48 h and then concentrated under reduced pressure to give 3.46 g (77%) of the title compound as an oil.

ESI/APCI(+): 241 (M+H); 263 (M+Na);
ESI/APCI(−): 239 (M−H).

Example 54

Preparation of 2-(2,4-dichloro-6-methylpyrimidin-5-yl)pentanoate

To a solution of methyl 2-(6-methyl-2,4-dioxo-1,2,3,4-tetrahydropyrimidin-5-yl)pentanoate (3.35 g; 13.94 mmol) in phosphorus oxychloride (19.50 mL; 209.15 mmol) was added N,N-dimethylaniline (2.46 mL; 19.52 mmol) and the reaction mixture was heated at 115° C. for 2 h. after cooling, the excess of phosphorus oxychloride was removed under reduced pressure and crushed-ice was added to the residue. The mixture was extracted with diethyl ether (3×50 mL) and the combined organics were washed with a saturated solution of sodium chloride, dried over magnesium sulphate, filtered and concentrated under reduced pressure. Purification by flash chromatography on silica gel using a gradient of ethyl acetate (5-40%) in heptane furnished 0.843 g (22%) of the title compound as a yellow oil.

ESI/APCI(+): 277 (M+H).

Example 55

Preparation of Methyl 2-(2-chloro-4-methyl-6-p-tolylpyrimidin-5-yl)pentanoate

To a suspension of mixture of methyl 2-(2,4-dichloro-6-methylpyrimidin-5-yl)pentanoate (2.56 g, 7.18 mmol) in a degassed mixture of 1,2-dimethoxyethane-water (3:1, 60 mL) were added p-tolylboronic acid (1.51 g; 10.77 mmol), tetrakis(triphenylphosphine)palladium (0.846 g; 0.732 mmol) and diisopropylethylamine (5 mL; 28.70 mmol). The resulting mixture was heated at 90° C. for 2 h. After cooling, the reaction mixture was partitioned between brine and ethyl acetate, the phases were separated and the aqueous layer was extracted with ethyl acetate. The combined organic extracts were dried over magnesium sulphate, filtered and concentrated under reduced pressure. Purification by flash-chromatography on silica gel using a gradient of ethyl acetate (3-20%) in heptane furnished 0.935 g (27%) of the title compound as an oil.

ESI/APCI(+): 333 (M+H).

Example 56

Preparation of Methyl 2-(2-(3,4-dihydroisoquinolin-2(1H)-yl)-4-methyl-6-p-tolylpyrimidin-5-yl)pentanoate This compound was prepared according to the method C from methyl 2-(2-chloro-4-methyl-6-p-tolylpyrimidin-5-yl)pentanoate (0.095 g; 0.285 mmol), 1,2,3,4-tetrahydroisoquinoline (0.108 mL; 0.856 mmol) and triethyl amine (0.200 mL; 1.43 mmol) in tetrahydrofuran (2 mL). Purification by flash-chromatography on silica gel using a gradient of ethyl acetate (2-30%) in heptane furnished 0.072 g (58%) of the titled compound as a colorless oil.

ESI/APCI(+): 430 (M+H).

Example 57

Preparation of 2-(2-(3,4-dihydroisoquinolin-2(1H)-yl)-4-methyl-6-p-tolylpyrimidin-5-yl)pentanoic acid A solution of sodium hydroxide 5N (1 mL) was added to a mixture of methyl 2-(2-(3,4-dihydroisoquinolin-2(1H)-yl)-4-methyl-6-p-tolylpyrimidin-5-yl)pentanoate (0.072 g; 0.168 mmol) in methanol (1 mL). The mixture was heated in a sealed tube at 100° C. for 18 h and then concentrated under reduced pressure. The residue was dissolved in water and the pH of the solution was adjusted between 2 and 3 by addition of a solution of hydrochloric acid 6N. The precipitate was collected by filtration and dried under reduced pressure over phosphorus pentoxide to give 0.050 g (72%) of the title compound as a yellow solid.
ESI/APCI(+): 416 (M+H);
ESI/APCI(−): 414 (M−H).

Example 58

Preparation of Methyl 2-(2-(4-benzyl-1,4-diazepan-1-yl)-4-methyl-6-p-tolylpyrimidin-5-yl)pentanoate This compound was prepared according to the method C from methyl 2-(2-chloro-4-methyl-6-p-tolylpyrimidin-5-yl)pentanoate (0.095 g; 0.285 mmol), 1-benzyl-1,4-diazepane (0.178 g, 0.937 mmol) and triethyl amine (0.200 mL; 1.43 mmol) in tetrahydrofuran (2 mL). Purification by flash chromatography on silica gel using a gradient of ethyl acetate (2-30%) in heptane furnished 0.083 g (54%) of the titled compound as a colorless oil.
ESI/APCI(+): 487 (M+H).

Example 59

Preparation of 2-(2-(4-benzyl-1,4-diazepan-1-yl)-4-methyl-6-p-tolylpyrimidin-5-yl)pentanoic acid A solution of sodium hydroxide 5N (0.5 mL) was added to a mixture of methyl 2-(2-(4-benzyl-1,4-diazepan-1-yl)-4-methyl-6-p-tolylpyrimidin-5-yl)pentanoate (0.083 g; 0.195 mmol) in methanol (1.5 mL). The mixture was heated in a sealed tube at 100° C. for 18 h and then concentrated under reduced pressure. The residue was dissolved in water and the pH of the solution was adjusted between 3 and 4 by addition of a solution of hydrochloric acid 6N. The precipitate was collected by filtration and dried under reduced pressure over phosphorus pentoxide to give 0.020 g (25%) of the title compound as a white solid.
ESI/APCI(+): 473 (M+H).

Example 60

Preparation of Methyl 2-(2-(3-(3-isopropyl-1,2,4-oxadiazol-5-yl)piperidin-1-yl)-4-methyl-6-p-tolylpyrimidin-5-yl)pentanoate This compound was prepared according to the method C from methyl 2-(2-chloro-4-methyl-6-p-tolylpyrimidin-5-yl)pentanoate (0.095 g; 0.285 mmol), 3-isopropyl-5-(piperidin-3-yl)-1,2,4-oxadiazole (0.167 g; 0.856 mmol) and triethyl amine (0.200 mL; 1.43 mmol) in tetrahydrofuran (2 mL). Purification by flash chromatography on silica gel using a gradient of ethyl acetate (2-30%) in heptane furnished 0.026 g (18%) of the titled compound as a colorless oil.
ESI/APCI(+): 492 (M+H); 514 (M+Na).

Example 61

Preparation of 2-(2-(3-(3-isopropyl-1,2,4-oxadiazol-5-yl)piperidin-1-yl)-4-methyl-6-p-tolylpyrimidin-5-yl)pentanoic acid A solution of sodium hydroxide 5N (1 mL) was added to a mixture of methyl 2-(2-(3-(3-isopropyl-1,2,4-oxadiazol-5-yl)piperidin-1-yl)-4-methyl-6-p-tolylpyrimidin-5-yl)pentanoate (0.026 g; 0.053 mmol) in methanol (1 mL). The mixture was heated in a sealed tube at 100° C. for 18 h and then concentrated under reduced pressure. The residue was dissolved in water and the pH of the solution was adjusted between 2 and 3 by addition of a solution of hydrochloric acid 6N. The precipitate was collected by filtration and dried under reduced pressure over phosphorus pentoxide to give 0.084 g (33%) of the title compound as a white solid.
ESI/APCI(+): 478 (M+H);
ESI/APCI(−): 476 (M−H).

Example 62

Preparation of Methyl 2-(4-methyl-2-(3-phenoxypiperidin-1-yl)-6-p-tolylpyrimidin-5-yl)pentanoate This compound was prepared according to the method C from methyl 2-(2-chloro-4-methyl-6-p-tolylpyrimidin-5-yl)pentanoate (0.095 g; 0.285 mmol), 3-phenoxypiperidine (0.152 g; 0.856 mmol) and triethyl amine (0.200 mL; 1.43 mmol) in tetrahydrofuran (2 mL). Purification by flash chromatography on silica gel using a gradient of ethyl acetate (2-30%) in heptane furnished 0.026 g (38%) of the titled compound as a colorless oil.
ESI/APCI(+): 474 (M+H), 496 (M+Na).

Example 63

Preparation of 2-(4-methyl-2-(3-phenoxypiperidin-1-yl)-6-p-tolylpyrimidin-5-yl)pentanoic acid A solution of sodium hydroxide 5N (1 mL) was added to a mixture of methyl 2-(4-methyl-2-(3-phenoxypiperidin-1-yl)-6-p-tolylpyrimidin-5-yl)pentanoate (0.050 g; 0.053 mmol) in methanol (1 mL). The mixture was heated in a sealed tube at 100° C. for 18 h and then concentrated under reduced pressure. The residue was dissolved in water and the pH of the solution was adjusted between 2 and 3 by addition of a solution of hydrochloric acid 6N. The aqueous layer was extracted with ethyl acetate, dried and concentrated under reduced pressure. Purification by preparative HPLC (HPLC method 4) furnished 0.013 g (26%) of the title compound as a white solid.
ESI/APCI(+): 460 (M+H);
ESI/APCI(−): 458 (M−H).

Example 64

Preparation of Methyl 2-(4-methyl-2-(3-phenylpiperidin-1-yl)-6-p-tolylpyrimidin-5-yl)pentanoate A mixture of methyl 2-(2-chloro-4-methyl-6-p-tolylpyrimidin-5-yl)pentanoate (0.104 g; 0.312 mmol), 3-phenylpiperidine (0.151 g; 0.937 mmol) and triethylamine (0.220 mL; 1.56 mmol) in tetrahydrofuran (2 mL) was heated to 110° C. in a sealed tube for 5 h. The reaction mixture was diluted with a saturated solution of hydrogen carbonate and extracted twice with ethyl acetate. The organic layers were washed with brine, dried over sodium sulphate, filtered and concentrated under reduced pressure. Purification by flash-chromatography on silica gel using a gradient of ethyl acetate (2-15%) in heptane furnished 0.047 g (33%) of the title compound as a colorless oil.
ESI/APCI(+): 458 (M+H).

Example 65

Preparation of 2-(4-methyl-2-(3-phenylpiperidin-1-yl)-6-p-tolylpyrimidin-5-yl)pentanoic acid A solution of sodium hydroxide 5N (0.5 mL) was added to a mixture of methyl 2-(4-methyl-2-(3-phenylpiperidin-1-yl)-

6-p-tolylpyrimidin-5-yl)pentanoate (0.047 g; 0.103 mmol) in methanol (1.5 mL). The mixture was heated in a sealed tube at 100° C. for 18 h and then concentrated under reduced pressure. The residue was dissolved in water and the pH of the solution was adjusted between 3 and 4 by addition of a solution of hydrochloric acid 6N. The aqueous layer was extracted with ethyl acetate, dried over sodium sulphate, filtered and concentrated under reduced pressure. Purification by preparative HPLC (HPLC method 4) furnished 0.014 g (31%) of the title compound as a white solid.

ESI/APCI(+): 444 (M+H);
ESI/APCI(−): 442 (M−H).

Example 66

Preparation of Methyl 2-(2-[(S)-3-(dimethylamino) pyrrolidin-1-yl]-4-methyl-6-p-tolylpyrimidin-5-yl) pentanoate A mixture of methyl 2-(2-chloro-4-methyl-6-p-tolylpyrimidin-5-yl)pentanoate (0.104 g; 0.312 mmol), (R)-N,N-dimethylaminopyrrolidine (0.119 mL; 0.937 mmol) and triethyl amine (0.220 mL; 1.56 mmol) in tetrahydrofuran (2 mL) was heated at 110° C. in a sealed tube for 5 h. The mixture was diluted with a saturated solution of sodium hydrogencarbonate, extracted twice with ethyl acetate and the combined organic layers were washed with brine, dried over sodium sulphate, filtered and concentrated under reduced pressure. Purification by flash-chromatography on silica gel using a gradient of methanol (1-10%) in dichloromethane furnished 0.053 g (42%) of the title compound as a colorless oil.

ESI/APCI(+): 411 (M+H).

Example 67

Preparation of 2-(2-((S)-3-(dimethylamino)pyrrolidin-1-yl)-4-methyl-6-p-tolylpyrimidin-5-yl)pentanoic acid A solution of sodium hydroxide 5N (0.5 mL) was added to a mixture of methyl 2-(2-((R)-3-(dimethylamino)pyrrolidin-1-yl)-4-methyl-6-p-tolylpyrimidin-5-yl)pentanoate (0.053 g; 0.116 mmol) in methanol (1.5 mL). The mixture was heated in a sealed tube at 100° C. for 18 h and then concentrated under reduced pressure. The residue was dissolved in water and the pH of the solution was adjusted between 3 and 4 by addition of a solution of hydrochloric acid 6N. The aqueous layer was extracted with ethyl acetate and concentrated under reduced pressure. Purification by preparative HPLC (HPLC method 5) furnished 0.007 g (14%) of the title compound as a white solid.

ESI/APCI(+): 397 (M+H);
ESI/APCI(−): 395(M−H).

Example 68

Preparation of Methyl 2-(2-(4-benzamidopiperidin-1-yl)-4-methyl-6-p-tolylpyrimidin-5-yl)pentanoate A mixture of methyl 2-(2-chloro-4-methyl-6-p-tolylpyrimidin-5-yl)pentanoate (0.104 g; 0.312 mmol), N-(piperidin-4-yl)benzamide (0.191 g; 0.937 mmol) and triethyl amine (0.220 mL; 1.56 mmol) in tetrahydrofuran (2 mL) was heated at 110° C. in a sealed tube for 5 h. The reaction mixture was diluted with a saturated solution of sodium hydrogen carbonate, extracted twice with ethyl acetate. The combined organic layers were washed with brine, dried over sodium sulphate, filtered and concentrated under reduced pressure. Purification by flash-chromatography on silica gel using a gradient of ethyl acetate (15-80%) in heptane furnished 0.049 g (34%) of the title compound as a colorless oil.

ESI/APCI(+): 501(M+H).

Example 69

Preparation of 2-(2-(4-benzamidopiperidin-1-yl)-4-methyl-6-p-tolylpyrimidin-5-yl)pentanoic acid A solution of sodium hydroxide 5N (1 mL) was added to a mixture of methyl 2-(2-(4-benzamidopiperidin-1-yl)-4-methyl-6-p-tolylpyrimidin-5-yl)pentanoate (0.049 g; 0.0979 mmol) in methanol (1.5 mL). The mixture was heated in a sealed tube at 100° C. for 18 h and then concentrated under reduced pressure. The residue was dissolved in water and the pH of the solution was adjusted between 3 and 4 by addition of a solution of hydrochloric acid 6N. The precipitate was collected by filtration and was purified by preparative HPLC (HPLC method 4) furnished 0.024 g (51%) of the title compound as a white solid.

ESI/APCI(+): 487 (M+H);
ESI/APCI(−): 485 (M−H).

Example 70

Preparation of Methyl 2-(2-(4-ethyl-1,4-diazepan-1-yl)-4-methyl-6-p-tolylpyrimidin-5-yl)pentanoate A mixture of methyl 2-(2-chloro-4-methyl-6-p-tolylpyrimidin-5-yl)pentanoate (0.104 g; 0.312 mmol), 1-ethyl-1,4-diazepane (0.120 g; 0.937 mmol) and triethyl amine (0.220 mL; 1.56 mmol) in tetrahydrofuran (2 mL) was heated at 110° C. in a sealed tube for 5 h. The mixture was diluted with a saturated solution of sodium hydrogencarbonate, extracted twice with ethyl acetate. The combined organic layers were washed with brine, dried over sodium sulphate, filtered and concentrated under reduced pressure. Purification by flash-chromatography on silica gel using a gradient of methanol (1-30%) in dichloromethane furnished 0.030 g (21%) of the title compound as a brown oil.

ESI/APCI(+): 425 (M+H).

Example 71

Preparation of 2-(2-(4-ethyl-1,4-diazepan-1-yl)-4-methyl-6-p-tolylpyrimidin-5-yl)pentanoic acid A solution of sodium hydroxide 5N (0.5 mL) was added to a mixture of methyl 2-(2-(4-ethyl-1,4-diazepan-1-yl)-4-methyl-6-p-tolylpyrimidin-5-yl)pentanoate (0.030 g; 0.070 mmol) in methanol (1.5 mL). The mixture was heated in a sealed tube at 100° C. for 18 h and then concentrated under reduced pressure. The residue was dissolved in water and the pH of the solution was adjusted between 3 and 4 by addition of a solution of hydrochloric acid 6N. The aqueous layer was extracted with ethyl acetate and concentrated under reduced pressure. The crude mixture was purified by preparative HPLC (HPLC method 5) furnished 0.016 g (60%) of the title compound as a white solid.

ESI/APCI(+): 411 (M+H);
ESI/APCI(−): 409 (M−H).

Example 72

Preparation of Methyl 2-(2-(indolin-1-yl)-4-methyl-6-p-tolylpyrimidin-5-yl)pentanoate A solution of methyl 2-(2-chloro-4-methyl-6-p-tolylpyrimidin-5-yl)pentanoate (0.104 g; 0.312 mmol), N,N-diisopropylethylamine (0.122 mL; 0.781 mmol), sodium iodide (0.047 mg; 0.312 mmol) and indoline (0.074 mL; 0.625 mmol) in a mixture of 1-methylpyrrolidin-2-one (0.5 mL) and acetonitrile (0.5 mL) was irradiated in a microwave oven at 160° C. for 30 min. The solution was partitioned between ethyl acetate and water and the organic layer was washed with a saturated solution of sodium thiosulphate, dried over sodium sulphate, filtered and concentrated under reduced pressure. Purification by flash-chromatography on silica using a gradient of ethyl acetate (2-20%) in heptane furnished 0.040 g (31%) of the title compound as a yellow oil.
ESI/APCI(+): 416 (M+H).

Example 73

Preparation of 2-(2-(indolin-1-yl)-4-methyl-6-p-tolylpyrimidin-5-yl)pentanoic acid A solution of sodium hydroxide 5N (0.5 mL) was added to a mixture of methyl 2-(2-(indolin-1-yl)-4-methyl-6-p-tolylpyrimidin-5-yl)pentanoate (0.040 g; 0.096 mmol) in methanol (1.5 mL). The mixture was heated in a sealed tube at 100° C. for 18 h and then concentrated under reduced pressure. The residue was dissolved in water and the pH of the solution was adjusted between 3 and 4 by addition of a solution of hydrochloric acid 6N. The precipitate was collected by filtration, dried under reduced pressure over phosphorous pentoxide and purified by preparative HPLC (HPLC method 5) furnished 0.010 g (25%) of the title compound as a white solid.
ESI/APCI(+): 402 (M+H);
ESI/APCI(−): 400 (M−H).

Example 74

Preparation of Methyl 2-(4-chloro-6-methyl-2-phenylpyrimidin-5-yl)pentanoate

To a suspension of methyl 2-(4-methyl-6-oxo-2-phenyl-1,6-dihydropyrimidin-5-yl)pentanoate (0.900 g; 3 mmol) in dry toluene (6 mL) under a nitrogen atmosphere were carefully added phosphorus oxychloride (3 mL), dimethylaniline (0.3 mL) and the reaction mixture was heated to reflux for 3 h. The volatiles were removed under reduced pressure, the residue was cooled down in an ice-bath and quenched by adding crushed-ice and a saturated solution of sodium hydrogencarbonate until neutralization. The product was extracted with ethyl acetate, the combined organics were dried over magnesium sulphate, filtered and concentrated under reduced pressure. Purification by flash-chromatography on silica gel using a gradient of ethyl acetate (2-40%) in heptane furnished 0.701 g (73%) of the title compound as a colorless oil.
ESI/APCI(+): 319 (M+H).

Example 75

Preparation of Methyl 2-(4-methyl-2-phenyl-6-(piperidin-1-yl)pyrimidin-5-yl)pentanoate Piperidine (0.198 mL; 2.00 mmol) was added to a solution of methyl 2-(4-chloro-6-methyl-2-phenylpyrimidin-5-yl)pentanoate (0.159 g; 0.5 mmol) in tetrahydrofuran (1.5 mL) and the reaction mixture was irradiated in a microwave oven at 100° C. for 30 min. The mixture was diluted with a saturated solution of sodium hydrogen carbonate and was extracted with ethyl acetate. The combined organics were washed with brine, dried over magnesium sulphate and concentrated under reduced pressure. Purification by flash-chromatography on silica gel using a gradient of ethyl acetate (2-40%) in heptane furnished 0.094 g (51%) of the title compound.
ESI/APCI(+): 368 (M+H).

Example 76

Preparation of 2-(4-methyl-2-phenyl-6-(piperidin-1-yl)pyrimidin-5-yl)pentanoic acid This compound was prepared according to general method D from methyl 2-(4-methyl-2-phenyl-6-(piperidin-1-yl)pyrimidin-5-yl)pentanoate (0.094 g; 0.256 mmol), a solution of sodium hydroxide 10N (0.256 mL; 2.56 mmol) in methanol (2.5 mL) to afford 0.050 g (56%) of the title compound as a white solid.
ESI/APCI(+): 354 (M+H);
ESI/APCI(−): 308 (M−CO$_2$H).

Example 77

Preparation of Methyl 2-(4-(azepan-1-yl)-6-methyl-2-phenylpyrimidin-5-yl)pentanoate Azepane (0.113 mL; 1.00 mmol) and triethylamine (0.277 mL; 2.00 mmol) were added to a solution of methyl 2-(4-chloro-6-methyl-2-phenylpyrimidin-5-yl)pentanoate (0.159 g; 0.5 mmol) in tetrahydrofuran (1.5 mL). The reaction vessel was sealed and heated at 100° C. for 18 h. The mixture was diluted with a saturated solution of sodium hydrogen carbonate and was extracted with ethyl acetate. The combined organics were washed with brine, dried over magnesium sulphate, filtered and concentrated under reduced pressure. Purification by flash-chromatography on silica gel using a gradient of ethyl acetate (2-40%) in heptane furnished 0.092 g (98%) of the title compound.
ESI/APCI(+): 382 (M+H).

Example 78

Preparation of 2-(4-(azepan-1-yl)-6-methyl-2-phenylpyrimidin-5-yl)pentanoic acid This compound was prepared according to general method D from methyl 2-(4-(azepan-1-yl)-6-methyl-2-phenylpyrimidin-5-yl)pentanoate (0.084 g; 0.220 mmol), sodium hydroxide 10N solution (0.220 mL; 2.2 mmol) in methanol (2.2 mL) to afford 0.058 g (69%) of the title compound as a white solid.
ESI/APCI(+): 368 (M+H);
ESI/APCI(−): 322 (M−CO$_2$H).

Example 79

Preparation of Methyl 2-(4-methyl-6-(4-methylpiperazin-1-yl)-2-phenylpyrimidin-5-yl)pentanoate 1-methylpiperazine (0.111 mL, 1.00 mmol) and triethylamine (0.277 mL; 2.00 mmol) were added to a solution of methyl 2-(4-chloro-6-methyl-2-phenylpyrimidin-5-yl)pen-

Example 80

Preparation of 2-(4-methyl-6-(4-methylpiperazin-1-yl)-2-phenylpyrimidin-5-yl)pentanoic acid This compound was prepared according to general method D from methyl 2-(4-methyl-6-(4-methylpiperazin-1-yl)-2-phenylpyrimidin-5-yl)pentanoate (0.120 g; 0.314 mmol), sodium hydroxide 10N (0.314 mL; 3.14 mmol) in methanol (3 mL) to afford 0.055 g (48%) of the title compound as a white solid.

ESI/APCI(+): 369 (M+H);
ESI/APCI(−): 323 (M−$CO_2$H).

Example 81

Preparation of Methyl 2-(4-(3,4-dimethylphenyl)-6-methyl-2-phenylpyrimidin-5-yl)pentanoate This compound was prepared according to general method E from methyl 2-(4-chloro-6-methyl-2-phenylpyrimidin-5-yl)pentanoate (0.159 g; 0.5 mmol) tetrakis(triphenylphosphine) palladium(0) (0.058 mg; 0.05 mmol), N,N-diisopropylethylamine (0.345 mL; 2 mmol) and 3,4-dimethylphenylboronic acid (0.225 g; 1.5 mmol) in DME-water (2 mL) for 1 h. Purification by flash-chromatography on silica gel using a gradient of ethyl acetate (2-40%) in heptane furnished 0.138 g (71%) of the title compound.

ESI/APCI(+): 389 (M+H).

Example 82

Preparation of 2-(4-(3,4-dimethylphenyl)-6-methyl-2-phenylpyrimidin-5-yl)pentanoic acid This compound was prepared according to general method D from methyl 2-(4-(3,4-dimethylphenyl)-6-methyl-2-phenylpyrimidin-5-yl)pentanoate (0.083 g; 0.214 mmol), sodium hydroxide 10N (0.214 mL; 2.14 mmol) in methanol (2 mL) to afford 0.066 g (81%) of the title compound as a white solid.

ESI/APCI(+): 375 (M+H).

Example 83

Preparation of Methyl 2-(4-methyl-6-(naphthalen-2-yl)-2-phenylpyrimidin-5-yl)pentanoate This compound was prepared according to general method E from methyl 2-(4-chloro-6-methyl-2-phenylpyrimidin-5-yl)pentanoate (0.159 g; 0.5 mmol), tetrakis(triphenylphosphine) palladium(0) (0.058 mg; 0.05 mmol), N,N-Diisopropylethylamine (0.345 mL; 2 mmol) and naphthalen-2-ylboronic acid (0.258 g; 1.5 mmol) in DME-water (2 mL) for 30 min. Purification by flash-chromatography on silica gel using a gradient of ethyl acetate (2-40%) in heptane furnished 0.147 g (71%) of the title compound.

ESI/APCI(+): 411 (M+H).

Example 84

Preparation of 2-(4-methyl-6-(naphthalen-2-yl)-2-phenylpyrimidin-5-yl)pentanoic acid This compound was prepared according to general method D from methyl 2-(4-methyl-6-(naphthalen-2-yl)-2-phenylpyrimidin-5-yl)pentanoate (0.090 g; 0.219 mmol), sodium hydroxide 10N (0.219 mL; 2.19 mmol) in methanol (2 mL) to afford 0.080 g (92%) of the title compound as a white solid.

ESI/APCI(+): 397 (M+H).

Example 85

Preparation of Methyl 2-(4-(2,3-dihydrobenzofuran-5-yl)-6-methyl-2-phenylpyrimidin-5-yl)pentanoate This compound was prepared according to general method E from methyl 2-(4-chloro-6-methyl-2-phenylpyrimidin-5-yl)pentanoate (0.159 g; 0.5 mmol), tetrakis(triphenylphosphine) palladium(0) (0.058 mg; 0.05 mmol), N,N-diisopropylethylamine (0.345 mL; 2 mmol) and 2,3-dihydrobenzofuran-5-ylboronic acid (0.246 g; 1.5 mmol) in DME-water (2 mL) for 30 min. Purification by flash-chromatography on silica gel using a gradient of ethyl acetate (2-40%) in heptane furnished 0.184 g (91%) of the title compound.

ESI/APCI(+): 403 (M+H).

Example 86

Preparation of 2-(4-(2,3-dihydrobenzofuran-5-yl)-6-methyl-2-phenylpyrimidin-5-yl)pentanoic acid This compound was prepared according to general method D from methyl 2-(4-(2,3-dihydrobenzofuran-5-yl)-6-methyl-2-phenylpyrimidin-5-yl)pentanoate (0.100 g; 0.248 mmol), sodium hydroxide 10N solution (0.248 mL; 2.48 mmol) in methanol (2.5 mL) to afford 0.089 g (91%) of the title compound as a white solid.

ESI/APCI(+): 389 (M+H).

Example 87

Preparation of Methyl 2-(4-(benzofuran-5-yl)-6-methyl-2-phenylpyrimidin-5-yl)pentanoate This compound was prepared according to general method E from methyl 2-(4-chloro-6-methyl-2-phenylpyrimidin-5-yl)pentanoate (0.159 g; 0.5 mmol), tetrakis(triphenylphosphine) palladium(0) (0.058 mg; 0.05 mmol), N,N-diisopropylethylamine (0.345 mL; 2 mmol) and 2-(benzofuran-5-yl)-4,4,5,5-tetramethyl-1,3,2-dioxaborolane (0.366 g; 1.5 mmol) in DME-water (2 mL) for 30 min. Purification by flash-chromatography on silica gel using a gradient of ethyl acetate (2-40%) in heptane furnished 0.171 g (85%) of the title compound.

ESI/APCI(+): 401 (M+H).

[continued from previous page] tanoate (0.159 g; 0.5 mmol) in tetrahydrofuran (1.5 mL). the reaction vessel was heated at 100° C. for 18 h. The mixture was diluted with a saturated solution of sodium hydrogen carbonate and was extracted with ethyl acetate. The combined organics were washed with brine, dried over magnesium sulphate, filtered and concentrated under reduced pressure. Purification by flash-chromatography on silica gel using a gradient of ethyl acetate (60-100%) in heptane furnished 0.120 g (63%) of the title compound.

ESI/APCI(+): 383 (M+H).

Example 88

Preparation of 2-(4-(benzofuran-5-yl)-6-methyl-2-phenylpyrimidin-5-yl)pentanoic acid This compound was prepared according to general method D from methyl 2-(4-(benzofuran-5-yl)-6-methyl-2-phenylpyrimidin-5-yl)pentanoate (0.114 g; 0.285 mmol), sodium hydroxide 10N (0.285 mL; 2.85 mmol) in methanol (3 mL) to afford 0.094 g (81%) of the title compound as a white solid.

ESI/APCI(+): 387 (M+H).

Example 89

Preparation of Methyl 2-(4-methyl-6-(1-methyl-1H-indol-5-yl)-2-phenylpyrimidin-5-yl)pentanoate This compound was prepared according to general method E from methyl 2-(4-chloro-6-methyl-2-phenylpyrimidin-5-yl)pentanoate (0.159 g; 0.5 mmol), tetrakis(triphenylphosphine) palladium(0) (0.058 mg; 0.05 mmol), N,N-diisopropylethylamine (0.345 mL; 2 mmol) and 1-methyl-5-(4,4,5,5-tetramethyl-1,3,2-dioxaborolan-2-yl)-1H-indole (0.321 g; 1.25 mmol) in DME-water (2 mL) for 30 min. Purification by flash-chromatography on silica gel using a gradient of ethyl acetate (5-40%) in heptane furnished 0.142 g (69%) of the title compound.

ESI/APCI(+): 414 (M+H).

Example 90

Preparation of 2-(4-methyl-6-(1-methyl-1H-indol-5-yl)-2-phenylpyrimidin-5-yl)pentanoic acid This compound was prepared according to general procedure D from methyl 2-(4-methyl-6-(1-methyl-1H-indol-5-yl)-2-phenylpyrimidin-5-yl)pentanoate (0.106 g; 0.256 mmol), sodium hydroxide 10N (0.256 mL; 2.56 mmol) in methanol (2.5 mL) to afford 0.079 g (76%) of the title compound as a white solid.

ESI/APCI(+): 400 (M+H).

Example 91

Preparation of Methyl 2-(4-(3,4-dihydroisoquinolin-2(1H)-yl)-6-methyl-2-phenylpyrimidin-5-yl)pentanoate 1,2,3,4-tetrahydroisoquinoline (0.190 mL, 1.5 mmol) and triethylamine (0.277 mL; 2 mmol) were added to a solution of methyl 2-(4-chloro-6-methyl-2-phenylpyrimidin-5-yl)pentanoate (0.159 g; 0.5 mmol) in tetrahydrofuran (1.5 mL) and heated in a sealed tube to 100° C. for 18 h. The mixture was diluted with a saturated solution of sodium hydrogen carbonate and extracted with ethyl acetate. The combined organics were washed with brine, dried over magnesium sulphate, filtered and concentrated under reduced pressure. Purification by flash-chromatography on silica gel using a gradient of ethyl acetate (5-40%) in heptane furnished 0.194 g (93%) of the title compound.

ESI/APCI(+): 416 (M+H).

Example 92

Preparation of 2-(4-(3,4-dihydroisoquinolin-2(1H)-yl)-6-methyl-2-phenylpyrimidin-5-yl)pentanoic acid This compound was prepared according to general method D from methyl 2-(4-(3,4-dihydroisoquinolin-2(1H)-yl)-6-methyl-2-phenylpyrimidin-5-yl)pentanoate (0.110 g; 0.265 mmol), sodium hydroxide 10N (0.265 mL; 2.65 mmol) in methanol (2.6 mL) to afford 0.073 g (69%) of the title compound as a white solid.

ESI/APCI(+): 402 (M+H).

Example 93

Preparation of Methyl 2-(4-methyl-6-phenoxy-2-phenylpyrimidin-5-yl)pentanoate

Phenol (0.141 g; 1.5 mmol) and cesium carbonate (0.489 g; 1.5 mmol) were added to a solution of methyl 2-(4-chloro-6-methyl-2-phenylpyrimidin-5-yl)pentanoate (0.159 g; 0.5 mmol) in tetrahydrofuran (1.5 mL) and heated in a seal tube to 100° C. for 18 h. The mixture was diluted with a saturated solution of sodium hydrogen carbonate and was extracted with ethyl acetate. The combined organics were washed with brine, dried over magnesium sulphate, filtered and concentrated under reduced pressure. Purification by flash-chromatography on silica gel using a gradient of ethyl acetate (2-40%) in heptane furnished 0.129 g (58%) of the title compound.

ESI/APCI(+): 377 (M+H).

Example 94

Preparation of 2-(4-methyl-6-phenoxy-2-phenylpyrimidin-5-yl)pentanoic acid

This compound was prepared according to general method D from methyl 2-(4-methyl-6-phenoxy-2-phenylpyrimidin-5-yl)pentanoate (0.082 g; 0.218 mmol), sodium hydroxide 10N (0.218 mL; 2.18 mmol) in methanol (2 mL) to afford 0.056 g (68%) of the title compound as a white solid.

ESI/APCI(+): 363 (M+H);
ESI/APCI(−): 361 (M−H).

Example 95

Preparation of Methyl 2-(4-(1H-indol-5-yl)-6-methyl-2-phenylpyrimidin-5-yl)pentanoate This compound was prepared according to general method E from methyl 2-(4-chloro-6-methyl-2-phenylpyrimidin-5-yl)pentanoate (0.159 g; 0.5 mmol), tetrakis(triphenylphosphine) palladium(0) (0.058 mg; 0.05 mmol), N,N-diisopropylethylamine (0.345 mL; 2 mmol) and 1H-indol-5-ylboronic acid (0.201 g; 1.25 mmol) in DME-water (2 mL) for 30 min. Purification by flash-chromatography on silica gel using a gradient of ethyl acetate (5-40%) in heptane furnished 0.161 g (81%) of the title compound.

ESI/APCI(+): 400 (M+H).

Example 96

Preparation of 2-(4-(1H-indol-5-yl)-6-methyl-2-phenylpyrimidin-5-yl)pentanoic acid This compound was prepared according to general method D from methyl 2-(4-(1H-indol-5-yl)-6-methyl-2-phenylpyrimidin-5-yl)pentanoate (0.098 g; 0.245 mmol), sodium hydroxide 10N (0.245 mL; 2.45 mmol) in methanol (2.5 mL) to afford 0.047 g (48%) of the title compound as a white solid.
ESI/APCI(+): 386 (M+H).

Example 97

Preparation of methyl 2-(4-(1H-indol-6-yl)-6-methyl-2-phenylpyrimidin-5-yl)pentanoate This compound was prepared according to general method E from methyl 2-(4-chloro-6-methyl-2-phenylpyrimidin-5yl)pentanoate (0.159 g; 0.5 mmol), tetrakis(triphenylphosphine) palladium(0) (0.058 mg; 0.05 mmol), N,N-diisopropylethylamine (0.345 mL; 2 mmol) and 1H-indol-6-ylboronic acid (0.201 g; 1.25 mmol) in DME-water (2 mL) for 30 min. Purification by flash-chromatography on silica gel using a gradient of ethyl acetate (5-40%) in heptane furnished 0.165 g (83%) of the title compound.
ESI/APCI(+): 400 (M+H);
ESI/APCI(−): 398 (M−H).

Example 98

Preparation of 2-(4-(1H-indol-6-yl)-6-methyl-2-phenylpyrimidin-5-yl)pentanoic acid This compound was prepared according to general method D from methyl 2-(4-(1H-indol-6-yl)-6-methyl-2-phenylpyrimidin-5-yl)pentanoate (0.108 g; 0.270 mmol), sodium hydroxide 10N (0.270 mL; 2.7 mmol) in methanol (2.7 mL). Purification by flash-chromatography on silica gel using a gradient of methanol (1-10%) in dichloromethane furnished 0.055 g (52%) of the title compound as a white solid.
ESI/APCI(+): 386 (M+H);
ESI/APCI(−): 769 (2M−H).

Example 99

Preparation of Methyl 2-(4-(3,4-dihydro-2H-benzo[b][1,4]dioxepin-7-yl)-6-methyl-2-phenylpyrimidin-5-yl)pentanoate This compound was prepared according to general method E from methyl 2-(4-chloro-6-methyl-2-phenylpyrimidin-5-yl)pentanoate (0.08 g; 0.25 mmol), tetrakis(triphenylphosphine) palladium(0) (0.029 mg; 0.025 mmol), N,N-diisopropylethylamine (0.173 mL; 1 mmol) and 3,4-dihydro-2H-benzo[b][1,4]dioxepin-7-ylboronic acid (0.097 g; 0.5 mmol) in DME-water (2 mL) for 30 min. Purification by flash-chromatography on silica gel using a gradient of ethyl acetate (2-40%) in heptane furnished 0.092 g (75%) of the title compound.
ESI/APCI(+): 433 (M+H).

Example 100

Preparation of 2-(4-(3,4-dihydro-2H-benzo[b][1,4]dioxepin-7-yl)-6-methyl-2-phenylpyrimidin-5-yl)pentanoic acid This compound was prepared according to general method D from methyl 2-(4-(3,4-dihydro-2H-benzo[b][1,4]dioxepin-7-yl)-6-methyl-2-phenylpyrimidin-5-yl)pentanoate (0.092 g; 0.213 mmol), sodium hydroxide 10N (0.213 mL; 2.13 mmol) in methanol (2.1 mL). Purification by flash-chromatography on silica gel using a gradient of methanol (1-10%) in dichloromethane furnished 0.063 g (70%) of the title compound as an oil.
ESI/APCI(+): 419 (M+H);
ESI/APCI(−): 373 (M−CO₂H); 835 (2M−H); 857 (2M−2H+Na).

Example 101

Preparation of Methyl 2-(4-methyl-6-(4-methyl-3,4-dihydro-2H-benzo[b][1,4]oxazin-7-yl)-2-phenylpyrimidin-5-yl)pentanoate This compound was prepared according to general method E from methyl 2-(4-chloro-6-methyl-2-phenylpyrimidin-5-yl)pentanoate (0.08 g; 0.25 mmol), tetrakis(triphenylphosphine) palladium(0) (0.029 mg; 0.025 mmol), N,N-diisopropylethylamine (0.173 mL; 1 mmol) and 4-methyl-7-(4,4,5,5-tetramethyl-1,3,2-dioxaborolan-2-yl)-3,4-dihydro-2H-benzo[b][1,4]oxazine (0.138 g; 0.5 mmol) in DME-water (2 mL) for 30 min. Purification by flash-chromatography on silica gel using a gradient of ethyl acetate (2-40%) in heptane furnished 0.075 g (68%) of the title compound.
ESI/APCI(+): 432 (M+H).

Example 102

Preparation of 2-(4-methyl-6-(4-methyl-3,4-dihydro-2H-benzo[b][1,4]oxazin-7-yl)-2-phenylpyrimidin-5-yl)pentanoic acid This compound was prepared according to general method D from methyl 2-(4-methyl-6-(4-methyl-3,4-dihydro-2H-benzo[b][1,4]oxazin-7-yl)-2-phenylpyrimidin-5-yl)pentanoate (0.075 g; 0.174 mmol), sodium hydroxide 10N (0.174 mL; 1.74 mmol) in methanol (1.7 mL) to afford 0.059 g (80%) of the title compound as a white solid.
ESI/APCI(+): 418 (M+H).

Example 103

Preparation of Methyl 2-(4-(benzo[b]thiophen-5-yl)-6-methyl-2-phenylpyrimidin-5-yl)pentanoate This compound was prepared according to general method E from methyl 2-(4-chloro-6-methyl-2-phenylpyrimidin-5-yl)pentanoate (0.08 g; 0.25 mmol), tetrakis(triphenylphosphine) palladium(0) (0.029 mg; 0.025 mmol), N,N-diisopropylethylamine (0.173 mL; 1 mmol) and 2-(benzo[b]thiophen-5-yl)-4,4,5,5-tetramethyl-1,3,2-dioxaborolane (0.131 g; 0.5 mmol) in DME-water (2 mL) for 30 min. Purification by flash-chromatography on silica gel using a gradient of ethyl acetate (2-40%) in heptane furnished 0.047 g (42%) of the title compound.
ESI/APCI(+): 417 (M+H).

Example 104

Preparation of 2-(4-(benzo[b]thiophen-5-yl)-6-methyl-2-phenylpyrimidin-5-yl)pentanoic acid 2 This compound was prepared according to general method D from methyl 2-(4-(benzo[b]thiophen-5-yl)-6-methyl-2-phenylpyrimidin-5-yl)pentanoate (0.047 g; 0.113 mmol), sodium hydroxide 10N (0.113 mL; 1.13 mmol) in methanol (1.1 mL) to afford 0.037 g (79%) of the title compound as a white solid.
ESI/APCI(+): 403 (M+H).

Example 105

Preparation of Methyl 2-(4-(chroman-6-yl)-6-methyl-2-phenylpyrimidin-5-yl)pentanoate This compound was prepared according to general method E from methyl 2-(4-chloro-6-methyl-2-phenylpyrimidin-5-yl)pentanoate (0.08 g; 0.25 mmol), tetrakis(triphenylphosphine) palladium(0) (0.029 mg; 0.025 mmol), N,N-diisopropylethylamine (0.173 mL; 1 mmol) and 2-(chroman-6-yl)-4,4,5,5-tetramethyl-1,3,2-dioxaborolane (0.131 g; 0.5 mmol) in DME-water (2 mL) for 30 min. Purification by flash-chromatography on silica gel using a gradient of ethyl acetate (2-40%) in heptane furnished 0.094 g (86%) of the title compound.
ESI/APCI(+): 417 (M+H).

Example 106

Preparation of 2-(4-(chroman-6-yl)-6-methyl-2-phenylpyrimidin-5-yl)pentanoic acid This compound was prepared according to general method D from methyl 2-(4-(chroman-6-yl)-6-methyl-2-phenylpyrimidin-5-yl)pentanoate (0.094 g; 0.226 mmol), sodium hydroxide 10N (0.226 mL; 2.26 mmol) in methanol (2.2 mL) to afford 0.070 g (74%) of the title compound as a white solid.
ESI/APCI(+): 403 (M+H).

Example 107

Preparation of Methyl 2-(4-methyl-6-(1-methyl-1H-indol-6-yl)-2-phenylpyrimidin-5-yl)pentanoate This compound was prepared according to general method E from methyl 2-(4-chloro-6-methyl-2-phenylpyrimidin-5-yl)pentanoate (0.08 g; 0.25 mmol), tetrakis(triphenylphosphine) palladium(0) (0.029 mg; 0.025 mmol), N,N-diisopropylethylamine (0.173 mL; 1 mmol) and 1-methyl-6-(4,4,5,5-tetramethyl-1,3,2-dioxaborolan-2-yl)-1H-indole (0.129 g; 0.5 mmol) in DME-water (2 mL) for 30 min. Purification by flash-chromatography on silica gel using a gradient of ethyl acetate (2-40%) in heptane furnished 0.076 g (61%) of the title compound.
ESI/APCI(+): 414 (M+H).

Example 108

Preparation of 2-(4-methyl-6-(1-methyl-1H-indol-6-yl)-2-phenylpyrimidin-5-yl)pentanoic acid This compound was prepared according to general method D from methyl 2-(4-methyl-6-(1-methyl-1H-indol-6-yl)-2-phenylpyrimidin-5-yl)pentanoate (0.076 g; 0.184 mmol), sodium hydroxide 10N (0.184 mL; 1.838 mmol) in methanol (1.8 mL) to afford 0.058 g (75%) of the title compound as a white solid.
ESI/APCI(+): 400 (M+H).

Example 109

Preparation of Methyl 2-(4-(4-chloro-2-fluorophenyl)-6-methyl-2-phenylpyrimidin-5-yl)pentanoate To a suspension of methyl 2-(4-chloro-6-methyl-2-phenylpyrimidin-5-yl)pentanoate (0.159 g; 0.5 mmol), tetrakis(triphenylphosphine) palladium(0) (0.059 mg; 0.05 mmol), and 4-chloro-2-fluorophenylboronic acid (0.131 g; 0.75 mmol) in a mixture of DME-water (2 mL) was added N,N-diisopropylethylamine (0.345 mL; 2 mmol) and the mixture was heated in a sealed tube to 100° C. for 3 h. The mixture was diluted with brine and extracted with ethyl acetate. The combined organics were dried over magnesium sulphate, filtered and concentrated under reduced pressure. Purification by flash-chromatography on silica gel using a gradient of ethyl acetate (2-40%) in heptane furnished 0.164 g (75%) of the title compound.
ESI/APCI(+): 413 (M+H).

Example 110

Preparation of 2-(4-(4-chloro-2-fluorophenyl)-6-methyl-2-phenylpyrimidin-5-yl)pentanoic acid This compound was prepared according to general method D from methyl 2-(4-(4-chloro-2-fluorophenyl)-6-methyl-2-phenylpyrimidin-5-yl)pentanoate (0.164 g; 0.397 mmol), sodium hydroxide 10N (0.397 mL; 3.97 mmol) in methanol (4 mL) to afford 0.082 g (49%) of the title compound as a white solid.
ESI/APCI(+): 399 (M+H).

Example 111

Preparation of Methyl 2-(4-methyl-6-(1-methylindolin-5-yl)-2-phenylpyrimidin-5-yl)pentanoate This compound was prepared according to general method E from methyl 2-(4-chloro-6-methyl-2-phenylpyrimidin-5-yl)pentanoate (0.08 g; 0.25 mmol), tetrakis(triphenylphosphine) palladium(0) (0.029 mg; 0.025 mmol), N,N-diisopropylethylamine (0.173 mL; 1 mmol) and 1-methyl-5-(4,4,5,5-tetramethyl-1,3,2-dioxaborolan-2-yl)indoline (0.130 g; 0.5 mmol) in DME-water (2 mL) for 30 min. Purification by flash-chromatography on silica gel using a gradient of ethyl acetate (2-40%) in heptane furnished 0.064 g (58%) of the title compound.
ESI/APCI(+): 416 (M+H).

Example 112

Preparation of 2-(4-methyl-6-(1-methylindolin-5-yl)-2-phenylpyrimidin-5-yl)pentanoic acid This compound was prepared according to general method D from methyl 2-(4-methyl-6-(1-methylindolin-5-yl)-2-phenylpyrimidin-5-yl)pentanoate (0.064 g; 0.154 mmol), sodium hydroxide 10N (0.154 mL; 1.54 mmol) in methanol (1.5 mL). Purification by flash-chromatography on silica gel using a gradient of methanol (1-10%) in dichloromethane followed by a purification by preparative HPLC (HPLC method 1) furnished 0.029 g (45%) of the title compound as a red oil.
ESI/APCI(+): 402 (M+H).

Example 113

Preparation of Methyl 2-(4-(2-fluoro-4-methylphenyl)-6-methyl-2-phenylpyrimidin-5-yl)pentanoate This compound was prepared according to general method E from methyl 2-(4-chloro-6-methyl-2-phenylpyrimidin-5-yl)pentanoate (0.08 g; 0.25 mmol), tetrakis(triphenylphosphine) palladium(0) (0.029 mg; 0.025 mmol), N,N-diisopropylethylamine (0.173 mL; 1 mmol) and 2-fluoro-4-methylphenylboronic acid (0.077 g; 0.5 mmol) in DME-water (2 mL) for 30 min. Purification by flash-chromatography on silica gel using a gradient of ethyl acetate (2-20%) in heptane furnished 0.067 g (67%) of the title compound.

ESI/APCI(+): 393 (M+H).

Example 114

Preparation of 2-(4-(2-fluoro-4-methylphenyl)-6-methyl-2-phenylpyrimidin-5-yl)pentanoic acid This compound was prepared according to general method D from methyl 2-(4-(2-fluoro-4-methylphenyl)-6-methyl-2-phenylpyrimidin-5-yl)pentanoate (0.067 g; 0.171 mmol), sodium hydroxide 10N (0.171 mL; 1.71 mmol) in methanol (1.7 mL) to afford 0.056 g (86%) of the title compound as a white solid.

ESI/APCI(+): 379 (M+H).

Example 115

Preparation of Methyl 2-(4-methyl-6-(2-oxo-2,3-dihydro-1H-benzo[d]imidazol-5-yl)-2-phenylpyrimidin-5-yl)pentanoate This compound was prepared according to general method E from methyl 2-(4-chloro-6-methyl-2-phenylpyrimidin-5-yl)pentanoate (0.159 g; 0.5 mmol), tetrakis(triphenylphosphine) palladium(0) (0.059 mg; 0.05 mmol), N,N-diisopropylethylamine (0.345 mL; 2 mmol) and 5-(4,4,5,5-tetramethyl-1,3,2-dioxaborolan-2-yl)-1H-benzo[d]imidazol-2(3H)-one (0.325 g; 1.25 mmol) in DME-water (2 mL) for 30 min. Purification by flash-chromatography on silica gel using a gradient of ethyl acetate (5-100%) in heptane furnished 0.273 g (85%) of the title compound.

ESI/APCI(+): 417 (M+H);
ESI/APCI(+): 415 (M–H).

Example 116

Preparation of 2-(4-methyl-6-(2-oxo-2,3-dihydro-1H-benzo[d]imidazol-5-yl)-2-phenylpyrimidin-5-yl)pentanoic acid This compound was prepared according to general method D from methyl 2-(4-methyl-6-(2-oxo-2,3-dihydro-1H-benzo[d]imidazol-5-yl)-2-phenylpyrimidin-5-yl)pentanoate (0.180 g; 0.432 mmol), sodium hydroxide 10N (0.432 mL; 4.32 mmol) in methanol (4.3 mL). Purification by preparative HPLC (HPLC method 2) furnished 0.024 g (13%) of the title compound as a white solid.

ESI/APCI(+): 403 (M+H);
ESI/APCI(–): 803 (2M–H).

Example 117

Preparation of Methyl 2-(4-(4-chlorophenyl)-6-methyl-2-phenylpyrimidin-5-yl)pentanoate This compound was prepared according to general method E from methyl 2-(4-chloro-6-methyl-2-phenylpyrimidin-5-yl)pentanoate (0.08 g; 0.25 mmol), tetrakis(triphenylphosphine) palladium(0) (0.029 mg; 0.025 mmol), N,N-diisopropylethylamine (0.173 mL; 1 mmol) and 4-chlorophenylboronic acid (0.058 g; 0.37 mmol) in DME-water (1 mL) for 2.5 h. Purification by flash-chromatography on silica gel using a gradient of ethyl acetate (2-20%) in heptane furnished 0.056 g (51%) of the title compound.

ESI/APCI(+): 395 (M+H).

Example 118

Preparation of 2-(4-(4-chlorophenyl)-6-methyl-2-phenylpyrimidin-5-yl)pentanoic acid This compound was prepared according to general method D from methyl 2-(4-(4-chlorophenyl)-6-methyl-2-phenylpyrimidin-5-yl)pentanoate (0.056 g; 0.142 mmol), sodium hydroxide 10N (0.142 mL; 1.42 mmol) in methanol (1.4 mL). Purification by flash-chromatography on silica gel using a gradient of methanol (1-10%) in dichloromethane followed by a purification by preparative HPLC (HPLC method 1) furnished 0.026 g (48%) of the title compound as a white solid.

ESI/APCI(+): 381 (M+H);
ESI/APCI(–): 335 (M–CO$_2$H).

Example 119

Preparation of 6-(4,4,5,5-tetramethyl-1,3,2-dioxaborolan-2-yl)indolin-2-one 6-bromoindolin-2-one (0.424 g; 2 mmol), potassium acetate (0.687 g; 7.0 mmol) and bis[pinacolato]diborane (0.762 g; 3.0 mmol) were placed in a 20 mL microwave vial, dissolved in dry DMF (13 mL) and the flask was purged with nitrogen. The catalyst [1,1'-Bis(diphenylphosphino)ferrocene]palladium(II) chloride, complex with dichloromethane (0.169 g; 0.20 mmol) was added, the flask was again purged with argon, sealed and the reaction was heated at 95° C. for 18 h. The reaction mixture was diluted with water and the suspension was extracted twice with ethyl acetate. The combined organics were washed with brine, dried over magnesium sulphate, filtered and concentrated under reduced pressure. Purification by flash-chromatography on silica gel using a gradient of ethyl acetate (10-80%) in heptane furnished 0.390 g (40%) of the title compound.

ESI/APCI(+): 260 (M+H);

$^1$H NMR (DMSO-d6) δ 10.40 (s, 1 H), 7.27 (dd, J=7.3, 0.8 Hz, 1 H), 7.21 (m, 1 H), 7.07 (s, 1 H), 3.50 (s, 2 H), 1.28 (s, 12 H).

Example 120

Preparation of Methyl 2-(4-methyl-6-(2-oxoindolin-6-yl)-2-phenylpyrimidin-5-yl)pentanoate This compound was prepared according to general method E from methyl 2-(4-chloro-6-methyl-2-phenylpyrimidin-5-yl)pentanoate (0.08 g; 0.25 mmol), tetrakis(triphenylphosphine) palladium(0) (0.029 mg; 0.025 mmol), N,N-diisopropylethylamine (0.173 mL; 1 mmol) and intermediate 17 6-(4,4,5,5-tetramethyl-1,3,2-dioxaborolan-2-yl)indolin-2-one (0.133 g; 0.75 mmol) in DME-water (2 mL) for 30 min. Purification by flash-chromatography on silica gel using a gradient of ethyl acetate (10-80%) in heptane furnished 0.066 g (56%) of the title compound.

ESI/APCI(+): 416 (M+H).

Example 121

Preparation of 2-(4-methyl-6-(2-oxoindolin-6-yl)-2-phenylpyrimidin-5-yl)pentanoic acid This compound was prepared according to general method D from methyl 2-(4-methyl-6-(2-oxoindolin-6-yl)-2-phenylpyrimidin-5-yl)pentanoate (0.066 g; 0.159 mmol), sodium hydroxide 10N (0.159 mL; 1.59 mmol) in methanol (1.5 mL). Purification by preparative HPLC (HPLC method 2) furnished 0.0012 g (2%) of the title compound as a white solid.
ESI/APCI(+): 402 (M+H);
ESI/APCI(−): 356 (M−CO$_2$H).

Example 122

Preparation of Methyl 2-(4-(4-isopropylphenyl)-6-methyl-2-phenylpyrimidin-5-yl)pentanoate This compound was prepared according to general method E from methyl 2-(4-chloro-6-methyl-2-phenylpyrimidin-5-yl)pentanoate (0.08 g; 0.25 mmol), tetrakis(triphenylphosphine palladium(0) (0.029 mg; 0.025 mmol), N,N-diisopropylethylamine (0.173 mL; 1 mmol) and 4-isopropylphenylboronic acid (0.082 g; 0.5 mmol) in DME-water (1 mL) for 20 min. Purification by flash-chromatography on silica gel using a gradient of ethyl acetate (2-20%) in heptane furnished 0.074 g (73%) of the title compound.
ESI/APCI(+): 403 (M+H).

Example 123

Preparation of 2-(4-(4-isopropylphenyl)-6-methyl-2-phenylpyrimidin-5-yl)pentanoic acid This compound was prepared according to general method D from methyl 2-(4-(4-isopropylphenyl)-6-methyl-2-phenylpyrimidin-5-yl)pentanoate (0.074 g; 0.184 mmol), sodium hydroxide 10N (0.184 mL; 1.84 mmol) in methanol (2 mL) to afford 0.060 g (83%) of the title compound as a white solid.
ESI/APCI(+): 389 (M+H).

Example 124

Preparation of Methyl 2-(4-methyl-2-phenyl-6-(4-(trifluoromethyl)phenyl)pyrimidin-5-yl)pentanoate This compound was prepared according to general method E from methyl 2-(4-chloro-6-methyl-2-phenylpyrimidin-5-yl)pentanoate (0.08 g; 0.25 mmol), tetrakis(triphenylphosphine) palladium(0) (0.029 mg; 0.025 mmol), N,N-diisopropylethylamine (0.173 mL; 1 mmol) and 4-(trifluoromethyl)phenylboronic acid (0.095 g; 0.5 mmol) in DME-water (1 mL) for 20 min. Purification by flash-chromatography on silica gel using a gradient of ethyl acetate (2-20%) in heptane furnished 0.061 g (57%) of the title compound.
ESI/APCI(+): 429 (M+H).

Example 125

Preparation of 2-(4-methyl-2-phenyl-6-(4-(trifluoromethyl)phenyl)pyrimidin-5-yl)pentanoic acid This compound was prepared according to general method D from methyl 2-(4-methyl-2-phenyl-6-(4-(trifluoromethyl) phenyl)pyrimidin-5-yl)pentanoate (0.061 g; 0.142 mmol), sodium hydroxide 10N (0.200 mL; 2.0 mmol) in methanol (2 mL) to afford 0.058 g (98%) of the title compound as a white solid.
ESI/APCI(+): 415 (M+H).

Example 126

Preparation of Methyl 2-(4-(4-chloro-2-methoxyphenyl)-6-methyl-2-phenylpyrimidin-5-yl)pentanoate A suspension of methyl 2-(4-chloro-6-methyl-2-phenylpyrimidin-5-yl)pentanoate (0.239 g; 0.75 mmol), tetrakis (triphenylphosphine) palladium(0) (0.087 mg; 0.075 mmol), N,N-diisopropylethylamine (0.517 mL; 3 mmol) and 4-chloro-2-methoxyphenylboronic acid (0.210 g; 1.125 mmol) in a mixture DME-water (2 mL) was heated in a sealed tube for 2.5 h. The mixture was diluted with brine and extracted with ethyl acetate. The combined organics were dried over magnesium sulphate, filtered and concentrated under reduced pressure. Purification by flash-chromatography on silica gel using a gradient of ethyl acetate (5-40%) in heptane furnished 0.190 g (60%) of the title compound as a colorless oil.
ESI/APCI(+): 425 (M+H).

Example 127

Preparation of 2-(4-(4-chloro-2-methoxyphenyl)-6-methyl-2-phenylpyrimidin-5-yl)pentanoic acid A solution of sodium hydroxide 10N (0.2 mL; 2 mmol) was added to a mixture of methyl 2-(4-(4-chloro-2-methoxyphenyl)-6-methyl-2-phenylpyrimidin-5-yl)pentanoate (0.063 g; 0.148 mmol) in methanol (2 mL). The mixture was heated at 60° C. in a sealed tube for 18 h and then concentrated under reduced pressure. The residue was dissolved in water and the pH of the solution was adjusted between 2 and 3 by addition of a solution of hydrochloric acid 6N until a precipitate formed. The precipitate was collected by filtration and dried under reduced pressure over phosphorus pentoxide to afford 0.048 g (77%) of the title compound as a white solid.
ESI/APCI(+): 411 (M+H).

Example 128

Preparation of 2-(4-(4-chloro-2-hydroxyphenyl)-6-methyl-2-phenylpyrimidin-5-yl)pentanoic acid To a cooled (−78° C.) stirred solution of methyl 2-(4-(4-chloro-2-methoxyphenyl)-6-methyl-2-phenylpyrimidin-5-yl)pentanoate (0.125 mg; 0.294 mmol) in dichloromethane (1.5 mL) was added a solution of boron tribromide (1M in dichloromethane) (0.340 mL; 0.340 mmol) dropwise. After 1 h the mixture was allowed to warm up to room temperature and the reaction was stirred for 16 h. The reaction was quenched by adding water and the mixture was extracted with ethyl acetate, dried over magnesium sulphate, filtered and concentrated under reduced pressure. Purifications by flash-chromatography on silica gel using a gradient of methanol (0-10%) in dichloromethane and by preparative TLC on silica gel using a mixture methanol-dichloromethane (5:95) as eluent furnished 0.0018 g (1.5%) of the title compound.
ESI/APCI(+): 397 (M+H);
ESI/APCI(−): 395 (M−H).

Example 129

Preparation of 6-(4,4,5,5-tetramethyl-1,3,2-dioxaborolan-2-yl)-2,3-dihydro-1H-inden-1-one 6-bromo-2,3-dihydro-1H-inden-1-one (0.422 g; 2 mmol), potassium acetate (0.687 g; 7.0 mmol) and bis[pinacolato]diborane (0.762 g; 3.0 mmol) were placed in a 20 mL microwave vial, dissolved in dry DMF (13 mL) and the flask was purged with nitrogen. The catalyst [1,1'-Bis(diphenylphosphino)ferrocene]palladium(II) chloride, complex with dichloromethane (0.169 g; 0.20 mmol) was added, the flask was again purged with argon, sealed and the reaction was heated at 95° C. for 18 h. The reaction mixture was diluted with water and the suspension was extracted twice with ethyl acetate. The combined organics were washed with brine, dried over magnesium sulphate, filtered and concentrated under reduced pressure. Purification by flash-chromatography on silica gel using a gradient of ethyl acetate (10-80%) in heptane furnished 0.467 g (90%) of the title compound.

Example 130

Preparation of Methyl 2-(4-methyl-6-(3-oxo-2,3-dihydro-1H-inden-5-yl)-2-phenylpyrimidin-5-yl)pentanoate This compound was prepared according to general method E from methyl 2-(4-chloro-6-methyl-2-phenylpyrimidin-5-yl)pentanoate (0.159 g; 0.5 mmol), tetrakis(triphenylphosphine) palladium(0) (0.059 mg; 0.05 mmol), N,N-diisopropylethylamine (0.345 mL; 2 mmol) and intermediate 18 6-(4,4,5,5-tetramethyl-1,3,2-dioxaborolan-2-yl)-2,3-dihydro-1H-inden-1-one (0.325 g; 1.25 mmol) in DME-water (2 mL) for 30 min. Purification by flash-chromatography on silica gel using a gradient of ethyl acetate (2-40%) in heptane furnished 0.117 g (56%) of the title compound.
ESI/APCI(+): 415 (M+H).

Example 131

Preparation of 2-(4-methyl-6-(3-oxo-2,3-dihydro-1H-inden-5-yl)-2-phenylpyrimidin-5-yl)pentanoic acid This compound was prepared according to general method D from methyl 2-(4-methyl-6-(3-oxo-2,3-dihydro-1H-inden-5-yl)-2-phenylpyrimidin-5-yl)pentanoate (0.177 g; 0.282 mmol), sodium hydroxide 10N (0.282 mL; 2.82 mmol) in methanol (2.8 mL). Purification by preparative HPLC (HPLC method 1) furnished 0.0016 g (1.4%) of the title compound as a brown solid.
ESI/APCI(+): 401 (M+H).

Example 132

Preparation of 6-(4,4,5,5-tetramethyl-1,3,2-dioxaborolan-2-yl)benzo[d]thiazole 6-bromobenzo[d]thiazole (0.428 g; 2 mmol), potassium acetate (0.687 g; 7.0 mmol) and bis[pinacolato]diborane (0.762 g; 3.0 mmol) were placed in a 20 mL microwave vial, dissolved in dry DMF (13 mL) and the flask was purged with nitrogen. The catalyst [1,1'-Bis(diphenylphosphino)ferrocene]palladium(II) chloride, complex with dichloromethane (0.169 g; 0.20 mmol) was added, the flask was again purged with argon, sealed and the reaction was heated at 95° C. for 18 h. The reaction mixture was diluted with water and the suspension was extracted twice with ethyl acetate. The combined organics were washed with brine, dried over magnesium sulphate, filtered and concentrated under reduced pressure. Purification by flash-chromatography on silica gel using a gradient of ethyl acetate (10-80%) in heptane furnished 0.510 g (98%) of the title compound.
$^1$H NMR (DMSO-d6) δ 9.49 (s, 1 H); 8.50 (s, 1 H); 8.09 (d, J=8.1 Hz, 1 H); 7.80 (dd, J=8.1, 0.6 Hz, 1 H); 1.33 (s, 12 H).

Example 133

Preparation of Methyl 2-(4-(benzo[d]thiazol-6-yl)-6-methyl-2-phenylpyrimidin-5-yl)pentanoate This compound was prepared according to general method E from methyl 2-(4-chloro-6-methyl-2-phenylpyrimidin-5-yl)pentanoate (0.08 g; 0.25 mmol), tetrakis(triphenylphosphine) palladium(0) (0.029 mg; 0.025 mmol), N,N-diisopropylethylamine (0.173 mL; 1 mmol) and intermediate 19 6-(4,4,5,5-tetramethyl-1,3,2-dioxaborolan-2-yl)benzo[d]thiazole (0.098 g; 0.5 mmol) in DME-water (1 mL) for 20 min. Purification by flash-chromatography on silica gel using a gradient of ethyl acetate (5-40%) in heptane furnished 0.041 g (39%) of the title compound.
ESI(+): 418 (M+H).

Example 134

Preparation of 2-(4-(benzo[d]thiazol-6-yl)-6-methyl-2-phenylpyrimidin-5-yl)pentanoic acid Methyl 2-(4-(benzo[d]thiazol-6-yl)-6-methyl-2-phenylpyrimidin-5-yl)pentanoate (0.041 g; 0.098 mmol) and lithium iodide (0.039 mg; 0.295 mmol) were placed in a microwave vial and dissolved in pyridine (0.7 mL). The vial was purged with nitrogen and heated to 125° C. for 48 h. The solvent was removed under reduced pressure, the residue was dissolved in water and the pH of the solution was adjusted between 2 and 3 by addition of a solution of hydrochloric acid 6N until a precipitate formed. The precipitate was collected by filtration and dried under reduced pressure over phosphorus pentoxide. Purification by flash-chromatography on silica gel using a gradient of methanol (1-10%) in dichloromethane furnished 0.015 g (35%) of the title compound as a brown solid.
ESI(+): 404 (M+H).

Example 135

Preparation of Methyl 2-(4-benzyl-6-methyl-2-phenylpyrimidin-5-yl)pentanoate

To a cooled (0° C.) solution of anhydrous zinc chloride (0.060 mg; 0.439 mmol) in tetrahydrofuran (0.8 mL) under nitrogen atmosphere was added dropwise a benzylmagnesium chloride solution (1M in THF) (0.408 mL; 0.408 mmol). After 15 min, the solution was allowed to warm up to room temperature for 10 min. To an argon purged reaction tube was added methyl 2-(4-chloro-6-methyl-2-phenylpyrimidin-5-yl)pentanoate (0.100 g; 0.314 mmol), (1,1'-Bis(diphenylphosphino)ferrocene)-dichloropalladium(II) complex with dichloromethane (0.015 g; 0.022 mmol) and tetrahydrofuran (3 mL). The milky benzylzinc solution was added dropwise, the mixture was stirred at room temperature for 30 min and then heated at 65° C. for 20 h. The reaction mixture was diluted with water and extracted twice with ethyl acetate. The combined organics were washed with a solution of ethylenediaminetetraacetic acid, water, brine, dried over magnesium sulphate, filtered and concentrated under reduced pressure. Purification by flash-chromatography on silica gel using a gradient of ethyl acetate (2-20%) in heptane furnished 0.095 g (81%) of the title compound as a colorless oil.

ESI(+): 375 (M+H).

Example 136

Preparation of 2-(4-benzyl-6-methyl-2-phenylpyrimidin-5-yl)pentanoic acid

A solution of sodium hydroxide 10N (0.300 mL; 3.0 mmol) was added to a mixture of methyl 2-(4-(4-chloro-2-methoxyphenyl)-6-methyl-2-phenylpyrimidin-5-yl)pentanoate (0.095 g; 0.254 mmol) in methanol (3 mL). The mixture was heated at 60° C. in a sealed tube for 18 h and then concentrated under reduced pressure. The residue was dissolved in water and the pH of the solution was adjusted between 2 and 3 by addition of a solution of hydrochloric acid 6N until a precipitate formed. The precipitate was collected by filtration and dried under reduced pressure over phosphorus pentoxide to afford 0.078 g (84%) of the title compound as a yellow solid.

ESI/APCI(+): 361 (M+H)

Example 137

Preparation of 2-methoxy-4-methylaniline

To a solution of 2-methoxy-4-methyl-1-nitrobenzene (5 g; 29.9 mmol) in methanol (200 mL) was added Tin(II) chloride dihydrate (33.7 g; 150 mmol) and the mixture was heated to reflux for 3 h. The solvent was removed under reduced pressure and the residue was dissolved in ethyl acetate. A saturated solution of sodium hydrogen carbonate was added until pH 8. A suspension formed and the mixture was filtered on a plug of celite. The organic phase was separated, washed with a saturated solution of sodium hydrogen carbonate solution and dried over magnesium sulphate. The solvent was removed under reduced pressure and the residue was used as such in the next reaction.

Example 138

Preparation of 2-methoxy-4-methylphenylboronic acid

Step 1:
To a solution of cupric bromide (6.35 g; 28.4 mmol) in acetonitrille (25 mL) was added tert-butyl nitrite (2.85 mL; 24.06 mmol) and the mixture was heated at 65° C. under a nitrogen atmosphere. A solution of 2-methoxy-4-methylaniline (3 g; 21.87 mmol) in acetonitrile (25 mL) was added carefully and the mixture was stirred for 20 min at 65° C. The solvent was removed under reduced pressure and the residue was dissolved in ethyl acetate and washed (×3) with an aqueous solution of ammonia 5%, water, a solution of ethylenediaminetetraacetic acid, water, brine and the mixture was concentrated under reduced pressure. Purification by flash-chromatography on silica gel using a gradient of ethyl acetate (2-50%) in heptane furnished 2.32 g (53%) of the title compound as a yellow oil.
Step 2:
To a cooled (−78° C.) solution of 1-bromo-2-methoxy-4-methylbenzene (0.5 g; 2.49 mmol) in dry THF (12.5 mL) under argon atmosphere was added dropwise a tert-butyllithium solution (1.6M in pentane) (3.65 mL; 5.47 mmol). After 10 min, trimethyl borate (0.424 mL; 3.73 mmol) was added dropwise as a neat liquid and the reaction was stirred at −78° C. for 1 h. The reaction was allowed to warm up to room temperature and was stirred for another 1 h. The mixture was quenched with a saturated solution of ammonium chloride and the mixture was concentrated under reduced pressure. The residue was acidified with a solution of hydrochloric acid 2N and the mixture was extracted with dichloromethane. The organic layer was washed with brine, dried over magnesium sulphate and concentrated under reduced pressure. The crude product was precipitated out off a mixture of dichloromethane-heptane, filtered, washed with heptane and dried under reduced pressure to afford 0.095 g (23%) of the title compound as an off-white solid.

Example 139

Preparation of Methyl 2-(4-(2-hydroxy-4-methylphenyl)-6-methyl-2-phenylpyrimidin-5-yl)pentanoate This compound was prepared according to general method E from methyl 2-(4-chloro-6-methyl-2-phenylpyrimidin-5-yl)pentanoate (0.10 g; 0.314 mmol), tetrakis(triphenylphosphine) palladium(0) (0.036 mg; 0.031 mmol), N,N-diisopropylethylamine (0.216 mL; 1.25 mmol) and 2-methoxy-4-methylphenylboronic acid (0.078 g; 0.47 mmol in DME-water (1 mL) for 20 min. Purification by flash-chromatography on silica gel using a gradient of ethyl acetate (2-20%) in heptane furnished 0.082 g (65%) of the title compound as a colorless oil.

ESI/APCI(+): 405 (M+H).

Example 140

Preparation of 2-(4-(2-hydroxy-4-methylphenyl)-6-methyl-2-phenylpyrimidin-5-yl)pentanoic acid and Example 116 Preparation of 2-(4-(2-methoxy-4-methylphenyl)-6-methyl-2-phenylpyrimidin-5-yl)pentanoic acid A solution of methyl 2-(4-(2-hydroxy-4-methylphenyl)-6-methyl-2-phenylpyrimidin-5-yl)pentanoate (0.040 g; 0.099 mmol) and lithium iodide (0.066 g; 0.494 mmol) in pyridine (0.5 mL) was irradiated at 170° C. in a microwave sealed tube for 3 h. The solvent was removed under reduced pressure, the residue was dissolved in water and the pH adjusted between 2 and 3 by addition of a solution of hydrochloric acid 6N. The suspension was extracted twice with ethyl acetate and the combined organic layers were concentrated under reduced pressure. The residue was again suspended in water, basified with a solution of sodium hydroxide 5N and washed with a mixture of heptane and ethyl acetate (1:1). The pH of the aqueous solution was adjusted between 2 and 3 by addition of a solution of hydrochloric acid 6N, extracted twice with ethyl acetate and the combined organic layers were dried over magnesium sulphate and concentrated under reduced pressure. Purification by preparative HPLC (HPLC method 1) furnished 0.008 g (21%) of 2-(4-(2-hydroxy-4-methylphenyl)-6-methyl-2-phenylpyrimidin-5-yl)pentanoic acid and 0.002 g (5%) of 2-(4-(2-methoxy-4-methylphenyl)-6-methyl-2-phenylpyrimidin-5-yl)pentanoic acid.

ESI/APCI(+): 377 (M+H);

ESI/APCI(−): 375 (M−H); 331 (M−CO$_2$H);

ESI/APCI(+): 391 (M+H).

Example 141

Preparation of Methyl 2-(4-methyl-2-(piperidin-1-yl)-6-p-tolylpyrimidin-5-yl)acetate To a solution of methyl 2-(2-chloro-4-methyl-6-p-tolylpyrimidin-5-yl)acetate (3 g; 10.32 mmol) in 2-methyltetrahydrofuran (20 ml) was added piperidine (4.09 mL; 41.3 mmol) and triethylamine (5.72 mL; 41.3 mmol). The reaction was heated under reflux for 5 h and the reaction mixture was partitioned between ethyl acetate and a saturated solution of sodium hydrogen carbonate. The phases were separated and the aqueous layer was extracted twice with ethyl acetate. The combined organic layers were dried over magnesium sulphate, filtered and concentrated under reduced pressure. Purification by flash-chromatography on silica gel using a gradient of ethyl acetate (2-20%) in heptane furnished 1.88 g (48%) of the title compound as a white solid.

ESI/APCI(+): 340 (M+H).

Example 142

Preparation of Methyl 4-methoxy-2-(4-methyl-2-(piperidin-1-yl)-6-p-tolylpyrimidin-5-yl)butanoate To a cooled (−15° C.) solution of methyl 2-(4-methyl-2-(piperidin-1-yl)-6-p-tolylpyrimidin-5-yl)acetate (0.100 g; 0.295 mmol) in dry DMF (1.5 mL) was wadded a 1N solution of LHMDS in THF (0.324 mL; 0.324 mmol) dropwise and the mixture was stirred at (−15° C.) for 15 min, followed by the dropwise addition of 2-bromoethyl methyl ether (0.083 mL; 0.884 mmol). After stirring for 2 h at (−15° C.) the mixture was allowed to warm up to room temperature. After 1 h the reaction was quenched by adding a saturated solution of ammonium chloride and the mixture was extracted twice with ethyl acetate and the combined organic layers were washed with brine, dried over magnesium sulphate, filtered and concentrated under reduced pressure. Purification by flash-chromatography on silica gel using a gradient of ethyl acetate (2-20%) in heptane furnished 0.018 g (15%) of the title compound as a colorless oil.

ESI/APCI(+): 421 (M+H).

Example 143

Preparation of 4-methoxy-2-(4-methyl-2-(piperidin-1-yl)-6-p-tolylpyrimidin-5-yl)butanoic acid This compound was prepared according to general method D from methyl 4-methoxy-2-(4-methyl-2-(piperidin-1-yl)-6-p-tolylpyrimidin-5-yl)butanoate (0.018 g; 0.045 mmol), sodium hydroxide 10N (0.045 mL; 0.45 mmol) in methanol (0.4 mL) to afford 0.007 g (38%) of the title compound as a white solid.

ESI/APCI(+): 384 (M+H).

Example 144

Preparation of Methyl 6,6,6-trifluoro-2-(4-methyl-2-(piperidin-1-yl)-6-p-tolylpyrimidin-5-yl)hexanoate To a cooled (−15° C.) solution of methyl 2-(4-methyl-2-(piperidin-1-yl)-6-p-tolylpyrimidin-5-yl)acetate (0.100 g; 0.295 mmol) in dry DMF (1.5 mL) was wadded a 1N solution of LHMDS in THF (0.324 mL; 0.324 mmol) dropwise and the mixture was stirred at (−15° C.) for 15 min, followed by the dropwise addition of 1,1,1-trifluoro-4-iodo-butane (0.076 mL; 0.589 mmol). After stirring for 2 h at (−15° C.) the mixture was allowed to warm up to room temperature. After 1 h the reaction was quenched by adding a saturated solution of ammonium chloride and the mixture was extracted twice with ethyl acetate and the combined organic layers were washed with brine, dried over magnesium sulphate, filtered and concentrated under reduced pressure. Purification by flash-chromatography on silica gel using a gradient of ethyl acetate (2-20%) in heptane furnished 0.102 g (66%) of the title compound as a colorless oil.

ESI/APCI(+): 450 (M+H).

Example 145

Preparation of 6,6,6-trifluoro-2-(4-methyl-2-(piperidin-1-yl)-6-p-tolylpyrimidin-5-yl)hexanoic acid This compound was prepared according to general method D from methyl 6,6,6-trifluoro-2-(4-methyl-2-(piperidin-1-yl)-6-p-tolylpyrimidin-5-yl)hexanoate (0.102 g; 0.227 mmol), sodium hydroxide 10N (0.227 mL; 2.27 mmol) in methanol (2.2 mL). Purification by preparative HPLC (HPLC method 1) furnished 0.062 g (60%) of the title compound as a white solid.

ESI/APCI(+): 436 (M+H);
ESI/APCI(−): 434 (M−H).

Example 146

Preparation of Methyl 2-(4-methyl-2-(piperidin-1-yl)-6-p-tolylpyrimidin-5-yl)-3-phenylpropanoate To a cooled (−15° C.) solution of methyl 2-(4-methyl-2-(piperidin-1-yl)-6-p-tolylpyrimidin-5-yl)acetate (0.100 g; 0.295 mmol) in dry DMF (1.5 mL) was wadded a 1N solution of LHMDS in THF (0.324 mL; 0.324 mmol) dropwise and the mixture was stirred at (−15° C.) for 15 min, followed by the dropwise addition of benzyl bromide (0.070 mL; 0.589 mmol). After stirring for 2 h at (−15° C.) the mixture was allowed to warm up to room temperature. After 1 h the reaction was quenched by adding a saturated solution of ammonium chloride and the mixture was extracted twice with ethyl acetate and the combined organic layers were washed with brine, dried over magnesium sulphate, filtered and concentrated under reduced pressure. Purification by flash-chromatography on silica gel using a gradient of ethyl acetate (2-20%) in heptane furnished 0.087 g (60%) of the title compound as a colorless oil.

ESI/APCI(+): 430 (M+H).

Example 147

Preparation of 2-(4-methyl-2-(piperidin-1-yl)-6-p-tolylpyrimidin-5-yl)-3-phenylpropanoic acid This compound was prepared according to general method D from methyl 2-(4-methyl-2-(piperidin-1-yl)-6-p-tolylpyrimidin-5-yl)-3-phenylpropanoate (0.087 g; 0.203 mmol), sodium hydroxide 10N (0.203 mL; 2.02 mmol) in methanol (2 mL) to afford 0.071 g (80%) of the title compound as a white solid.

ESI/APCI(+): 416 (M+H);
ESI/APCI(−): 414 (M−H); 371 (M−CO$_2$H).

Example 148

Preparation of Methyl 3-methyl-2-(4-methyl-2-(piperidin-1-yl)-6-p-tolylpyrimidin-5-yl)pentanoate To a cooled (−15° C.) solution of intermediate 23: methyl 2-(4-methyl-2-(piperidin-1-yl)-6-p-tolylpyrimidin-5-yl)acetate (0.100 g; 0.295 mmol) in dry DMF (1.5 mL) was wadded a 1N solution of LHMDS in THF (0.324 mL; 0.324 mmol) dropwise and the mixture was stirred at (−15° C.) for 15 min, followed by the dropwise addition of 2-iodobutane (0.068 mL; 0.589 mmol). After stirring for 2 h at (−15° C.) the mixture was allowed to warm up to room temperature. After 1 h the reaction was quenched by adding a saturated solution of ammonium chloride and the mixture was extracted twice with ethyl acetate and the combined organic layers were washed with brine, dried over magnesium sulphate, filtered and concentrated under reduced pressure. Purification by flash-chromatography on silica gel using a gradient of ethyl acetate (2-20%) in heptane furnished 0.039 g (33%) of the title compound as a colorless oil.

ESI/APCI(+): 396 (M+H).

Example 149

Preparation of 3-methyl-2-(4-methyl-2-(piperidin-1-yl)-6-p-tolylpyrimidin-5-yl)pentanoic acid This compound was prepared according to general method D from methyl 3-methyl-2-(4-methyl-2-(piperidin-1-yl)-6-p-tolylpyrimidin-5-yl)pentanoate (0.039 g; 0.099 mmol), sodium hydroxide 10N (0.100 mL; 0.1 mmol) in methanol (1 mL) to afford 0.028 g (73%) of the title compound as a white solid.

ESI/APCI(+): 382 (M+H);
ESI/APCI(−): 380 (M−H).

Example 150

Preparation of Methyl 2-(4-methyl-6-oxo-2-(piperidin-1-yl)-1,6-dihydropyrimidin-5-yl)pentanoate Step 1:

To a solution of piperidine-1-carboximidamide (dimer complexated with $H_2SO_4$) (5 g; 39.3 mmol) in methanol (56 mL) was added slowly sodium methoxide (25 w % in MeOH) (17.98 mL; 79 mmol) and diethyl 2-acetyl-3-propylsuccinate (10.15 g; 39.3 mmol). The reaction was heated to reflux for 18 h and after cooling to room temperature, the mixture was concentrated under reduced pressure and dissolved in concentrated hydrochloric acid. The slurry was concentrated under reduced pressure and the crude product used as such in the next step.

ESI/APCI(+): 294 (M+H).

Step 2:

To a cooled (0° C.) solution of the crude mixture from the last step in methanol (110 mL) was added dropwise thionyl chloride (5.93 mL; 82 mmol) and the reaction mixture was heated to reflux for 18 h. The reaction mixture was concentrated under reduced pressure, the residue was dissolved in water and neutralized with a saturated solution of sodium hydrogen carbonate. The suspension was extracted with ethyl acetate (2×200 mL) and the combined organic layers were washed with brine, dried over magnesium sulphate, filtered and concentrated under reduced pressure. The crude product was used as such in the next reaction.

ESI/APCI(+): 308 (M+H).

Example 151

Preparation of Methyl 2-(4-chloro-6-methyl-2-(piperidin-1-yl)pyrimidin-5-yl)pentanoate To a suspension of methyl 2-(4-methyl-6-oxo-2-(piperidin-1-yl)-1,6-dihydropyrimidin-5-yl)pentanoate (5.97 g; 19.42 mmol) in dry toluene (40 mL) under nitrogen atmosphere were carefully added phosphorus oxychloride (18.05 mL; 194 mmol) and dimethylaniline (1.961 mL, 15.54 mmol). The reaction was heated to reflux for 3 h and after cooling at room temperature, the volatiles were removed under reduced pressure and the remaining residue was cooled in an ice-bath and quenched by adding crushed ice and a saturated solution of sodium hydrogen carbonate until neutralization. The product was extracted twice with ethyl acetate and the combined organic layers were dried over magnesium sulphate, filtered and concentrated under reduced pressure. Purification by flash-chromatography on silica gel using a gradient of ethyl acetate (1-10%) in heptane furnished 2.45g (39%) of the title compound as a yellow oil.

ESI/APCI(+): 326 (M+H);
$^1$H NMR (DMSO-d6) δ: 4.01 (dd, $J_1$=9.1 Hz, $J_2$=5.5 Hz, 1 H); 3.68 (m, 4 H), 3.60 (s, 3 H); 2.29 (s, 3 H); 2.09 (m, 1 H); 1.65 (m, 3 H); 1.51 (m, 4 H); 1.29 (m, 1 H); 1.11 (m, 1 H); 0.86 (t, J=7.2 Hz, 3 H).

Example 152

Preparation of Methyl 2-(4-(2,4-difluorophenyl)-6-methyl-2-(piperidin-1-yl)pyrimidin-5-yl)pentanoate This compound was prepared according to general method E from methyl 2-(4-chloro-6-methyl-2-(piperidin-1-yl)pyrimidin-5-yl)pentanoate (0.081 g; 0.25 mmol), tetrakis(triphenylphosphine) palladium(0) (0.029 g; 0.025 mmol), N,N-diisopropylethylamine (0.172 mL; 1.00 mmol) and 2,4-difluorophenylboronic acid (0.079 g; 0.500 mmol) in DME-water (1 mL) for 20 min. Purification by flash-chromatography on silica gel using a gradient of ethyl acetate (1-10%) in heptane furnished 0.056 g (55%) of the title compound.

ESI/APCI(+): 422 (M+H).

Example 153

Preparation of 2-(4-(2,4-difluorophenyl)-6-methyl-2-(piperidin-1-yl)pyrimidin-5-yl)pentanoic acid This compound was prepared according to general method D from methyl 2-(4-(2,4-difluorophenyl)-6-methyl-2-(piperidin-1-yl)pyrimidin-5-yl)pentanoate (0.056 g; 0.139 mmol), sodium hydroxide 10N (0.200 mL; 2.00 mmol) in methanol (2 mL) at 60° C. for 18 h to afford 0.039 g (69%) of the title compound as a white solid.

ESI/APCI(+): 390 (M+H);
ESI/APCI(−): 388 (M−H).

Example 154

Preparation of Methyl 2-(4-(2,4-dimethylphenyl)-6-methyl-2-(piperidin-1-yl)pyrimidin-5-yl)pentanoate This compound was prepared according to general method E from methyl 2-(4-chloro-6-methyl-2-(piperidin-1-yl)pyrimidin-5-yl)pentanoate (0.081 g; 0.25 mmol), tetrakis(triphenylphosphine) palladium(0) (0.029 g; 0.025 mmol), N,N-diisopropylethylamine (0.172 mL; 1.00 mmol) and 2,4-dimethylphenylboronic acid (0.075 g; 0.500 mmol) in DME-water (1 mL) for 20 min. Purification by flash-chromatography on silica gel using a gradient of ethyl acetate (1-10%) in heptane furnished 0.073 g (74%) of the title compound.
ESI/APCI(+): 396 (M+H).

Example 155

Preparation of 2-(4-(2,4-dimethylphenyl)-6-methyl-2-(piperidin-1-yl)pyrimidin-5-yl)pentanoic acid This compound was prepared according to general method D from 2 methyl 2-(4-(2,4-dimethylphenyl)-6-methyl-2-(piperidin-1-yl)pyrimidin-5-yl)pentanoate (0.073 g; 0.185 mmol), sodium hydroxide 10N (0.200 mL; 2.00 mmol) in methanol (2 mL) at 60° C. for 18 h to afford 0.063 g (88%) of the title compound as a white solid.
ESI/APCI(+): 382 (M+H);
ESI/APCI(−): 381 (M−H).

Example 156

Preparation of Methyl 2-(4-(4-isopropylphenyl)-6-methyl-2-(piperidin-1-yl)pyrimidin-5-yl)pentanoate This compound was prepared according to general method E from methyl 2-(4-chloro-6-methyl-2-(piperidin-1-yl)pyrimidin-5-yl)pentanoate (0.081 g; 0.25 mmol), tetrakis(triphenylphosphine) palladium(0) (0.029 g; 0.025 mmol), N,N-diisopropylethylamine (0.172 mL; 1.00 mmol) and 4-isopropylphenylboronic acid (0.082 g; 0.500 mmol) in DME-water (1 mL) for 20 min. Purification by flash-chromatography on silica gel using a gradient of ethyl acetate (1-10%) in heptane furnished 0.074 g (71%) of the title compound.
ESI/APCI(+): 393 (M+H).

Example 157

Preparation of 2-(4-(4-isopropylphenyl)-6-methyl-2-(piperidin-1-yl)pyrimidin-5-yl)pentanoic acid This compound was prepared according to general method D from methyl 2-(4-(4-isopropylphenyl)-6-methyl-2-(piperidin-1-yl)pyrimidin-5-yl)pentanoate (0.074 g; 0.181 mmol), sodium hydroxide 10N (0.200 mL; 2.00 mmol) in methanol (2 mL) at 60° C. for 18 h furnished 0.054 g (73%) of the title compound as a white solid.
ESI/APCI(+): 396 (M+H).
ESI/APCI(−): 394 (M−H).

Example 158

Preparation of Methyl 2-(4-(2-fluoro-4-methoxyphenyl)-6-methyl-2-(piperidin-1-yl)pyrimidin-5-yl)pentanoate This compound was prepared according to general method E from methyl 2-(4-chloro-6-methyl-2-(piperidin-1-yl)pyrimidin-5-yl)pentanoate (0.081 g; 0.25 mmol), tetrakis(triphenylphosphine) palladium(0) (0.029 g; 0.025 mmol), N,N-diisopropylethylamine (0.172 mL; 1.00 mmol) and 2-fluoro-4-methoxyphenylboronic acid (0.085 g; 0.500 mmol) in DME-water (1 mL) for 20 min. Purification by flash-chromatography on silica gel using a gradient of ethyl acetate (1-10%) in heptane furnished 0.072 g (68%) of the title compound.
ESI/APCI(+): 416 (M+H).

Example 159

Preparation of 2-(4-(2-fluoro-4-methoxyphenyl)-6-methyl-2-(piperidin-1-yl)pyrimidin-5-yl)pentanoic acid This compound was prepared according to general method D from methyl 2-(4-(2-fluoro-4-methoxyphenyl)-6-methyl-2-(piperidin-1-yl)pyrimidin-5-yl)pentanoate (0.072 g; 0.173 mmol), sodium hydroxide 10N (0.200 mL; 2.00 mmol) in methanol (2 mL) at 60° C. for 18 h to afford 0.065 g (89%) of the title compound as a white solid.
ESI/APCI(+): 402 (M+H);
ESI/APCI(−): 400 (M−H).

Example 160

Preparation of Methyl 2-(4-methyl-2-(piperidin-1-yl)-6-(quinolin-5-yl)pyrimidin-5-yl)pentanoate This compound was prepared according to general method E from methyl 2-(4-chloro-6-methyl-2-(piperidin-1-yl)pyrimidin-5-yl)pentanoate (0.081 g; 0.25 mmol), tetrakis(triphenylphosphine) palladium(0) (0.029 g; 0.025 mmol), N,N-diisopropylethylamine (0.172 mL; 1.00 mmol) and quinolin-5-ylboronic acid (0.086 g; 0.500 mmol) in DME-water (1 mL) for 20 min. Purification by flash-chromatography on silica gel using a gradient of ethyl acetate (5-40%) in heptane furnished 0.070 g (67%) of the title compound.
ESI/APCI(+): 419 (M+H).

Example 161

Preparation of 2-(4-methyl-2-(piperidin-1-yl)-6-(quinolin-5-yl)pyrimidin-5-yl)pentanoic acid This compound was prepared according to general method D from methyl 2-(4-methyl-2-(piperidin-1-yl)-6-(quinolin-5-yl)pyrimidin-5-yl)pentanoate (0.070 g; 0.167 mmol), sodium hydroxide 10N (0.200 mL; 2.00 mmol) in methanol (2 mL) at 60° C. for 18 h to afford 0.063 g (88%) of the title compound as a yellow solid.
ESI/APCI(+): 405 (M+H);
ESI/APCI(−): 403 (M−H).

Example 162

Preparation of Methyl 2-(4-methyl-2-(piperidin-1-yl)-6-(quinolin-8-yl)pyrimidin-5-yl)pentanoate This compound was prepared according to general method E from methyl 2-(4-chloro-6-methyl-2-(piperidin-1-yl)pyrimidin-5-yl)pentanoate (0.081 g; 0.25 mmol), tetrakis(triphenylphosphine) palladium(0) (0.029 g; 0.025 mmol), N,N-diisopropylethylamine (0.172 mL; 1.00 mmol) and quinolin-8-ylboronic acid (0.086 g; 0.500 mmol) in DME-water (1 mL) for 20 min. Purification by flash-chromatography on silica gel using a gradient of ethyl acetate (5-40%) in heptane furnished 0.057 g (52%) of the title compound.
ESI/APCI(+): 419 (M+H).

Example 163

Preparation of 2-(4-methyl-2-(piperidin-1-yl)-6-(quinolin-8-yl)pyrimidin-5-yl)pentanoic acid This compound was prepared according to general method D from methyl 2-(4-methyl-2-(piperidin-1-yl)-6-(quinolin-8-yl)pyrimidin-5-yl)pentanoate (0.057 g; 0.136 mmol), sodium hydroxide 10N solution (0.200 mL; 2.00 mmol) in methanol (2 mL) at 60° C. for 18 h. Purification by flash-chromatography on silica gel using a gradient of methanol (1-10%) in dichloromethane, followed by a purification by preperative HPLC (HPLC method 1) furnished 0.0059 g (9%) of the title compound.

ESI/APCI(+): 405 (M+H).

Example 164

Preparation of Methyl 2-(4-methyl-2-(piperidin-1-yl)-6-(2,4,5-trifluorophenyl)pyrimidin-5-yl)pentanoate This compound was prepared according to general method E from methyl 2-(4-chloro-6-methyl-2-(piperidin-1-yl)pyrimidin-5-yl)pentanoate (0.081 g; 0.25 mmol), tetrakis(triphenylphosphine) palladium(0) (0.029 g; 0.025 mmol), N,N-diisopropylethylamine (0.172 mL; 1.00 mmol) and 2,4,5-trifluorophenylboronic acid (0.088 g; 0.500 mmol) in DME-water (1 mL) for 20 min. Purification by flash-chromatography on silica gel using a gradient of ethyl acetate (1-10%) in heptane furnished 0.080 g (76%) of the title compound.

ESI/APCI(+): 422 (M+H).

Example 165

Preparation of 2-(4-methyl-2-(piperidin-1-yl)-6-(2,4,5-trifluorophenyl)pyrimidin-5-yl)pentanoic acid This compound was prepared according to general method D from methyl 2-(4-methyl-2-(piperidin-1-yl)-6-(2,4,5-trifluorophenyl)pyrimidin-5-yl)pentanoate (0.080 g; 0.190 mmol), sodium hydroxide 10N (0.200 mL; 2.00 mmol) in methanol (2 mL) at 60° C. for 18 h. Purification by flash-chromatography on silica gel using a gradient of methanol (1-10%) in dichloromethane and then by preperative HPLC (HPLC method 1) furnished 0.0024 g (31%) of the title compound as a white solid.

ESI/APCI(+): 408 (M+H);
ESI/APCI(−): 406 (M−H).

Example 166

Preparation of Methyl 2-(4-(2-chloro-4-methylphenyl)-6-methyl-2-(piperidin-1-yl)pyrimidin-5-yl)pentanoate A suspension of methyl 2-(4-chloro-6-methyl-2-(piperidin-1-yl)pyrimidin-5-yl)pentanoate (0.081 g; 0.25 mmol), tetrakis(triphenylphosphine) palladium(0) (0.029 g; 0.025 mmol), N,N-diisopropylethylamine (0.172 mL; 1.00 mmol) and 2-chloro-4-methylphenylboronic acid (0.064 g; 0.375 mmol) in a mixture of DME-water (3:1, 1 mL) was heated at 100° C. in a sealed tube for 2.5 h. The mixture was diluted with brine and extracted with ethyl acetate. The combined organics were dried over magnesium sulphate, filtered and concentrated under reduced pressure. Purification by flash-chromatography on silica gel using a gradient of methanol (1-10%) in dichloromethane furnished 0.069 g (64%) of the title compound as a colorless oil.

ESI/APCI(+): 420 (M+H).

Example 167

Preparation of 2-(4-(2-chloro-4-methylphenyl)-6-methyl-2-(piperidin-1-yl)pyrimidin-5-yl)pentanoic acid This compound was prepared according to general method D from methyl 2-(4-(2-chloro-4-methylphenyl)-6-methyl-2-(piperidin-1-yl)pyrimidin-5-yl)pentanoate (0.069 g; 0.166 mmol), sodium hydroxide 10N (0.200 mL; 2.00 mmol) in methanol (2 mL) at 60° C. for 18 h. Purification by flash-chromatography on silica gel using a gradient of methanol (1-10%) in dichloromethane furnished 0.033 g (44%) of the title compound as a white solid.

ESI/APCI(+): 402 (M+H);
ESI/APCI(−): 400 (M−H).

Example 168

Preparation of Methyl 2-(4-(4-chloro-2-fluorophenyl)-6-methyl-2-(piperidin-1-yl)pyrimidin-5-yl)pentanoate A suspension of methyl 2-(4-chloro-6-methyl-2-(piperidin-1-yl)pyrimidin-5-yl)pentanoate (0.081 g; 0.25 mmol), tetrakis(triphenylphosphine) palladium(0) (0.029 g; 0.025 mmol), N,N-diisopropylethylamine (0.172 mL; 1.00 mmol) and 4-chloro-2-fluorophenylboronic acid (0.065 g; 0.375 mmol) in a mixture of DME-water (3:1, 1 mL) was heated at 100° C. for 2.5 h. The mixture was partitioned between brine and dichloromethane, filtered over a phase separator filter (1PS) and concentrated under reduced pressure. Purification by flash-chromatography on silica gel using a gradient of ethyl acetate (1-10%) in heptane furnished 0.049 g (38%) of the title compound as a colorless oil.

ESI/APCI(+): 420 (M+H)

Example 169

Preparation of 2-(4-(4-chloro-2-fluorophenyl)-6-methyl-2-(piperidin-1-yl)pyrimidin-5-yl)pentanoic acid This compound was prepared according to general method D from methyl 2-(4-(4-chloro-2-fluorophenyl)-6-methyl-2-(piperidin-1-yl)pyrimidin-5-yl)pentanoate (0.049 g; 0.117 mmol), sodium hydroxide 10N (0.200 mL; 2.00 mmol) in methanol (2 mL) at 60° C. for 18 h. Purification by flash-chromatography on silica gel using a gradient of methanol (1-10%) in dichloromethane, followed by a purification by preparative HPLC (HPLC method 1) furnished 0.009 g (19%) of the title compound as a white solid.

ESI/APCI(+): 406 (M+H);
ESI/APCI(−): 404 (M−H).

Example 170

Preparation of Methyl 2-(4-methyl-2,6-di(piperidin-1-yl)pyrimidin-5-yl)pentanoate A suspension of methyl 2-(4-chloro-6-methyl-2-(piperidin-1-yl)pyrimidin-5-yl)pentanoate (0.081 g; 0.25 mmol), piperidine (0.122 mL; 1.228 mmol) and potassium carbonate (0.102 mg; 0.737 mmol) in acetonitrile (1 mL) was irradiated at 130° C. for 2 h in a microwave oven. The mixture was partitioned between brine and ethyl acetate, the phases were separated and the aqueous layer was extracted with ethyl acetate. The combined organic layers were dried over magnesium sulphate, filtered and concentrated under reduced pressure. Purification by flash-chromatography on silica gel using a gradient of ethyl acetate (1-10%) in heptane furnished 0.042 g (46%) of the title compound as a colorless oil.
ESI/APCI(+): 375 (M+H).

Example 171

Preparation of 2-(4-methyl-2,6-di(piperidin-1-yl)pyrimidin-5-yl)pentanoic acid

This compound was prepared according to general method D from methyl 2-(4-methyl-2,6-di(piperidin-1-yl)pyrimidin-5-yl)pentanoate (0.042 g; 0.112 mmol), sodium hydroxide 10N (0.150 mL; 1.50 mmol) in methanol (2 mL) at 60° C. for 18 h. Purification by flash-chromatography on silica gel using a gradient of methanol (1-10%) in dichloromethane, followed by a purification by preparative HPLC (HPLC method 2) furnished 0.013 g (31%) of the title compound as a white solid.
ESI/APCI(+): 361 (M+H).

Example 172

Preparation of 2-(1,2-dihydroacenaphthylen-5-yl)-4,4,5,5-tetramethyl-1,3,2-dioxaborolane 5-bromo-1,2-dihydroacenaphthylene (0.466 g; 2 mmol), potassium acetate (0.687 g; 7.00 mmol) and bis[pinacolato]diborane (0.762 g; 3.00 mmol) were placed in a microwave vial, dissolved in dry DMF (13 mL) and the flask was purged with nitrogen. The catalyst [1,1'-Bis(diphenylphosphino)ferrocene]palladium(II) chloride, complex with dichloromethane (0.169 g; 0.200 mmol) was added, the flask was purged with argon, sealed and the reaction was heated at 95° C. for 18 h. The reaction mixture was diluted with water and the suspension extracted with ethyl acetate (3×). The combined organic layers were washed with brine, dried over magnesium sulphate, filtered and concentrated under reduced pressure. Purification by flash chromatography on silica gel using a gradient of ethyl acetate (2-20%) in heptane furnished 0.309 g (46%) of the title compound as a tan solid.
ESI/APCI(+): 281 (M+H);
1H NMR δ: 8.23 (d, J=8.3 Hz, 1 H); 7.92 (d, J=6.9 Hz, 1 H); 7.50 (dd, J1=8.1 Hz, J2=7.0 Hz); 7.32 (d, J =6.9 Hz, 2 H); 3.36 (s, 4 H); 1.36 (s, 12 H).

Example 173

Preparation of Methyl 2-(4-(1,2-dihydroacenaphthylen-5-yl)-6-methyl-2-(piperidin-1-yl)pyrimidin-5-yl)pentanoate This compound was prepared according to general method E from methyl 2-(4-chloro-6-methyl-2-(piperidin-1-yl)pyrimidin-5-yl)pentanoate (0.081 g; 0.25 mmol), tetrakis(triphenylphosphine) palladium(0) (0.029 g; 0.025 mmol), N,N-diisopropylethylamine (0.172 mL; 1.00 mmol) and 2-(1,2-dihydroacenaphthylen-5-yl)-4,4,5,5-tetramethyl-1,3,2-dioxaborolane (0.105 g; 0.375 mmol) in DME-water (1 mL) for 20 min. Purification by flash-chromatography on silica gel using a gradient of ethyl acetate (1-10%) in heptane furnished 0.040 g (36%) of the title compound as a yellow oil.
ESI/APCI(+): 444 (M+H).

Example 174

Preparation of 2-(4-(1,2-dihydroacenaphthylen-5-yl)-6-methyl-2-(piperidin-1-yl)pyrimidin-5-yl)pentanoic acid This compound was prepared according to general method D from methyl 2-(4-(1,2-dihydroacenaphthylen-5-yl)-6-methyl-2-(piperidin-1-yl)pyrimidin-5-yl)pentanoate (0.040 g; 0.090 mmol), sodium hydroxide 10N (0.150 mL; 1.50 mmol) in methanol (1.5 mL) at 60° C. for 18 h. Purification by flash-chromatography on silica gel using a gradient of methanol (1-10%) in dichloromethane, followed by a purification by preparative HPLC (HPLC method 1) furnished 0.042 g (100%) of the title compound as a white solid.
ESI/APCI(+): 430 (M+H);
ESI/APCI(-): 428 (M-H).

Example 175

Preparation of Methyl 4,4-dimethyl-2-(4-methyl-2-(piperidin-1-yl)-6-p-tolylpyrimidin-5-yl)pentanoate To a cooled (-15° C.) solution of methyl 2-(4-methyl-2-(piperidin-1-yl)-6-p-tolylpyrimidin-5-yl)acetate (0.200 g; 0.589 mmol) in a mixture of dry DMF (1.2 mL) and HMPA (0.3 mL) was wadded a 1N solution of KHMDS in THF (0.825 mL; 0.825 mmol) dropwise and the mixture was stirred at (-15° C.) for 15 min, followed by the dropwise addition of 1-iodo-2,2-dimethylpropane (0.313 mL; 2.357 mmol). After stirring for 1 h at (-15° C.) the mixture was allowed to warm up to room temperature and stirring was carried on 4 h. The reaction was quenched by adding a saturated solution of ammonium chloride and the mixture was extracted twice with ethyl acetate and the combined organic layers were washed with brine, dried over magnesium sulphate, filtered and concentrated under reduced pressure. Purification by flash-chromatography on silica gel using a gradient of ethyl acetate (2-20%) in heptane furnished 0.024 g (9%) of the title compound.
ESI/APCI(+): 410 (M+H).

Example 176

Preparation of 4,4-dimethyl-2-(4-methyl-2-(piperidin-1-yl)-6-p-tolylpyrimidin-5-yl)pentanoic acid This compound was prepared according to general method D from methyl 4,4-dimethyl-2-(4-methyl-2-(piperidin-1-yl)-6-p-tolylpyrimidin-5-yl)pentanoate (0.024 g; 0.059 mmol), sodium hydroxide 10N (0.100 mL; 1.00 mmol) in methanol (1 mL) at 60° C. for 18 h. Purification by flash-chromatography on silica gel using a gradient of methanol (1-10%) in dichloromethane, followed by a purification by preparative HPLC (HPLC method 1) furnished 0.007 g (29%) of the title compound as a colorless oil.
ESI/APCI(+): 361 (M+H).

Example 177

Preparation of Ethyl 6-methyl-2-oxo-4-p-tolyl-1,2,3,4-tetrahydropyrimidine-5-carboxylate A suspension of urea (2,70 g; 45 mmol), copper (I) chloride (0,297 g; 3 mmol), p-tolualdehyde (3,53 ml; 30 mmol), ethyl acetoacetate (3,81 ml; 30 mmol), acetic acid (0,172 ml; 3 mmol) and boron trifluoride etherate (4,90 ml; 39 mmol) in dry tetrahydrofuran (60 mL) was heated to reflux for 21 h. After cooling to room temperature, the reaction mixture was quenched by adding a saturated solution of sodium hydrogen carbonate and the aqueous solution was extracted with ethyl acetate. The organic layer was concentrated under reduced pressure, the residue was suspended in toluene and left standing at room temperature for 24 h. The formed solid was filtered, washed with toluene and dried under reduced pressure to afford 7,45 g (91%) of the title compound as a green solid.

ESI/APCI(+): 275 (M+H);
ESI/APCI(−): 274 (M−H);
$^1$H NMR (300 MHz, DMSO-$d_6$) δ ppm 9.16 (s, 1 H); 7.69 (s, 1 H); 7.11 (s, 4 H); 5.10 (s, 1 H); 3.98 (q, J=6.8 Hz, 2 H); 2.26 (s, 3 H); 2.24 (s, 3 H); 1.10 (t, J=6.8 Hz, 3 H).

Example 178

Preparation of Ethyl 6-methyl-2-oxo-4-p-tolyl-1,2-dihydropyrimidine-5-carboxylate To a cold (0° C.) mixture of nitric acid (70%) (34 ml) and water (6 mL) was added ethyl 6-methyl-2-oxo-4-p-tolyl-1,2,3,4-tetrahydropyrimidine-5-carboxylate (6 g; 21,87 mmol) in small portions (within 3 min). The mixture was stirred for 30 min while gradually allowed to reach room temperature. The reaction was poured onto crushed ice and neutralized by adding potassium carbonate until pH 8. The aqueous layer was extracted with chloroform (3 times) and the combined organics were dried over sodium sulphate, filtered and concentrated under reduced pressure. The obtained green oil was dissolved in dichloromethane and concentrated under reduced pressure to afford a green solid, which was crystallized from ethanol and the obtained greenish crystals were triturated with heptane to furnish 3.7 g (60%) of the title compound as a white-to-green solid.

ESI/APCI(+): 273 (M+H).

Example 179

Preparation of Ethyl 4-methyl-2-(piperidin-1-yl)-6-p-tolylpyrimidine-5-carboxylate To a stirred solution of ethyl 6-methyl-2-oxo-4-p-tolyl-1,2-dihydropyrimidine-5-carboxylate (2 g; 7,34 mmol) in dioxane (35 mL) were added PyBrOP (3,77 g; 8,08 mmol), triethyl amine (2,06 mL; 14,69 mmol) and piperidine (0,945 mL; 9,55 mmol) and the mixture was stirred at room temperature for 4 days. The reaction mixture was diluted with ethyl acetate and washed with a saturated solution of ammonium chloride and brine, dried over sodium sulphate, filtered and concentrated under reduced pressure. Purification by flash-chromatography on silica gel using a gradient of ethyl acetate (2-20%) in heptane furnished 2 g (80%) of the title as a yellow oil.

ESI/APCI(+): 340 (M+H).

Example 180

Preparation of (4-methyl-2-(piperidin-1-yl)-6-p-tolylpyrimidin-5-yl)methanol

To a solution of ethyl 4-methyl-2-(piperidin-1-yl)-6-p-tolylpyrimidine-5-carboxylate (2 g; 5,89 mmol) in dry dichloromethane (20 mL) at (−78° C.) under nitrogen atmosphere was slowly added a solution of diisobutylaluminium hydride (1M in dichloromethane) (13 mL; 13 mmol) and the reaction was stirred for 1 h at (−78° C.), then allowed to warm up to 0° C. and the stirring was carried on 2 h more. The reaction was quenched by adding a solution of hydrochloric acid 1N and the mixture was vigorously stirred for 1 h. The phases were separated and the aqueous layer was extracted with dichloromethane. The combined organic layers were washed with a saturated solution of sodium potassium tartrate and brine, dried over magnesium sulphate, filtered and concentrated under reduced pressure. The desired compound was obtained as a white solid (1.48 g; 84%) and used as such in the next step.

ESI/APCI(+): 298 (M+H);
$^1$H NMR (300 MHz, DMSO-$d_6$) δ ppm 7.62 (d, J=7.9 Hz, 2 H); 7.26 (d, J=7.9 Hz, 2 H); 4.97 (t, J=4.3 Hz, 1 H); 4.31 (d, J=4.1 Hz, 2 H); 3.75 (t, J=4.7 Hz, 4 H); 2.46 (s, 3 H); 2.37 (s, 3 H); 1.56-1.69 (m, 2 H); 1.42-1.56 (m, 4 H).

Example 181

Preparation of 4-methyl-2-(piperidin-1-yl)-6-p-tolylpyrimidine-5-carbaldehyde

To a solution of (4-methyl-2-(piperidin-1-yl)-6-p-tolylpyrimidin-5-yl)methanol (0.800 g; 2,69 mmol) in dichloromethane (27 mL) was added molecular sieves (4 Å) and pyridinium dichromate (1,52 g; 4,04 mmol). The reaction was stirred at room temperature for 21 h. An excess of celite was added to the reaction and the suspension was stirred for 30 min, filtered on a plug of celite and concentrated under reduced pressure. Purification by flash-chromatography on silica gel using a gradient of ethyl acetate (2-20%) in heptane furnished 0.487 g (61%) of the desired compound as a white solid.

ESI/APCI(+): 296 (M+H);
$^1$H NMR (300 MHz, DMSO-$d_6$) δ ppm 9.71 (s, 1 H); 7.46 (d, J=7.9 Hz, 2 H); 7.33 (d, J=7.9 Hz, 2 H); 3.91 (bs, 4 H); 2.61 (s, 3 H); 2.39 (s, 3 H); 1.47-1.73 (m, 6 H).

Example 182

Preparation of 2-(4-methyl-2-(piperidin-1-yl)-6-p-tolylpyrimidin-5-yl)-2-(trimethylsilyloxy)acetonitrile To a cold (0° C.) mixture of 4-methyl-2-(piperidin-1-yl)-6-p-tolylpyrimidine-5-carbaldehyde (0.48 g; 1,625 mmol) and zinc iodide (0.259 g; 0,813 mmol) in dichloromethane (8 mL) was added trimethylsilylcyanide (0,436 mL; 3,25 mmol) and the reaction mixture was stirred at room temperature for 1.5 h. The reaction mixture was diluted with dichloromethane and quenched with water. The aqueous layer was extracted with dichloromethane, the combine organics were washed with water and a brine, dried over sodium sulphate, filtered and concentrated under reduced pressure. The crude product was used as such in the next reaction.

ESI/APCI(+): 395 (M+H).

Example 183

Preparation of methyl 2-hydroxy-2-(4-methyl-2-(piperidin-1-yl)-6-p-tolylpyrimidin-5-yl)acetate To a cooled (0° C.), stirred solution of methanol (4 mL) under an argon atmosphere was added dropwise sulfuric acid (0.8 mL). The solution was warmed to room temperature and used immediately to dissolve 2-(4-methyl-2-(piperidin-1-yl)-6-p-tolylpyrimidin-5-yl)-2-(trimethylsilyloxy)acetonitrile (0.529 g; 1.39 mmol). The resulting mixture was heated at reflux for 24 h. After cooling, the volatiles were removed under reduced pressure, the remaining residue was partitioned between ethyl acetate and a saturated solution of sodium hydrogen carbonate. The phases were separated and the aqueous layer was extracted with ethyl acetate. The combined organics were washed with brine, dried over magnesium sulphate, filtered and concentrated under reduced pressure. Purification by flash-chromatography on silica gel using a gradient of ethyl acetate (5-40%) in heptane furnished 0.591 g (44%) of the title compound.

ESI/APCI(+): 356 (M+H).

Example 184

Preparation of methyl 2-tert-butoxy-2-(4-methyl-2-(piperidin-1-yl)-6-p-tolylpyrimidin-5-yl)acetate To a solution of methyl 2-hydroxy-2-(4-methyl-2-(piperidin-1-yl)-6-p-tolylpyrimidin-5-yl)acetate (0.135 g; 0.380 mmol) in tert-butyl acetate (1.5 mL; 11.23 mmol) under nitrogen atmosphere was added perchloric acid 70% (0.049 mL; 0.570 mmol) and the reaction was stirred at room temperature for 2 days. The reaction was quenched by adding a saturated solution of sodium hydrogen carbonate. The mixture was extracted with ethyl acetate and the combined organic layers were dried over magnesium sulphate, filtered a,d concentrated under reduced pressure. Purification by flash-chromatography on silica gel using a gradient of ethyl acetate (1-40%) in heptane furnished 0.063 g (40%) of the title compound as a colorless oil.

ESI/APCI(+): 412 (M+H).

Example 185

Preparation of 2-tert-butoxy-2-(4-methyl-2-(piperidin-1-yl)-6-p-tolylpyrimidin-5-yl)acetic acid To a mixture of methyl 2-tert-butoxy-2-(4-methyl-2-(piperidin-1-yl)-6-p-tolylpyrimidin-5-yl)acetate (0.030 g; 0.073 mmol) in a mixture dichloromethane-methanol (10:1) (0.55 ml) was added a solution of sodium hydroxide (2N in methanol) (0.075 ml; 0.150 mmol) and the reaction was stirred at room temperature for 24 h. The solvent was removed under reduced pressure, the residue diluted with water and washed with diethyl ether. The pH of the aqueous layer was adjusted to 2 with a solution of hydrochloric acid 2N and the suspension was extracted twice with dichloromethane. The combined organic layers were dried over sodium sulphate, filtered and concentrated under reduced pressure to furnish 0.020 g (65%) of the title compound as a white solid.

ESI/APCI(+): 398 (M+H);
ESI/APCI(−): 396 (M−H).

Example 186

Preparation of Diethyl 2-benzoyl-3-propylsuccinate

To a solution of ethyl benzoyacetate (8.71 mL; 50 mmol) in dry DMF (25 mL) under nitrogen atmosphere was added potassium carbonate (7.6 g; 55 mmol), which has been dried at 120° C. for 12 h before using. After stirring for 15 min at room temperature, ethyl 2-bromovalerate (8.53 mL; 50 mmol) was slowly added under nitrogen and the mixture was vigorously stirred at room temperature for 24 h. The reaction mixture was poured in water (240 mL) and neutralized by adding a solution of hydrochloric acid 6N. The product was extracted with diethyl ether (2×240 mL) and the combined organic layers were dried over magnesium sulphate, filtered and concentrated under reduced pressure. Purification by distillation under reduced pressure furnished 6 g (37%) of the title compound as a colorless liquid.

ESI/APCI(+): 321 (M+H).

Example 187

Preparation of 2-(6-oxo-4-phenyl-2-(piperidin-1-yl)-1,6-dihydropyrimidin-5-yl)pentanoic acid To a solution of piperidine-1-carboximidamide (dimer complexed with $H_2SO_4$) (0.6 g; 4.71 mmol) and diethyl 2-benzoyl-3-propylsuccinate (1.51 g; 4.71 mmol) in methanol (5 mL) was slowly added a solution of sodium methoxide in methanol (25% w:w) (2.16 mL; 9.43 mmol) and the reaction was heated to reflux for 21 h. The volatiles were removed under reduced pressure and the crude residue was used as such in the next reaction.

ESI/APCI(−): 354 (M−H).

Example 188

Preparation of Methyl 2-(6-oxo-4-phenyl-2-(piperidin-1-yl)-1,6-dihydropyrimidin-5-yl)pentanoate To a solution cold solution of methanol (20 mL) was added thionyl chloride (2.90 mL; 40 mmol) dropwise. The acidic solution was added to a flask containing 2-(6-oxo-4-phenyl-2-(piperidin-1-yl)-1,6-dihydropyrimidin-5-yl)pentanoic acid (1.67 g; 4.71 mmol) and the mixture was heated to reflux for 18 h. The reaction mixture was concentrated under reduced pressure, the residue was dissolved in water and neutralized with a saturated solution of sodium hydrogen carbonate. The suspension was extracted twice with ethyl acetate and the combined organic layers were washed with brine, dried over magnesium sulphate, filtered and concentrated under reduced pressure. The product was used as such in the next reaction.

ESI/APCI(+): 370 (M+H).

Example 189

Preparation of Methyl 2-(4-chloro-6-phenyl-2-(piperidin-1-yl)pyrimidin-5-yl)pentanoate To a suspension of methyl 2-(6-oxo-4-phenyl-2-(piperidin-1-yl)-1,6-dihydropyrimidin-5-yl)pentanoate (1.74 g; 4,71 mmol) in dry toluene (10 mL) under nitrogen atmosphere were carefully added phosphorus oxychloride (4.38 mL; 47.1 mmol) and dimethylaniline (0.476 mL; 3.77 mmol) and the reaction mixture was heated to reflux for 3 h. The volatiles were removed under reduced pressure (while the reaction mixture was still at elevated temperature), the residue was cooled in an ice-bath and quenched by adding crushed ice and a saturated solution of sodium hydrogen carbonate until neutralization. The aqueous layer was extracted with ethyl acetate, the organics were collected, dried over magnesium sulphate, filtered and concentrated under reduced pressure. Purification by flash-chromatography on silica gel using a gradient of ethyl acetate (1-10%) in heptane furnished 0.040 g (1.6%, over 3 last steps) of the title compound as a yellow oil.

ESI/APCI(+): 388 (M+H).

Example 190

Preparation of methyl 2-(4-phenyl-2-(piperidin-1-yl)-6-p-tolylpyrimidin-5-yl)pentanoate methyl-2-(4-chloro-6-phenyl-2-(piperidin-1-yl)pyrimidin-5-yl)pentanoate (0.031 g; 0.228 mmol), p-tolylboronic acid (0.031 g; 0.228 mmol), tetrakis(triphenylphosphine) palladium(0) (0.013 g; 0.011 mmol) were placed in a 5 mL reaction tube and dissolved in a mixture of degassed DME (0.75 mL) and water (0.25 mL). N,N-Diisopropylethylamine (0.060 mL; 0.344 mmol) was added, the tube was sealed and irradiated in a microwave oven at 130° C. for 30 min. The reaction mixture was partitioned between a solution of hydrochloric acid 1N and ethyl acetate. The phases were separated and the organic phase was washed with a 1N sodium bicarbonate solution and a saturated sodium chloride solution. The organic phase was dried over magnesium sulfate and concentrated under reduced pressure. The crude material was purified by flash chromatography on silica gel using a linear gradient of ethylacetate (0-10%) in heptane to give 0.018 g (45%) of the title compound.
ESI/APCI(+): 444 (M+H).

Example 191

Preparation of 2-(4-phenyl-2-(piperidin-1-yl)-6-p-tolylpyrimidin-5-yl)pentanoic acid This compound was prepared according to general method D from methyl-2-(4-phenyl-2-(piperidin-1-yl)-6-p-tolylpyrimidin-5-yl)pentanoate (0.018 g; 0.041 mmol), sodium hydroxide 5N (0.100 mL; 0.50 mmol) in methanol (1 mL) at 60° C. for 72 h. The reaction mixture was concentrated under reduced pressure, the residue was dissolved in water and extracted with diethyl ether. The pH of the aqueous layer was adjusted between 2 and 3 by addition of a solution of hydrochloric acid 6N until a precipitate was formed. The suspension was extracted twice with ethyl acetate and the combined organic layers were dried over sodium sulfate and concentrated under reduced pressure to give 0.012 g (68%) of the title compound.
ESI/APCI(+): 430 (M+H)
ESI/APCI(−): 428 (M−H); 384 (M−CO2H)

Example 192

Preparation of Diethyl 2-propionyl-3-propylsuccinate

To a solution of ethyl 3-oxopentanoate (7.21 mL; 50 mmol) in dry DMF (25 mL) under nitrogen atmosphere was added potassium carbonate (7.6 g; 55 mmol), which has been dried at 120° C. for 12 h before using. After stirring for 15 min at room temperature, ethyl 2-bromovalerate (8.53 mL; 50 mmol) was slowly added under nitrogen and the mixture was vigorously stirred at room temperature for 24 h. The reaction mixture was poured in water (240 mL) and neutralized by adding a solution of hydrochloric acid 6N. The product was extracted with diethyl ether (2×240 mL) and the combined organic layers were dried over magnesium sulphate, filtered and concentrated under reduced pressure. Purification by distillation under reduced pressure furnished 7.9 g (58%) of the title compound as a colorless liquid (bp. 130-135° C., 4 mbar, temperature of the oil bath 150° C.).
ESI/APCI(+): 273 (M+H);
ESI/APCI(−): 271 (M−H).

Example 193

Preparation of 2-(4-ethyl-6-oxo-2-(piperidin-1-yl)-1,6-dihydropyrimidin-5-yl)pentanoic acid To a solution of piperidine-1-carboximidamide (dimer complexated with $H_2SO_4$) (1 g; 7.86 mmol) and diethyl 2-propionyl-3-propylsuccinate (2.14 g; 7.86 mmol) in methanol (8 mL) was slowly added a solution of sodium methoxide in methanol (25% w:w) (3.60 mL; 15.72 mmol) and the reaction was heated under reflux for 18 h. The mixture was concentrated under reduced pressure and the curde residue was used as such in the next reaction.
ESI/APCI(+): 330 (M+Na); 308 (M+H);
ESI/APCI(−): 306 (M−H).

Example 194

Preparation of methyl 2-(4-ethyl-6-oxo-2-(piperidin-1-yl)-1,6-dihydropyrimidin-5-yl)pentanoate To a solution cold solution of methanol (40 mL) was added thionyl chloride (5.8 mL; 80 mmol) dropwise. The acidic solution was added to a flask containing 2-(4-ethyl-6-oxo-2-(piperidin-1-yl)-1,6-dihydropyrimidin-5-yl)pentanoic acid (2.416 g; 7.86 mmol) and the mixture was heated to reflux for 18 h. The reaction mixture was concentrated under reduced pressure and the product was used as such in the next reaction.
ESI/APCI(+): 322 (M+H)
ESI/APCI(−): 320 (M−H)

Example 195

Preparation of methyl 2-(4-chloro-6-ethyl-2-(piperidin-1-yl)pyrimidin-5-yl)pentanoate To a suspension of methyl 2-(4-ethyl-6-oxo-2-(piperidin-1-yl)-1,6-dihydropyrimidin-5-yl)pentanoate (2.53 g; 7.86 mmol) in dry toluene (15 mL) under nitrogen atmosphere were 5carefully added phosphorus oxychloride (7.30 mL; 79 mmol) and dimethylaniline (0.794 mL; 6.29 mmol) and the reaction mixture was heated under reflux for 3 h. The volatiles were removed under reduced pressure (while the reaction mixture was still at elevated temperature), the residue was cooled in an ice-bath and quenched by adding crushed ice and a saturated solution of sodium hydrogen carbonate until neutralization. The aqueous layer was extracted with ethyl acetate, the organics were collected, dried over magnesium sulphate, filtered and concentrated under reduced pressure. Purification by flash-chromatography on silica gel using a gradient of ethyl acetate (1-10%) in heptane furnished 0.352 g (8.6%, over 3 last steps) of the title compound as a yellow oil.
ESI/APCI(+): 340 (M+H)

Example 196

Preparation of methyl 2-(4-ethyl-2-(piperidin-1-yl)-6-p-tolylpyrimidin-5-yl)pentanoate methyl 2-(4-chloro-6-ethyl-2-(piperidin-1-yl)pyrimidin-5-yl)pentanoate (0.190 g; 0.559 mmol), p-tolylboronic acid (114 mg; 0.839 mmol), tetrakis(triphenylphosphine) palladium(0) (64.6 mg; 0.056 mmol) were placed in a 5 mL reaction tube and dissolved in a mixture of degassed DME (1.50 mL) and water (0.5 mL). N,N-Diisopropylethylamine (0.344 mL; 2.236 mmol) was added, the tube was sealed and irradiated in a microwave oven at 130° C. for 30 min. The reaction mixture was partitioned between brine and dichloromethane, filtered over a phase separator filter (1PS) and concentrated under reduced pressure. The crude material was purified by flash chromatography on silica gel using a linear gradient of ethylacetate (2-20%) in heptane to give 85 mg (35%) of the title compound as a yellow oil.

Example 197

Preparation of 2-(4-ethyl-2-(piperidin-1-yl)-6-p-tolylpyrimidin-5-yl)pentanoic acid This compound was prepared according to general method D from methyl 2-(4-ethyl-2-(piperidin-1-yl)-6-p-tolylpyrimidin-5-yl)pentanoate (0.085 g; 0.215 mmol), sodium hydroxide 10N (0.15 mL; 1.50 mmol) in methanol (1.5 mL) at 60° C. for 18 h. The reaction mixture was concentrated under reduced pressure, the residue was dissolved in water and extracted with diethyl ether. The pH of the aqueous layer was adjusted between 2 and 3 by addition of a solution of hydrochloric acid 6N until a precipitate was formed. The suspension was extracted twice with ethyl acetate and the combined organic layers were dried over sodium sulfate and concentrated under reduced pressure to give 0.061 g (74%) of the title compound.

ESI/APCI(+): 382 (M+H)
ESI/APCI(−): 380 (M−H); 336 (M−CO2H)

Example 198

Preparation of methyl 2-(2-(2-fluorophenyl)-4-methyl-6-p-tolylpyrimidin-5-yl)pentanoate Methyl 2-(2-chloro-4-methyl-6-p-tolylpyrimidin-5-yl)pentanoate (100 mg; 0.300 mmol), 2-fluorophenylboronic acid (126 mg; 0.901 mmol), tetrakis(triphenylphosphine) palladium(0) (34.7 mg; 0.030 mmol) were placed in a 5 mL reaction tube and dissolved in a mixture of degassed DME (1.50 mL) and water (0.5 mL). N,N-Diisopropylethylamine (0.185 mL; 1.202 mmol) was added, the tube was sealed and irradiated in a microwave oven at 130° C. for 1 h. The reaction mixture was partitioned between brine and dichloromethane, filtered over a phase separator filter (1PS) and concentrated under reduced pressure. The crude material was purified by flash chromatography on silica gel using a linear gradient of ethylacetate (5-40%) in heptane to give 69 mg (41%) of the title compound as a colorless oil.

ESI/APCI(+): 393 (M+H).

Example 199

Preparation of 2-(2-(2-fluorophenyl)-4-methyl-6-p-tolylpyrimidin-5-yl)pentanoic acid This compound was prepared according to general method D from methyl 2-(2-(2-fluorophenyl)-4-methyl-6-p-tolylpyrimidin-5-yl)pentanoate (0.069 g; 0.176 mmol), sodium hydroxide 10N (0.10 mL; 1.00 mmol) in methanol (1 mL) at 60° C. for 18 h. The reaction mixture was concentrated under reduced pressure, the residue was dissolved in water and extracted with diethyl ether. The pH of the aqueous layer was adjusted between 2 and 3 by addition of a solution of hydrochloric acid 6N until a precipitate was formed. The suspension was extracted twice with ethyl acetate and the combined organic layers were dried over sodium sulfate and concentrated under reduced pressure to give 0.006 g (9%) of the title compound.

ESI/APCI(+): 379 (M+H).

Example 200

Preparation of methyl 2-(2-(2-hydroxyphenyl)-4-methyl-6-p-tolylpyrimidin-5-yl)pentanoate Methyl 2-(2-chloro-4-methyl-6-p-tolylpyrimidin-5-yl)pentanoate (100 mg; 0.300 mmol), 2-hydroxyphenylboronic acid (124 mg; 0.901 mmol), tetrakis(triphenylphosphine) palladium(0) (34.7 mg; 0.030 mmol) were placed in a 5 mL reaction tube and dissolved in a mixture of degassed DME (1.50 mL) and water (0.5 mL). N,N-Diisopropylethylamine (0.185 mL; 1.202 mmol) was added, the tube was sealed and irradiated in a microwave oven at 130° C. for 1 h. The reaction mixture was partitioned between brine and ethyl acetate, the phases were separated and the aqueous layer was extracted with ethyl acetate. The combined organic layers were dried over magnesium sulfate and concentrated under reduced pressure. The crude material was purified by flash chromatography on silica gel using a linear gradient of ethylacetate (5-40%) in heptane to yield 83 mg (49%) of the title compound.

ESI/APCI(+): 391 (M+H).

Example 201

Preparation of 2-(2-(2-hydroxyphenyl)-4-methyl-6-p-tolylpyrimidin-5-yl)pentanoic acid This compound was prepared according to general method D from methyl 2-(2-(2-hydroxyphenyl)-4-methyl-6-p-tolylpyrimidin-5-yl)pentanoate (0.083 g; 0.213 mmol), sodium hydroxide 10N (0.10 mL; 1.00 mmol) in methanol (1 mL) at 60° C. for 18 h. The reaction mixture was concentrated under reduced pressure, the residue was dissolved in water and extracted with diethyl ether. The pH of the aqueous layer was adjusted between 2 and 3 by addition of a solution of hydrochloric acid 6N until a precipitate was formed. The suspension was extracted twice with ethyl acetate and the combined organic layers were dried over sodium sulfate and concentrated under reduced pressure to give 0.041 g (51%) of the title compound.

ESI/APCI(+): 377 (M+H).

Example 202

Preparation of methyl 2-(4-methyl-2-(quinolin-5-yl)-6-p-tolylpyrimidin-5-yl)pentanoate Methyl 2-(2-chloro-4-methyl-6-p-tolylpyrimidin-5-yl)pentanoate (100 mg; 0.300 mmol), quinolin-5-ylboronic acid (156 mg; 0.901 mmol), tetrakis(triphenylphosphine) palladium(0) (34.7 mg; 0.030 mmol) were placed in a 5 mL reaction tube and dissolved in a mixture of degassed DME (1.50 mL) and water (0.5 mL). N,N-Diisopropylethylamine (0.185 mL; 1.202 mmol) was added, the tube was sealed and irradiated in a microwave oven at 130° C. for 1 h. The reaction mixture was partitioned between brine and dichloromethane, filtered over a phase separator filter (1PS) and concentrated under reduced pressure. The crude material was purified by flash chromatography on silica gel using a linear gradient of ethylacetate (10-80%) in heptane to give 84 mg (43%) of the title compound as a colorless oil.

ESI/APCI(+): 426 (M+H).

Example 203

Preparation of 2-(4-methyl-2-(quinolin-5-yl)-6-p-tolylpyrimidin-5-yl)pentanoic acid This compound was prepared according to general method D from methyl 2-(4-methyl-2-(quinolin-5-yl)-6-p-tolylpyrimidin-5-yl)pentanoate (0.084 g; 0.197 mmol), sodium hydroxide 10N (0.10 mL; 1.00 mmol) in methanol (1 mL) at 60° C. for 18 h. The reaction mixture was concentrated under reduced pressure, the residue was dissolved in water and extracted with diethyl ether. The pH of the aqueous layer was adjusted between 2 and 3 by addition of a solution of hydrochloric acid 6N until a precipitate was formed. The suspension was extracted twice with ethyl acetate and the combined organic layers were dried over sodium sulfate and concentrated under reduced pressure to give 0.021 g (26%) of the title compound.

ESI/APCI(+): 412 (M+H).

Example 204:

Preparation of methyl 2-(4-methyl-2-(1-methyl-1H-pyrazol-4-yl)-6-p-tolylpyrimidin-5-yl)pentanoate Methyl 2-(2-chloro-4-methyl-6-p-tolylpyrimidin-5-yl)pentanoate (100 mg; 0.300 mmol), 1-Methyl-1H-pyrazole-4-boronic acid, pinacol ester (188 mg; 0.901 mmol), tetrakis(triphenylphosphine) palladium(0) (34.7 mg; 0.030 mmol) were placed in a 5 mL reaction tube and dissolved in a mixture of degassed DME (1.50 mL) and water (0.5 mL). N,N-Diisopropylethylamine (0.185 mL; 1.202 mmol) was added, the tube was sealed and irradiated in a microwave oven at 130° C. for 1 h. The reaction mixture was partitioned between brine and dichloromethane, filtered over a phase separator filter (1PS) and concentrated under reduced pressure. The crude material was purified by flash chromatography on silica gel using a linear gradient of ethylacetate (10-80%) in heptane to give 114 mg (63%) of the title compound as a colorless oil.

ESI/APCI(+): 379 (M+H).

Example 205

Preparation of 2-(4-methyl-2-(1-methyl-1H-pyrazol-4-yl)-6-p-tolylpyrimidin-5-yl)pentanoic acid This compound was prepared according to general method D from methyl 2-(4-methyl-2-(1-methyl-1H-pyrazol-4-yl)-6-p-tolylpyrimidin-5-yl)pentanoate (0.114 g; 0.301 mmol), sodium hydroxide 10N (0.10 mL; 1.00 mmol) in methanol (1 mL) at 60° C. for 18 h. The reaction mixture was concentrated under reduced pressure, the residue was dissolved in water and extracted with diethyl ether. The pH of the aqueous layer was adjusted between 2 and 3 by addition of a solution of hydrochloric acid 6N until a precipitate was formed. The suspension was extracted twice with ethyl acetate and the combined organic layers were dried over sodium sulfate and concentrated under reduced pressure to give 0.017 g (15%) of the title compound.

ESI/APCI(+): 365 (M+H).

Example 206

Preparation of methyl 2-(4-methyl-2-(phenylthio)-6-p-tolylpyrimidin-5-yl)pentanoate Methyl 2-(2-chloro-4-methyl-6-p-tolylpyrimidin-5-yl)pentanoate (100 mg; 0.300 mmol), cesium carbonate (294 mg; 0.901 mmol) and thiophenol (0.092 mL; 0.901 mmol) were placed in a 2 mL reaction tube and dissolved in tetrahydrofuran (0.6 mL). The tube was sealed and irradiated in a microwave oven at 130° C. for 30 min. The reaction mixture was partitioned between brine and dichloromethane, filtered over a phase separator filter (1PS) and concentrated under reduced pressure. The crude material was purified by flash chromatography on silica gel using a linear gradient of ethylacetate (5-40%) in heptane to give 57 mg (32%) of the title compound as a colorless oil.

ESI/APCI(+): 407 (M+H).

Example 207

Preparation of 2-(4-methyl-2-(phenylthio)-6-p-tolylpyrimidin-5-yl)pentanoic acid This compound was prepared according to general method D from methyl 2-(4-methyl-2-(phenylthio)-6-p-tolylpyrimidin-5-yl)pentanoate (0.057 g; 0.140 mmol), sodium hydroxide 10N (0.10 mL; 1.00 mmol) in methanol (1 mL) at 60° C. for 18 h. The reaction mixture was concentrated under reduced pressure, the residue was dissolved in water and extracted with diethyl ether. The pH of the aqueous layer was adjusted between 2 and 3 by addition of a solution of hydrochloric acid 6N until a precipitate was formed. The suspension was extracted twice with ethyl acetate and the combined organic layers were dried over sodium sulfate and concentrated under reduced pressure to give 0.035 g (64%) of the title compound.

ESI/APCI(+): 393 (M+H).

Example 208

Preparation of methyl 2-(4-methyl-2-(phenylamino)-6-p-tolylpyrimidin-5-yl)pentanoate Methyl 2-(2-chloro-4-methyl-6-p-tolylpyrimidin-5-yl)pentanoate (100 mg; 0.300 mmol), aniline (0.033 mL; 0.361 mmol), palladium acetate (2 mg, 0.009 mmol) and xantphos (10 mg; 0.018 mmol) were placed in a 2 mL reaction tube and dissolved in dioxane (1 mL), the tube was purged with argon, sealed and irradiated in a microwave oven at 160° C. for 15 min. The reaction mixture was partitioned between a saturated sodium chloride solution and dichloromethane, filtered over a phase separator filter (1PS) and concentrated under reduced pressure. The crude material was purified by flash chromatography on silica gel using a linear gradient of ethylacetate (5-40%) in heptane to yield 58 mg (39%) of the title compound as a colorless oil.

ESI/APCI(+): 390 (M+H).

Example 209

Preparation of 2-(4-methyl-2-(phenylamino)-6-p-tolylpyrimidin-5-yl)pentanoic acid This compound was prepared according to general method D from methyl 2-(4-methyl-2-(phenylamino)-6-p-tolylpyrimidin-5-yl)pentanoate (0.058 g; 0.149 mmol), sodium hydroxide 10N (0.10 mL; 1.00 mmol) in methanol (1 mL) at 60° C. for 18 h. The reaction mixture was concentrated under reduced pressure, the residue was dissolved in water and extracted with diethyl ether. The pH of the aqueous layer was adjusted between 2 and 3 by addition of a solution of hydrochloric acid 6N until a precipitate was formed. The suspension was extracted twice with ethyl acetate and the combined organic layers were dried over sodium sulfate and concentrated under reduced pressure to give 0.035 g (62%) of the title compound.

ESI/APCI(+): 376 (M+H);
ESI/APCI(−): 374 (M−H).

Example 210

Preparation of methyl 2-(2-(benzylamino)-4-methyl-6-p-tolylpyrimidin-5-yl)pentanoate Methyl 2-(2-chloro-4-methyl-6-p-tolylpyrimidin-5-yl)pentanoate (100 mg; 0.300 mmol), and benzylamine (0.164 mL; 1.502 mmol) were placed in a 2 mL reaction tube and dissolved in isopropanol (1.5 mL). The tube was sealed and irradiated in a microwave oven at 180° C. for 1 h. The reaction mixture was partitioned between brine and dichloromethane, filtered over a phase separator filter (1PS) and concentrated under reduced pressure. The crude material was purified by flash chromatography on silica gel using a linear gradient of ethylacetate (5-40%) in heptane to give 55 mg (33%) of the title compound as a colorless oil.
ESI/APCI(+): 404 (M+H).

Example 211

Preparation of 2-(2-(benzylamino)-4-methyl-6-p-tolylpyrimidin-5-yl)pentanoic acid This compound was prepared according to general method D from methyl 2-(2-(benzylamino)-4-methyl-6-p-tolylpyrimidin-5-yl)pentanoate (0.055 g; 0.136 mmol), sodium hydroxide 10N (0.10 mL; 1.00 mmol) in methanol (1 mL) at 60° C. for 18 h. The reaction mixture was concentrated under reduced pressure, the residue was dissolved in water and extracted with diethyl ether. The pH of the aqueous layer was adjusted between 2 and 3 by addition of a solution of hydrochloric acid 6N until a precipitate was formed. The suspension was extracted twice with ethyl acetate and the combined organic layers were dried over sodium sulfate and concentrated under reduced pressure to give 0.049 g (92%) of the title compound.
ESI/APCI(+): 390 (M+H);
ESI/APCI(−): 388 (M−H).

Example 212

Preparation of methyl 2-(4-methyl-2-(4-methylphenylsulfonamido)-6-p-tolylpyrimidin-5-yl)pentanoate Methyl 2-(2-chloro-4-methyl-6-p-tolylpyrimidin-5-yl)pentanoate (100 mg; 0.300 mmol), p-toluenesulfonamide (0.061 mg; 0.361 mmol), palladium acetate (2 mg, 0.009 mmol) and xantphos (10 mg; 0.018 mmol) were placed in a 2 mL reaction tube and dissolved in dioxane (1 mL), the tube was purged with argon, sealed and irradiated in a microwave oven at 160° C. for 30 min. The reaction mixture was partitioned between a saturated sodium chloride solution and dichloromethane, filtered over a phase separator filter (1PS) and concentrated under reduced pressure. The crude material was purified by flash chromatography on silica gel using a linear gradient of ethylacetate (10-80%) in heptane to yield 32 mg (22%) of the title compound as a colorless oil.
ESI/APCI(+): 468 (M+H).

Example 213

Preparation of 2-(4-methyl-2-(4-methylphenylsulfonamido)-6-p-tolylpyrimidin-5-yl)pentanoic acid This compound was prepared according to general method D from methyl 2-(4-methyl-2-(4-methylphenylsulfonamido)-6-p-tolylpyrimidin-5-yl)pentanoate (0.032 g; 0.068 mmol), sodium hydroxide 10N (0.10 mL; 1.00 mmol) in methanol (1 mL) at 60° C. for 18 h. The reaction mixture was concentrated under reduced pressure, the residue was dissolved in water and extracted with diethyl ether. The pH of the aqueous layer was adjusted between 2 and 3 by addition of a solution of hydrochloric acid 6N until a precipitate was formed. The suspension was extracted twice with ethyl acetate and the combined organic layers were dried over sodium sulfate and concentrated under reduced pressure to give 0.029 g (93%) of the title compound.
ESI/APCI(+): 454 (M+H);
ESI/APCI(−): 452 (M−H).

Example 214

Preparation of methyl 2-(2-(2,6-difluorophenyl)-4-methyl-6-p-tolylpyrimidin-5-yl)pentanoate Methyl 2-(2-chloro-4-methyl-6-p-tolylpyrimidin-5-yl)pentanoate (100 mg; 0.300 mmol), 2,6-difluorophenylboronic acid (142 mg; 0.901 mmol), tetrakis(triphenylphosphine) palladium(0) (34.7 mg; 0.030 mmol) were placed in a 5 mL reaction tube and dissolved in a mixture of degassed DME (1.50 mL) and water (0.5 mL). N,N-Diisopropylethylamine (0.185 mL; 1.202 mmol) was added, the tube was sealed and irradiated in a microwave oven at 130° C. for 1 h. The reaction mixture was partitioned between brine and dichloromethane, filtered over a phase separator filter (1PS) and concentrated under reduced pressure. The crude material was purified by flash chromatography on silica gel using a linear gradient of ethylacetate (10-80%) in heptane to give 33 mg (16%) of the title compound as a colorless oil.
ESI/APCI(+): 411 (M+H).

Example 215

Preparation of 2-(2-(2,6-difluorophenyl)-4-methyl-6-p-tolylpyrimidin-5-yl)pentanoic acid This compound was prepared according to general method D from methyl 2-(2-(2,6-difluorophenyl)-4-methyl-6-p-tolylpyrimidin-5-yl)pentanoate (0.033 g; 0.080 mmol), sodium hydroxide 10N (0.10 mL; 1.00 mmol) in methanol (1 mL) at 60° C. for 18 h. The reaction mixture was concentrated under reduced pressure, the residue was dissolved in water and extracted with diethyl ether. The pH of the aqueous layer was adjusted between 2 and 3 by addition of a solution of hydrochloric acid 6N until a precipitate was formed. The suspension was extracted twice with ethyl acetate and the combined organic layers were dried over sodium sulfate and concentrated under reduced pressure to give 0.022 g (69%) of the title compound.
ESI/APCI(+): 397 (M+H);
ESI/APCI(−): 395 (M−H).

Example 216

Preparation of methyl 2-(4-methyl-2-(neopentylamino)-6-p-tolylpyrimidin-5-yl)pentanoate Methyl 2-(2-chloro-4-methyl-6-p-tolylpyrimidin-5-yl)pentanoate (100 mg; 0.300 mmol), and neopentyl amine (0.177 mL; 1.502 mmol) were placed in a 2 mL reaction tube and dissolved in isopropanol (1.5 mL). The tube was sealed and irradiated in a microwave oven at 180° C. for 1 h. The reaction mixture was partitioned between brine and dichloromethane, filtered over a phase separator filter (1PS) and

Example 217

Preparation of 2-(4-methyl-2-(neopentylamino)-6-p-tolylpyrimidin-5-yl)pentanoic acid This compound was prepared according to general method D from methyl 2-(4-methyl-2-(neopentylamino)-6-p-tolylpyrimidin-5-yl)pentanoate (0.057 g; 0.149 mmol), sodium hydroxide 10N (0.10 mL; 1.00 mmol) in methanol (1 mL) at 60° C. for 18 h. The reaction mixture was concentrated under reduced pressure, the residue was dissolved in water and extracted with diethyl ether. The pH of the aqueous layer was adjusted between 2 and 3 by addition of a solution of hydrochloric acid 6N until a precipitate was formed. The suspension was extracted twice with ethyl acetate and the combined organic layers were dried over sodium sulfate and concentrated under reduced pressure to give 0.048 g (87%) of the title compound.
ESI/APCI(+): 370 (M+H);
ESI/APCI(−): 368 (M−H).

Example 218

Preparation of Triethyl pentane-1,1,2-tricarboxylate

To a solution of diethyl malonate (8.01 g; 50 mmol) in dry DMF (25 mL) under nitrogen atmosphere was added potassium carbonate (7.6 g; 55 mmol), which has been dried at 120° C. for 12 h before using. After stirring for 15 min at room temperature, ethyl 2-bromovalerate (8.53 mL; 50 mmol) was slowly added under nitrogen and the mixture was vigorously stirred at room temperature for 24 h. The reaction mixture was poured in water (240 mL) and neutralized by adding a solution of hydrochloric acid 6N. The product was extracted with diethyl ether (2x240 mL) and the combined organic layers were dried over magnesium sulphate, filtered and concentrated under reduced pressure. Purification by distillation under reduced pressure furnished 12.8 g (99%) of the title compound as a colorless liquid (bp. 117° C., 2 mbar, temperature of the oil bath 165° C.).
ESI/APCI(+): 259 (M+H);
ESI/APCI(−): 257 (M−H).

Example 219

Preparation of 2-(4,6-dihydroxy-2-(piperidin-1-yl)pyrimidin-5-yl)pentanoic acid

To a solution of piperidine-1-carboximidamide (dimer complexated with $H_2SO_4$) (1.32 g; 10.4 mmol) and triethyl pentane-1,1,2-tricarboxylate (3 g; 10.4 mmol) in methanol (15 mL) was slowly added a solution of sodium methoxide in methanol (25% w:w) (4.76 mL; 20.81 mmol) and the reaction was heated to reflux for 18 h. The volatiles were removed under reduced pressure and the crude residue was used as such in the next reaction.

Example 220

Preparation of methyl 2-(4,6-dioxo-2-(piperidin-1-yl)-1,4,5,6-tetrahydropyrimidin-5-yl)pentanoate To a solution cold solution of methanol (50 mL) was added thionyl chloride (7.25 mL; 100 mmol) dropwise. The acidic solution was added to a flask containing 2-(4,6-dihydroxy-2-(piperidin-1-yl)pyrimidin-5-yl)pentanoic acid (3.07 g; 10.4 mmol) and the mixture was heated to reflux for 18 h. The reaction mixture was concentrated under reduced pressure and the product was used as such in the next reaction.

Example 221

Preparation of methyl 2-(4,6-dichloro-2-(piperidin-1-yl)pyrimidin-5-yl)pentanoate To a suspension of methyl 2-(4,6-dioxo-2-(piperidin-1-yl)-1,4,5,6-tetrahydropyrimidin-5-yl)pentanoate (1 eq) in dry toluene (2 mL/mmol) under a nitrogen atmosphere is carefully added phosphorus oxychloride (10 eq) and dimethylaniline (0.8 eq) and the reaction mixture is heated under reflux for 3 h. The volatiles are removed under reduced pressure, the residue is cooled in an ice-bath and quenched by adding crushed ice and a saturated solution of sodium hydrogen carbonate until neutralization. The aqueous layer is extracted with ethyl acetate, the organics are collected, dried over magnesium sulphate, filtered and concentrated under reduced pressure. Purification is performed by flash-chromatography on silica gel using a gradient of ethyl acetate in heptane.

Example 222

Preparation of methyl 2-(4-chloro-2-(piperidin-1-yl)-6-p-tolylpyrimidin-5-yl)pentanoate methyl 2-(4,6-dichloro-2-(piperidin-1-yl)pyrimidin-5-yl)pentanoate (1 eq), p-tolylboronic acid (1 eq), tetrakis(triphenylphosphine)palladium(0) (0.1 eq) are placed in a reaction tube and dissolved in a mixture of degassed DME and water (3/1 v/v; 5 mL/mmol). N,N-Diisopropylethylamine (4 eq) is added, the tube is sealed and irradiated in a microwave oven at 130° C. for 30 min. The reaction mixture is partitioned between brine and dichloromethane, filtered over a phase separator filter (1PS) and concentrated under reduced pressure. Purification of the crude material is performed by flash chromatography on silica gel using a linear gradient of ethyl acetate in heptane.

Example 223

Preparation of methyl 2-(6-oxo-2-(piperidin-1-yl)-4-p-tolyl-1,6-dihydropyrimidin-5-yl)pentanoate A mixture of methyl 2-(4-chloro-2-(piperidin-1-yl)-6-p-tolylpyrimidin-5-yl)pentanoate in acetic acid and water (4/1 v/v; 30 mL/mmol) is stirred at 150° C. until completion. The reaction mixture is concentrated under reduced pressure, dissolved in dichloromethane and purified by flash chromatography on silica gel using a linear gradient of ethyl acetate in heptane.

Example 224

Preparation of 2-(6-oxo-2-(piperidin-1-yl)-4-p-tolyl-1,6-dihydropyrimidin-5-yl)pentanoic acid This compound is prepared according to general method D from methyl 2-(6-oxo-2-(piperidin-1-yl)-4-p-tolyl-1,6-dihydropyrimidin-5-yl)pentanoate (1 eq), sodium hydroxide 10N (10 eq) in methanol (6 mL/mmol) at 60° C. for 18 h. The reaction mixture is concentrated under reduced pressure, the residue is dissolved in water and extracted with diethyl ether.

--- concentrated under reduced pressure. The crude material was purified by flash chromatography on silica gel using a linear gradient of ethylacetate (2-20%) in heptane to give 57 mg (49%) of the title compound as a colorless oil.
ESI/APCI(+): 384 (M+H).

The pH of the aqueous layer is adjusted between 2 and 3 by addition of a solution of hydrochloric acid 6N. The suspension is extracted twice with ethyl acetate and the combined organic layers are dried over sodium sulfate and concentrated under reduced pressure to yield the title compound.

Example 225

Preparation of 2-(1-methyl-6-oxo-2-(piperidin-1-yl)-4-p-tolyl-1,6-dihydropyrimidin-5-yl)pentanoic acid LHMDS (1M in THF; 2 eq) is added to a cold (−10° C.) stirred solution of methyl 2-(6-oxo-2-(piperidin-1-yl)-4-p-tolyl-1,6-dihydropyrimidin-5-yl)pentanoate (1 eq) in dry DMF (2 mL/mmol of the limiting reagent). After stirring for 5 minutes, methyl iodide (2 eq) is added and the reaction mixture is stirred at room temperature for 18 hours. A saturated solution of ammonium chloride is then added and the aqueous layer is extracted with ethyl acetate. The organic layer is dried over magnesium sulphate, filtered and evaporated to dryness. The crude material is purified by flash chromatography on silica gel to provide the methyl 2-(1-methyl-6-oxo-2-(piperidin-1-yl)-4-p-tolyl-1,6-dihydropyrimidin-5-yl)pentanoate which is deprotected following general method D yielding to the title compound.

Example 226

Preparation of 2-(1-ethyl-6-oxo-2-(piperidin-1-yl)-4-p-tolyl-1,6-dihydropyrimidin-5-yl)pentanoic acid LHMDS (1M in THF; 2 eq) is added to a cold (−10° C.) stirred solution of methyl 2-(6-oxo-2-(piperidin-1-yl)-4-p-tolyl-1,6-dihydropyrimidin-5-yl)pentanoate (1 eq) in dry DMF (2 mL/mmol of the limiting reagent). After stirring for 5 minutes, ethyl iodide (2 eq) is added and the reaction mixture is stirred at room temperature for 18 hours. A saturated solution of ammonium chloride is then added and the aqueous layer is extracted with ethyl acetate. The organic layer is dried over magnesium sulphate, filtered and evaporated to dryness. The crude material is purified by flash chromatography on silica gel to provide the methyl 2-(1-ethyl-6-oxo-2-(piperidin-1-yl)-4-p-tolyl-1,6-dihydropyrimidin-5-yl)pentanoate which is deprotected following general method D yielding to the title compound.

Example 227

Preparation of 2-(1-benzyl-6-oxo-2-(piperidin-1-yl)-4-p-tolyl-1,6-dihydropyrimidin-5-yl)pentanoic acid LHMDS (1M in THF; 2 eq) is added to a cold (−-10° C.) stirred solution of methyl 2-(6-oxo-2-(piperidin-1-yl)-4-p-tolyl-1,6-dihydropyrimidin-5-yl)pentanoate (1 eq) in dry DMF (2 mL/mmol of the limiting reagent). After stirring for 5 minutes, benzyl bromide (2 eq) is added and the reaction mixture is stirred at room temperature for 18 hours. A saturated solution of ammonium chloride is then added and the aqueous layer is extracted with ethyl acetate. The organic layer is dried over magnesium sulphate, filtered and evaporated to dryness. The crude material is purified by flash chromatography on silica gel to provide the methyl 2-(1-benzyl-6-oxo-2-(piperidin-1-yl)-4-p-tolyl-1,6-dihydropyrimidin-5-yl)pentanoate which is deprotected following general method D yielding to the title compound.

Example 228

Preparation of methyl 2-(4-(2,3-dihydropyrano[4,3,2-de]quinolin-7-yl)-6-methyl-2-(piperidin-1-yl)pyrimidin-5-yl)pentanoate This compound is prepared according to general method E starting from methyl 2-(4-chloro-6-methyl-2-(piperidin-1-yl)pyrimidin-5-yl)pentanoate and 2,3-dihydropyrano[4,3,2-de]quinolin-7-ylboronic acid.

Example 229

Preparation of 2-(4-(2,3-dihydropyrano[4,3,2-de]quinolin-7-yl)-6-methyl-2-(piperidin-1-yl)pyrimidin-5-yl)pentanoic acid This compound is prepared according to general method D starting from methyl 2-(4-(2,3-dihydropyrano[4,3,2-de]quinolin-7-yl)-6-methyl-2-(piperidin-1-yl)pyrimidin-5-yl)pentanoate.

Example 230

Preparation of methyl 2-(4-(8-fluoro-5-methylchroman-6-yl)-6-methyl-2-(piperidin-1-yl)pyrimidin-5-yl)pentanoate This compound is prepared according to general method E starting from methyl 2-(4-chloro-6-methyl-2-(piperidin-1-yl)pyrimidin-5-yl)pentanoate and 2-(8-fluoro-5-methylchroman-6-yl)-4,4,5,5-tetramethyl-1,3,2-dioxaborolane.

Example 231

Preparation of 2-(4-(8-fluoro-5-methylchroman-6-yl)-6-methyl-2-(piperidin-1-yl)pyrimidin-5-yl)pentanoic acid This compound is prepared according to general method D starting from methyl 2-(4-(8-fluoro-5-methylchroman-6-yl)-6-methyl-2-(piperidin-1-yl)pyrimidin-5-yl)pentanoate.

Example 232

Preparation of methyl 2-(4-(5-chlorochroman-6-yl)-6-methyl-2-(piperidin-1-yl)pyrimidin-5-yl)pentanoate This compound is prepared according to general method E starting from methyl 2-(4-chloro-6-methyl-2-(piperidin-1-yl)pyrimidin-5-yl)pentanoate and 2-(5-chlorochroman-6-yl)-4,4,5,5-tetramethyl-1,3,2-dioxaborolane.

Example 233

Preparation of 2-(4-(5-chlorochroman-6-yl)-6-methyl-2-(piperidin-1-yl)pyrimidin-5-yl)pentanoic acid This compound is prepared according to general method D starting from methyl 2-(4-(5-chlorochroman-6-yl)-6-methyl-2-(piperidin-1-yl)pyrimidin-5-yl)pentanoate.

Example 234

Preparation of methyl 2-tert-butoxy-2-(4-tert-butyl-6-methyl-2-(piperidin-1-yl)pyrimidin-5-yl)acetate This compound is prepared following the same procedure as described for example 184 wherein methyl 2-hydroxy-2-

(4-methyl-2-(piperidin-1-yl)-6-p-tolylpyrimidin-5-yl)acetate is replaced by methyl 2-(4-tert-butyl-6-methyl-2-(piperidin-1-yl)pyrimidin-5-yl)-2-hydroxyacetate.

Example 235

Preparation of 2-tert-butoxy-2-(4-tert-butyl-6-methyl-2-(piperidin-1-yl)pyrimidin-5-yl)acetic acid This compound is prepared following the same procedure as described for example 185 wherein methyl 2-tert-butoxy-2-(4-methyl-2-(piperidin-1-yl)-6-p-tolylpyrimidin-5-yl)acetate is replaced by methyl 2-tert-butoxy-2-(4-tert-butyl-6-methyl-2-(piperidin-1-yl)pyrimidin-5-yl)acetate.

Example 236

Preparation of methyl 2-(4-ethyl-6-methyl-2-phenylpyrimidin-5-yl)pentanoate This compound is prepared from methyl 2-(4-chloro-6-methyl-2-phenylpyrimidin-5-yl)pentanoate and ethylmagnesium chloride in THF at −10° C. in the presence of CuI as described in the following reference: Chemistry-A European Journal, 15(29), 7167-7179, S7167/1-S7167/121; 2009.

Example 237

Preparation of 2-(4-ethyl-6-methyl-2-phenylpyrimidin-5-yl)pentanoic acid

This compound is prepared according to general method D starting from methyl 2-(4-ethyl-6-methyl-2-phenylpyrimidin-5-yl)pentanoate.

Part B: Antiviral Activity of the Compounds

Example 238

Evaluation of the Anti-HIV Activity of the Compounds of the Invention

A rapid and automated assay procedure was used for the in vitro evaluation of anti-HIV agents. An HTLV-1 transformed T4-cell line MT-4, which was previously shown to be highly susceptible to and permissive for HIV infection, served as the target cell line. Inhibition of the HIV-induced cytopathogenic effect was used as the end point. The viability of both HIV- and mock-infected cells was assessed spectrophotometrically via in situ reduction of 3-(4,5-dimethylthiazol-2-yl)-2,5-diphenyltetrazolium bromide (MTT). The 50% cytotoxic concentration ($CC_{50}$ in µg/ml) was defined as the concentration of compound that reduced the absorbance of the mock-infected control sample by 50%. The percent protection achieved by the compound in HIV-infected cells was calculated by the following formula:

$$\frac{(OD_T)_{HIV} - (OD_C)_{HIV}}{(OD_C)_{MOCK} - (OD_C)_{HIV}} \text{ expressed in \%}$$

whereby $(OD_T)_{HIV}$ is the optical density measured with a given concentration of the test compound in HIV-infected cells; $(OD_C)_{HIV}$ is the optical density measured for the control untreated HIV-infected cells; $(OD_C)_{MOCK}$ is the optical density measured for the control untreated mock-infected cells; all optical density values were determined at 540 nm. The dose achieving 50% protection according to the above formula was defined as the 50% inhibitory concentration ($IC_{50}$ in µg/ml). The ratio of $CC_{50}$ to $IC_{50}$ was defined as the selectivity index (SI). The compounds of formula (9 and 13) were shown to inhibit HIV effectively. Examples of $IC_{50}$, $CC_{50}$ and SI values for inhibition of proliferation of HIV by particular compounds of formula (I) are listed in table 7 herein below.

Examples of inhibition of cell proliferation by particular compounds of formula (I) can be found by looking at the respective $CC_{50}$ values in the MT-4 cell line.

Cells: MT-4 cells (Miyoshi et al., 1982) were grown and maintained in RPMI 1640 medium supplemented with 10% heat-inactivated fetal calf serum, 2 mM l-glutamine, 0.1% sodium bicarbonate, and 20 æg of gentamicin per ml.

Viruses: The HIV-1 (NL4.3) strain (Adachi et al., 1986) is a molecular clone obtained from the National Institutes of Health (Bethesda, Md.). The HIV-2 (ROD) (Barr,-Sinoussi et al., 1983) stock was obtained from culture supernatant of HIV-2 infected cell lines.

References:
Adachi, A., Gendelman, H., Koenig, S., Folks, T., Willey, R., Rabson, A. and Martin, M (1986) Production of acquired immunodeficiency syndrome-associated retrovirus in human and nonhuman cells transfected with an infectious molecular clone, *J. Virol.*, 59, 284-291. Barr-Sinoussi, F., Chermann, J. C., Rey, F., Nugeyre, M. T., Chamaret, S., Gruest, J., Dauguet, C., Axler-Blin, C., V,zinet-Brun, F., Rouzioux, C., Rozenbaum, W., Montagnier, L. (1983) Isolation of a T-lymphotropic retrovirus from patient at risk for AIDS, *Science* (Wash D.C.) 220, 868-871. Miyoshi, I., Taguchi, H., Kobonishi, I., Yoshimoto, S., Ohtsuki, Y., Shiraishi, Y. and Akagi, T. (1982) Type C virus-producing cell lines derived from adult T cell leukemia, *Gann mongr*, 28, 219-228.

Example 239

Alphascreen Assay to Measure the LEDGF-Integrase Interaction Inhibitory Activity of Compounds of the Invention The AlphaScreen assay was performed according to the manufacturer's protocol (Perkin Elmer, Benelux). Reactions were performed in 25 µl final volume in 384-well Optiwell™ microtiter plates (Perkin Elmer). The reaction buffer contained 25 mM Tris-HCl (pH 7.4), 150 mM NaCl, 1 mM $MgCl_2$, 0.01% (v/v) Tween-20 and 0.1% (w/v) bovine serum albumin. $His_6$-tagged integrase (300 nM final concentration) was incubated with the compounds for 30 min at 4° C. The compounds were added at varying concentrations spanning a wide range from 0.1 up to 100 µM. Afterwards 100 nM flag-LEDGF/p75 was added and incubation was prolonged for an additional hour at 4° C. Subsequently 5 µl of Ni-chelate-coated acceptor beads and 5 µl anti-flag donor beads were added to a final concentration of 20 µg/ml of both beads. Proteins and beads were incubated for 1 h at 30° C. in order to allow association to occur. Exposure of the reaction to direct light was omitted as much as possible and the emission of light from the acceptor beads was measured in the EnVision plate reader (Perkin Elmer, Benelux) and analyzed using the EnVision manager software. IN/DNA binding was analyzed in a similar setting using $His_6$-tagged integrase (1 µM final concentration) and an oligodeoxynucleotide mimicking the IN ELISA oligonucleotide substrate (30 nM final concentration). Counterscreens with JPO2 or PogZ, respectively, were essentially performed as described previously.

Expression and purification of recombinant proteins: $His_6$-tagged HIV-1 integrase, 3×flag-tagged LEDGF/p75, MBP- JPO2 and MBP-PogZ were purified for AlphaScreen applications as described previously 23,25,56.

References

Bartholomeeusen, K., et al. Differential interaction of HIV-1 integrase and JPO2 with the C terminus of LEDGF/p75. J. Mol. Biol. 372, 407-421 (2007).

Bartholomeeusen, K., et al. Lens Epithelium Derived Growth Factor/p75 interacts with the transposase derived DDE domain of pogZ. J. Biol. Chem. (2009).

Busschots, K., et al. The interaction of LEDGF/p75 with integrase is lentivirus-specific and promotes DNA binding. J. Biol. Chem. 280, 17841-17847 (2005).

Representative compounds of the invention with their biological activity according to examples 238 and 239 are listed in Table 2.

| code | $IC_{50}$ in IN-LEDGF alphascreen (μM) [or with *: % inhibition at 100 μM] | $CC_{50}$ in MT4-IIIB (μm) | $EC_{50}$ in MT4-IIIB (μm) | SI |
|---|---|---|---|---|
| cpd 2 | 36.71 | 164.2 | / | |
| cpd 6 | 45.59 | 98.72 | / | |
| cpd 10 | 30.88 | 110.45 | 35.89 | 3 |
| cpd 12 | 25.21 | 81.8 | 48.33 | 2 |
| cpd 14 | 22.08 | 119.65 | 23.37 | 5 |
| cpd 16 | ND | >250 | 152.32 | >1 |
| cpd 18 | 89.94 | 125 | / | |
| cpd 20 | 12.47 | 119.55 | 15.87 | 8 |
| cpd 22 | 4.74 | 100 | 9.16 | 11 |
| cpd 24 | ND | >125 | 79.99 | >2 |
| cpd 26 | ND | >125 | 70.86 | >2 |
| cpd 30 | 4.61 | 143 | 16.1 | 9 |
| cpd 32 | 53.74 | >250 | / | |
| cpd 34 | 17.55 | 57 | / | |
| cpd 36 | 11.16 | 58 | / | |
| cpd 38 | 10.88 | 144 | 5.97 | 24 |
| cpd 40 | 25.06 | 120 | 24.58 | 5 |
| cpd 42 | 17.3 | 26 | / | |
| cpd 44 | 10.98 | 7 | / | |
| cpd 46 | 80.8 | 42 | / | |
| cpd 48 | 9.49 | 25 | / | |
| cpd 50 | 82.24 | 28 | / | |
| cpd 52 | 3.62 | 101 | / | |
| cpd 54 | 3.9 | 67 | / | |
| cpd 56 | 73.78 | >250 | 100.82 | >2 |
| cpd 58 | 17.85 | 38.66 | 2.91 | 13 |
| cpd 60 | 4.71 | 61 +/− 1 | 13.25 | 5 |
| cpd 62 | 6.71 | 131 | 29.76 | 4 |
| cpd 64 | ND | >250 | 197.14 | >1 |
| cpd 66 | 28.28 | 120 | / | |
| cpd 68 | *[61%] | 53 | / | |
| cpd 70 | 14.94 | 90 | 42.05 | 2 |
| cpd 72 | 14.73 | 110 | 46.3 | 2 |
| cpd 74 | *[46%] | 129 | / | |
| cpd 76 | 93.03 | 74 | / | |
| cpd 78 | *[58%] | 102 | / | |
| cpd 86 | *[46%] | 118 | / | |
| cpd 88 | 66.69 | 121 | / | |
| cpd 90 | 61.86 | 125 | / | |
| cpd 92 | *[51%] | 113 | / | |
| cpd 94 | 7.25 | 81 | 19.04 | 4 |
| cpd 98 | 13.52 | 113 | 35.85 | 3 |
| cpd 100 | 70.75 | 96 | / | |
| cpd 102 | 13.38 | 143 | 13.42 | 11 |
| cpd 106 | 56.6 | 32 | / | |
| cpd 108 | 100 | 47 | / | |
| cpd 110 | *[40%] | 94 | / | |
| cpd 111 | 1.97 | 97 | 26.43 | 4 |
| cpd 117 | 6.1 | >250 | / | |
| cpd 119 | 21.89 | 119.66 | 29.43 | 4 |
| cpd 120 | *[48%] | 124 | / | |
| cpd 122 | 59.74 | >250 | 21.49 | >12 |
| cpd 124 | 19.73 | 124 | 5.3 | 23 |
| cpd 126 | 27 | 67 | / | |
| cpd 130 | 17.43 | 99 | 22.68 | 4 |
| cpd 132 | 22.95 | 84.5 | 30.15 | 3 |
| cpd 136 | 20.7 | 127 | 48.97 | 3 |
| cpd 142 | 50.46 | 79 | / | |
| cpd 144 | 5.92 | 72.5 | 7.93 | 9 |
| cpd 146 | 10.79 | 72 | 9.38 | 8 |
| cpd 148 | 34.07 | 137.5 | 18.09 | 8 |
| cpd 152 | 6.9 | 72 | 3.48 | 21 |
| cpd 154 | ND | 118 | 1.06 | 111 |
| cpd 158 | ND | 119 | 17.79 | 7 |
| cpd 162 | ND | >250 | 72.12 | >3 |
| cpd 168 | ND | 127.7 | 23.95 | 5 |
| cpd 174 | ND | 155 | 25 | 6 |

All publications and patent applications cited herein are incorporated by reference to the same extent as if each individual publication or patent application was specifically and individually indicated to be incorporated by reference. Specifically cited sections or pages of the above cited works are incorporated by reference with specificity. The invention has been described in detail sufficient to allow one of ordinary skill in the art to make and use the subject matter of the described embodiments. Many modifications are possible in the embodiments without departing from the teachings thereof. All such modifications are intended to be encompassed within the claims of the invention.

The invention claimed is:

1. A compound a according to the formula (A1):

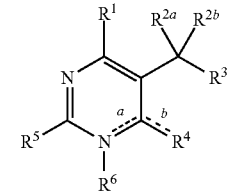

(A1)

wherein,
each dotted line represents an optional double bond, whereby if the dotted line "a" forms a double bond, the dotted line "b" does not form a double bond and whereby if the dotted line "b" forms a double bond, the dotted line "a" does not form a double bond;

$R^1$ is independently selected from alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl or heterocycle-heteroalkynyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more $Z^1$;

$R^{2a}$ is hydrogen;
$R^{2b}$ is selected from the group consisting of $C_3$-$C_4$-alkyl, O—($C_1$-$C_4$-alkyl) and arylalkyl;

wherein said alkyl, or arylalkyl, can be unsubstituted or substituted with one or more $Z^1$;

$R^3$ is —C(O)OH or —C(O)O-alkyl;

when the dotted line "a" forms a double bond, $R^4$ is independently selected from hydrogen; halogen; cyano; hydroxyl; alkyl; alkenyl, alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; and heterocycle-alkynyl; heterocycle-heteroalkyl; heterocycle-heteroalkenyl; and heterocycle-heteroalkynyl; and when the dotted line "b" forms a double bond, $R^4$ is independently selected from O and S;

wherein said alkyl, alkenyl, alkynyl, heteroalkyl, heteroalkenyl, heteroalkynyl, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl or heterocycle-heteroalkynyl can be unsubstituted or substituted with one or more $Z^1$;

when the dotted line "a" forms a double bond, $R^6$ is not present and when the dotted line "b" forms a double bond, $R^6$ is independently selected from hydrogen; alkyl; alkenyl, alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; heterocycle-heteroalkynyl;

wherein said alkyl, alkenyl, alkynyl, heteroalkyl, heteroalkenyl, heteroalkynyl, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl or heterocycle-heteroalkynyl can be unsubstituted or substituted with one or more $Z^1$;

$R^5$ is selected from halogen; cyano; —$NR^{10}R^{11}$; alkyl; alkenyl; alkynyl; heteroalkyl; heteroalkenyl; heteroalkynyl; aryl; arylalkyl; arylalkenyl; arylalkynyl; arylheteroalkyl; arylheteroalkenyl; arylheteroalkynyl; heterocycle; heterocycle-alkyl; heterocycle-alkenyl; heterocycle-alkynyl; heterocycle-heteroalkyl, heterocycle-heteroalkenyl, or heterocycle-heteroalkynyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more $R^{20}$;

each $R^{10}$ and $R^{11}$ is independently selected from hydrogen; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl; or $R^{10}$ and $R^{11}$ can be taken together with the nitrogen to which they are attached to in order to form a 4-, 5-, 6-, 7- or 8-membered heterocycle which can be unsubstituted or substituted with one or more $R^{20}$;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more $R^{20}$;

each $R^{20}$ is independently selected from the group consisting of halogen; —$OR^{21}$; =O; —$SR^{21}$; =S; —$S(O)R^{22}$; —$S(O)_2R^{22}$; —$S(O)_2NR^{23}R^{24}$; trifluoromethyl; nitro; —$NR^{23}R^{24}$; —$NR^{21}S(O)_2R^{22}$; cyano; —$NR^{21}C(O)R^{22}$; —$NR^{21}C(O)NR^{23}R^{24}$; —$C(O)OR^{21}$; —$C(O)NR^{23}R^{24}$; —$C(O)R^{22}$; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more $Z^1$;

each $R^{21}$ is independently selected from hydrogen; alkyl; alkenyl; alkynyl; heteroalkyl; heteroalkenyl; heteroalkynyl; aryl; arylalkyl; arylalkenyl; arylalkynyl; arylheteroalkyl; arylheteroalkenyl; arylheteroalkynyl; heterocycle; heterocycle-alkyl; heterocycle-alkenyl; heterocycle-alkynyl; heterocycle-heteroalkyl; heterocycle-heteroalkenyl; and heterocycle-heteroalkynyl;

wherein said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, heterocycle, heterocycle-alkyl, heterocycle-alkenyl, heterocycle-alkynyl, heterocycle-heteroalkyl, heterocycle-heteroalkenyl, and heterocycle-heteroalkynyl can be unsubstituted or substituted with one or more $Z^1$;

each $R^{22}$ is independently selected from hydrogen; hydroxyl; alkyl; alkenyl; alkynyl; heteroalkyl; heteroalkenyl; heteroalkynyl; aryl; arylalkyl; arylalkenyl; arylalkynyl; arylheteroalkyl; arylheteroalkenyl; arylheteroalkynyl; heterocycle; heterocycle-alkyl; heterocycle-alkenyl; heterocycle-alkynyl; heterocycle-heteroalkyl; heterocycle-heteroalkenyl; and heterocycle-heteroalkynyl;

wherein said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, heterocycle, heterocycle-alkyl, heterocycle-alkenyl, heterocycle-alkynyl, heterocycle-heteroalkyl, heterocycle-heteroalkenyl, and heterocycle-heteroalkynyl can be unsubstituted or substituted with one or more $Z^1$;

each $R^{23}$ and $R^{24}$ is independently selected from hydrogen; alkyl; alkenyl; alkynyl; heteroalkyl; heteroalkenyl; heteroalkynyl; aryl; arylalkyl; arylalkenyl; arylalkynyl; arylheteroalkyl; arylheteroalkenyl; arylheteroalkynyl; heterocycle; heterocycle-alkyl; heterocycle-alkenyl; heterocycle-alkynyl; heterocycle-heteroalkyl; heterocycle-heteroalkenyl; and heterocycle-heteroalkynyl; or $R^{23}$ and $R^{24}$ can be taken together with the nitrogen to which they are attached to in order to form a 4-, 5-, 6-, 7- or 8-membered heterocycle which can be unsubstituted or substituted with one or more $Z^1$;

wherein said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, heterocycle, heterocycle-alkyl, heterocycle-alkenyl, heterocycle-alkynyl, heterocycle-heteroalkyl, heterocycle-heteroalkenyl, and heterocycle-heteroalkynyl can be unsubstituted or substituted with one or more $Z^1$;

each $Z^1$ is independently selected from the group consisting of hydrogen; halogen; $-OZ^2$; $=O$; $-SZ^2$; $=S$; $-S(O)Z^3$; $-S(O)_2Z^3$; $-S(O)_2NZ^4Z^5$; trifluoromethyl; nitro; $-NZ^4Z^5$; $-NZ^2S(O)_2Z^3$; cyano; $-NZ^2C(O)Z^3$; $-NZ^2C(O)NZ^4Z^5$; $-C(O)OZ^2$; $-C(O)NZ^4Z^5$; $-C(O)Z^3$; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more $Z^{11}$;

or two $Z^1$ on the same carbon atom or nitrogen atom can be taken together with the 4-, 5-, 6-, 7- or 8-membered ring they are attached to form a spiro-cycloalkyl; a spiro-cycloalkenyl; or a saturated or unsaturated spiro-heterocycle;

each $Z^{11}$ is independently selected from the group consisting of hydrogen; halogen; $-OZ^{12}$; $=O$; $-SZ^{12}$; $=S$; $-S(O)Z^{13}$; $-S(O)_2Z^{13}$; $-S(O)_2NZ^{14}Z^{15}$; trifluoromethyl; nitro; $-NZ^{14}Z^{15}$; $-NZ^{12}S(O)_2Z^{13}$; cyano; $-NZ^{12}C(O)Z^{13}$; $-NZ^{12}C(O)NZ^{14}Z^{15}$; $-C(O)OZ^{12}$; $-C(O)NZ^{14}Z^{15}$; $-C(O)Z^{13}$; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from the group of alkyl, alkenyl, alkynyl, heteroalkyl, heteroalkenyl, heteroalkynyl, hydroxyl, $=O$, halogen, $-SH$, $=S$, trifluoromethyl, $-O$-alkyl, $-OCF_3$, cyano, nitro, $-C(O)OH$ or $-NH_2$;

each $Z^2$ and $Z^{12}$ is independently selected from hydrogen; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with alkyl, alkenyl, alkynyl, heteroalkyl, heteroalkenyl, heteroalkynyl, hydroxyl, $=O$, halogen, $-SH$, $=S$, trifluoromethyl, $-O$-alkyl, $-OCF_3$, cyano, nitro, $-C(O)OH$ or $-NH_2$;

each $Z^3$ and $Z^{13}$ is independently selected from hydroxyl; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more selected from the group of alkyl, alkenyl, alkynyl, heteroalkyl, heteroalkenyl, heteroalkynyl, hydroxyl, $=O$, halogen, $-SH$, $=S$, trifluoromethyl, $-O$-alkyl, $-OCF_3$, cyano, nitro, $-C(O)OH$ or $-NH_2$;

each $Z^4$, $Z^5$, $Z^{14}$ and $Z^{15}$ is independently selected from hydrogen; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl, or heterocycle-heteroalkynyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more selected from the group of alkyl, alkenyl, alkynyl, heteroalkyl, heteroalkenyl, heteroalkynyl, hydroxyl, $=O$, halogen, $-SH$, $=S$, trifluoromethyl, $-O$-alkyl, $-OCF_3$, cyano, nitro, $-C(O)OH$ or $-NH_2$;

or wherein $Z^4$ and $Z^5$, and $Z^{14}$ and $Z^{15}$ respectively, can be taken together in order to form a (4-, 5-, 6-, 7-, or 8-membered) heterocycle which can be unsubstituted or substituted with alkyl, alkenyl, alkynyl, heteroalkyl, heteroalkenyl, heteroalkynyl, hydroxyl, halogen, $-SH$, trifluoromethyl, $-O$-alkyl, $-OCF_3$, cyano, nitro, $-C(O)OH$ or $-NH_2$;

and tautomers, stereo-isomers, solvates, hydrates, or salts thereof.

2. The compound according to claim 1, wherein $R^3$ is $-C(O)OH$.

3. The compound according to claim 1, wherein $R^1$ is selected from aryl or heteroaryl, wherein said aryl or heteroaryl can be unsubstituted or substituted with one or more $Z^1$.

4. The compound according to claim 3, wherein $R^1$ is selected from benzothiazolyl, quinolinyl, piperidinyl, 1-H-azepinyl, 4-methyl-piperazinyl, naphtyl, benzothiophenyl, benzofuranyl, indazolyl, N-methyl-indazolyl, chromanyl, 4H-isoquinolinyl, isochromanyl, 5-F-8-Me-isochromanyl, 5 Cl-isochromanyl, t-butyl, ethyl, phenyl, and phenyl substituted with 1, 2 or 3 substituents independently selected from the group consisting of $C_1$-$C_4$-alkyl, chloro, fluoro, hydroxy, methoxy, trifluoromethyl.

5. The compound according to claim 1, wherein $R^5$ is selected from $NR^{10}R^{11}$; aryl; arylalkyl; arylalkenyl; NH-aryl, and heterocycle; wherein said aryl, arylalkyl, — and heterocycle can be unsubstituted or substituted with one or more substituents independently selected from the group consisting of halogen; —OH; —O-phenyl, —N(CH_3)_2, NH(CO)(phenyl); —C(O)NH($C_1$-$C_4$-alkyl); $C_1$-$C_4$-alkyl; phenyl; 1,2,4-oxadiazolyl; benzyl; phenylethylenyl, wherein said 1,2,4-oxadiazolyl is further substituted with one C1-C4-alkyl, preferably with isopropyl.

6. The compound according to claim 1, wherein the compound has a structure according to formula (C2),

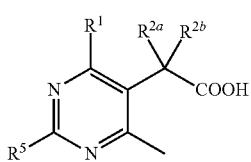

(C2)

wherein each of $R^1$, $R^{2a}$, $R^{2b}$ and $R^5$ are as in claim 1.

7. The compound according to claim 1, wherein the compound has a structure according to formula (E),

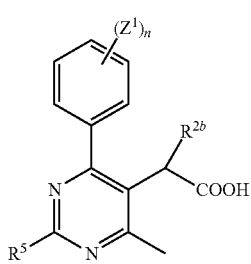

(E2)

wherein each of $R^{2b}$, $R^5$ and $Z^1$ are as in claim 1.

8. The compound according to claim 1, wherein the compound has a structure according to formula (G1),

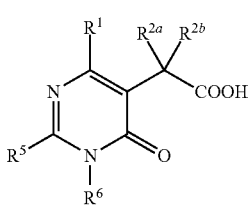

(G1)

wherein each of $R^1$, $R^{2a}$, $R^{2b}$, $R^5$ and $R^6$ are as in claim 1.

9. The compounds according to claim 1 selected from the list of:
methyl 2-(2-(dimethylamino)-4-methyl-6-phenylpyrimidin-5-yl)pentanoate
2-(2-(dimethylamino)-4-methyl-6-phenylpyrimidin-5-yl)pentanoic acid
methyl 2-(2-benzyl-4-methyl-6-phenylpyrimidin-5-yl)pentanoate
2-(2-benzyl-4-methyl-6-phenylpyrimidin-5-yl)pentanoic acid
(E)-methyl 2-(4-methyl-6-phenyl-2-styrylpyrimidin-5-yl)pentanoate
(E)-2-(4-methyl-6-phenyl-2-styrylpyrimidin-5-yl)pentanoic acid
methyl 2-(4-methyl-2-phenethyl-6-phenylpyrimidin-5-yl)pentanoate
2-(4-methyl-2-phenethyl-6-phenylpyrimidin-5-yl)pentanoic acid
methyl 2-(4-methyl-2,6-dip-tolylpyrimidin-5-yl)pentanoate
2-(4-methyl-2,6-dip-tolylpyrimidin-5-yl)pentanoic acid
methyl 2-(2-(cyclohexyl(methyl)amino)-4-methyl-6-p-tolylpyrimidin-5-yl)pentanoate
2-(2-(cyclohexyl(methyl)amino)-4-methyl-6-p-tolylpyrimidin-5-yl)pentanoic acid
methyl 2-(4-methyl-2-phenyl-6-p-tolylpyrimidin-5-yl)pentanoate
2-(4-methyl-2-phenyl-6-p-tolylpyrimidin-5-yl)pentanoic acid
methyl 2-(2-(2-chlorophenyl)-4-methyl-6-phenylpyrimidin-5-yl)pentanoate
2-(2-(2-chlorophenyl)-4-methyl-6-phenylpyrimidin-5-yl)pentanoic acid
methyl 2-(2-(2-chlorophenyl)-4-methyl-6-p-tolylpyrimidin-5-yl)pentanoate
2-(2-(2-chlorophenyl)-4-methyl-6-p-tolylpyrimidin-5-yl)pentanoic acid
methyl 2-(4-methyl-6-phenyl-2-(piperidin-1-yl)pyrimidin-5-yl)pentanoate
2-(4-methyl-6-phenyl-2-(piperidin-1-yl)pyrimidin-5-yl)pentanoic acid
methyl 2-(4-methyl-2-(piperidin-1-yl)-6-p-tolylpyrimidin-5-yl)pentanoate
2-(4-methyl-2-(piperidin-1-yl)-6-p-tolylpyrimidin-5-yl)pentanoic acid
methyl 2-(4-methyl-2,6-diphenylpyrimidin-5-yl)pentanoate
2-(4-methyl-2,6-diphenylpyrimidin-5-yl)pentanoic acid
methyl 2-(4-(3-hydroxyphenyl)-6-methyl-2-phenylpyrimidin-5-yl)pentanoate
2-(4-(3-hydroxyphenyl)-6-methyl-2-phenylpyrimidin-5-yl)pentanoic acid
methyl 2-(4-methyl-2-morpholino-6-p-tolylpyrimidin-5-yl)pentanoate
2-(4-methyl-2-morpholino-6-p-tolylpyrimidin-5-yl)pentanoic acid
methyl 2-(4-methyl-2-(pyrrolidin-1-yl)-6-p-tolylpyrimidin-5-yl)pentanoate
2-(4-methyl-2-(pyrrolidin-1-yl)-6-p-tolylpyrimidin-5-yl)pentanoic acid
methyl 2-(4-methyl-2-(4-methylpiperazin-1-yl)-6-p-tolylpyrimidin-5-yl)pentanoate
2-(4-methyl-2-(4-methylpiperazin-1-yl)-6-p-tolylpyrimidin-5-yl)pentanoic acid
methyl 2-(2-(3,5-dimethylpiperidin-1-yl)-4-methyl-6-p-tolylpyrimidin-5-yl)pentanoate
2-(2-(3,5-dimethylpiperidin-1-yl)-4-methyl-6-p-tolylpyrimidin-5-yl)pentanoic acid
methyl 2-(2-(azepan-1-yl)-4-methyl-6-p-tolylpyrimidin-5-yl)pentanoate
2-(2-(azepan-1-yl)-4-methyl-6-p-tolylpyrimidin-5-yl)pentanoic acid
methyl 2-(2-(3-(isobutylcarbamoyl)piperidin-1-yl)-4-methyl-6-p-tolylpyrimidin-5-yl)pentanoate
2-(2-(3-(isobutylcarbamoyl)piperidin-1-yl)-4-methyl-6-p-tolylpyrimidin-5-yl)pentanoic acid methyl 2-(4-methyl-2-(3-methylpiperidin-1-yl)-6-p-tolylpyrimidin-5-yl)pentanoate
2-(4-methyl-2-(3-methylpiperidin-1-yl)-6-p-tolylpyrimidin-5-yl)pentanoic acid
methyl 2-(2-(3,4-dihydroisoquinolin-2(1H)-yl)-4-methyl-6-p-tolylpyrimidin-5-yl)pentanoate
2-(2-(3,4-dihydroisoquinolin-2(1H)-yl)-4-methyl-6-p-tolylpyrimidin-5-yl)pentanoic acid
methyl 2-(2-(4-benzyl-1,4-diazepan-1-yl)-4-methyl-6-p-tolylpyrimidin-5-yl)pentanoate
2-(2-(4-benzyl-1,4-diazepan-1-yl)-4-methyl-6-p-tolylpyrimidin-5-yl)pentanoic acid
methyl 2-(2-(3-(3-isopropyl-1,2,4-oxadiazol-5-yl)piperidin-1-yl)-4-methyl-6-p-tolylpyrimidin-5-yl)pentanoic acid
2-(2-(3-(3-isopropyl-1,2,4-oxadiazol-5-yl)piperidin-1-yl)-4-methyl-6-p-tolylpyrimidin-5-yl)pentanoic acid
methyl 2-(4-methyl-2-(3-phenoxypiperidin-1-yl)-6-p-tolylpyrimidin-5-yl)pentanoate
2-(4-methyl-2-(3-phenoxypiperidin-1-yl)-6-p-tolylpyrimidin-5-yl)pentanoic acid
methyl 2-(4-methyl-2-(3-phenylpiperidin-1-yl)-6-p-tolylpyrimidin-5-yl)pentanoate
2-(4-methyl-2-(3-phenylpiperidin-1-yl)-6-p-tolylpyrimidin-5-yl)pentanoic acid
methyl 2-(2-((S)-3-(dimethylamino)pyrrolidin-1-yl)-4-methyl-6-p-tolylpyrimidin-5-yl)pentanoate
2-(2-((S)-3-(dimethylamino)pyrrolidin-1-yl)-4-methyl-6-p-tolylpyrimidin-5-yl)pentanoic acid
methyl 2-(2-(4-benzamidopiperidin-1-yl)-4-methyl-6-p-tolylpyrimidin-5-yl)pentanoate
2-(2-(4-benzamidopiperidin-1-yl)-4-methyl-6-p-tolylpyrimidin-5-yl)pentanoic acid
methyl 2-(2-(4-ethyl-1,4-diazepan-1-yl)-4-methyl-6-p-tolylpyrimidin-5-yl)pentanoate
2-(2-(4-ethyl-1,4-diazepan-1-yl)-4-methyl-6-p-tolylpyrimidin-5-yl)pentanoic acid
methyl 2-(2-(indolin-1-yl)-4-methyl-6-p-tolylpyrimidin-5-yl)pentanoate
2-(2-(indolin-1-yl)-4-methyl-6-p-tolylpyrimidin-5-yl)pentanoic acid
methyl 2-(4-methyl-2-phenyl-6-(piperidin-1-yl)pyrimidin-5-yl)pentanoate
2-(4-methyl-2-phenyl-6-(piperidin-1-yl)pyrimidin-5-yl)pentanoic acid
methyl 2-(4-(azepan-1-yl)-6-methyl-2-phenylpyrimidin-5-yl)pentanoate
2-(4-(azepan-1-yl)-6-methyl-2-phenylpyrimidin-5-yl)pentanoic acid
methyl 2-(4-methyl-6-(4-methylpiperazin-1-yl)-2-phenylpyrimidin-5-yl)pentanoate
2-(4-methyl-6-(4-methylpiperazin-1-yl)-2-phenylpyrimidin-5-yl)pentanoic acid
methyl 2-(4-(3,4-dimethylphenyl)-6-methyl-2-phenylpyrimidin-5-yl)pentanoate
2-(4-(3,4-dimethylphenyl)-6-methyl-2-phenylpyrimidin-5-yl)pentanoic acid
methyl 2-(4-methyl-6-(naphthalen-2-yl)-2-phenylpyrimidin-5-yl)pentanoate
2-(4-methyl-6-(naphthalen-2-yl)-2-phenylpyrimidin-5-yl)pentanoic acid
methyl 2-(4-(2,3-dihydrobenzofuran-5-yl)-6-methyl-2-phenylpyrimidin-5-yl)pentanoate
2-(4-(2,3-dihydrobenzofuran-5-yl)-6-methyl-2-phenylpyrimidin-5-yl)pentanoic acid
methyl 2-(4-(benzofuran-5-yl)-6-methyl-2-phenylpyrimidin-5-yl)pentanoate
2-(4-(benzofuran-5-yl)-6-methyl-2-phenylpyrimidin-5-yl)pentanoic acid
methyl 2-(4-methyl-6-(1-methyl-1H-indol-5-yl)-2-phenylpyrimidin-5-yl)pentanoate
2-(4-methyl-6-(1-methyl-1H-indol-5-yl)-2-phenylpyrimidin-5-yl)pentanoic acid
methyl 2-(4-(3,4-dihydroisoquinolin-2(1H)-yl)-6-methyl-2-phenylpyrimidin-5-yl)pentanoate
2-(4-(3,4-dihydroisoquinolin-2(1H)-yl)-6-methyl-2-phenylpyrimidin-5-yl)pentanoic acid
methyl 2-(4-methyl-6-phenoxy-2-phenylpyrimidin-5-yl)pentanoate
2-(4-methyl-6-phenoxy-2-phenylpyrimidin-5-yl)pentanoic acid
methyl 2-(4-(1H-indol-5-yl)-6-methyl-2-phenylpyrimidin-5-yl)pentanoate
2-(4-(1H-indol-5-yl)-6-methyl-2-phenylpyrimidin-5-yl)pentanoic acid
methyl 2-(4-(1H-indol-6-yl)-6-methyl-2-phenylpyrimidin-5-yl)pentanoate
2-(4-(1H-indol-6-yl)-6-methyl-2-phenylpyrimidin-5-yl)pentanoic acid
methyl 2-(4-(3,4-dihydro-2H-benzo[b][1,4]dioxepin-7-yl)-6-methyl-2-phenylpyrimidin-5-yl)pentanoate
2-(4-(3,4-dihydro-2H-benzo[b][1,4]dioxepin-7-yl)-6-methyl-2-phenylpyrimidin-5-yl)pentanoic acid
methyl 2-(4-methyl-6-(4-methyl-3,4-dihydro-2H-benzo[b][1,4]oxazin-7-yl)-2-phenylpyrimidin-5-yl)pentanoate
2-(4-methyl-6-(4-methyl-3,4-dihydro-2H-benzo[b][1,4]oxazin-7-yl)-2-phenylpyrimidin-5-yl)pentanoic acid
methyl 2-(4-(benzo[b]thiophen-5-yl)-6-methyl-2-phenylpyrimidin-5-yl)pentanoate
2-(4-(benzo[b]thiophen-5-yl)-6-methyl-2-phenylpyrimidin-5-yl)pentanoic acid
methyl 2-(4-(chroman-6-yl)-6-methyl-2-phenylpyrimidin-5-yl)pentanoate
2-(4-(chroman-6-yl)-6-methyl-2-phenylpyrimidin-5-yl)pentanoic acid
methyl 2-(4-methyl-6-(1-methyl-1H-indol-6-yl)-2-phenylpyrimidin-5-yl)pentanoate
2-(4-methyl-6-(1-methyl-1H-indol-6-yl)-2-phenylpyrimidin-5-yl)pentanoic acid
methyl 2-(4-(4-chloro-2-fluorophenyl)-6-methyl-2-phenylpyrimidin-5-yl)pentanoate
2-(4-(4-chloro-2-fluorophenyl)-6-methyl-2-phenylpyrimidin-5-yl)pentanoic acid
methyl 2-(4-methyl-6-(1-methylindolin-5-yl)-2-phenylpyrimidin-5-yl)pentanoate
2-(4-methyl-6-(1-methylindolin-5-yl)-2-phenylpyrimidin-5-yl)pentanoic acid
methyl 2-(4-(2-fluoro-4-methylphenyl)-6-methyl-2-phenylpyrimidin-5-yl)pentanoate
2-(4-(2-fluoro-4-methylphenyl)-6-methyl-2-phenylpyrimidin-5-yl)pentanoic acid
methyl 2-(4-methyl-6-(2-oxo-2,3-dihydro-1H-benzo[d]imidazol-5-yl)-2-phenylpyrimidin-5-yl)pentanoate
2-(4-methyl-6-(2-oxo-2,3-dihydro-1H-benzo[d]imidazol-5-yl)-2-phenylpyrimidin-5-yl)pentanoic acid
methyl 2-(4-(4-chlorophenyl)-6-methyl-2-phenylpyrimidin-5-yl)pentanoate
2-(4-(4-chlorophenyl)-6-methyl-2-phenylpyrimidin-5-yl)pentanoic acid
methyl 2-(4-methyl-6-(2-oxoindolin-6-yl)-2-phenylpyrimidin-5-yl)pentanoate
2-(4-methyl-6-(2-oxoindolin-6-yl)-2-phenylpyrimidin-5-yl)pentanoic acid methyl 2-(4-(4-isopropylphenyl)-6-methyl-2-phenylpyrimidin-5-yl)pentanoate
2-(4-(4-isopropylphenyl)-6-methyl-2-phenylpyrimidin-5-yl)pentanoic acid
methyl 2-(4-methyl-2-phenyl-6-(4-(trifluoromethyl)phenyl)pyrimidin-5-yl)pentanoate
2-(4-methyl-2-phenyl-6-(4-(trifluoromethyl)phenyl)pyrimidin-5-yl)pentanoic acid
methyl 2-(4-(4-chloro-2-methoxyphenyl)-6-methyl-2-phenylpyrimidin-5-yl)pentanoate
2-(4-(4-chloro-2-methoxyphenyl)-6-methyl-2-phenylpyrimidin-5-yl)pentanoic acid
2-(4-(4-chloro-2-hydroxyphenyl)-6-methyl-2-phenylpyrimidin-5-yl)pentanoic acid
methyl 2-(4-methyl-6-(3-oxo-2,3-dihydro-1H-inden-5-yl)-2-phenylpyrimidin-5-yl)pentanoate
2-(4-methyl-6-(3-oxo-2,3-dihydro-1H-inden-5-yl)-2-phenylpyrimidin-5-yl)pentanoic acid
methyl 2-(4-(benzo[d]thiazol-6-yl)-6-methyl-2-phenylpyrimidin-5-yl)pentanoate
2-(4-(benzo[d]thiazol-6-yl)-6-methyl-2-phenylpyrimidin-5-yl)pentanoic acid
methyl 2-(4-benzyl-6-methyl-2-phenylpyrimidin-5-yl)pentanoate
2-(4-benzyl-6-methyl-2-phenylpyrimidin-5-yl)pentanoic acid
methyl 2-(4-(2-hydroxy-4-methylphenyl)-6-methyl-2-phenylpyrimidin-5-yl)pentanoate
2-(4-(2-hydroxy-4-methylphenyl)-6-methyl-2-phenylpyrimidin-5-yl)pentanoic acid
2-(4-(2-methoxy-4-methylphenyl)-6-methyl-2-phenylpyrimidin-5-yl)pentanoic acid
methyl 6,6,6-trifluoro-2-(4-methyl-2-(piperidin-1-yl)-6-p-tolylpyrimidin-5-yl)hexanoate
6,6,6-trifluoro-2-(4-methyl-2-(piperidin-1-yl)-6-p-tolylpyrimidin-5-yl)hexanoic acid
methyl 2-(4-methyl-2-(piperidin-1-yl)-6-p-tolylpyrimidin-5-yl)-3-phenylpropanoate
2-(4-methyl-2-(piperidin-1-yl)-6-p-tolylpyrimidin-5-yl)-3-phenylpropanoic acid
methyl 3-methyl-2-(4-methyl-2-(piperidin-1-yl)-6-p-tolylpyrimidin-5-yl)pentanoate
3-methyl-2-(4-methyl-2-(piperidin-1-yl)-6-p-tolylpyrimidin-5-yl)pentanoic acid
methyl 2-(4-(2,4-difluorophenyl)-6-methyl-2-(piperidin-1-yl)pyrimidin-5-yl)pentanoate
2-(4-(2,4-difluorophenyl)-6-methyl-2-(piperidin-1-yl)pyrimidin-5-yl)pentanoic acid
methyl 2-(4-(2,4-dimethylphenyl)-6-methyl-2-(piperidin-1-yl)pyrimidin-5-yl)pentanoate
2-(4-(2,4-dimethylphenyl)-6-methyl-2-(piperidin-1-yl)pyrimidin-5-yl)pentanoic acid
methyl 2-(4-(4-isopropylphenyl)-6-methyl-2-(piperidin-1-yl)pyrimidin-5-yl)pentanoate
2-(4-(4-isopropylphenyl)-6-methyl-2-(piperidin-1-yl)pyrimidin-5-yl)pentanoic acid
methyl 2-(4-(2-fluoro-4-methoxyphenyl)-6-methyl-2-(piperidin-1-yl)pyrimidin-5-yl)pentanoate
2-(4-(2-fluoro-4-methoxyphenyl)-6-methyl-2-(piperidin-1-yl)pyrimidin-5-yl)pentanoic acid
methyl 2-(4-methyl-2-(piperidin-1-yl)-6-(quinolin-5-yl)pyrimidin-5-yl)pentanoate
2-(4-methyl-2-(piperidin-1-yl)-6-(quinolin-5-yl)pyrimidin-5-yl)pentanoic acid
methyl 2-(4-methyl-2-(piperidin-1-yl)-6-(quinolin-8-yl)pyrimidin-5-yl)pentanoate
2-(4-methyl-2-(piperidin-1-yl)-6-(quinolin-8-yl)pyrimidin-5-yl)pentanoic acid
methyl 2-(4-methyl-2-(piperidin-1-yl)-6-(2,4,5-trifluorophenyl)pyrimidin-5-yl)pentanoate
2-(4-methyl-2-(piperidin-1-yl)-6-(2,4,5-trifluorophenyl)pyrimidin-5-yl)pentanoic acid
methyl 2-(4-(2-chloro-4-methylphenyl)-6-methyl-2-(piperidin-1-yl)pyrimidin-5-yl)pentanoate
2-(4-(2-chloro-4-methylphenyl)-6-methyl-2-(piperidin-1-yl)pyrimidin-5-yl)pentanoic acid
methyl 2-(4-(4-chloro-2-fluorophenyl)-6-methyl-2-(piperidin-1-yl)pyrimidin-5-yl)pentanoate
2-(4-(4-chloro-2-fluorophenyl)-6-methyl-2-(piperidin-1-yl)pyrimidin-5-yl)pentanoic acid
methyl 2-(4-methyl-2,6-di(piperidin-1-yl)pyrimidin-5-yl)pentanoate
2-(4-methyl-2,6-di(piperidin-1-yl)pyrimidin-5-yl)pentanoic acid
methyl 2-(4-(1,2-dihydroacenaphthylen-5-yl)-6-methyl-2-(piperidin-1-yl)pyrimidin-5-yl)pentanoate
2-(4-(1,2-dihydroacenaphthylen-5-yl)-6-methyl-2-(piperidin-1-yl)pyrimidin-5-yl)pentanoic acid
methyl 4,4-dimethyl-2-(4-methyl-2-(piperidin-1-yl)-6-p-tolylpyrimidin-5-yl)pentanoate
4,4-dimethyl-2-(4-methyl-2-(piperidin-1-yl)-6-p-tolylpyrimidin-5-yl)pentanoic acid
methyl 2-tert-butoxy-2-(4-methyl-2-(piperidin-1-yl)-6-p-tolylpyrimidin-5-yl)acetate
2-tert-butoxy-2-(4-methyl-2-(piperidin-1-yl)-6-p-tolylpyrimidin-5-yl)acetic acid
methyl 2-(4-(2,3-dihydropyrano[4,3,2-de]quinolin-7-yl)-6-methyl-2-(piperidin-1-yl)pyrimidin-5-yl)pentanoate
2-(4-(2,3-dihydropyrano[4,3,2-de]quinolin-7-yl)-6-methyl-2-(piperidin-1-yl)pyrimidin-5-yl)pentanoic acid
methyl 2-(4-(8-fluoro-5-methylchroman-6-yl)-6-methyl-2-(piperidin-1-yl)pyrimidin-5-yl)pentanoate
2-(4-(8-fluoro-5-methylchroman-6-yl)-6-methyl-2-(piperidin-1-yl)pyrimidin-5-yl)pentanoic acid
methyl 2-(4-(5-chlorochroman-6-yl)-6-methyl-2-(piperidin-1-yl)pyrimidin-5-yl)pentanoate
2-(4-(5-chlorochroman-6-yl)-6-methyl-2-(piperidin-1-yl)pyrimidin-5-yl)pentanoic acid
2-(1-methyl-6-oxo-2-(piperidin-1-yl)-4-p-tolyl-1,6-dihydropyrimidin-5-yl)pentanoic acid
2-(1-ethyl-6-oxo-2-(piperidin-1-yl)-4-p-tolyl-1,6-dihydropyrimidin-5-yl)pentanoic acid
2-(1-benzyl-6-oxo-2-(piperidin-1-yl)-4-p-tolyl-1,6-dihydropyrimidin-5-yl)pentanoic acid
methyl 2-tert-butoxy-2-(4-tert-butyl-6-methyl-2-(piperidin-1-yl)pyrimidin-5-yl)acetate
2-tert-butoxy-2-(4-tert-butyl-6-methyl-2-(piperidin-1-yl)pyrimidin-5-yl)acetic acid
methyl 2-(4-ethyl-6-methyl-2-phenylpyrimidin-5-yl)pentanoate
2-(4-ethyl-6-methyl-2-phenylpyrimidin-5-yl)pentanoic acid
methyl 2-(2-(2-fluorophenyl)-4-methyl-6-p-tolylpyrimidin-5-yl)pentanoate
2-(2-(2-fluorophenyl)-4-methyl-6-p-tolylpyrimidin-5-yl)pentanoic acid
methyl 2-(2-(2-hydroxyphenyl)-4-methyl-6-p-tolylpyrimidin-5-yl)pentanoate
2-(2-(2-hydroxyphenyl)-4-methyl-6-p-tolylpyrimidin-5-yl)pentanoic acid
methyl 2-(4-methyl-2-(quinolin-5-yl)-6-p-tolylpyrimidin-5-yl)pentanoate 2-(4-methyl-2-(quinolin-5-yl)-6-p-tolylpyrimidin-5-yl)
  pentanoic acid
methyl 2-(4-methyl-2-(1-methyl-1H-pyrazol-4-yl)-6-p-
  tolylpyrimidin-5-yl)pentanoate
2-(4-methyl-2-(1-methyl-1H-pyrazol-4-yl)-6-p-tolylpyri-
  midin-5-yl)pentanoic acid
methyl 2-(4-methyl-2-(phenylthio)-6-p-tolylpyrimidin-5-
  yl)pentanoate
2-(4-methyl-2-(phenylthio)-6-p-tolylpyrimidin-5-yl)pen-
  tanoic acid
methyl 2-(4-methyl-2-(phenylamino)-6-p-tolylpyrimidin-
  5-yl)pentanoate
2-(4-methyl-2-(phenylamino)-6-p-tolylpyrimidin-5-yl)
  pentanoic acid
methyl 2-(2-(benzylamino)-4-methyl-6-p-tolylpyrimidin-
  5-yl)pentanoate
2-(2-(benzylamino)-4-methyl-6-p-tolylpyrimidin-5-yl)
  pentanoic acid
methyl 2-(2-(2,6-difluorophenyl)-4-methyl-6-p-tolylpyri-
  midin-5-yl)pentanoate
2-(2-(2,6-difluorophenyl)-4-methyl-6-p-tolylpyrimidin-
  5-yl)pentanoic acid
methyl 2-(4-methyl-2-(neopentylamino)-6-p-tolylpyrimi-
  din-5-yl)pentanoate
2-(4-methyl-2-(neopentylamino)-6-p-tolylpyrimidin-5-
  yl)pentanoic acid

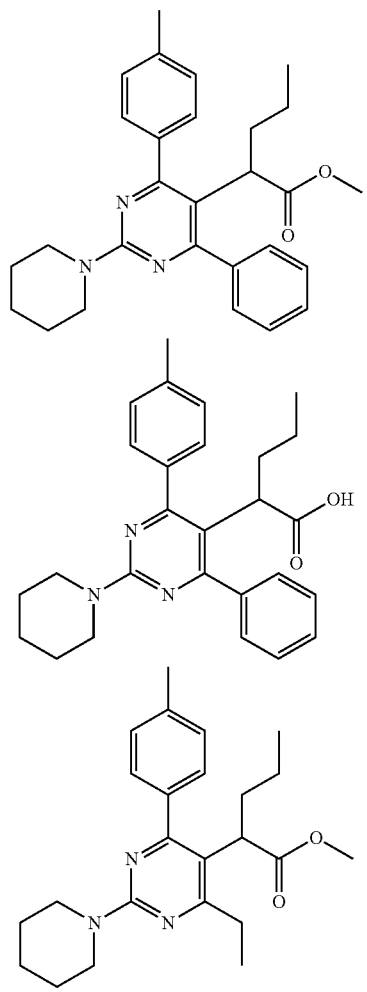

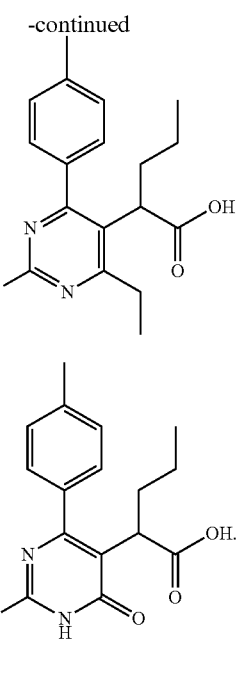

10. A method for the preparation of the compounds according to claim 1 comprising the steps of:
   preparing a substituted or non-substituted 2-(4-oxo-2-thioxo-1,2,3,4-tetrahydropyrimidin-5-yl)acetic acid derivative;
   converting a substituted or non-substituted 2-(4-oxo-2-thioxo-1,2,3,4-tetrahydropyrimidin-5-yl)acetic acid derivative into a substituted or non-substituted 2-(2,4-dioxo-1,2,3,4-tetrahydropyrimidin-5-yl)acetic acid derivative which is ultimately converted in a substituted or non-substituted 2-(pyrimidin-5-yl)acetate;
   preparing a substituted or non-substituted 2-(6-oxo-1,6-dihydropyrimidin-5-yl)acetic acid derivative;
   converting a substituted or non-substituted 2-(6-oxo-1,6-dihydropyrimidin-5-yl)acetic acid derivative into a substituted or non-substituted 2-(pyrimidin-5-yl)acetate;
   substituting a 2-(pyrimidin-5-yl)acetate derivative on position 2 and/or 4 of the pyrimidine moiety and/or on position 2 of the acetate side chain sequentially and in a specific manner (amination, alkylation, arylation) with suitable chemical reagents to obtain the desired compounds; and
   hydrolyzing the obtained compounds in the previous step to obtain the desired 2-(pyrimidin-5-yl)acetic acid derivatives.

11. A pharmaceutical composition comprising the compounds according to claim 1 as an active ingredient in admixture with at least a pharmaceutically acceptable carrier.

12. The pharmaceutical composition according to claim 11, wherein said pharmaceutical composition has an activity selected from the group consisting of anti-HIV-1 and anti-HIV-2 activity.

13. The pharmaceutical composition according to claim 11, further comprising a compound with antiviral activity selected from reverse transcriptase inhibitors, protease inhibitors, integrase inhibitors, entry inhibitors and compounds with other mechanisms of action.

14. A method of treatment of an HIV-1 or HIV-2 infection in an animal or mammal, comprising administering to the animal or mammal in need of such treatment a therapeutically effective amount of a compound according to any of the claim 1.

* * * * *

UNITED STATES PATENT AND TRADEMARK OFFICE
CERTIFICATE OF CORRECTION

PATENT NO.      : 8,906,906 B2
APPLICATION NO. : 13/388712
DATED           : December 9, 2014
INVENTOR(S)     : Chaltin et al.

Page 1 of 1

It is certified that error appears in the above-identified patent and that said Letters Patent is hereby corrected as shown below:

<u>In the claims:</u>

In claim 4, col. 200, line 66, change "5 Cl-isochromanyl" to --5-Cl-isochromanyl--.

In claim 5, col. 201, line 5, change "arylalkyl;arylalkenyl" to --arylalkyl; arylalkenyl--.

In claim 5, col. 201, line 6, delete "–".

In claim 9, col. 203, line 14, change "pentanoic acid" to --pentanoate--.

In claim 13, col. 208, line 58, change "11" to --12--.

Signed and Sealed this
Twenty-first Day of July, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,906,906 B2 | Page 1 of 1 |
| APPLICATION NO. | : 13/388712 | |
| DATED | : December 9, 2014 | |
| INVENTOR(S) | : Chaltin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 242 days.

Signed and Sealed this
Twenty-second Day of September, 2015

Michelle K. Lee
*Director of the United States Patent and Trademark Office*